US012746360B2

(12) United States Patent
Huddart et al.

(10) Patent No.: US 12,746,360 B2
(45) **Date of Patent: *Sep. 29, 2026**

(54) HEADGEAR ASSEMBLIES AND INTERFACE ASSEMBLIES WITH HEADGEAR

(71) Applicant: Fisher & Paykel Healthcare Limited, Auckland (NZ)

(72) Inventors: Brett John Huddart, Auckland (NZ); Jeroen Hammer, Auckland (NZ); Matthew Robert Geoff Slight, Auckland (NZ); Vitaly Kapelevich, Auckland (NZ); David Monroy Felix, Auckland (NZ); Jason Allan Klenner, Auckland (NZ); Andrew Paul Maxwell Salmon, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 757 days.

This patent is subject to a terminal disclaimer.

(21) Appl. No.: 18/194,975

(22) Filed: Apr. 3, 2023

(65) Prior Publication Data

US 2023/0347090 A1 Nov. 2, 2023

Related U.S. Application Data

(63) Continuation of application No. 16/838,963, filed on Apr. 2, 2020, now Pat. No. 11,648,365, which is a (Continued)

(51) Int. Cl.
*A61M 16/06* (2006.01)
*A61M 16/08* (2006.01)

(52) U.S. Cl.
CPC ........ *A61M 16/0683* (2013.01); *A61M 16/06* (2013.01); *A61M 16/0672* (2014.02); *A61M 16/0816* (2013.01); *A61M 16/0825* (2014.02)

(58) Field of Classification Search
CPC .......... A61M 16/0488; A61M 16/0683; A62B 18/084; B63C 2011/128; A44B 11/06; A44B 11/065; A44B 19/303
See application file for complete search history.

(56) References Cited

U.S. PATENT DOCUMENTS

| | | |
|---|---|---|
| 301,111 A | 7/1884 | Genese |
| 472,238 A | 4/1892 | Van Orden |

(Continued)

FOREIGN PATENT DOCUMENTS

| | | |
|---|---|---|
| CA | 996301 | 9/1976 |
| CA | 1311662 | 12/1992 |

(Continued)

OTHER PUBLICATIONS cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.

(Continued)

*Primary Examiner* — Joseph D. Boecker
(74) *Attorney, Agent, or Firm* — VIA LLP

(57) ABSTRACT

A headgear system and/or an interface assembly incorporating a headgear system that, in some configurations, is configured to transform from elasticated or "stretchy" behavior to "inelastic" behavior at least in response to normal or expected forces encountered during the intended therapy. In some configurations, upon fitment to the head of a user, the system automatically adjusts toward or to an appropriate size.

19 Claims, 86 Drawing Sheets

Related U.S. Application Data continuation of application No. 14/856,193, filed on Sep. 16, 2015, now Pat. No. 10,646,680.

(60) Provisional application No. 62/196,672, filed on Jul. 24, 2015, provisional application No. 62/138,304, filed on Mar. 25, 2015, provisional application No. 62/062,720, filed on Oct. 10, 2014, provisional application No. 62/053,026, filed on Sep. 19, 2014.

(56) References Cited

U.S. PATENT DOCUMENTS 577,926 A 3/1897 Miller
718,470 A 1/1903 Jones
751,091 A 2/1904 Moran
770,013 A 9/1904 Linn
1,364,104 A 1/1921 Geer
1,635,545 A 7/1927 Drager
1,942,442 A 1/1934 Motsinger
2,199,690 A 5/1940 Bullard
2,296,150 A 9/1942 Dockson et al.
2,353,643 A 7/1944 Bulbulian
2,359,506 A 10/1944 Battley et al.
2,388,604 A 11/1945 Eisenbud
2,390,233 A 12/1945 Akerman et al.
2,508,050 A 5/1950 Valente
2,586,851 A 2/1952 Monro et al.
2,611,897 A 9/1952 Adams
2,661,514 A 12/1953 Ada
2,693,800 A 11/1954 Caldwell
2,738,788 A 3/1956 Matheson et al.
2,843,121 A 7/1958 Hudson
2,859,748 A 11/1958 Hudson
3,045,672 A 7/1962 Croasdaile
3,156,922 A 11/1964 Anderson
3,295,529 A 1/1967 Corrigall et al.
3,416,521 A 12/1968 Humphrey
3,457,564 A 7/1969 Holloway
3,490,452 A 1/1970 Greenfield
3,500,474 A 3/1970 Austin
3,530,031 A 9/1970 Loew
3,792,702 A 2/1974 Delest
3,834,682 A 9/1974 McPhee
3,850,171 A 11/1974 Ball et al.
3,887,968 A 6/1975 Lynam
3,972,321 A 8/1976 Proctor
3,990,757 A 11/1976 Gill
3,992,720 A 11/1976 Nicolinas
3,994,022 A 11/1976 Villari et al.
3,994,521 A 11/1976 Van Gompel
4,051,556 A 10/1977 Davenport et al.
4,062,068 A 12/1977 Davenport et al.
4,090,510 A 5/1978 Segersten
4,106,165 A 8/1978 Clowers et al.
D250,047 S 10/1978 Lewis et al.
D250,131 S 10/1978 Lewis et al.
4,127,130 A 11/1978 Naysmith
D252,322 S 7/1979 Johnson
4,167,185 A 9/1979 Lewis
4,201,205 A 5/1980 Bartholomew
4,266,540 A 5/1981 Panzik et al.
4,278,082 A 7/1981 Blackmer
4,288,891 A 9/1981 Boden
4,313,437 A 2/1982 Martin
4,328,605 A 5/1982 Hutchinson et al.
4,354,488 A 10/1982 Bartos
4,367,735 A 1/1983 Dali
4,402,316 A 9/1983 Gadberry
4,413,382 A 11/1983 Siegmann
4,437,462 A 3/1984 Piljay
4,450,603 A 5/1984 Hirsch
4,453,292 A 6/1984 Bakker
4,458,373 A 7/1984 Maslow
4,477,928 A 10/1984 Graff
4,606,077 A 8/1986 Phillips
D293,613 S 1/1988 Wingler
4,734,940 A 4/1988 Galet et al.
4,753,233 A 6/1988 Grimes
4,782,832 A 11/1988 Trimble et al.
4,817,596 A 4/1989 Gallet
4,848,334 A 7/1989 Bellm
4,853,275 A 8/1989 Tracy et al.
4,856,508 A 8/1989 Tayebi
4,915,105 A 4/1990 Lee
4,941,467 A 7/1990 Takata
4,944,310 A 7/1990 Sullivan
4,947,488 A 8/1990 Ashinoff
D310,431 S 9/1990 Bellm
4,971,051 A 11/1990 Toffolon
4,986,269 A 1/1991 Hakkinen
5,010,925 A 4/1991 Atkinson et al.
5,016,625 A 5/1991 Hsu et al.
5,042,478 A 8/1991 Kopala et al.
D320,677 S 10/1991 Kumagai et al.
5,052,084 A 10/1991 Braun
D321,419 S 11/1991 Wallace
5,065,756 A 11/1991 Rapoport
5,074,297 A 12/1991 Venegas
5,094,236 A 3/1992 Tayebi
5,113,857 A 5/1992 Dickerman et al.
5,148,578 A 9/1992 Clarke et al.
5,148,802 A 9/1992 Sanders et al.
5,191,882 A 3/1993 Vogliano
5,231,979 A 8/1993 Rose
5,245,995 A 9/1993 Sullivan et al.
D340,317 S 10/1993 Cole
5,269,296 A 12/1993 Landis et al.
5,279,020 A 1/1994 Coe
D354,128 S 1/1995 Rinehart
D355,484 S 2/1995 Rinehart
5,388,743 A 2/1995 Silagy
5,438,979 A 8/1995 Johnson et al.
5,477,852 A 12/1995 Landis et al.
5,488,948 A 2/1996 Dubruille
5,513,634 A 5/1996 Jackson
5,529,062 A 6/1996 Byrd
5,533,506 A 7/1996 Wood
5,546,605 A 8/1996 Mallardi
5,551,419 A 9/1996 Froehlich et al.
5,566,395 A 10/1996 Nebeker
5,595,174 A 1/1997 Gwaltney
5,601,078 A 2/1997 Schaller et al.
D378,610 S 3/1997 Reischel et al.
5,657,752 A 8/1997 Landis et al.
5,724,965 A 3/1998 Handke et al.
5,752,510 A 5/1998 Goldstein
5,755,578 A 5/1998 Contant et al.
5,774,901 A 7/1998 Minami
5,823,020 A 10/1998 Benda
5,884,624 A 3/1999 Barnett et al.
5,921,239 A 7/1999 McCall et al.
5,941,245 A 8/1999 Hannah et al.
5,941,856 A 8/1999 Kovacs et al.
6,017,315 A 1/2000 Starr et al.
6,019,101 A 2/2000 Cotner et al.
6,044,844 A 4/2000 Kwok et al.
6,050,260 A 4/2000 Daniell et al.
6,119,694 A 9/2000 Correa et al.
6,192,886 B1 2/2001 Rudolph
D440,302 S 4/2001 Wolfe
6,256,798 B1 7/2001 Egolf et al.
6,272,690 B1 8/2001 Carey et al.
6,282,725 B1 9/2001 Vanidestine, Jr.
6,298,850 B1 10/2001 Argraves
6,338,342 B1 1/2002 Fecteau et al.
6,347,631 B1 2/2002 Hansen et al.
D455,891 S 4/2002 Biedrzycki
6,418,928 B1 7/2002 Bordewick et al.
6,422,238 B1 7/2002 Lithgow
6,431,172 B1 8/2002 Bordewick
6,435,181 B1 8/2002 Jones, Jr. et al.
6,439,234 B1 8/2002 Curti et al.
6,470,886 B1 10/2002 Jestrabek-Hart
6,478,026 B1 11/2002 Wood

(56) References Cited

U.S. PATENT DOCUMENTS

| | | | |
|---|---|---|---|
| 6,491,034 | B1 | 12/2002 | Gunaratnam et al. |
| 6,536,435 | B1 | 3/2003 | Fecteau et al. |
| 6,561,188 | B1 | 5/2003 | Ellis |
| 6,561,191 | B1 | 5/2003 | Kwok |
| 6,571,854 | B1 | 6/2003 | Palmer |
| 6,581,594 | B1 | 6/2003 | Drew et al. |
| 6,581,601 | B2 | 6/2003 | Ziaee |
| 6,588,424 | B2 | 7/2003 | Bardel |
| 6,631,718 | B1 | 10/2003 | Lovell |
| 6,637,434 | B2 | 10/2003 | Noble |
| 6,644,315 | B2 | 11/2003 | Ziaee |
| 6,651,658 | B1 | 11/2003 | Hill et al. |
| 6,659,102 | B1 | 12/2003 | Sico |
| 6,662,803 | B2 | 12/2003 | Gradon et al. |
| 6,679,257 | B1 | 1/2004 | Robertson et al. |
| 6,679,265 | B2 | 1/2004 | Strickland et al. |
| 6,772,761 | B1 | 8/2004 | Rucker, Jr. |
| 6,851,425 | B2 | 2/2005 | Jaffre et al. |
| 6,883,519 | B2 | 4/2005 | Schmidtke et al. |
| 6,886,564 | B2 | 5/2005 | Sullivan et al. |
| 6,892,729 | B2 | 5/2005 | Smith et al. |
| 6,907,882 | B2 | 6/2005 | Ging et al. |
| 6,951,218 | B2 | 10/2005 | Gradon et al. |
| 7,004,165 | B1 | 2/2006 | Salcido |
| D520,140 | S | 5/2006 | Chaggares |
| 7,036,508 | B2 | 5/2006 | Kwok |
| 7,062,795 | B2 | 6/2006 | Skiba et al. |
| 7,066,179 | B2 | 6/2006 | Eaton et al. |
| D526,094 | S | 8/2006 | Chen |
| 7,096,864 | B1 | 8/2006 | Mayer et al. |
| 7,096,867 | B2 | 8/2006 | Smith et al. |
| 7,201,169 | B2 | 4/2007 | Wilkie et al. |
| 7,207,333 | B2 | 4/2007 | Tohara |
| 7,210,481 | B1 | 5/2007 | Lovell et al. |
| 7,219,669 | B1 | 5/2007 | Lovell et al. |
| 7,225,811 | B2 | 6/2007 | Ruiz et al. |
| 7,318,437 | B2 | 1/2008 | Gunaratnam et al. |
| 7,353,826 | B2 | 4/2008 | Sleeper et al. |
| 7,353,827 | B2 | 4/2008 | Geist |
| 7,814,911 | B2 | 10/2010 | Bordewick et al. |
| 7,845,352 | B2 | 12/2010 | Sleeper et al. |
| 7,861,715 | B2 | 1/2011 | Jones et al. |
| 7,870,860 | B2 | 1/2011 | McCormick et al. |
| 7,896,003 | B2 | 3/2011 | Matula et al. |
| 7,913,692 | B2 | 3/2011 | Kwok |
| 7,967,014 | B2 | 6/2011 | Heidmann |
| 8,042,539 | B2 | 10/2011 | Chandran et al. |
| 8,047,893 | B2 | 11/2011 | Fenske |
| 8,074,651 | B2 | 12/2011 | Bierman et al. |
| 8,104,473 | B2 | 1/2012 | Woodard et al. |
| 8,132,270 | B2 | 3/2012 | Lang et al. |
| 8,136,524 | B2 | 3/2012 | Ging et al. |
| 8,209,995 | B2 | 7/2012 | Kieling et al. |
| 8,297,285 | B2 | 10/2012 | Henry et al. |
| 8,371,302 | B2 | 2/2013 | Ging et al. |
| 8,443,807 | B2 | 5/2013 | McAuley et al. |
| D686,313 | S | 7/2013 | Matula et al. |
| 8,479,741 | B2 | 7/2013 | McAuley et al. |
| 8,505,538 | B2 | 8/2013 | Amarasinghe |
| 8,517,025 | B2 | 8/2013 | Ho et al. |
| 8,522,785 | B2 | 9/2013 | Berthon-Jones et al. |
| 8,573,201 | B2 | 11/2013 | Rummery et al. |
| 8,596,271 | B2 | 12/2013 | Matula, Jr. et al. |
| 8,596,274 | B2 | 12/2013 | Hieber et al. |
| 8,631,793 | B2 | 1/2014 | Omura et al. |
| 8,636,005 | B2 | 1/2014 | Gradon et al. |
| 8,636,007 | B2 | 1/2014 | Rummery et al. |
| 8,636,008 | B2 | 1/2014 | Flory et al. |
| 8,757,157 | B2 | 6/2014 | Price et al. |
| 8,783,257 | B2 | 7/2014 | McAuley et al. |
| 8,794,239 | B2 | 8/2014 | Gunaratnam |
| 8,839,789 | B2 | 9/2014 | Guney et al. |
| 8,856,975 | B2 | 10/2014 | Lang et al. |
| 8,857,435 | B2 | 10/2014 | Matula, Jr. et al. |
| 8,915,251 | B2 | 12/2014 | Lubke et al. |
| 8,950,404 | B2 | 2/2015 | Formica et al. |
| 8,997,742 | B2 | 4/2015 | Moore et al. |
| 9,032,955 | B2 | 5/2015 | Lubke et al. |
| 9,044,564 | B2 | 6/2015 | Dravitzki et al. |
| 9,103,161 | B2 | 8/2015 | Mader |
| 9,138,555 | B2 | 9/2015 | McAuley et al. |
| 9,149,596 | B2 | 10/2015 | Valcic et al. |
| 9,265,909 | B2 | 2/2016 | Ho et al. |
| 9,302,065 | B2 | 4/2016 | Smith et al. |
| 9,320,866 | B2 | 4/2016 | McAuley et al. |
| 9,333,315 | B2 | 5/2016 | McAuley et al. |
| 9,339,622 | B2 | 5/2016 | McAuley et al. |
| 9,480,809 | B2 | 11/2016 | Guney et al. |
| 9,517,320 | B2 | 12/2016 | Barlow et al. |
| 9,550,038 | B2 | 1/2017 | McAuley et al. |
| 9,555,943 | B2 | 1/2017 | Breen, IV et al. |
| 9,592,336 | B2 | 3/2017 | Nielsen et al. |
| 9,629,974 | B2 | 4/2017 | Gibson |
| 9,656,038 | B2 | 5/2017 | Rummery et al. |
| 9,744,385 | B2 | 8/2017 | Henry |
| 9,782,554 | B2 | 10/2017 | Mazzone et al. |
| 9,878,118 | B2 | 1/2018 | Formica |
| D810,277 | S | 2/2018 | Amarasinghe |
| 9,884,160 | B2 | 2/2018 | Mcauley |
| 9,901,700 | B2 | 2/2018 | McAuley et al. |
| 9,925,349 | B2 | 3/2018 | Jablonski |
| 9,974,914 | B2 | 5/2018 | McAuley |
| 9,993,606 | B2 | 6/2018 | Gibson et al. |
| 10,039,665 | B2 | 8/2018 | Blaszczykiewicz et al. |
| 10,065,010 | B2 | 9/2018 | Smith et al. |
| 10,071,217 | B2 | 9/2018 | Grashow |
| 10,080,856 | B2 | 9/2018 | McLaren |
| 10,137,319 | B2 | 11/2018 | Carr et al. |
| 10,207,072 | B2 | 2/2019 | Dunn et al. |
| 10,279,138 | B2 | 5/2019 | Ovzinsky |
| 10,456,546 | B2 | 10/2019 | McLaren et al. |
| 10,646,680 | B2 | 5/2020 | Huddart et al. |
| 10,668,242 | B2 | 6/2020 | Bearne |
| 10,675,428 | B2 | 6/2020 | Guney et al. |
| 10,792,451 | B2 | 10/2020 | Allan et al. |
| 10,828,449 | B2 | 11/2020 | Higgins et al. |
| 10,828,452 | B2 | 11/2020 | Huddart et al. |
| 10,874,814 | B2 | 12/2020 | Huddart et al. |
| 11,000,663 | B2 | 5/2021 | Felix et al. |
| 11,253,668 | B2 | 2/2022 | Freestone |
| 11,331,449 | B2 | 5/2022 | McLaren et al. |
| 11,419,999 | B2 | 8/2022 | Patel et al. |
| 11,607,518 | B2 | 3/2023 | Hammer et al. |
| 11,648,365 | B2 | 5/2023 | Huddart et al. |
| 11,701,486 | B2 | 7/2023 | Mashal et al. |
| 11,850,365 | B2 | 12/2023 | Freestone et al. |
| 12,102,765 | B2 * | 10/2024 | Huddart ............ A61M 16/0825 |
| 2002/0005198 | A1 | 1/2002 | Kwok et al. |
| 2002/0020416 | A1 | 2/2002 | Namey |
| 2002/0046755 | A1 | 4/2002 | Voss |
| 2002/0052568 | A1 | 5/2002 | Houser et al. |
| 2002/0053347 | A1 | 5/2002 | Ziaee |
| 2002/0059935 | A1 | 5/2002 | Wood |
| 2002/0096178 | A1 | 7/2002 | Ziaee |
| 2002/0157668 | A1 | 10/2002 | Bardel |
| 2003/0005933 | A1 | 1/2003 | Izuchukwu |
| 2003/0051732 | A1 | 3/2003 | Smith et al. |
| 2003/0079749 | A1 | 5/2003 | Strickland et al. |
| 2003/0084903 | A1 | 5/2003 | Fecteau et al. |
| 2003/0111080 | A1 | 6/2003 | Olsen et al. |
| 2003/0121519 | A1 | 7/2003 | Estes et al. |
| 2003/0164170 | A1 | 9/2003 | Drew et al. |
| 2003/0172936 | A1 | 9/2003 | Wilkie et al. |
| 2003/0196656 | A1 | 10/2003 | Moore |
| 2003/0196659 | A1 | 10/2003 | Gradon et al. |
| 2003/0196664 | A1 | 10/2003 | Jacobson |
| 2003/0200970 | A1 | 10/2003 | Stenzler et al. |
| 2004/0067333 | A1 | 4/2004 | Amarasinghe |
| 2004/0211427 | A1 | 10/2004 | Jones et al. |
| 2004/0226566 | A1 | 11/2004 | Gunaratnam et al. |
| 2005/0011524 | A1 | 1/2005 | Thomlinson et al. |
| 2005/0016067 | A1 | 1/2005 | Pettit |
| 2005/0028822 | A1 | 2/2005 | Sleeper et al. |
| 2005/0033247 | A1 | 2/2005 | Thompson |

(56) References Cited

U.S. PATENT DOCUMENTS

| | | | |
|---|---|---|---|
| 2005/0066976 | A1 | 3/2005 | Wondka |
| 2005/0076913 | A1 | 4/2005 | Ho et al. |
| 2005/0098183 | A1 | 5/2005 | Nash et al. |
| 2005/0150497 | A1 | 7/2005 | Eifler et al. |
| 2005/0161049 | A1 | 7/2005 | Wright |
| 2005/0199239 | A1 | 9/2005 | Lang et al. |
| 2005/0199242 | A1 | 9/2005 | Matula et al. |
| 2005/0205096 | A1 | 9/2005 | Matula |
| 2005/0235999 | A1 | 10/2005 | Wood et al. |
| 2005/0262619 | A1 | 12/2005 | Musal |
| 2006/0060200 | A1 | 3/2006 | Ho et al. |
| 2006/0081250 | A1 | 4/2006 | Bordewick et al. |
| 2006/0096596 | A1 | 5/2006 | Occhialini et al. |
| 2006/0107958 | A1 | 5/2006 | Sleeper |
| 2006/0113147 | A1 | 6/2006 | Harris |
| 2006/0118117 | A1 | 6/2006 | Berthon-Jones et al. |
| 2006/0124131 | A1 | 6/2006 | Chandran |
| 2006/0137690 | A1 | 6/2006 | Gunaratnam et al. |
| 2006/0174887 | A1 | 8/2006 | Chandran et al. |
| 2006/0174892 | A1 | 8/2006 | Leksutin et al. |
| 2006/0196510 | A1 | 9/2006 | McDonald et al. |
| 2006/0196511 | A1 | 9/2006 | Lau et al. |
| 2006/0237018 | A1 | 10/2006 | McAuley et al. |
| 2007/0000492 | A1 | 1/2007 | Hansel et al. |
| 2007/0010786 | A1 | 1/2007 | Casey et al. |
| 2007/0089749 | A1 | 4/2007 | Ho et al. |
| 2007/0125385 | A1 | 6/2007 | Ho et al. |
| 2007/0125387 | A1 | 6/2007 | Zollinger et al. |
| 2007/0130663 | A1 | 6/2007 | Lang et al. |
| 2007/0137653 | A1 | 6/2007 | Wood |
| 2007/0163600 | A1 | 7/2007 | Hoffman |
| 2007/0169777 | A1 | 7/2007 | Amarasinghe et al. |
| 2007/0175480 | A1 | 8/2007 | Gradon et al. |
| 2007/0209663 | A1 | 9/2007 | Marque et al. |
| 2007/0215161 | A1 | 9/2007 | Frater et al. |
| 2007/0235033 | A1 | 10/2007 | Reier et al. |
| 2007/0295335 | A1 | 12/2007 | Nashed |
| 2008/0041388 | A1 | 2/2008 | McAuley et al. |
| 2008/0041393 | A1 | 2/2008 | Bracken |
| 2008/0047560 | A1 | 2/2008 | Veliss et al. |
| 2008/0052806 | A1 | 3/2008 | McDaniel |
| 2008/0053450 | A1 | 3/2008 | Van Kerkwyk et al. |
| 2008/0060648 | A1 | 3/2008 | Thornton et al. |
| 2008/0060653 | A1 | 3/2008 | Hallet et al. |
| 2008/0060657 | A1 | 3/2008 | McAuley et al. |
| 2008/0065015 | A1 | 3/2008 | Fiser |
| 2008/0083412 | A1 | 4/2008 | Henry et al. |
| 2008/0092906 | A1 | 4/2008 | Gunaratnam et al. |
| 2008/0099024 | A1 | 5/2008 | Gunaratnam et al. |
| 2008/0110464 | A1 | 5/2008 | Davidson et al. |
| 2008/0134480 | A1 | 6/2008 | Shiue |
| 2008/0196728 | A1 | 8/2008 | Ho |
| 2008/0230068 | A1 | 9/2008 | Rudolph |
| 2008/0230069 | A1 | 9/2008 | Valcic et al. |
| 2008/0264422 | A1 | 10/2008 | Fishman |
| 2008/0302366 | A1 | 12/2008 | McGinnis et al. |
| 2008/0314388 | A1 | 12/2008 | Brambilla et al. |
| 2009/0000624 | A1 | 1/2009 | Lee et al. |
| 2009/0014007 | A1 | 1/2009 | Brambilla et al. |
| 2009/0032026 | A1 | 2/2009 | Price et al. |
| 2009/0044808 | A1 | 2/2009 | Guney et al. |
| 2009/0044809 | A1 | 2/2009 | Welchel et al. |
| 2009/0120442 | A1 | 5/2009 | Ho |
| 2009/0133697 | A1 | 5/2009 | Kwok et al. |
| 2009/0145429 | A1 | 6/2009 | Ging et al. |
| 2009/0173349 | A1 | 7/2009 | Hernandez et al. |
| 2009/0178680 | A1 | 7/2009 | Chang |
| 2009/0183739 | A1 | 7/2009 | Wondka |
| 2009/0211583 | A1 | 8/2009 | Carroll |
| 2009/0250060 | A1 | 10/2009 | Hacke et al. |
| 2009/0320187 | A1 | 12/2009 | Petzl et al. |
| 2010/0000538 | A1 | 1/2010 | Edwards et al. |
| 2010/0000544 | A1 | 1/2010 | Blaszczykiewicz et al. |
| 2010/0018534 | A1 | 1/2010 | Veliss et al. |
| 2010/0037897 | A1 | 2/2010 | Wood |
| 2010/0154798 | A1 | 6/2010 | Henry et al. |
| 2010/0224199 | A1 | 9/2010 | Smith et al. |
| 2010/0258132 | A1 | 10/2010 | Moore |
| 2010/0258136 | A1 | 10/2010 | Doherty et al. |
| 2010/0282265 | A1 | 11/2010 | Melidis et al. |
| 2010/0307502 | A1 | 12/2010 | Rummery et al. |
| 2010/0313532 | A1 | 12/2010 | Stjernfelt et al. |
| 2010/0313891 | A1 | 12/2010 | Veliss et al. |
| 2010/0319700 | A1 | 12/2010 | Ng et al. |
| 2011/0048425 | A1 | 3/2011 | Chang |
| 2011/0191938 | A1 | 8/2011 | Elliott |
| 2011/0197341 | A1 | 8/2011 | Formica |
| 2011/0220113 | A1 | 9/2011 | Newman |
| 2011/0247628 | A1 | 10/2011 | Ho |
| 2011/0259335 | A1 | 10/2011 | Sullivan |
| 2011/0265791 | A1 | 11/2011 | Ging et al. |
| 2011/0265796 | A1 | 11/2011 | Amarasinghe et al. |
| 2012/0067349 | A1 | 3/2012 | Barlow et al. |
| 2012/0125339 | A1 | 5/2012 | Ho et al. |
| 2012/0132209 | A1 | 5/2012 | Rummery |
| 2012/0138063 | A1 | 6/2012 | Eves et al. |
| 2012/0174355 | A1 | 7/2012 | Fraze |
| 2012/0222680 | A1 | 9/2012 | Eves et al. |
| 2012/0247490 | A1 | 10/2012 | Matthews |
| 2012/0285464 | A1 | 11/2012 | Birch et al. |
| 2012/0304999 | A1 | 12/2012 | Swift et al. |
| 2013/0000648 | A1 | 1/2013 | Madaus et al. |
| 2013/0008449 | A1 | 1/2013 | Busch |
| 2013/0139822 | A1 | 6/2013 | Gibson |
| 2013/0152918 | A1 | 6/2013 | Rummery et al. |
| 2013/0152937 | A1 | 6/2013 | Jablonski |
| 2013/0160769 | A1 | 6/2013 | Ng et al. |
| 2013/0220327 | A1 | 8/2013 | Barlow et al. |
| 2013/0247916 | A1 | 9/2013 | Symons |
| 2013/0319421 | A1 | 12/2013 | Hitchcock et al. |
| 2014/0026888 | A1 | 1/2014 | Matula |
| 2014/0026890 | A1 | 1/2014 | Haskard et al. |
| 2014/0083428 | A1 | 3/2014 | Rothermel et al. |
| 2014/0102456 | A1 | 4/2014 | Ovizinsky |
| 2014/0137870 | A1 | 5/2014 | Barlow |
| 2014/0158726 | A1 | 6/2014 | Malara |
| 2014/0166019 | A1 | 6/2014 | Ho et al. |
| 2014/0190486 | A1 | 7/2014 | Dunn et al. |
| 2014/0209098 | A1 | 7/2014 | Dunn |
| 2014/0209298 | A1 | 7/2014 | Baldasaro et al. |
| 2014/0216452 | A1 | 8/2014 | Miller et al. |
| 2014/0305439 | A1 | 10/2014 | Chodkowski |
| 2014/0358054 | A1 | 12/2014 | Capra |
| 2015/0000615 | A1 | 1/2015 | Imran et al. |
| 2015/0005685 | A1 | 1/2015 | Chetlapalli et al. |
| 2015/0028519 | A1 | 1/2015 | Lang et al. |
| 2015/0033457 | A1 | 2/2015 | Tryner et al. |
| 2015/0051000 | A1 | 2/2015 | Henn |
| 2015/0090268 | A1 | 4/2015 | Madaus et al. |
| 2015/0128953 | A1 | 5/2015 | Formica et al. |
| 2015/0151070 | A1 | 6/2015 | Capra et al. |
| 2015/0190262 | A1 | 7/2015 | Capra et al. |
| 2015/0202397 | A1 | 7/2015 | Pastoor |
| 2015/0217150 | A1 | 8/2015 | Harris |
| 2015/0285337 | A1 | 10/2015 | Dingley et al. |
| 2015/0290415 | A1 | 10/2015 | Dunn |
| 2016/0022944 | A1 | 1/2016 | Chodkowski et al. |
| 2016/0038707 | A1 | 2/2016 | Allan et al. |
| 2016/0045700 | A1 | 2/2016 | Amarasinghe |
| 2016/0082214 | A1 | 3/2016 | Barlow et al. |
| 2016/0166793 | A1 | 6/2016 | McLaren et al. |
| 2016/0178027 | A1 | 6/2016 | Wetzel |
| 2016/0256655 | A1 | 9/2016 | Mah |
| 2016/0278463 | A1 | 9/2016 | Stevenson |
| 2016/0375214 | A1 | 12/2016 | Chodkowski et al. |
| 2017/0136269 | A1 | 5/2017 | Jacotey et al. |
| 2017/0182276 | A1 | 6/2017 | Hammer |
| 2017/0189636 | A1 | 7/2017 | Gibson et al. |
| 2017/0216548 | A1 | 8/2017 | Gerhardt |
| 2018/0209618 | A1 | 7/2018 | Pontano |
| 2018/0214655 | A1 | 8/2018 | Kooij et al. |
| 2018/0264218 | A1 | 9/2018 | Chodkowski |
| 2018/0339123 | A1 | 11/2018 | Smith et al. |
| 2019/0111227 | A1 | 4/2019 | Veliss et al. |

(56) References Cited

U.S. PATENT DOCUMENTS

| | | | |
|---|---|---|---|
| 2019/0117026 | A1 | 4/2019 | Guerra |
| 2019/0118009 | A1 | 4/2019 | Vogus |
| 2019/0151592 | A1 | 5/2019 | Bornholdt |
| 2019/0220327 | A1 | 7/2019 | Otenko |
| 2020/0129720 | A1 | 4/2020 | McLaren et al. |
| 2020/0230343 | A1 | 7/2020 | Sims et al. |
| 2020/0338294 | A1 | 10/2020 | McLaren et al. |
| 2021/0008316 | A1 | 1/2021 | McLaren et al. |
| 2021/0016041 | A1 | 1/2021 | Huddart et al. |
| 2022/0126049 | A1 | 4/2022 | Amarasinghe |
| 2022/0331542 | A1 | 10/2022 | McLaren et al. |
| 2023/0201510 | A1 | 6/2023 | Hammer |
| 2024/0024606 | A1 | 1/2024 | McLaren et al. |
| 2024/0033461 | A1 | 2/2024 | Felix et al. |
| 2024/0077763 | A1 | 3/2024 | Yoon et al. |
| 2024/0139456 | A1 | 5/2024 | Freestone |
| 2024/0165360 | A1 | 5/2024 | Smith et al. |
| 2024/0181194 | A1 | 6/2024 | Hammer |
| 2026/0108694 | A1 | 4/2026 | Huddart |

FOREIGN PATENT DOCUMENTS

| | | | |
|---|---|---|---|
| CA | 2995960 | A1 | 2/2017 |
| CN | 2172538 | | 7/1994 |
| CN | 2504493 | Y | 8/2002 |
| CN | 2562067 | Y | 7/2003 |
| CN | 1784250 | | 6/2006 |
| CN | 1901963 | A | 1/2007 |
| CN | 201033204 | | 3/2008 |
| CN | 201171846 | | 12/2008 |
| CN | 101432039 | A | 5/2009 |
| CN | 100502972 | C | 6/2009 |
| CN | 101516427 | | 8/2009 |
| CN | 202822396 | U | 3/2013 |
| CN | 103536996 | | 1/2014 |
| DE | 895692 | | 11/1953 |
| DE | 2706284 | | 8/1978 |
| DE | 3122034 | | 12/1982 |
| DE | 3907428 | | 9/1990 |
| DE | 10254399 | | 6/2004 |
| DE | 10341550 | A1 | 3/2005 |
| DE | 102006011151 | | 9/2007 |
| DE | 102012010775 | | 12/2013 |
| EP | 0 350 322 | | 1/1990 |
| EP | 0352948 | A2 | 1/1990 |
| EP | 0 401 307 | | 8/1995 |
| EP | 0 879 565 | | 11/1998 |
| EP | 0 982 049 | | 3/2000 |
| EP | 1 187 650 | | 12/2005 |
| EP | 2 060 294 | | 5/2009 |
| EP | 2 130 563 | | 12/2009 |
| EP | 2 517 757 | | 10/2012 |
| EP | 2 022 528 | | 3/2016 |
| FR | 2390116 | | 3/1938 |
| FR | 2618340 | | 11/1970 |
| FR | 825960 | | 1/1989 |
| FR | 2658725 | | 8/1991 |
| FR | 2749176 | | 12/1997 |
| FR | 2804421 | | 8/2001 |
| GB | 190224431 | | 12/1902 |
| GB | 339522 | | 12/1930 |
| GB | 826198 | | 12/1959 |
| GB | 880824 | | 10/1961 |
| GB | 1467828 | | 3/1977 |
| GB | 2133275 | | 7/1984 |
| GB | 2188236 | | 9/1987 |
| GB | 1211268 | | 4/2000 |
| GB | 2478305 | | 9/2011 |
| GB | 2491227 | | 11/2012 |
| GB | 2553475 | | 3/2018 |
| JP | S46-12114 | | 4/1971 |
| JP | 46-016719 | | 6/1971 |
| JP | S55-89072 | | 7/1980 |
| JP | H0368861 | | 7/1991 |
| JP | 2004-016488 | | 1/2004 |
| JP | 2003-053874 | | 9/2004 |
| JP | 2009-125306 | | 6/2009 |
| JP | 2010-090973 | | 4/2010 |
| JP | 2000-102624 | | 5/2013 |
| JP | 2018-127729 | | 8/2018 |
| KR | 10-2011-0028950 | | 3/2011 |
| NZ | 585295 | | 12/2011 |
| TW | 201340900 | | 10/2013 |
| WO | WO 95/12432 | | 5/1995 |
| WO | WO 97/32494 | | 9/1997 |
| WO | WO 98/003225 | | 1/1998 |
| WO | WO 98/018514 | | 5/1998 |
| WO | WO 99/04842 | | 2/1999 |
| WO | WO 99/058181 | | 11/1999 |
| WO | WO 00/50122 | | 8/2000 |
| WO | WO 00/069497 | | 11/2000 |
| WO | WO 00/074758 | | 12/2000 |
| WO | WO 01/041854 | | 6/2001 |
| WO | WO 01/097892 | | 12/2001 |
| WO | WO 02/44749 | | 6/2002 |
| WO | WO 02/047749 | | 6/2002 |
| WO | WO 02/074372 | | 9/2002 |
| WO | WO 04/039185 | | 5/2004 |
| WO | WO 04/041341 | | 5/2004 |
| WO | WO 04/073778 | | 9/2004 |
| WO | WO 05/021075 | | 3/2005 |
| WO | WO 05/032634 | | 4/2005 |
| WO | WO 05/046776 | | 5/2005 |
| WO | WO 05/051468 | | 6/2005 |
| WO | WO 05/063328 | | 7/2005 |
| WO | WO 05/118042 | | 12/2005 |
| WO | WO 05/123166 | | 12/2005 |
| WO | WO 06/130903 | | 12/2006 |
| WO | WO 06/138416 | | 12/2006 |
| WO | WO 07/022562 | | 3/2007 |
| WO | WO 07/041786 | | 4/2007 |
| WO | WO 07/068044 | | 6/2007 |
| WO | WO 07/125487 | | 11/2007 |
| WO | WO 07/147088 | | 12/2007 |
| WO | WO 08/007985 | | 1/2008 |
| WO | WO 08/060295 | | 5/2008 |
| WO | WO 08/070929 | | 6/2008 |
| WO | WO 08/106716 | | 9/2008 |
| WO | WO 08/148086 | | 12/2008 |
| WO | WO 09/026627 | | 3/2009 |
| WO | WO 09/038918 | | 3/2009 |
| WO | WO 09/052560 | | 4/2009 |
| WO | WO 09/059353 | | 5/2009 |
| WO | WO 09/092057 | | 7/2009 |
| WO | WO 09/108994 | | 9/2009 |
| WO | WO 09/108995 | | 9/2009 |
| WO | WO 09/139647 | | 11/2009 |
| WO | WO 09/148956 | | 12/2009 |
| WO | WO 10/066004 | | 6/2010 |
| WO | WO 10/081295 | | 7/2010 |
| WO | WO 10/131189 | | 11/2010 |
| WO | WO 10/139014 | | 12/2010 |
| WO | WO 11/072739 | | 6/2011 |
| WO | WO 11/077254 | | 6/2011 |
| WO | WO 11/112401 | | 9/2011 |
| WO | WO 12/07300 | | 1/2012 |
| WO | WO 12/045127 | | 4/2012 |
| WO | WO 12/069951 | | 5/2012 |
| WO | WO 12/071300 | | 5/2012 |
| WO | WO 12/143822 | | 10/2012 |
| WO | WO 12/154883 | | 11/2012 |
| WO | WO 12/177152 | | 12/2012 |
| WO | WO 13/006913 | | 1/2013 |
| WO | WO 13/026091 | | 2/2013 |
| WO | WO 13/026092 | | 2/2013 |
| WO | WO 13/064930 | | 5/2013 |
| WO | WO 14/020469 | | 2/2014 |
| WO | WO 14/025267 | | 2/2014 |
| WO | WO 14/031673 | | 2/2014 |
| WO | WO 14/075141 | | 5/2014 |
| WO | WO 14/077708 | | 5/2014 |
| WO | WO 14/110622 | | 7/2014 |
| WO | WO 14/110626 | | 7/2014 |
| WO | WO 14/129913 | | 8/2014 |

(56) References Cited

FOREIGN PATENT DOCUMENTS

| | | | |
|---|---|---|---|
| WO | WO 14/175752 | 10/2014 | |
| WO | WO 14/175753 | 10/2014 | |
| WO | WO-2014175752 A2 * | 10/2014 | ........ A61M 16/0816 |
| WO | WO 15/033287 | 3/2015 | |
| WO | WO 15/043229 | 4/2015 | |
| WO | WO 15/070289 | 5/2015 | |
| WO | WO 15/079396 | 6/2015 | |
| WO | WO 15/083060 | 6/2015 | |
| WO | WO 15/151019 | 10/2015 | |
| WO | WO 15/187986 | 12/2015 | |
| WO | WO 16/043603 | 3/2016 | |
| WO | WO 17/030447 | 2/2017 | |
| WO | WO 17/059476 | 4/2017 | |
| WO | WO 17/150990 | 9/2017 | |
| WO | WO 17/158474 | 9/2017 | |
| WO | WO 17/158544 | 9/2017 | |
| WO | WO 17/160166 | 9/2017 | |
| WO | WO 17/216708 | 12/2017 | |
| WO | WO 19/003094 | 1/2019 | |

OTHER PUBLICATIONS

Pad A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.

Philips Respironics 'System One Heated Humidifier—User Manual', 2011, pp. 1-16, [retrieved on Nov. 25, 2013] from the internet: URL: http://www.cpapxchange.com/cpap-machines-biap- machines/system-one-60-series-cpap-humidifier-manual.pdf.

Langnau, Jan. 2, 2012, Tips on Clips Part 2: Make it Snappy, https://www,makepartsfast,com/tips-on-clips-part-2-make-it-snappy/, 9 pp.

* cited by examiner

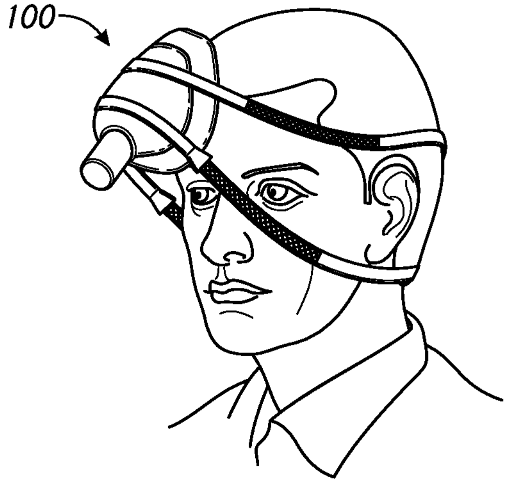
FIG. 4.1
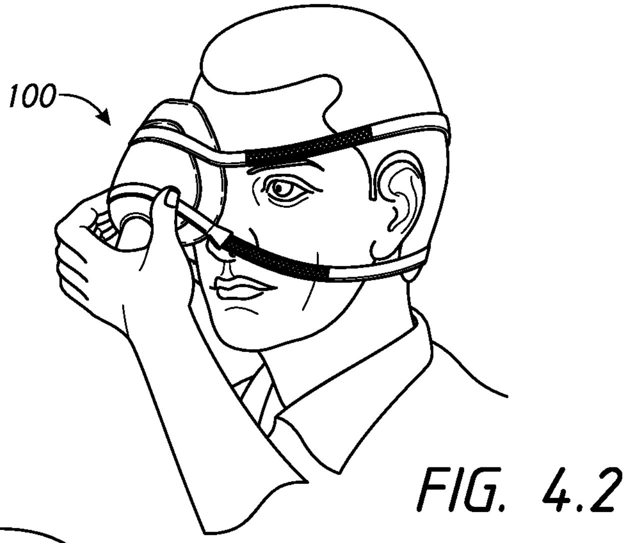
FIG. 4.2
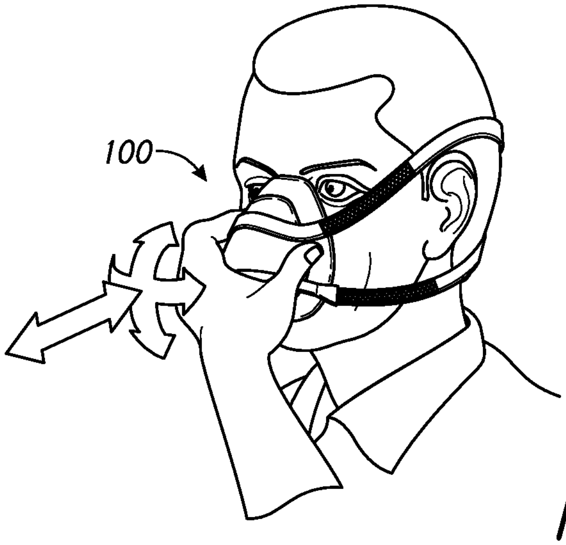
FIG. 4.3

Multi-Interface Configurations

Less Stability → More Stability

| | | Full Face | Nasal | Pillows / Prongs | Cannula |
|---|---|---|---|---|---|
| 1-plane | 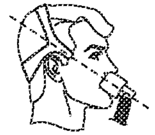 | Not practical | Yes | Yes | Yes |
| 2-plane (fwd converge | 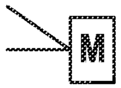 | Somewhat practical | Yes | Yes | Yes |
| 2-plane (rear converge | 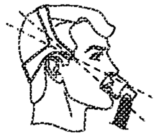 | Yes | Yes | Yes, less practical | Yes, not practical |
| 2-plane (separated/ angled) | 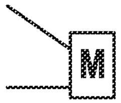 | Yes | Yes | Yes, less practical | Yes, not practical |
| 2-plane (horizontal/ parallel) | 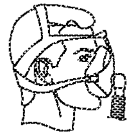 | Yes | Yes | Yes, not practical | Yes, not practical |

*FIG. 13.1*

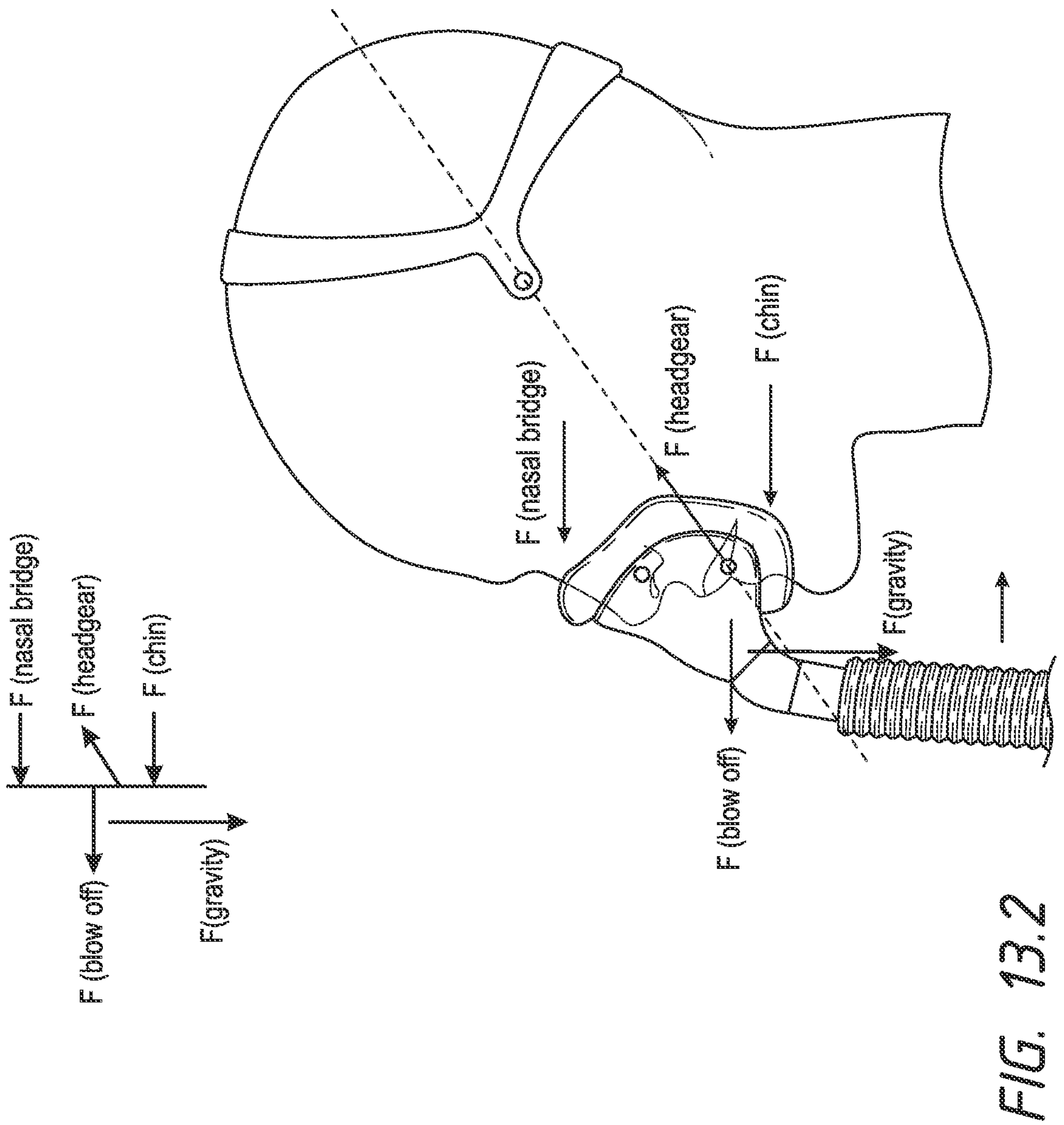
FIG. 13.2

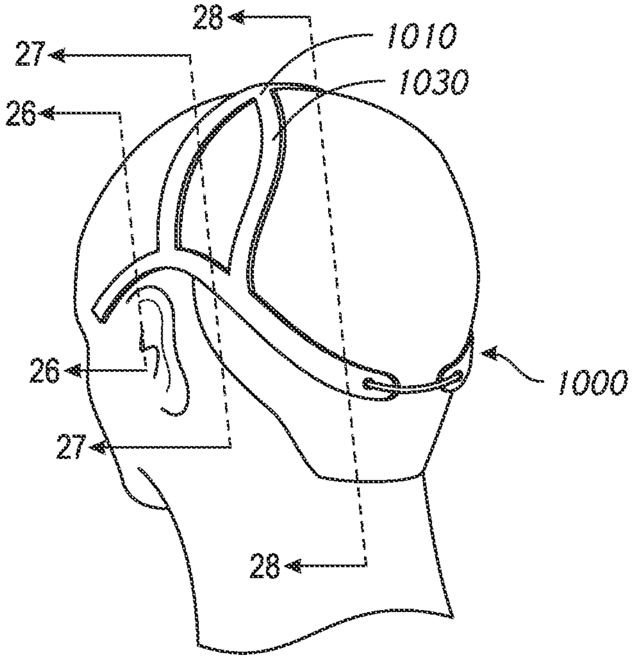
FIG. 25
FIG. 26
FIG. 27
FIG. 28
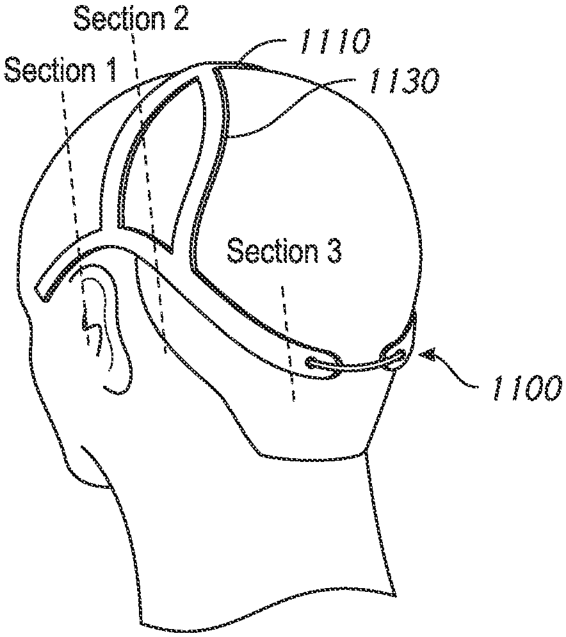
Section 1 ~ Polypropylene
Section 2 ~ TPU / TPE 70 shore A
Section 3 ~ TPE 40 shore D
FIG. 29

HEADGEAR ASSEMBLIES AND INTERFACE ASSEMBLIES WITH HEADGEAR

INCORPORATION BY REFERENCE TO ANY PRIORITY APPLICATIONS

Any and all applications for which a foreign or domestic priority claim is made in connection with the present application are hereby incorporated by reference and made a part of the disclosure.

BACKGROUND

Field

The present disclosure relates to respiratory therapy systems. In particular, the disclosure relates to interface assemblies for use in respiratory therapy.

Description of Related Art

The treatment of respiratory ailments or conditions with therapies such as non-invasive ventilation (NIV), Bi-level or continuous positive airway pressure (CPAP) therapy involves the delivery of pressurized air to the airways of a human via a conduit and an interface (e.g., a mask). Some types of interfaces create at least a substantial "seal" on or around the nose and/or the mouth of the user.

The result of creating this "seal" is that the combination of the enclosure area of the interface and its internal pressure creates a resulting force (a "blow off" force) that attempts to push the mask off the face. To restrain this force it is normal to use a headgear arrangement having one or more straps that pass around the back of the head.

The strap(s) require some form of adjustment to account for variation in head size, this adjustment mechanism is typically provided via an adjustment loop between the mask body and the head gear. The adjustment loop can have a hook-and-loop or similar fastener that permits an end of the strap to be passed through a mounting location on the mask or through a clip that attaches to the mask and then attached to another section of the strap. Such an arrangement permits adjustment of the headgear by positioning the end of the strap at a desired location on the other section of the strap to vary a size of the adjustment loop.

These types of mechanism are one solution to providing an adjustment mechanism for the headgear and, thus, the interface assembly. Such systems also require a reasonable level of user interaction and, as a result, is prone to misuse or mis-adjustment (e.g., over-tightening). As a practical matter, micro-adjustment of such systems is difficult and time-consuming to accomplish. The creation of practical and not so practical solutions to this has been the subject of considerable development effort from a number of organisations, which has resulted in numerous patents.

SUMMARY

The systems, methods and devices described herein have innovative aspects, no single one of which is indispensable or solely responsible for their desirable attributes. Without limiting the scope of the claims, some of the advantageous features will now be summarized.

A headgear system and/or an interface assembly incorporating a headgear system that upon fitment to the head of a user automatically adjusts to the correct size and, once in use, transforms in properties from an elasticated "stretchy" strap/strapping to an "inelastic" strap/strapping.

In some configurations, a headgear assembly for supporting a respiratory interface on a user includes a substantially inelastic rear portion, a substantially inelastic front portion, a first elastic side portion on a first side of the headgear assembly, and a second elastic side portion of a second side of the headgear assembly. At least one filament extends through or along the first and second elastic side portions. The at least one filament coupled to one of the inelastic rear portion and the inelastic front portion, and at least one restriction arrangement. The at least one filament passes through the at least one restriction arrangement. The at least one restriction arrangement is configured to selectively engage the at least one filament to resist movement of the at least one filament relative to the at least one restriction arrangement.

In some configurations, the at least one restriction arrangement is configured to provide a first resistance force to movement or attempted movement of the at least one filament in a direction that allows the inelastic rear portion and the inelastic front portion to move away from one another.

In some configurations, the at least one restriction arrangement is configured to provide a second resistance force to movement or attempted movement of the at least one filament in a direction that allows the inelastic rear portion and the inelastic front portion to move toward one another, wherein the second resistance force is less than the first resistance force.

In some configurations, the inelastic front portion is rigid.

In some configurations, the inelastic front portion is configured to be connected to a respiratory interface.

In some configurations, the inelastic front portion defines at least one collection passage that accommodates a portion of the at least one filament.

In some configurations, each of the first and second elastic side portions comprises an end cap having an opening through which the at least one filament passes. The end cap can be overmolded onto the respective one of the first and second elastic side portions. The end cap can be coupled to the inelastic front portion.

In some configurations, the inelastic rear portion, the inelastic front portion, the first elastic side portion and the second elastic side portion define a closed loop perimeter.

In some configurations, the at least one filament comprises a first filament associated with the first elastic side portion and a second filament associated with the second elastic side portion. The at least one restriction arrangement can comprise a first restriction arrangement associated with the first elastic side portion and a second restriction arrangement associated with the second elastic side portion.

In some configurations, the at least one collection passage comprises a first collection passage that accommodates a portion of the first filament and a second collection passage that accommodates a portion of the second filament.

In some configurations, the restriction arrangement comprises a pair of lock jaws that define a space therebetween through which the filament passes. The lock jaws have a first relative position engaging the filament to provide the first resistance force and a second relative position that provides the second resistance force.

In some configurations, the interface includes a forehead support and the at least one collection passage is located on the forehead support.

In some configurations, the headgear comprises upper and lower elastic side portions on each side, upper and lower filaments and upper and lower restriction arrangements. In some such configurations, the there is an upper collection passage and lower collection passage. These upper and lower collection passages on each side of the headgear can be separate from one another.

In some configurations, inelastic front portion defines an opening configured to receive a portion of the respiratory interface, wherein the at least one collection passage comprises a first collection passage and a second collection passage, wherein at least a portion of the first collection passage is located above the opening and at least a portion of the second collection passage is located below the opening.

In some configurations, the inelastic front portion is configured to connect to a plurality of different interfaces.

In some configurations, the inelastic front portion comprises separate portions on each side of the headgear assembly.

In some configurations, a headgear assembly for supporting a respiratory interface on a user defines a perimeter that surrounds a head of the user. The headgear assembly can include a first portion having a fixed length along the perimeter and a second portion having a fixed length along the perimeter. At least one elastic portion has a variable length along the perimeter, wherein the at least one elastic portion has a first length and a second length that is greater than the first length. At least one filament is secured to one of the first portion and the second portion and extends through the at least one elastic portion and into at least one collection passage of the other of the first portion and the second portion. The at least one filament has a filament length that is greater than the second length of the at least one elastic portion. At least one restriction arrangement is configured to selectively engage the at least one filament to resist movement of the at least one filament relative to the at least one restriction arrangement. The at least one restriction arrangement is located at an entrance to the at least one collection passage.

In some configurations, the first portion is a front portion of the headgear assembly.

In some configurations, the second portion is a rear portion of the headgear assembly.

In some configurations, the first portion defines the at least one collection passage.

In some configurations, the at least one elastic portion is restricted to a maximum length.

In some configurations, the at least one elastic portion comprises an inelastic element that defines the maximum length.

In some configurations, the at least one elastic portion comprises a first elastic portion and a second elastic portion, wherein each of the first elastic portion and the second elastic portion extend between the first portion and the second portion.

In some configurations, the at least one filament comprises a first filament associated with the first elastic portion and a second filament associated with the second elastic portion. The at least one restriction arrangement comprises a first restriction arrangement associated with the first elastic side portion and a second restriction arrangement associated with the second elastic side portion.

In some configurations, the at least one collection passage comprises a first collection passage that accommodates a portion of the first filament and a second collection passage that accommodates a portion of the second filament.

In some configurations, the restriction arrangement comprises a pair of lock jaws that define a space therebetween through which the filament passes. The lock jaws have a first relative position engaging the filament to provide a first level of resistance and a second relative position that provides a second level or resistance that is lower that the first level.

In some configurations, a directional lock includes a housing defining an interior space, a first opening and a second opening. Each of the first and second openings communicates with the interior space. At least one lock element is pivotally coupled to the housing for rotation about a fixed pivot axis. The lock element has an aperture configured to receive a core element. The lock element is movable between a first position, in which the aperture is aligned with the first opening and the second opening, and a second position, in which the aperture is not aligned with the first opening and the second opening.

In some configurations, the lock element is a lock washer.

In some configurations, at least one of the first opening and the second opening is elongate in a direction perpendicular to the pivot axis such that the at least one of the first opening and the second opening can accommodate a core element that passes through the aperture of the at least one lock element in both the first position and the second position.

In some configurations, the at least one lock element comprises a first lock element and a second lock element.

In some configurations, the housing comprises and internal wall positioned between the first lock element and the second lock element.

In some configurations, a headgear assembly for supporting a respiratory interface on a user includes a rear headgear portion configured to contact the rearward and/or upper portions of a head of the user. Each side of the rear headgear portion comprises a mounting portion configured to be located forwardly of an ear of the user in use. The rear headgear portion has no structure passing below the ear of the user that would inhibit removal of the rear headgear portion in an upward direction. An interface connection arrangement is provided to the mounting portion on each side of the headgear assembly. Each interface connection arrangement is configured to be directly or indirectly coupled to the respiratory interface. Each interface connection arrangement comprises at least one length adjusting arrangement. Each length adjusting arrangement comprises an elastic element, a core member and a restriction arrangement. The core member is associated with the elastic element and is fixed relative to one end of the elastic element. The core member passes through the restriction arrangement. The restriction arrangement is configured to selectively engage the core member to resist movement of the core member relative to the restriction arrangement.

In some configurations, each of the interface connection arrangements comprises at least a first length adjusting arrangement and a second length adjusting arrangement.

In some configurations, the first length adjusting arrangement and the second length adjusting arrangement are spaced apart from one another on the mounting portion.

In some configurations, a location of at least one of the first length adjusting arrangement and the second length adjusting arrangement on the mounting portion is adjustable.

In some configurations, at least one connector is configured to connect the interface connection arrangements to the respiratory interface.

In some configurations, the at least one connector comprises at least one collection passage configured to receive a portion of the core members.

In some configurations, a single connector is configured to connect both of the interface connection arrangements to the respiratory interface.

In some configurations, the connector defines an opening configured to receive a portion of the respiratory interface, wherein the at least one collection passage comprises a first collection passage and a second collection passage, wherein at least a portion of the first collection passage is located above the opening and at least a portion of the second collection passage is located below the opening.

In some configurations, the connector is configured to connect to a plurality of different interfaces.

In some configurations, the at least one connector comprises a connector on each side of the headgear assembly.

In some configurations, the restriction arrangement comprises a pair of lock jaws that define a space therebetween through which the core member passes. The lock jaws have a first relative position engaging the core member to provide a first level of resistance and a second relative position that provides a second level or resistance that is lower that the first level.

In some configurations, a headgear assembly for supporting a respiratory interface on a user comprises at least one inelastic portion and at least one elastic portion having a first end and a second end. At least one filament extends through or along the at least one elastic portion. The first end of the at least one elastic portion is fixed relative to the at least one inelastic portion and the at least one filament. The second end of the at least one elastic portion is movable relative to the at least one inelastic portion and the at least one filament. The headgear assembly also comprises at least one restriction arrangement. The at least one filament passes through the at least one restriction arrangement. The at least one restriction arrangement is configured to selectively engage the at least one filament to resist movement of the at least one filament relative to the at least one restriction arrangement. The at least one restriction arrangement is located remotely from each of the first end and the second end of the at least one elastic portion.

In some configurations, the inelastic portion is a rear headgear portion configured to contact a rearward and/or upper portion of the user's head in use, wherein the at least one restriction arrangement is located on the rear headgear portion.

In some configurations, the rear headgear portion comprises a top strap and the at least one restriction arrangement is located on the top strap.

In some configurations, the headgear assembly is configured such that the at least one restriction arrangement is located on the top of the user's head in use.

In some configurations, the rear headgear portion comprises a rear strap and the at least one restriction arrangement is located on the rear strap.

In some configurations, the headgear assembly is configured such that the at least one restriction arrangement is located behind the user's ear in use.

In some configurations, a guide for the at least one filament is provided between the restriction arrangement and one of the first and second ends of the at least one elastic portion.

In some configurations, the restriction arrangement comprises a pair of lock jaws that define a space therebetween through which the filament passes. The lock jaws have a first relative position engaging the filament to provide a first level of resistance and a second relative position that provides a second level or resistance that is lower that the first level.

In some configurations, a patient interface system comprises a body portion sized and shaped to surround the nose and/or mouth of a user and adapted to create at least a substantial seal with the user's face. A coupling permits the patient interface to be coupled to a gas delivery system. A headgear system allows the body portion to be positioned and retained on an users head, with the head-gear system providing the ability to transform from an elastic type elongation behaviour to a non-elongating type behaviour when the interface system is in use.

In some configurations, the transformational locking behaviour is provided by a group of directional locking features.

In some configurations, the transformational locking behaviour is provided by a group of directional locking features which are located on retention planes.

In some configurations, the transformational locking behaviour is provided by a group of directional locking features which enable independent relative movement to each other.

In some configurations, the transformational locking behaviour is provided by a group of directional locking features which have dependent movement to each other.

In some configurations, the interface system contains a combination of independent and dependent movement.

In some configurations, the transformational locking behaviour is provided by a directional locking feature/s which are located on the mask body.

In some configurations, the transformational locking behaviour is provided by a directional locking feature/s which are located on or within the headgear system.

In some configurations, a combination of directional locking feature/s located on the mask body and located on or within the headgear system are used.

In some configurations, the directional lock is positioned in a location that is proximal with the connection point to the headgear.

In some configurations, the directional lock is positioned in a location that is distal with the connection point to the headgear.

In some configurations, the directional lock module incorporates a mechanism which enables user attachment/detachment between it and the mask body.

In some configurations, the directional lock module incorporates a mechanism which enables user attachment/detachment between it and the remainder of the headgear system.

In some configurations, the non-stretch behaviour of the headgear system is such that there is less than 4 mm of mask movement when the patient interface system is subjected to variable pressure waveform.

In some configurations, a patient interface system comprises a body portion sized and shaped to provide a cannulated gas delivery system into the nasal passages. A coupling permits the patient interface to be coupled to a gas delivery system. A headgear system allows the body portion to be positioned and retained on an users head, with the head-gear system providing the ability to transform from an elastic type elongation behaviour to a non-elongating type behaviour when the interface system is in use.

In some configurations, a patient interface system includes a body portion sized and shaped to surround the nose and/or mouth of a user and adapted to create at least a substantial seal with the user's face. A coupling permits the patient interface to be coupled to a gas delivery system. A headgear system allows the body portion to be positioned and retained on an users head, with the head-gear system providing the ability to transform from an elastic type elongation behaviour to a non-elongating type behaviour when the interface system is in use.

In some configurations, the positional stability of the headgear system is achieved via two principal portions, one that passes on or below the occipital protruberance, the other passing over the top of the head in loosely the position of the crown of the head. The relative position of these two is maintained by the material of the headgear being shape sustaining.

In some configurations, the positional stability of the headgear system is achieved via two principal portions, one that passes on or below the occipital protuberance, the other passing over the top of the head in loosely the position of the crown of the head. The relative position of these two is maintained by the gusset or connecting member/s.

In some configurations, the non-stretch behaviour of the body portion of the headgear is achieved through constructing it from a single inelastic material and variable cross sectional geometry.

In some configurations, the non-stretch behaviour of the body portion of the headgear is achieved through constructing it from a single thermoplastic material and variable cross sectional geometry.

In some configurations, the non-stretch behaviour of the body portion of the headgear is achieved through constructing it from a single thermoset material and variable cross sectional geometry.

In some configurations, the non-stretch behaviour of the body portion of the headgear is achieved through constructing it from multiple thermoplastic materials.

In some configurations, the non-stretch behaviour of the body portion of the headgear is achieved through constructing it from multiple thermoset materials.

In some configurations, the non-stretch behaviour of the body portion of the headgear is achieved through constructing it from multiple thermoplastic materials & variable cross sectional geometry.

In some configurations, the non-stretch behaviour of the body portion of the headgear is achieved through constructing it from thermoplastic material/s and an incorporated lining or padding.

In some configurations, the non-stretch behaviour of the body portion of the headgear is achieved through constructing it from thermoset material/s and an incorporated lining or padding.

In some configurations, a headgear assembly for a respiratory interface includes a rear headgear portion, an interface coupling portion, and a length adjusting portion that adjusts a length of the headgear assembly or a perimeter length of the interface assembly when coupled to a respiratory interface. The headgear assembly exhibits an elastic force tending to contract the headgear length or the perimeter length and a non-elastic lock force tending to inhibit elongation of the headgear length or the perimeter length.

In some configurations, the headgear assembly comprises at least one retention plane.

In some configurations, the headgear assembly comprises two retention planes.

In some configurations, the retention planes converge in a direction moving from rearward to forward.

In some configurations, the retention planes converge in a direction moving from forward to rearward.

In some configurations, one of the retention planes is angled relative to the other retention plane.

In some configurations, the retention planes are separated from one another at the interface attachment locations.

In some configurations, the retention planes are generally parallel with one another.

In some configurations, the retention planes are generally horizontal.

In some configurations, the headgear assembly further comprises a manually-adjustable length adjusting portion In some configurations, the interface coupling portion can be connected to a plurality of types of interfaces.

In some configurations, the length adjusting portion comprises at least a first portion and a second portion.

In some configurations, the first portion and the second portion are on opposite sides of the headgear assembly.

In some configurations, the interface coupling portion extends between the first portion and the second portion.

In some configurations, the first portion and the second portion are on the same side of the headgear assembly.

In some configurations, the interface coupling portion extends between the first portion and the second portion.

In some configurations, at least one core member forms a portion of the headgear length or perimeter length and can be locked relative to another portion of the headgear assembly or interface assembly to inhibit elongation of the headgear length or perimeter length.

In some configurations, a length of the core member is greater than a maximum extended length of the length adjusting portion.

In some configurations, a length of the rear headgear portion is greater than or equal to a length of the core member.

In some configurations, a length of the rear headgear portion is greater than or equal to a length of the core member.

In some configurations, at least one core collector accommodates an excess portion of the core that, at any particular headgear length or perimeter length, does not form a portion of the headgear length or perimeter length.

In some configurations, a length of the core member is less than a combined length of the core collector and a maximum extended length of the length adjusting portion.

In some configurations, a length of the rear headgear portion and a length of the core collector is fixed, and adjustment of a length of the length adjusting member provides substantially all of a length adjustment of the headgear length or the perimeter length.

In some configurations, a nasal cannula system comprises a nasal cannula and a headgear. At least one adjustment arrangement allows adjustment of a perimeter length of the nasal cannula system. The at least one adjustment arrangement includes a core member coupled to one of the headgear and the nasal cannula and a lock coupled to the other of the headgear and the nasal cannula. The lock can engage the core member to retain the nasal cannula system in a desired adjusted perimeter length.

In some configurations, the lock can retain the desired adjusted perimeter length in response to normal or expected forces in use, such as the weight of the nasal cannula and hose pull forces, for example.

In some configurations, the lock allows slippage of the core member at forces above a threshold such that the perimeter length can be increased beyond the desired adjusted perimeter length.

In some configurations, the lock is a directional lock and allows movement of the core member in a direction that reduces the perimeter length at a relatively low force, which is lower than the normal or expected forces in use.

In some configurations, the directional lock is of any structure or arrangement disclosed herein.

In some configurations, at least one biasing element applies a force to the nasal cannula system tending to reduce the perimeter length.

In some configurations, the biasing element allows the nasal cannula system to be self-fitting or automatically adjustable.

In some configurations, the nasal cannula system comprises at least one quick release arrangement that allows the perimeter loop to be quickly and easily broken, such as for removal or application of the nasal cannula system from or to a user.

In some configurations, the headgear is a single strap or a bifurcated strap arrangement.

In some configurations, the nasal cannula comprises a body having a rigid frame portion and a softer user-contacting portion.

In some configurations, an excess portion of the at least one core member that is not actively defining a portion of the perimeter length is accommodated in either the nasal cannula or the headgear. In some such configurations, the excess portion is internal to the nasal cannula or the headgear. In some such configurations, the excess portion is accommodated in a circular accumulator.

In some configurations, multiple adjustment arrangements are provided. In some such configurations, an adjustment arrangement is provided on each side of the nasal cannula system. In some such configurations, the excess portions of the core members of each side are positioned above and below one another on or within the nasal cannula.

In some configurations, a nasal cannula system comprises a nasal cannula and a headgear. At least one adjustment arrangement allows adjustment of a perimeter length of the nasal cannula system. The at least one adjustment arrangement includes a core member coupled to one portion of the headgear and a lock coupled to another portion of the headgear that is movable relative to the first portion. The lock can engage the core member to retain the nasal cannula system in a desired adjusted perimeter length.

In some configurations, the lock can retain the desired adjusted perimeter length in response to normal or expected forces in use, such as the weight of the nasal cannula and hose pull forces, for example.

In some configurations, the lock allows slippage of the core member at forces above a threshold such that the perimeter length can be increased beyond the desired adjusted perimeter length.

In some configurations, the lock is a directional lock and allows movement of the core member in a direction that reduces the perimeter length at a relatively low force, which is lower than the normal or expected forces in use.

In some configurations, the directional lock is of any structure or arrangement disclosed herein.

In some configurations, at least one biasing element applies a force to the nasal cannula system tending to reduce the perimeter length.

In some configurations, the biasing element allows the nasal cannula system to be self-fitting or automatically adjustable.

In some configurations, the nasal cannula system comprises at least one quick release arrangement that allows the perimeter loop to be quickly and easily broken, such as for removal or application of the nasal cannula system from or to a user.

In some configurations, the headgear is a single strap or a bifurcated strap arrangement.

In some configurations, the nasal cannula comprises a body having a rigid frame portion and a softer user-contacting portion.

In some configurations, an excess portion of the at least one core member that is not actively defining a portion of the perimeter length is accommodated in the headgear. In some such configurations, the excess portion is internal to the headgear. In some such configurations, the excess portion is accommodated in a circular accumulator.

In some configurations, multiple adjustment arrangements are provided. In some such configurations, an adjustment arrangement is provided on each side of the nasal cannula system.

In some configurations, a directional lock includes a lock member having an aperture or opening and is configured to engage a core member or filament that passes through the opening. The opening can change cross-sectional dimensions between one side of the lock member and the other side of the lock member and/or the profile of the opening can be tapered.

In some configurations, the side of the opening that defines a working edge of the lock member that engages the core member in a locked position is smaller than the opposite side of the opening.

In some configurations, the profile of the opening tapers towards a pivot axis of the lock member.

In some configurations, a directional lock includes a first lock member and a second lock member, each having an aperture or opening and is configured to engage a core member or filament that passes through the opening. A motion transfer element causes movement of the second lock member in response to movement of the first lock member.

In some configurations, the motion transfer element pushes the second lock member in response to movement of the first lock member, but allows the second lock member to move away from the first lock member.

In some configurations, the motion transfer element is a link, which deflects to allow the second lock member to move away from the first lock member.

BRIEF DESCRIPTION OF THE DRAWINGS

Preferred embodiments of the present invention will be described with reference to the accompanying drawings.

FIG. 4.1 illustrates a position of the exemplary headgear arrangement at a start of donning onto a user.

FIG. 4.2 illustrates a position of the exemplary headgear arrangement at a start of retraction.

FIG. 4.3 illustrates a position of the exemplary headgear arrangement at an end of donning.

FIG. 13.1 is a stability chart of various headgear types.

FIG. 13.2 illustrates a single retention plane interface assembly.

FIG. 25 is a rear perspective view of an exemplary headgear assembly on a user.

FIG. 26 is a sectional view of the exemplary headgear assembly along a line 26-26 in FIG. 25.

FIG. 27 is a sectional view of the exemplary headgear assembly along a line 27-27 in FIG. 25.

FIG. 28 is a sectional view of the exemplary headgear assembly along a line 28-28 in FIG. 25.

FIG. 29 is a rear perspective view of an exemplary headgear assembly illustrating portions of the exemplary headgear constructed from various material types.

FIG. 108 is an enlarged view of the lock member of FIG. 107 in an unlocked position.

Figures 109A, 109B, 109C:
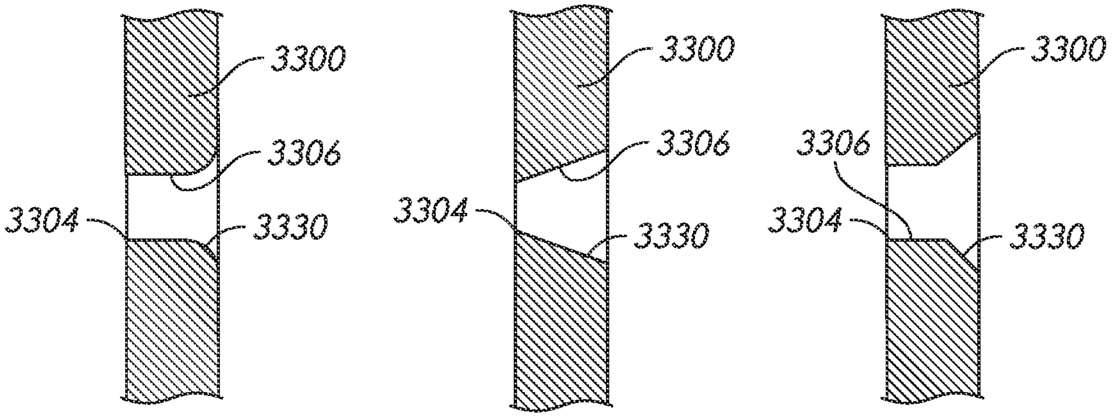

FIGS. 109*a*-109*c* illustrate several lock members with different possible cross-sectional opening shapes.

Figure 110:
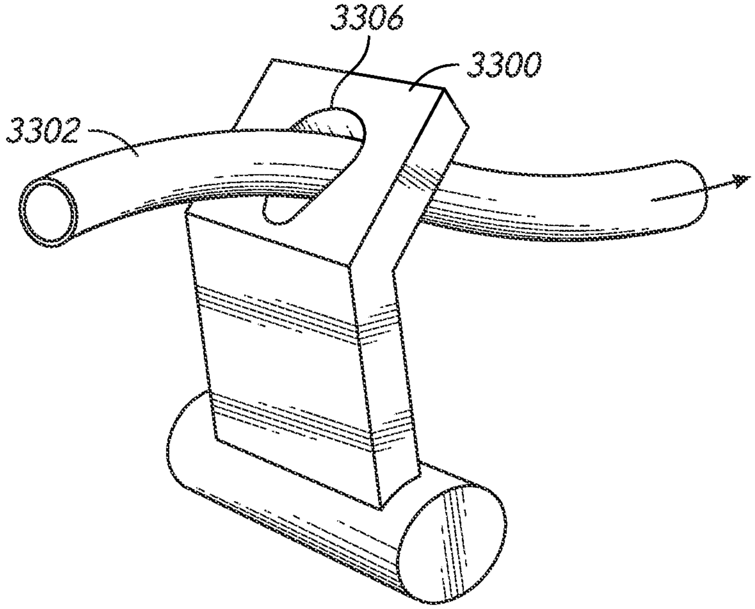

FIG. 110 is a perspective view of a lock member having a tapered hole geometry.

Figure 111A:
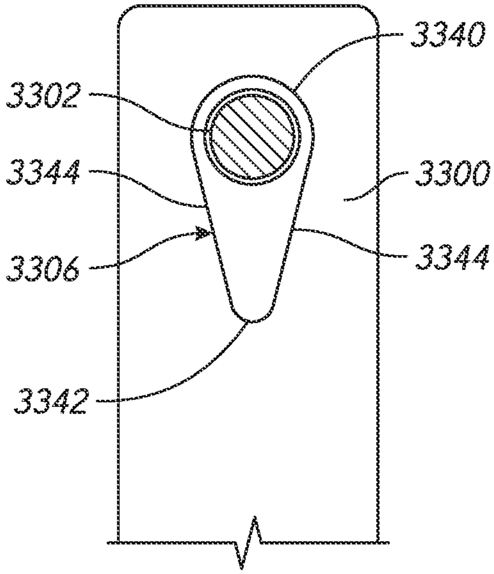
Figure 111B:
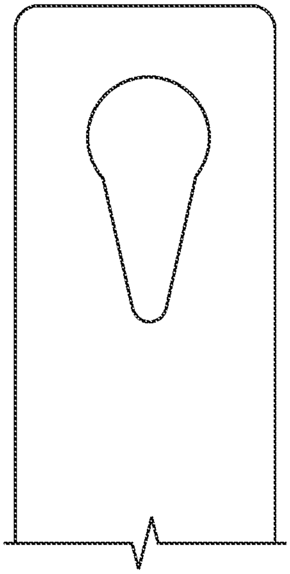

FIGS. 111*a* and 111*b* illustrate lock members having alternative tapered hole geometries.

Figure 112:
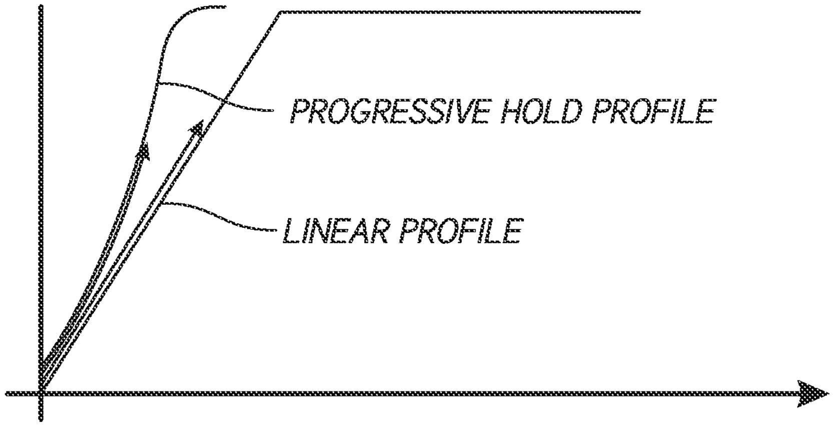

FIG. 112 is a graph of force versus distance illustrating the progressive holding force profile of the tapered hole geometries in comparison with a linear holding force profile.

Figure 113A:
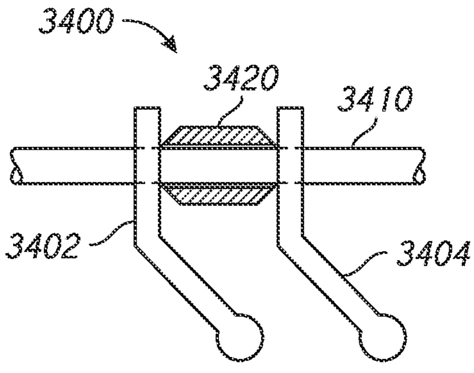
Figure 113B:
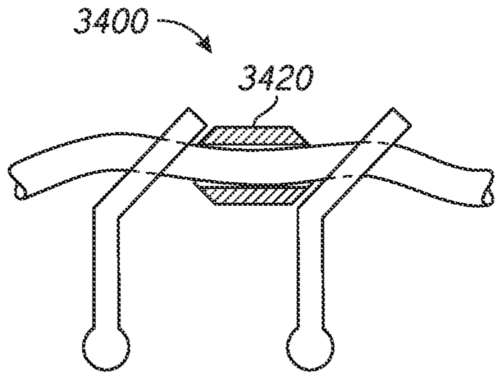

FIGS. 113*a* and 113*b* illustrate a directional lock arrangement comprising a pair of lock members and a motion transfer element for transferring motion between the lock members. FIG. 113*a* illustrates the directional lock arrangement in an unlocked position and FIG. 113*b* illustrates the directional lock arrangement in a locked position.

Figure 114A:
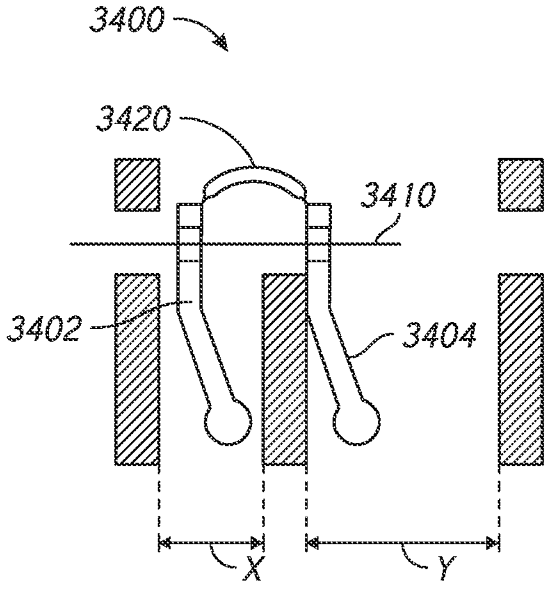
Figure 114B:
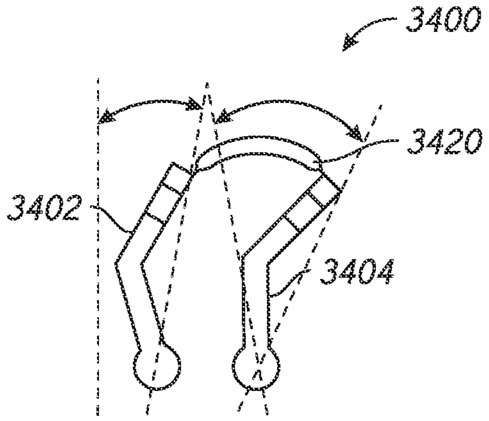

FIGS. 114*a* and 114*b* illustrate another directional lock arrangement comprising a pair of lock members and an alternative motion transfer element for transferring motion between the lock members. FIG. 114*a* illustrates the directional lock arrangement in an unlocked position and FIG. 114*b* illustrates the directional lock arrangement in a locked position.

Figure 115:
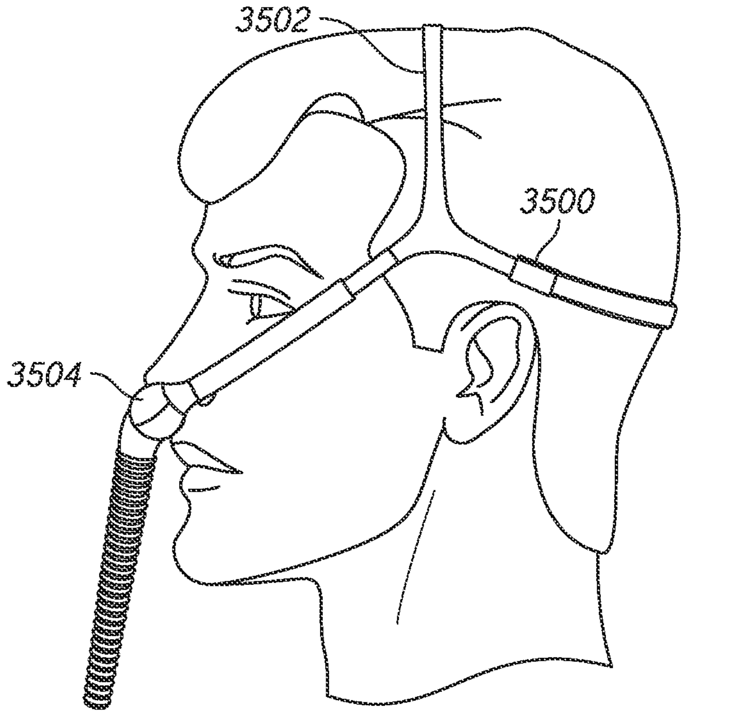

FIG. 115 illustrates a respiratory mask system comprising a headgear arrangement incorporating at least one directional lock arrangement. The directional lock arrangement is located behind the ear of the user.

Figure 116:
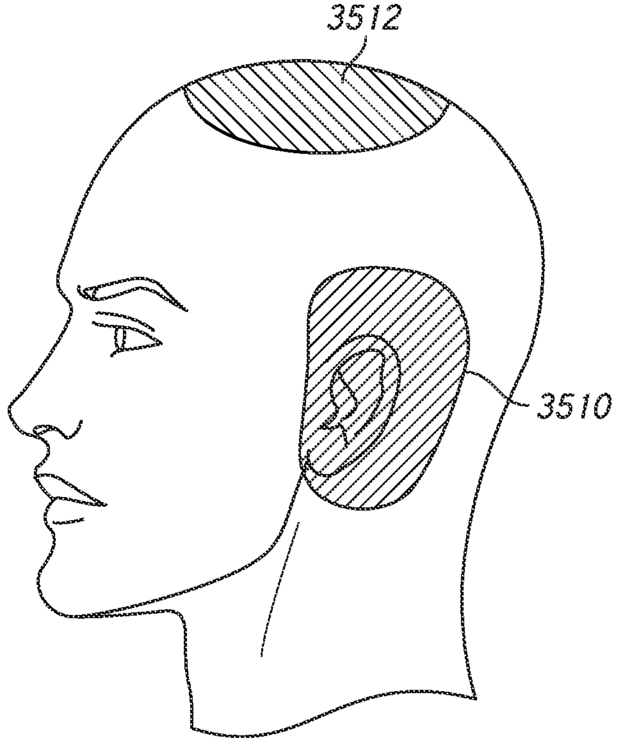

FIG. 116 illustrates possible locations for placement of a directional lock arrangement on a user.

Figure 117:
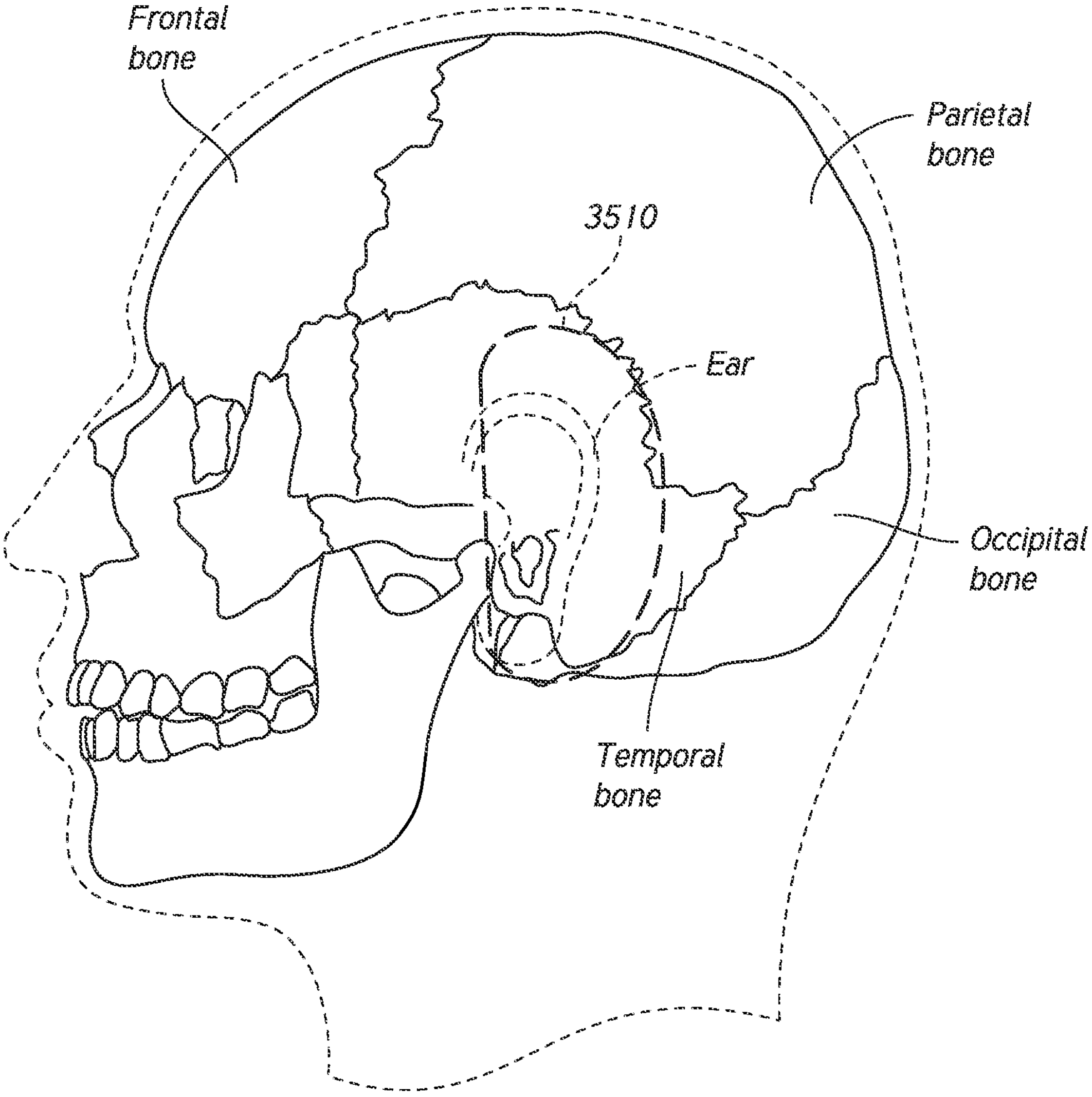

FIG. 117 illustrates a possible location for placement of a directional lock behind an ear of the user, with the placement area shown relative to bones of the skull.

Throughout the drawings, reference numbers can be reused to indicate general correspondence between reference elements. The drawings are provided to illustrate example embodiments described herein and are not intended to limit the scope of the disclosure.

DETAILED DESCRIPTION

Some embodiments disclosed herein involve a headgear system and/or an interface assembly incorporating a headgear system that upon fitment to the head of a user automatically adjusts to the correct size and, once in use, transforms in properties from an elasticated "stretchy" strap/strapping to an "inelastic" strap/strapping. In some configurations, the headgear (alone or as integrated in an interface assembly) exhibits a relatively small contraction force that tends to shorten the headgear. When coupled to a mask, the headgear and mask cooperate to define a perimeter of the interface assembly, which is reduced in length as a result of the contraction force toward a minimum perimeter length. Although not likely to be perfectly circular, the perimeter length is often referred to as a "circumference." Thus, with such an arrangement, the interface assembly can be positioned on the user's head and will automatically contract to or very near a proper head size, in a manner similar to an elasticated or "stretchy" headgear. The contraction force preferably is sufficient to support the weight of the interface assembly and at least substantially keep the interface assembly in place on the user's head at the smallest head size or minimum useful perimeter length of the interface assembly, which may or may not coincide with the minimum perimeter length. In some configurations, the retraction force can be sufficient to support the weight of a nasal cannula or other small interface, which can have a weight of about 50 grams, for example. In other configurations, the retraction force can be between about 0.5 Newtons and about 5.2 Newtons, or between about 1 Newton and about 2.6 Newtons, or between about 1 Newton and about 1.5 Newtons, including any value and sub-range within these ranges. In other configurations, the retraction force may be insufficient to support the weight of the interface and may require manual assistance to move the interface to a sealed position on the user's face. However, preferably, once the headgear is sufficiently retracted, it is then held in place by, for example, the directional lock(s). In some configurations, the contraction force is only sufficient or is configured to support the weight of the headgear.

However, in at least some configurations, the contraction force is less than is necessary to maintain the mask in sealed contact with the user's face during treatment/use. That is, the contraction force, alone, cannot resist the blow-off force. In some configurations, the contraction force is insufficient to resist the blow-off force throughout a range of usable perimeter lengths or headgear sizes. Therefore, the headgear and/or interface assembly also exhibits an inelastic behavior in response to forces tending to elongate the headgear or increase the perimeter length of the interface assembly. The headgear and/or interface assembly can have a locked mode that can produce a locking force tending to resist expansion, elongation or lengthening of the perimeter length. The locking force can be sufficient to resist elongation, or at least any significant elongation, of the perimeter length in response to blow-off forces. In some configurations, the locking force is sufficient to resist elongation in response to the highest blow-off forces expected with a variety of uses or treatments (e.g., Bi-Level or CPAP, NIV, etc.). In some configurations, the locking force may be selected for one or more particular uses/therapies, but may not be suitable for all uses/therapies. In some configurations, the locking force may be selected to resist elongation in response to forces in addition to blow-off forces, such as hose pull forces, for example. Such additional forces can be referred to collectively herein as "hose pull forces" and such additional resistance to elongation can be referred to herein as a "reserve."

In some configurations, the headgear and/or interface assembly also exhibits a yield force, above which expansion or elongation of the perimeter length is permitted. Preferably, the yield force is greater than the expected blow-off force. In some configurations, the yield force is greater than the expected blow-off force and the hose pull force. Thus, such a headgear and/or interface assembly has a reserve. Preferably, the yield force is set low enough that a user can at least relatively conveniently apply an elongation force to the headgear and/or interface assembly sufficient to exceed the yield force in order to permit the interface assembly to lengthen and to be applied to the user's head. As described above, the contraction force reduces the perimeter length toward a proper head size.

In some configurations, the headgear and/or interface assembly automatically transitions between a contraction mode, a locked mode and a yield mode in response to the presence or absence of external forces. For example, the headgear and/or interface assembly moves toward or to the minimum perimeter length in the absence of external lengthening or expanding forces. A lengthening or expansion force that is greater than the yield force can be applied to increase the perimeter length of the headgear and/or interface assembly to a length sufficient to permit the interface assembly to be positioned on the user's head. Once the lengthening or expansion force is removed (or reduced to below the contraction force), the contraction force acts to automatically reduce the perimeter length to or substantially to the proper head size such that the interface assembly is supported on the user's head. Upon the start of treatment (application of blow-off force) and/or application of hose pull force, the headgear and/or interface assembly automatically transforms to the locked mode to resist elongation, or at least resist any significant elongation, or increase of the perimeter length. At the end of treatment, or at any time as desired, a force above the yield force can be applied to the headgear and/or interface assembly to increase the perimeter length and permit removal of the interface assembly from the user's head.

Advantageously, with such an arrangement, micro-adjustments of the perimeter length of the headgear and/or interface assembly can be accomplished quickly and conveniently. For example, during treatment or use, the mask can be manipulated to effect micro-adjustment of the perimeter length. For instance, in the event of a leak between the mask and the user's face, the mask can be wiggled or otherwise moved to effect a micro-adjustment of the perimeter length to address the leak. In some cases, the seal of the mask may be compressed against the user's face, which can allow the contraction force to automatically reduce the perimeter length. Upon release of the mask, the headgear and/or interface assembly locks at, or very near, the reduced perimeter length. Thus, such configurations permit the headgear and/or interface assembly to micro-adjust, or move to an adjusted perimeter length, as a result of small manipulations (e.g., wiggling) of the mask. Manipulation of other portions of the interface assembly (e.g., headgear or breathing tube/gases conduit) can similarly result in micro-adjustment. Because of the nature of the human head and/or the conditions under which interface assemblies are used, quick and convenient micro-adjustment can dramatically improve performance and user satisfaction of an interface assembly. Treatment often occurs at night and/or under other situations when the user is lying down. Thus, the headgear can be in contact with surface, such as a pillow or bed. Movement of the user's head relative to such surfaces can cause movement of the headgear, which can alter the fit of the headgear. For example, hair can move or "compress" beneath the headgear, which can alter the fit. The headgear straps may move up, down or rotationally on the head, which can alter the fit. Such alterations in fit can result in leaks between the mask and the user's face. The above-described adjustment technology can permit such changes in fit to be addressed automatically or with small manipulations of the mask or other portions of the interface assembly. Moreover, the interface assembly can be removed and reapplied and automatically adjust to at or very near a proper headgear size. In contrast, if conventional non-stretch headgear is moved from its desired adjustment position, such as by mistake or as a result of cleaning, it can be difficult and time-consuming to reestablish the desired adjustment position. Conventional elasticated headgear addresses the adjustment issue, but because the contraction force must resist the highest expected blow-off and hose pull forces at the smallest useable headgear size, elasticated headgear applies a relatively large pressure to the user's head that is only partially relieved by the application of blow-off force. Such pressure may be substantial for a user with a relatively large head size and low treatment pressure.

As is described below with reference to specific directional lock arrangements, in some configurations, some amount of movement occurs in the headgear and/or interface assembly during transition from the elastic mode to the locked mode. For example, with some directional lock arrangements, the perimeter length may increase slightly during the transition from elastic mode to locked mode. In some cases, there exists a compromise between increased yield force and reduced perimeter length change during transition. Thus, references to any particular positions of the headgear and/or interface assembly or perimeter lengths can include such slight length changes during transition, if present.

The following example of the above-described adjustment technology is based on the delivery of CPAP. The series of graphs describe a typical operating envelope that a headgear system must be designed to operate over and how various current embodiments operate relative to that envelope. The envelope may comprise an entire CPAP treatment universe, that is, an entire range of typical, probable or possible CPAP pressures and an entire range of typical, probable or possible head sizes. Or, the envelope may comprise a subset of the CPAP treatment universe, such as a subset of pressures (e.g., low pressure or high pressure CPAP) or head (headgear or interface assembly) sizes (e.g., small, medium or large). The principles discussed in connection with CPAP treatment may apply to other treatments, as well.

Figure 1:
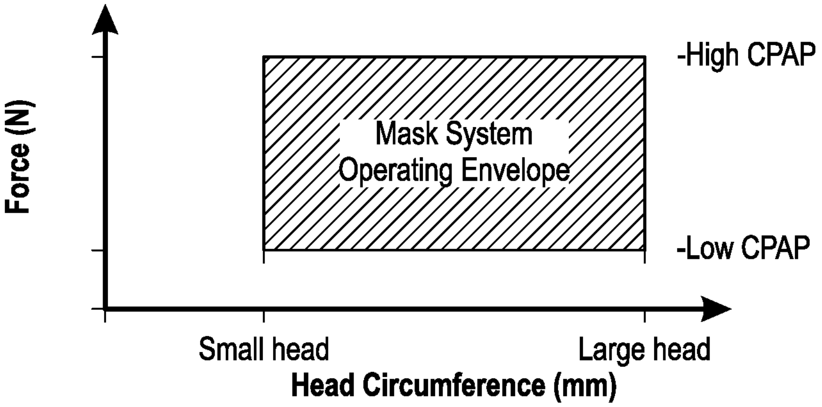
FIG. 1 is a graph illustrating an operating envelope representing a relationship between a force created when a mask enclosure is pressurised and a headgear sizing range of potential patients.

FIG. 1 is a graph that illustrates a relationship between the force that is created when a mask enclosure is pressurised and the headgear sizing range that is likely to be encountered across the range of potential patients. The operating envelope is illustrated as a rectangular area defined between minimum and maximum forces and minimum and maximum head sizes (circumferences).

Figure 2:
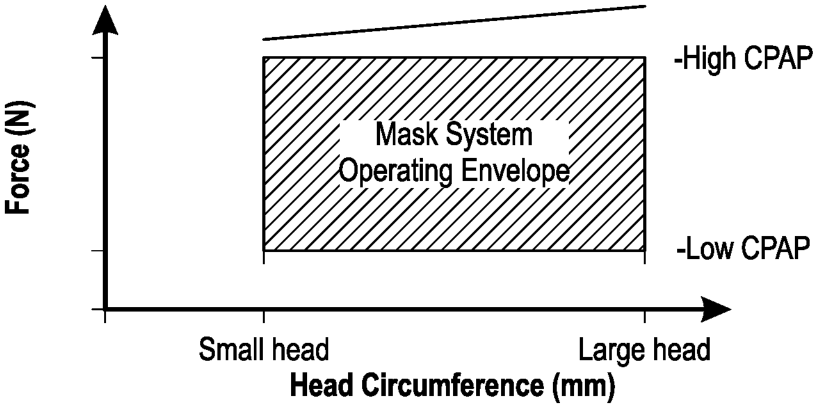
FIG. 2 illustrates the operating envelope of FIG. 1 with a force curve of an elasticated headgear system superimposed.

FIG. 2 illustrates the operating envelope of FIG. 1 with the performance characteristics (force curve) of an elasticated headgear system superimposed. It is apparent that for the elasticated system to offer sufficient performance across the mask system operating envelope, it must provide a greater force than the mask system can generate. Thus, at low CPAP pressures, the headgear provides a much greater force than is necessary to counteract the blow-off force. The additional force is applied a pressure to the user over an area defined by the mask and headgear, which is concentrated primarily at the mask and at the back of the head. The area of the headgear can be increased to apply the force over a larger area, thereby reducing the applied pressure. However, large headgear can be annoying or uncomfortable. For example, such large headgear can retain heat over a larger area than desirable.

Figure 3:
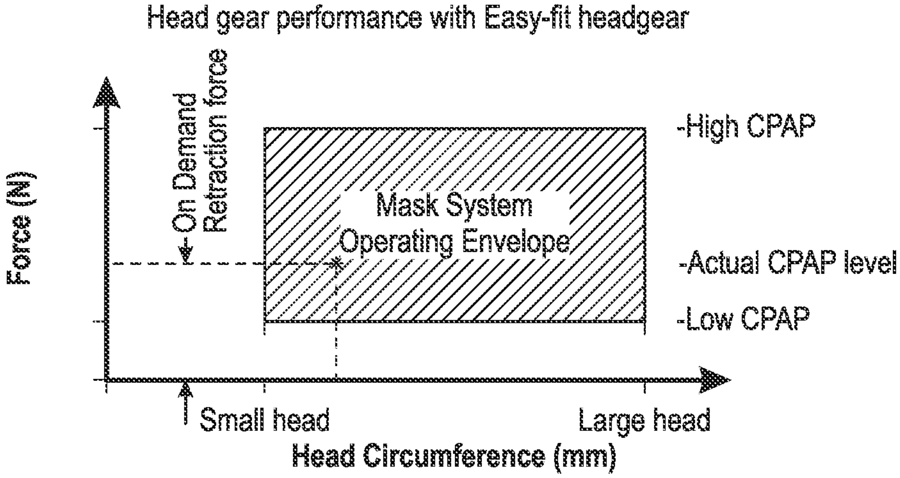
FIG. 3 illustrates the operating envelope of FIG. 1 with a force curve of an exemplary embodiment superimposed.

FIG. 3 illustrates the operating envelope of FIG. 1 with the performance of an example of a headgear system having the above-described automatic adjustment technology superimposed. In the illustrated example, the force generated by the headgear and/or interface assembly is sufficient to balance the forces generated by the pressurization of the enclosed area of the mask. In essence, the example headgear system automatically adjusts to the appropriate head size (circumference or perimeter length) with a relatively low contraction force and then provides a retention force "on-demand" that is matched to the actual CPAP pressure. Thus, the example headgear system can automatically adjust to meet the needs of any potential point within the CPAP envelope.

Figure 4:
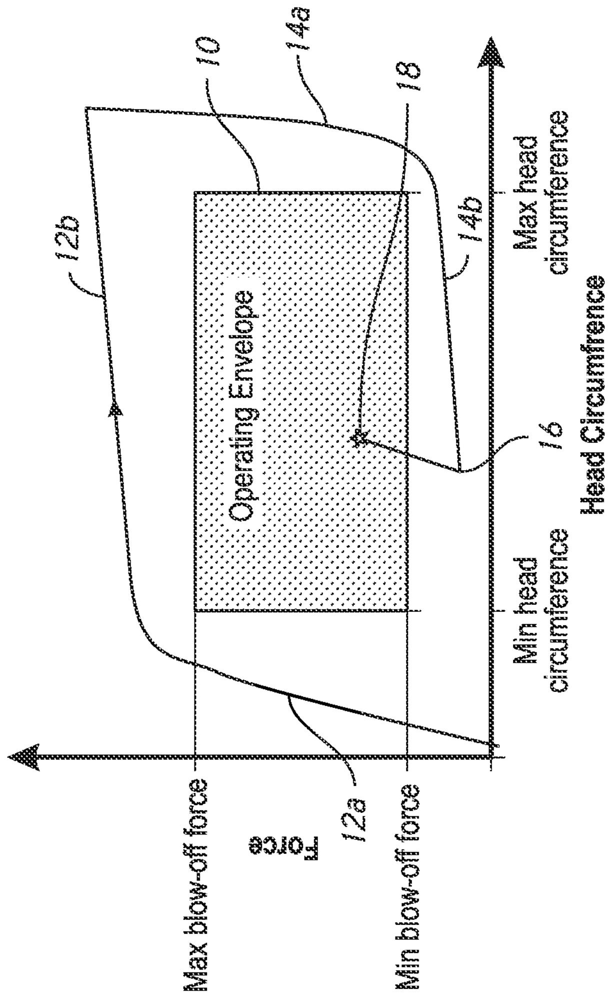
FIG. 4 is a graph of a force-deflection curve of an exemplary headgear arrangement.

FIG. 4 illustrates a graph of a force-deflection curve of an example of a headgear arrangement or interface assembly comprising a headgear arrangement. The deflection axis of the graph may represent the circumference or perimeter length of the headgear arrangement or interface assembly. The circumference or perimeter length, in turn, can represent the head circumference of a particular user when the headgear arrangement or interface assembly is fitted to the user. FIGS. 4.1-4.3 illustrate several discrete positions of a user putting on ("donning") and micro-adjusting an example interface assembly comprising a headgear arrangement. The graph of FIG. 4 is described below with additional reference to the donning positions of FIGS. 4.1-4.3.

The graph of FIG. 4 also illustrates an operating envelope 10 relevant to the headgear arrangement or interface assembly, which may be the same operating envelope as shown and described above with respect to FIGS. 1-3. The operating envelope 10 is illustrated as a rectangular area defined between minimum and maximum forces applied to the headgear arrangement or interface assembly as a result of the therapy and minimum and maximum head sizes or circumferences/perimeter lengths of the headgear arrangement. The operating envelope 10 can be specific to a therapy (e.g., CPAP or bi-level PAP) or can cover multiple therapies. Similarly, the head size or circumference/perimeter length can be specific to a size of headgear arrangement or can cover multiple sizes. The operating envelope 10 can be used to establish functional or behavioral criteria of a particular headgear arrangement and is utilized herein to illustrate features or behaviors of certain disclosed embodiments.

A graph containing an example force-deflection curve of an example headgear arrangement or interface assembly (referred to as "headgear" for convenience in the discussion of the graph) is illustrated relative to the example operating envelope 10. The curve originates at or near the origin of the graph, which may represent approximately zero force and a minimum circumference or perimeter length (referred to as "circumference" for convenience in the discussion of the graph) of the headgear. The minimum circumference is greater than zero, but typically at a value below a minimum head circumference (taking into consideration the interface, if any) of the intended user or range of users.

As illustrated in FIG. 4.1, to place the headgear 100 onto the user, typically, the headgear 100 will be elongated to a circumference greater than the actual head circumference of the user. Typically, a rear portion of the headgear 100 will be placed on the rear of the user's head and the user will grasp the front of the headgear 100 (e.g., the mask or other interface) and apply a pulling force to elongate the headgear 100 and move the mask or other interface over the crown of the head and toward the face.

As illustrated in the graph of FIG. 4, the example force-deflection curve initially rises with a steep pitch, in which the force increases a substantial amount with a relatively small increase in the circumference. In some configurations, the force-deflection curve rises above the maximum force level of the operating envelope 10 before reaching the minimum circumference of the operating envelope 10. This portion of the curve can be referred to as an initial elongation portion 12*a*.

At some location above the maximum force of the operating envelope 10, the force-deflection curve transitions to a shallower pitch, in which the circumference increases a substantial amount with a relatively small increase in the force. This shallow pitch portion of the force-deflection curve can relate to a yield force of the retention arrangement of the headgear 100. Preferably, the shallow pitch portion, which can be referred to as an elongation portion 12*b*, of the force-deflection curve extends at or above the maximum force level of the operating envelope 10 along a portion or an entirety of the circumference range of the operating envelope 10. In some configurations, the elongation portion 12*b* extends beyond the maximum circumference level of the operating envelope 10. That is, the headgear 100 can be configured to achieve a greater circumference than the intended maximum head circumference to allow the headgear 100 to be conveniently placed onto a user having the maximum head circumference of the operating envelope 10 of the headgear 100. In use, especially with users having head sizes on the smaller end of the operating envelope 10, the headgear 100 may not be elongated to a maximum circumference during donning and, in some cases, may not be elongated beyond the maximum circumference level of the operating envelope 10.

After the headgear 100 has been elongated to the maximum circumference, to a circumference greater than the operating envelope 10 or, in use, to some other circumference sufficient to allow donning onto the user, the illustrated force-deflection curve drops steeply (initial retraction portion 14*a*) and then transitions to a relatively shallow portion, in which the circumference reduces substantially with a relatively small change in force. This shallow portion of the curve can be referred to as a retraction portion 14*b* and is partially illustrated by FIG. 4.2. Preferably, in the retraction portion 14*b*, the headgear 100 reduces in circumference at a relatively low force level until the headgear 100 reaches an appropriate circumference to fit the user's head. The headgear 100 can be positioned on the user's head at this low force level (the left end of the retraction portion 14*b* or "fit point 16") until therapy is initiated or until another force attempting to elongate the headgear 100 is applied.

Advantageously, this relatively low force level allows the headgear 100 to be comfortable for the user. In some configurations, the retraction portion 14*b* of the force-deflection curve is at or below the minimum force level of the operating envelope 10. Thus, in such an arrangement, the retraction force of the headgear 100 can be lower than that necessary or desirable to resist minimum forces induced in the headgear 100 by the therapy (e.g., a low CPAP level). Accordingly, even at low therapy levels, the headgear 100 can be configured to produce only enough retention force to resist the therapy-induced forces because the minimum force level of the operating envelope 10 is above the retraction portion 14*b* of the force-deflection curve. In some configurations, as described below, the retraction portion 14*b* of the force deflection curve could fall within the operating envelope 10. Such an arrangement can be referred to as exhibiting "composite" behavior. However, preferably, the retraction portion 14*b* of a composite-behavior headgear force-deflection curve remains below the maximum force level of the operating envelope 10.

When therapy is commenced, or another elongating force is applied to the headgear 100, the force deflection curve rises relatively steeply from the fit point 16 to a point within the operating envelope 10 at which the retention force of the headgear 100 balances with the force induced by the therapy and/or other forces (e.g., hose pull forces) attempting to elongate the headgear 100. Such a point can be referred to as a balanced fit point 18. The force-deflection curve between the fit point 16 and the balanced fit point 18 can have substantially the same slope as the initial elongation portion 12*a*. The actual location of the balanced fit point 18 can be anywhere within the operating envelope 10 depending on the actual force induced by the therapy and the actual head size of the user. In any particular case, the force in the headgear 100, which is applied over an area related to headgear size as a pressure to the user, is substantially only the force necessary to counteract the forces induced by the therapy. Thus, in at least some configurations, the pressure applied to the user can be minimized for any particular headgear size and shape for the particular level of therapy utilized. The elongation portion 12*b* of the force-deflection curve can be spaced above the maximum force level of the operating envelope 10 to provide a reserve in which additional forces (e.g., hose pull forces) can be applied without elongation of the headgear 100. Once sufficient force is applied to the headgear 100 to reach the elongation portion 12*b* of the force-deflection curve, elongation of the headgear 100 can occur. However, the headgear 100 can be designed or configured to have a force-deflection curve that accommodates expected or usual therapy forces and hose pull forces or any combination thereof.

As described above, in at least some configurations, the user can manipulate the headgear 100 to cause a micro-adjustment of the perimeter length. Advantageously, such an arrangement allows the user to, for example, address leaks or tighten or loosen the headgear 100 (reduce the perimeter length) to a desired level by simply grasping the mask or other interface and moving (e.g., wiggling) the mask or other interface relative to the user's face and a rear portion of the headgear 100, as illustrated in FIG. 4.3. As indicated by the arrows in FIG. 4.3, the mask or other interface can be moved or adjusted in a plurality of directions, including toward and away from the user's face or in a rotational manner (e.g., about a vertical or horizontal/lateral axis). Movement toward the face can result in a reduction of the perimeter length or tightening of the headgear 100 to, for example, achieve a fit that is toward the tight end of the spectrum of an acceptable or desirable fit, which can be referred to as a "tight fit." Movement away from the face can result in elongation of the perimeter length or loosening of the headgear 100 to, for example, achieve a fit that is toward the loose end of the spectrum of an acceptable or desirable fit, which can be referred to as a "loose fit." Rotational movement about a vertical axis can cause one side of the headgear 100 to tighten and the other side to remain the same or loosen. Rotation about a horizontal or lateral axis can cause one of an upper or lower portion of the headgear 100 to tighten and the other of the upper or lower portion to loosen.

As described above, it is not necessary in all configurations that the retraction portion 14*b* of the force-deflection curve be located below a minimum force level of the operating envelope 10. The headgear 100 can be designed or configured to position the retraction portion 14*b* of the force-deflection curve within the operating envelope 10 and at a level that provides a sufficient degree of comfort to the user. In some cases, the user may desire that the headgear 100 apply some degree of force in order to provide the user with some tactile feedback that provides a feeling of comfort that the headgear 100 is securely holding the interface in place. Such force applied by the headgear 100 may, for some users, fall within the operating envelope 10 of the particular therapy. Thus, with such an arrangement, under at least some conditions, the retraction force of the headgear 100 may be sufficient to resist therapy forces at least as some lower therapy levels and/or certain larger head sizes.

Figure 5:
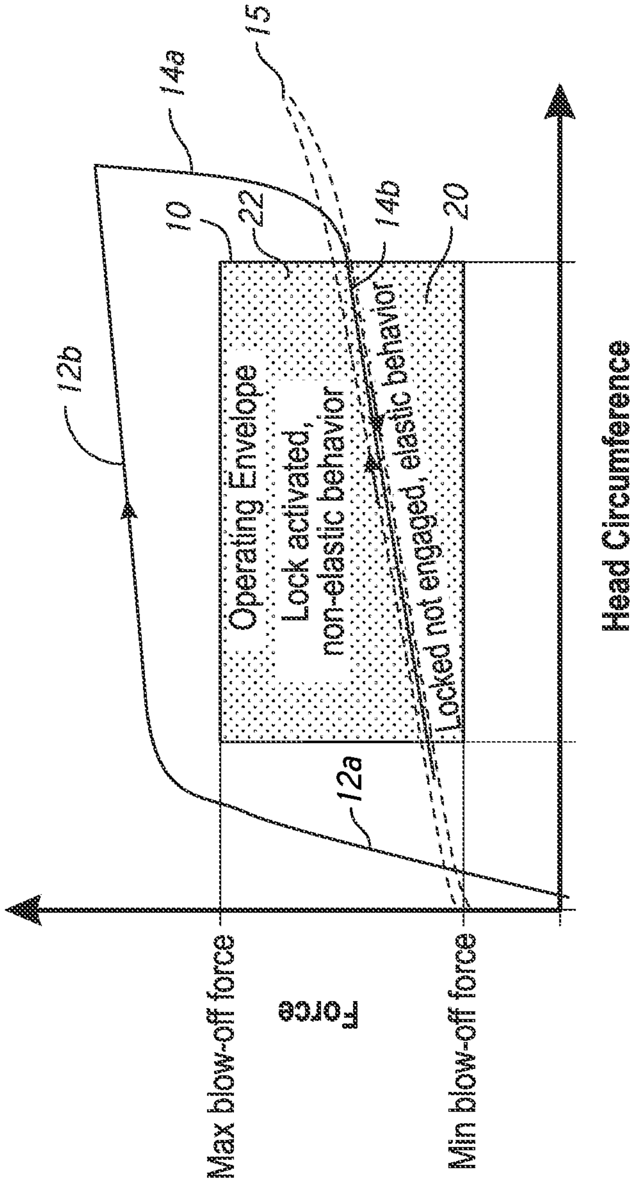
FIG. 5 is a graph containing an exemplary "composite" force-deflection curve.

FIG. 5 illustrates a graph containing an example "composite" force-deflection curve. For the sake of illustration, an example of an elastic headgear force-deflection curve is illustrated in the graph in addition to the composite force-deflection curve. The composite force-deflection curve can be substantially similar or identical to the force-deflection curve described above in connection with FIG. 4 except the composite force-deflection curve positions the retraction portion 14*b* within the operating envelope. The retraction portion 14*b* of the force-deflection curve divides the operating envelope into a lower portion 20 and an upper portion 22. The headgear can absorb forces in the lower portion 20 below the retraction portion 14*b* of the force-deflection curve utilizing the retraction force of the headgear, which can be provided by one or more elastic elements. Forces in the upper portion 22 above the retraction portion 14*b* of the force-deflection curve can be absorbed by the retention force of the headgear, which can be provided by one or more retention elements (e.g., locks), in a manner similar to that described above in connection with FIG. 4.

An example of an elastic headgear force curve 15 is illustrated overlying the retraction portion 14 of the force-deflection curve. The elastic headgear force curve 15 includes upper and lower curve portions separated by a relatively small vertical distance representing the internal frictional losses or hysteresis within the headgear. The force necessary to elongate the headgear is slightly greater than the retraction force of the headgear. An elastic headgear exhibiting the illustrated elastic force-deflection curve 15 can only accommodate applied therapy or other forces below the force-deflection curve 15. Applied forces above the force-deflection curve 15 will result in elongation of the elastic headgear. Thus, the force-deflection curve 15 of an elastic headgear must be positioned above the maximum force level of the operating envelope to avoid undesired elongation under at least some conditions (e.g., high therapy forces or small head size). The level of pressure applied to a user as a result of such a force-deflection curve 15 is likely to be uncomfortable under at least some conditions (e.g., low therapy forces or large head size).

In contrast, the composite force-deflection curve (or the balanced fit force-deflection curve shown and described in connection with FIG. 4) exhibits a relatively large vertical distance between the upper portion 12*b* of the curve and the lower portion 14*b* of the curve. At least a portion of the operating envelope falls within the vertical space between the upper portion 12*b* of the curve and the lower portion 14*b* of the curve. Accordingly, a headgear exhibiting such a force-deflection curve can resist relatively high forces while applying a relatively low force or pressure to the user in the absence of therapy or other elongation forces. In addition, once therapy is commenced, the force or pressure applied to the user remains the same (if below the retraction portion 14*b* of the force-deflection curve in a composite arrangement) or increases only to substantially the level needed to resist the applied force.

Figure 6:
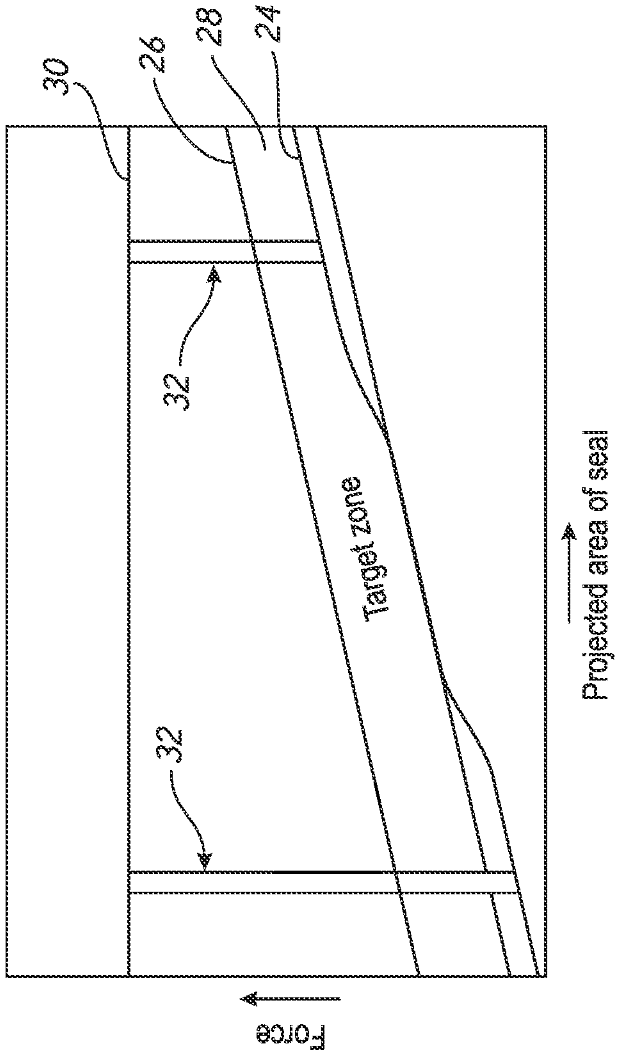
FIG. 6 is a force-area graph for maintaining an interface in sealed contact.

The forces applied to the headgear by the interface typically relate to a projected area of the seal of the interface. Smaller interfaces, such as nasal pillows or nasal masks, seal around a smaller area and, thus, produce a smaller force relative to larger interfaces, such as full face masks. Some interfaces (e.g., nasal cannula) may not create a seal with the face of the user and, thus, the forces applied to the headgear may relate primarily to the weight of the interface. FIG. 6 illustrates a graph of the force required to keep the interface in sealed contact with the user's face as it relates to the projected area of the seal. In general, the greater the projected area of the seal, the greater the force required to keep the interface in sealed contact with the user's face and, thus, the greater force that need to be resisted by the headgear. Such force can be referred to as a retention force of the headgear.

The graph of FIG. 6 includes two lines 24, 26 defining upper and lower limits of a range of acceptable retention forces for interfaces having different projected seal areas. The two lines 24, 26 are vertically spaced from one another and extend upwardly from left to right with a moderate slope. The lower line 24 can represent a minimum force necessary or desirable to maintain a seal with the user's face. The upper line 26 can represent a maximum desirable force, which can be greater than necessary to maintain a seal, but preferably is low enough to maintain user comfort or avoid excessive seal collapse. The space between the lower line 24 and the upper line 26 can represent a usable or target range 28 of adjustment to accommodate user preference, with the lower line 24 representing a usable or acceptable loose fit and the upper line 26 representing a usable or acceptable tight fit. The lower line 24 can include one or more relatively short, steep upward pitched sections that represent a transition between types of interfaces, such as nasal pillows to nasal mask and nasal mask to full face mask. The upper line 26 is illustrated as straight, but could include steep pitched sections corresponding to those of the lower line 24 to maintain a constant target adjustment range.

The graph of FIG. 6 also includes a flat or horizontal line 30 at a force level above the target range or target zone 28. This line 30 represents a force that will or is likely to cause skin damage to a user over a relatively short period of continued use of a particular headgear. This line 30 can be referred to as the maximum force line 30. The actual force value may vary depending on characteristics of the particular headgear, such as contact area or type of material. A vertical distance between the target zone 28 and the maximum force line 30 represents a margin of error 32 for adjustment of a headgear force. As illustrated, the margin for error 32 is reduced for an interface having a larger projected seal area, such as a full face mask, in comparison with an interface having a smaller projected seal area, such as nasal pillows or a nasal mask. Accordingly, especially with larger projected seal area interfaces, it is desirable that a headgear be easily or conveniently capable of adjustment to within or close to the target zone 28. Conventional inelastic headgear incorporates relatively coarse adjustments, such as one or more adjustable loops that are secured with hook-and-loop fasteners. Such headgear can be difficult to adjust to within the target zone 28, especially in environments in which the wearer of the headgear is not the person making the adjustments, which often occurs in hospital settings, for example.

Figure 7:
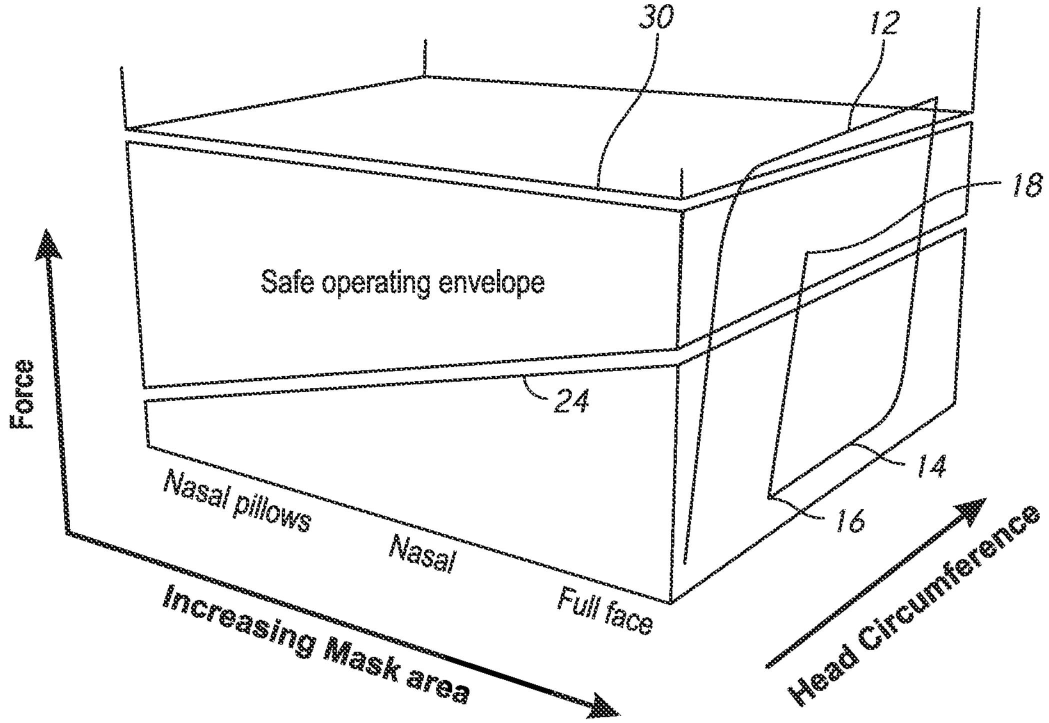
FIG. 7 is a three-dimensional graph of a relationship between headgear force, projected seal area and head circumference.

FIG. 7 illustrates a three-dimensional graph of a relationship between headgear force, projected seal area and circumference. The graph of FIG. 7 is a combination of the graph of FIG. 6 and the graph of FIG. 4. The graph of FIG. 7 illustrates the minimum force 24 for creating a seal between the interface and the user's face (the lower line 24 of the target zone 28 of FIG. 6). Below the minimum force line 24, the headgear force can be insufficient to create or maintain a seal. The graph of FIG. 7 also illustrates the maximum force line 30 above which skin damage is likely to occur. In between the minimum force line 24 and the maximum force line 30 is a safe operating envelope for the headgear force. The upper line of the target range is omitted for clarity.

The graph of FIG. 7 also illustrates a force-deflection curve of an example headgear. The force-deflection curve can be located within any plane along the projected seal area axis to illustrate design criteria for a headgear intended for use with a particular type of interface having a particular projected seal area. A headgear could also be designed taking into consideration the headgear forces and circumferences along a segment or an entirety of the projected seal area axis to design a headgear that will operate with multiple types of interfaces or that is universal for all types of interfaces (at least with respect to a particular therapy). In some configurations, as illustrated by the force-deflection curve in FIG. 7, the elongation portion 12 of the force-deflection curve can be located above the maximum force line 30.

In at least some configurations, headgear exhibiting a balanced fit or composite force-deflection curve, as described above, advantageously provides a retention force that falls within the safe operating envelope and, preferably, within the target zone. In at least some configurations, such headgear automatically adjusts to a suitable retention force within the safe operating envelope and, preferably, within the target zone. Thus, under-tightening or over-tightening by the user or by another can be reduced or eliminated.

As described above, the example headgear system performs several functions in the process of fitting, using and removing an interface or mask system. For fitment, the headgear system extends in length to enable it to be placed over a user's head. The headgear system retracts in length during the "fitment" process and provides sufficient force to the mask system such that the user feels that the mask system is secure. Once airway pressure is applied, the headgear system "transforms" in performance from an elastic or stretchy behaviour to one of inelastic behaviour. The headgear system also provides for micro-adjustment to tighten or loosen the mask based on the user's preference during use. For removal, the headgear system extends in length to enable it to be removed over a user's head. The combination of one or more, including all, of these features provides a mask system that requires minimal user interaction to fit and remove. This removes the potential for misuse and may help with improved usability of the mask system. The example headgear system can also mitigate the effects of excess pressure on the skin by reducing the probability, or even the possibility, of over-tightening of the head gear. The example headgear system can improve the overall compliance with the therapy. An additional feature to this is one which has a high degree of positional location and stability. This is both in terms of the activities of removal and refitting of the mask and during its use. Disclosed herein are one or more concepts for achieving a repeatable and stable positioning of the headgear and associated interface assembly on a patient or user's head. Also disclosed herein are one or more concepts for achieving a headgear system that supports transformational behaviour by providing portions that can selectively be made either elastic or inelastic and portions that provide an inelastic behaviour.

Figure 8B:
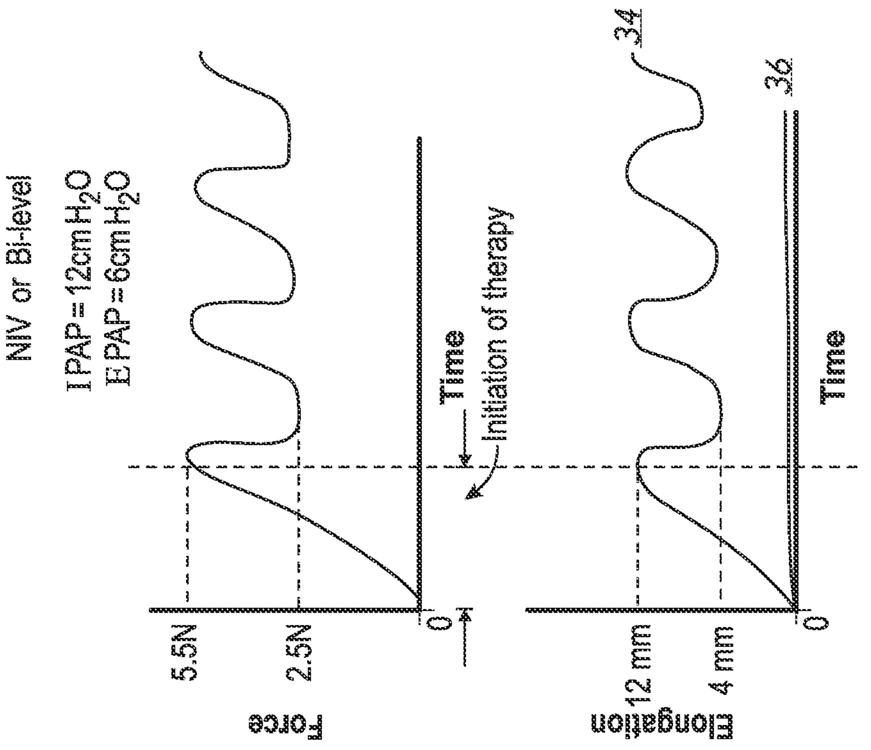
FIG. 8B shows a force profile and elongation profile of a variable pressure therapy for elastic and inelastic headgear systems.
Figure 8A:
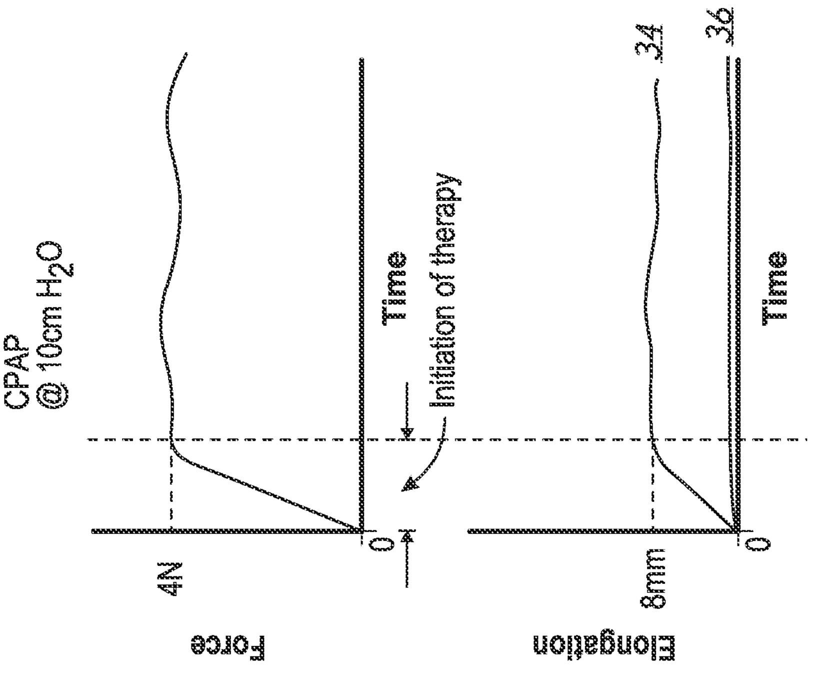
FIG. 8A shows a force profile and elongation profile of a constant pressure therapy for elastic and inelastic headgear systems.

FIGS. 8A and 8B illustrate the force profiles of constant pressure therapy and variable pressure therapy, respectively, along with associated elongation behaviour of elastic and inelastic headgear systems in graphical form for a full face mask. FIG. 8A includes two graphs of force and elongation, respectively, induced in the headgear over time with application of constant pressure therapy, such as CPAP at 10 cm of H2O. The upper graph illustrates the force that is induced in the headgear by the combination of the applied gas pressure and the mask enclosure area or, simply, the mask area. Despite the constant delivery pressure of the therapy, the force curve includes small oscillations that result from the user breathing and causing pressure changes within the mask. The lower graph illustrates the resulting elongation or movement in the headgear system and, thus, the mask body as the result of the forces applied. There are two elongation lines 34, 36 shown in the lower, elongation graph. The first line 34 illustrates the elongation behavior of a state-of-the-art elastic headgear, which elongates in response to the application of force. In the illustrated example, the elastic headgear elongates about 8 mm at the CPAP pressure compared to the length without CPAP pressure. The second line 36 illustrates the elongation behavior of the state-of-the-art inelastic headgear. As illustrated, the inelastic headgear exhibits very little elongation in response to applied force.

FIG. 8B similarly includes a graph of force and elongation, respectively, induced in the headgear over time with the application of oscillatory or variable pressure therapy, such as NIV or Bi-level PAP. For example, the illustrated therapy varies between a pressure of about 5 cm of H2O (e.g., expiratory positive airway pressure—EPAP) and about 12 cm of H2O (e.g., inspiratory positive airway pressure—IPAP). The upper graph illustrates the force that is induced in the headgear by the combination of the applied gas pressure and the mask enclosure area or, simply, the mask area. The lower graph illustrates the resulting elongation or movement in the headgear system and, thus, the mask body as the result of the forces applied. There are two elongation lines 34, 36 shown in the elongation graph. The first line 34, illustrates the elongation behavior of a state-of-the-art elastic headgear, which elongates and contracts along with increases and reductions in applied force. In the illustrated example, the elastic headgear elongates moves between about 4 mm and about 12 mm (at low pressure and high pressure, respectively) in response to the variable force curve compared to the length without CPAP pressure. Typical practice to reduce or prevent this movement is to over tighten the headgear system such that the force required elongate the headgear is greater than which is being produced by the combination of mask area and ventilation pressure. The application of this practice frequently leads to skin damage and the resulting wound care practices. The second line 36 illustrates the elongation behavior of the state-of-the-art inelastic headgear, which, as in FIG. 8A, exhibits very little elongation, but has the above-described limitations and drawbacks.

As shown in the example, state-of-the-art headgear systems when used with a full face mask, and which have not been over tightened, will elongate in length such that the mask body would move about 8 mm to about 12 mm during the change from peak inspiratory pressure to end expiratory pressure for NIV or IPAP to EPAP for bi-level ventilation. In at least some configurations, the present directional locking headgear systems exhibit behavior similar to the inelastic headgear in response to application of force in a direction tending to elongate the headgear. However, such configurations of the directional locking headgear systems exhibit one or more benefits of elastic headgear (e.g., automatic size adjustment or automatic fit) without the drawbacks associated with inelastic headgear (e.g., time-consuming and difficult adjustment). In at least some configurations, a headgear system incorporating a directional locking arrangement provides headgear elongation or mask movement of less than about 4 mm in response to applied force during therapy compared to a condition as applied to the user but without system pressure. In some configurations, a headgear system incorporating a directional locking arrangement provides headgear elongation or mask movement of less than about 4 mm between a high or maximum therapy pressure condition and a low or minimum therapy pressure condition (e.g., peak inspiratory pressure and end expiratory pressure for NIV).

The functional behaviour of the example headgear system involves the various headgear elements having elongation properties in design-specific locations, so that the elasticated or stretching behaviour can be switched on and off on demand, preferably with one or more of the directional locks and/or directional friction mechanisms disclosed herein. This can involve various features of the headgear being configured to deliver specific performance attributes in specific locations. With patient interfaces used in respiratory applications, the location of these features can depend on the interface type and the number of retention planes that are desired. A retention plane can be defined as a plane or planes through which forces that are generated in the interface assembly are resolved.

Figure 9:
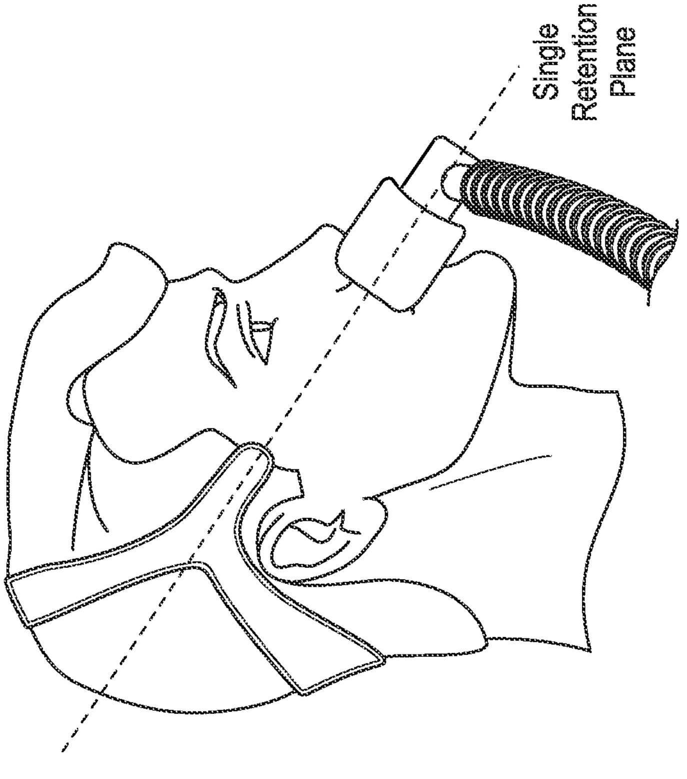
FIG. 9 is a side view of a nasal interface having a single retention plane.

For example, FIG. 9 illustrates a nasal interface, such as a nasal pillows mask, nasal mask or nasal cannula having a single retention plane. A first line extends between a mounting point on a first side of the nasal interface and a mounting point on the first side of a rear portion of the headgear. A second line extends between a mounting point on a second side of the nasal interface and a mounting point on the second side of the rear portion of the headgear. The first line and the second line cooperate to define the single retention plane. The retention plane can extend through or near a center of the nasal interface, which can be a geometric center or vertical center, for example. In some configurations, the retention plane can be off-center, such as in configurations in which it may be desirable to apply a bias force (e.g., upper or lower bias) to the nasal interface. The retention plane can extend generally from a location at or near (e.g., somewhat below) the underside of the user's nose to a location close to but somewhat above the user's ear. Such an arrangement may cause the retention plane to have an upward tilt in a front-to-back direction.

Figure 10:
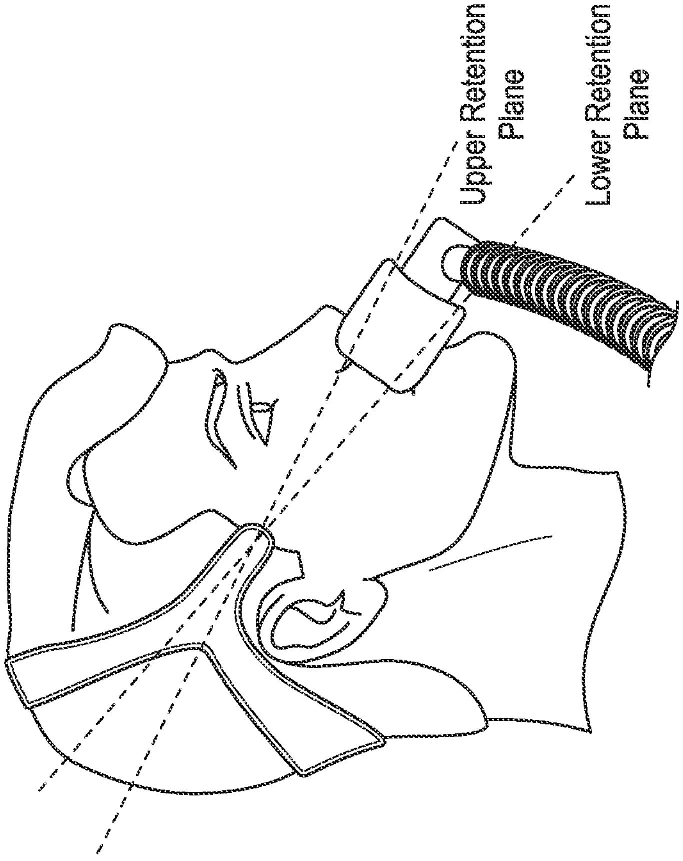
FIG. 10 is a side view of a nasal interface having two retention planes.

FIG. 10 illustrates a nasal interface, such as a nasal pillows mask, nasal mask or nasal cannula having multiple (e.g., two) retention planes. As described with respect to FIG. 9, each retention plane is defined by lines on each side of the interface assembly, which lines extend between points on the nasal interface and a rear portion of the headgear. In the arrangement of FIG. 10, the retention planes are offset from one another to define an angle in a front-to-back direction or from a side view. In the illustrated arrangement, a first retention plane extends through a relatively upper point on the nasal interface and a second retention plane extends through a relatively lower point on the nasal interface. The first and second retention planes can extend through a single point on the rear portion of the headgear (or very near one another) or can be spaced apart on the rear portion of the headgear, with the planes intersecting one another (crossing one another) between the nasal interface and the rear portion of the headgear or can be spaced apart between the nasal interface and the rear portion of the headgear. In the illustrated arrangement, the first retention plane is positioned at or near an upper edge of the inlet, breathing tube connector or gases conduit connector and the second retention plane is positioned at or near a lower edge of the inlet, breathing tube or gases conduit. In some configurations, the retention plane(s) can extend along a physical portion of the headgear or interface assembly. However, in other configurations, the retention plane(s) may not extend along a physical portion of the headgear or interface assembly. That is, for example, the retention plane(s) may not be aligned with a strap of the headgear.

Figure 11:
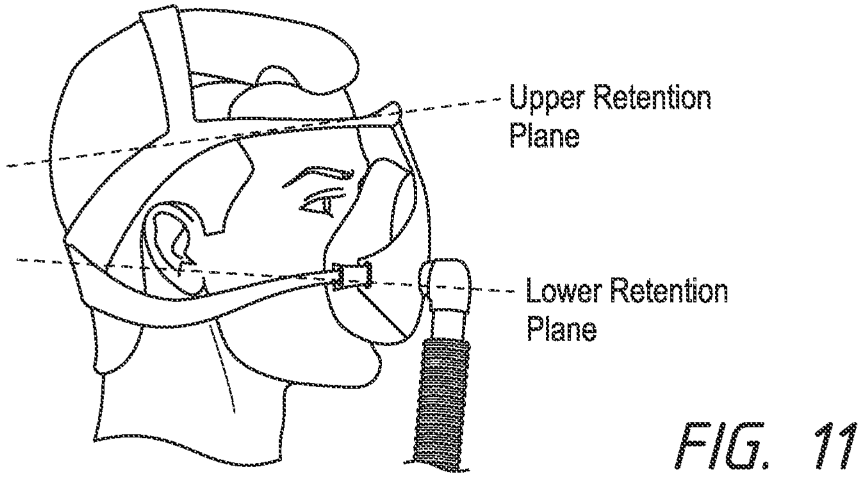
FIG. 11 is a side view of a full face mask having two retention planes.

Other types of interface assemblies can similarly utilize retention planes between the interface and a rear portion of the headgear. For example, FIG. 11 illustrates a full face mask having two retention planes. The illustrated full face mask includes an upwardly-extending frame portion or T-piece, which extends from a lower portion of the mask toward or to the user's forehead. In the illustrated arrangement, a first or upper retention plane extends between the T-piece and an upper location on a rear portion of the headgear. The upper retention plane can extend above the user's eyes and ears. The upper retention plane can be generally horizontal, but can be tilted somewhat in a front-to-back direction. For example, the upper retention plane can be tilted somewhat downward in a front-to-back direction to pass between the user's forehead and a center or rearward-most point on the back of the user's head. A second or lower retention plane extends between a base portion of the mask and a lower location on the rear portion of the headgear. The lower retention plane can extend between a point at about the user's mouth to a point below the user's ear. The lower retention plane can be generally horizontal, but can be tilted somewhat in a front-to-back direction. For example, the lower retention plane can be tilted somewhat upward in a front-to-back direction. The upper retention plane can extend along an upper strap of the headgear. The lower retention plane can extend generally along a lower strap of the headgear; however, the lower strap can be curved to accommodate the user's ear such that the lower retention plane overlies end portions of the lower strap, but does not overlie at least an intermediate portion of the lower strap. In other configurations, one or both of the upper and lower retention planes can partially or fully overlie an associated strap, can be partially or fully spaced from an associated strap or any combination of the two.

Figure 12:
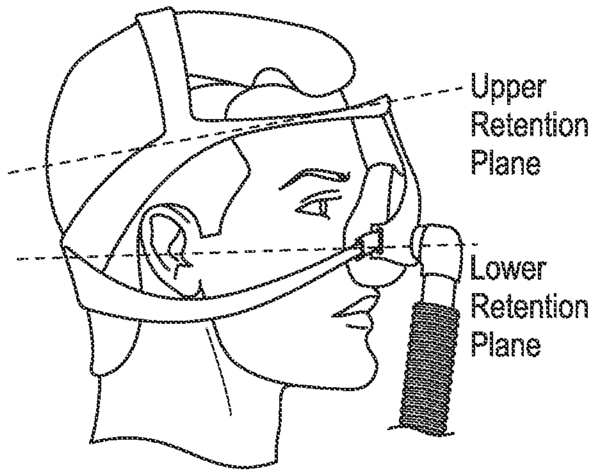
FIG. 12 is a side view of a nasal mask having two retention planes.

FIG. 12 illustrates a nasal mask having two retention planes. Similar to the full face mask of FIG. 11, the illustrated nasal mask includes an upwardly-extending frame portion or T-piece, which extends from a lower portion of the mask toward or to the user's forehead. In the illustrated arrangement, a first or upper retention plane extends between the T-piece and an upper location on a rear portion of the headgear. The upper retention plane can extend above the user's eyes and ears. The upper retention plane can be generally horizontal, but can be tilted somewhat in a front-to-back direction. For example, the upper retention plane can be tilted somewhat downward in a front-to-back direction to pass between the user's forehead and a center or rearward-most point on the back of the user's head. A second or lower retention plane extends between a base portion of the mask and a lower location on the rear portion of the headgear. The lower retention plane can extend between a point at about the user's nose to a point aligned with or below the user's ear. The lower retention plane can be generally horizontal, but can be tilted somewhat in a front-to-back direction. For example, the lower retention plane can be tilted somewhat downward in a front-to-back direction. The upper retention plane can extend along an upper strap of the headgear. The lower retention plane can extend between forward and rearward end portions of a lower strap of the headgear. The illustrated lower strap can be curved to accommodate the user's ear such that the lower retention plane does not overlie an intermediate portion of the lower strap. In either of the interface assemblies of FIGS. 11 and 12, the lower retention plane can pass through an inlet, breathing tube connector or gases conduit connector of the interface, such as through or near a center of the inlet or connector.

Figure 13:
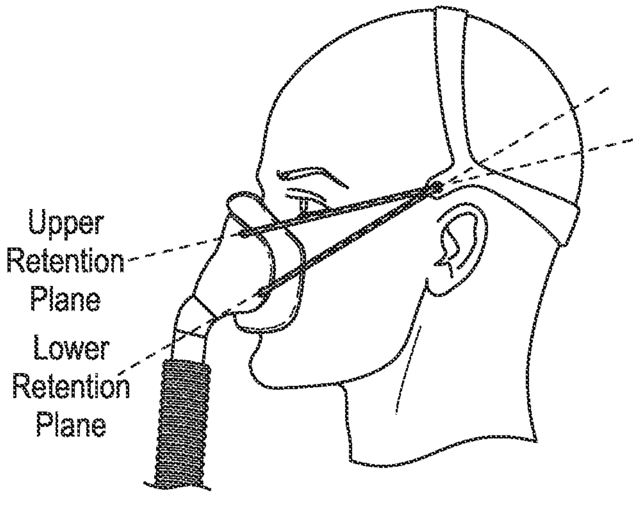
FIG. 13 is a side view of a mask having two retention planes that converge to a single point.

FIG. 13 illustrates an alternate arrangement that is applicable to a either a full face mask or a nasal mask in which there are two retention planes that converge to a single point within the head gear system. The retention planes can be vertically spaced from one another on the interface to provide some degree of stability to the interface. For example, in a full face mask, an upper retention plane can pass through or above the underside of the nose of the user and a lower retention plane can pass near or below the mouth of the user. In a nasal mask, the upper retention plane can pass above the underside of the nose of the user and the lower retention plane can pass below the underside of the nose of the user. The retention planes can intersect at a point generally above and/or forward of the ear of the user. The portions of the interface assembly coupling the mask to a rear portion of the headgear can be separate or interconnected, such that a single adjustment can at least potentially alter a length of both upper and lower portions. The length ratio of the upper and lower portions can be easily adjusted by moving the point of the interconnected portions that is located at the headgear connection point. The illustrated full face mask does not include a forehead rest or "T-piece." However, in some configurations, a T-piece could be provided. If desired, additional headgear element(s) or strap(s) could couple a rear portion of the headgear to the T-piece of the mask.

FIG. 13.1 is a chart that identifies a number of general categories of headgear types on the basis of the number and/or relative positioning of retention planes. The chart also identifies a number of interface types and provides an indication of the desirability or practicality of the resulting combinations of headgear type and interface type. Because of the automatic fit of at least some of the headgear assemblies disclosed herein, it is possible that a single headgear type can be utilized with multiple types of interfaces. Examples of possible combinations are described with reference to FIG. 13.1. The headgear types are listed from top to bottom in order of those that provide relatively less stability to those that provide relatively more stability, at least in certain configurations, such as those in which little to no external source of resistance to rotation of the interface is provided. The headgear types listed in the chart of FIG. 13.1 is not exclusive. Other headgear types may be used with the concepts disclosed herein, including modifications and hybrids of the illustrated headgear types.

In general, more stable headgear configurations can be universal or can provide at least an acceptable level of support to many or all interface types, or at least those interface types illustrated. In contrast, less stable headgear configurations may not be capable of providing a desirable or acceptable level of support to all interface types, at least without specific provisions to increase the stability of such inherently less stable configurations. In general, larger interfaces require or benefit from headgear that provides greater stability. It is often desirable or sometimes necessary to provide at least two retention planes for larger interfaces, such as full face masks. It can be advantageous for the two retention planes to be separated from one another in a vertical or height direction of the interface at the interface (e.g., at the points of attachment to the interface). In general, for a given headgear arrangement, the further the separation of the retention planes at the interface, the more stable the configuration. In some configurations, it can be advantageous for at least one of the retention planes to include an upward vector component.

One example headgear type provides a single retention plane. An example of such an arrangement is discussed herein with reference to FIG. 9. In general, single retention plane headgear can be impractical for use with full face interface types because the single retention plane headgear does not provide a desirable level of stability to the mask. Thus, the headgear may be able to secure the mask in place and maintain a seal, but the mask may be permitted to move and break the seal with relative ease or the interface assembly, although operable, may not provide a secure feeling to the user. In some cases, single retention plane headgear may not provide an acceptable level of stability to the mask. However, it is possible that some configurations of a single retention plane headgear could be suitable for use with a full face mask. For example, a single retention plane headgear utilizing rigid materials and/or configurations (e.g., shapes) could be suitable for use with a full face mask by providing resistance to rotation of the mask about a lateral axis. In addition, a single retention plane headgear can be suitable for use with a full face mask with careful location of the single retention plane relative to the full face mask, as illustrated in and described below with respect to FIG. 13.2. A single retention plane interface may be suitable or practical for use with nasal interfaces, such as nasal masks, nasal pillows or prongs and cannula.

FIG. 13.2 illustrated a single retention plane interface assembly comprising a headgear assembly and an interface, which is in the form of a full face mask. The illustrated mask omits a forehead rest or T-piece; however, in other configurations a T-piece could be provided. The headgear assembly includes a headgear rear portion and a headgear length or perimeter adjusting portion that allows adjustment of a position of the mask relative to the headgear rear portion. The single retention plane can extend from the mask to the headgear rear portion at a location above the user's ear, for example.

Forces acting on the mask can be summarized as a blow-off force created by pressure within the mask acting on the sealed area of the user's face and attempting to move the mask away from the user's face, a headgear force acting on the mask to resist the blow-off force, a force applied by the user's face along the contact area between the mask and the user's face, and a gravity force that acts on the mass of the mask and CPAP hose. The force applied by the user's face can be summarized by an upper force and a lower force. The upper force can be a force located at or near the nasal bridge of the user's nose ("nasal bridge force"), which can be generally the highest point or region of contact in a vertical direction. The lower force can be a force located at or near the chin of the user ("chin force"), which can be generally the lowest point or region of contact in a vertical direction.

The distributed gravity force can be summarized as a single point force ("gravity force") acting on the mask and CPAP hose at a center of gravity, which may be determined by the particular size and shape of the mask. In some configurations, the single retention plane extends between or passes through a point between the chin force and the blow-off force in a vertical direction.

The distributed blow-off force can be summarized as a single point force ("blow-off force") acting on the mask at a particular location, which may be determined by the particular size and shape of the mask and/or the specific shape of the user's face. The blow-off force can be located generally in a lower half of the mask height, such as at or near a geometric center of the mask. Assuming a generally triangular mask, the blow-off force can be located at approximately ⅓ of the height from the bottom of the mask. In some configurations, the single retention plane extends between or passes through a point between the chin force and the blow-off force in a vertical direction. Advantageously, such an arrangement can provide a desirable level of stability for a full face mask with a single retention plane. However, this arrangement can be applied to a multi-retention plane arrangement, as well, with the additional retention plane(s) providing additional stability.

The nasal bridge area can be a sensitive anatomical area and it can be desirable to avoid excessive force or pressure in this area. Thus, if the nasal bridge force is zero or minimal, the headgear force can be the only force countering the blow-off force. If the headgear force passes through a point vertically higher than the blow-off force, the nasal bridge force will be increased, which is generally undesirable. If the headgear force is too low, or too close to the chin force, the headgear force may not be able to counter the blow-off force or may provide an undesirably low level of counteraction of the blow-off force such that the sealing performance of the interface assembly is compromised. As described herein, preferably the retention plane comprises directional lock arrangement that provides an appropriate resistance to elongation of the headgear in response to the blow-off force. In combination with positioning of the retention plane as described herein, the resultant interface or headgear assembly can provide a suitable level of stability for a full face mask with a single retention plane type headgear. As with other headgear assemblies described herein, proper stability can be achieved without over-tightening of the headgear, which often occurs with prior art headgear arrangements.

Another example headgear type provides two retention planes that converge at a forward location (i.e., toward or at the interface). As used in herein in connection with FIG. 13.1, the term "converge" is intended to describe retention planes that lack substantial separation from one another at the interface or attachment locations. It is possible that the retention planes may meet at a single attachment point; however, convergent headgear types may also include those in which the retention planes are attached next to or close to one another. A two retention plane, forward converge headgear type can be suitable or at least somewhat practical for use with a full face headgear, because the additional retention plane may provide sufficient additional stability relative to a single retention plane headgear. As described with respect to single retention plane headgear types, the two retention plane, forward converge headgear type can employ rotation-resisting materials and/or configurations to provide improved performance with full face masks. A two retention plane, forward converge headgear type may be suitable or practical for use with nasal interfaces, such as nasal masks, nasal pillows or prongs and cannula.

Yet another example headgear type provides two retention planes that converge at a rearward location (i.e., away from the interface, such as at a rear portion of the headgear). A two retention plane, rearward converge headgear type can provide a sufficient level of stability to be suitable or practical for use with full face masks and with nasal masks. Examples of such a headgear type are shown and described herein in connection with FIGS. 10 and 13 with a nasal interface and a full face interface, respectively. A two retention plane, rearward converge headgear type may be less practical for use with pillows or prongs interface types because such interface types typically have a relatively small vertical or height dimension. The small height of pillows and prongs interface types can limit the ability to space the attachment locations of the retention planes on the interface and provide triangulation of the retention planes, at least without increasing the height dimension above what is required, which can be undesirable because pillows and prongs are often elected by users precisely due to their relatively small height dimension. A two retention plane, rearward converge headgear type may be impractical for use with cannula because it is not necessary to create a sealing force for a cannula. Thus, a two retention plane headgear type can be excessive for use with cannula. In addition, a two retention, rearward converge headgear type can be impractical for use with cannula for the same reasons as pillows and prongs. Cannula generally have an even smaller height dimension than pillows and prongs. However, in at least some configurations or under some circumstances, it may be practical or even desirable to use a two retention plane, rearward converge headgear type with pillows, prongs or cannula.

Still another example headgear type provides two retention planes that are separated and angled relative to one another or are non-parallel. In some configurations, the upper retention plane can be angled upward in a forward to rearward direction. The lower retention plane can be generally horizontal or angled. In other configurations, the lower retention plane can be angled in either direction. The upper retention plane can be generally horizontal or angled. A two retention plane, separated/angled headgear type can provide a sufficient level of stability to be suitable or practical for use with full face masks and with nasal masks. A two retention plane, separated/angled headgear type may be less practical for use with pillows or prongs interface types because such interface types typically have a relatively small vertical or height dimension for the reasons described above with respect to two retention plane, rearward converge headgear types. Similarly, a two retention plane, separated/angled headgear type may be impractical for use with cannula for the same reasons as pillows and prongs, as described above.

Another example headgear type provides two retention planes that are relatively, generally or substantially horizontal or parallel with one another. Examples of such two retention plane, parallel headgear types are shown and described in connection with FIGS. 11 and 12. A two retention plane, parallel headgear type can provide a sufficient level of stability to be suitable or practical for use with full face masks and with nasal masks. A two retention plane, parallel headgear type may be less practical for use with pillows or prongs interface types because such interface types typically have a relatively small vertical or height dimension for the reasons described above with respect to two retention plane, rearward converge headgear types. A two retention plane, parallel headgear type may be impractical for use with cannula for the same reasons as pillows and prongs, for the reasons described with respect to two retention plane, rearward converge headgear types.

Positioned or otherwise configured to act along at least one of the retention planes or lines is at least one mechanism or feature ("locking mechanism") that provides the ability to transform the function of the head gear from an elongating behaviour to a non-elongating behaviour. Along this plane, the directional locking functionality may be configured to operate as a single mechanism for the given retention plane or, preferably, to provide two independent locking mechanisms. The single mechanism arrangement is capable of varying the circumference or perimeter length of the headgear or interface assembly. The two locking mechanism arrangement (e.g., one mechanism on each side of the headgear or interface assembly) provides independent left and right control for fine adjustment for the fitting of the mask or other interface. In other arrangements, more than two locking mechanisms can be provided. In such arrangements, multiple locking mechanisms can be provided on each side of the headgear or interface assembly. Alternatively, the locking mechanisms can be otherwise located (e.g., one on each side and additional mechanism(s) on the top and/or rear) and can cooperate to allow for adjustment of the circumference or perimeter length of the headgear or interface assembly.

Figure 14:
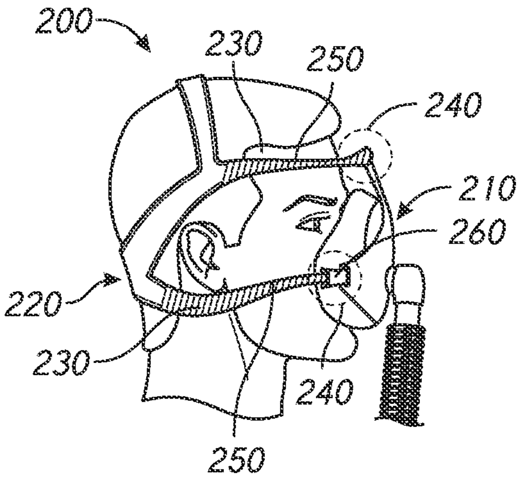
FIG. 14 is a side view of a full face mask with forehead support having a directional locking mechanism positioned at a connection between the headgear and the mask.
Figure 15:
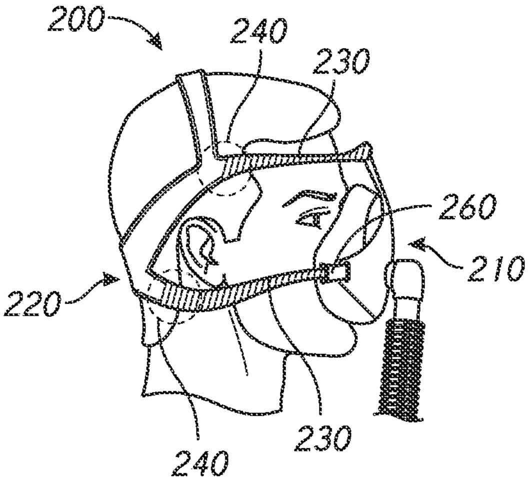
FIG. 15 is a side view of a full face mask with forehead support having a directional locking mechanism positioned within the headgear.

In some configurations, at least one locking mechanism is provided on each side of the interface assembly between the mask (or other interface) and a rear portion of the headgear. In some configurations, such as a full face mask 210 with forehead support or T-piece as illustrated in FIGS. 14 and 15, the mask 210 is connected to a rear portion of the headgear 220 by upper and lower connecting portions in the form of straps 230, for example, on each side of the interface assembly 200. The arrangements of FIGS. 14 and 15 illustrate a number of example locations where the locking feature or mechanism 240 can be located. In the illustrated arrangements, the interface assembly 200 includes an elasticated retraction feature or mechanism 250 in combination with or which acts in cooperation with the directional locking mechanism 240. The elasticated retraction mechanism 250 and the directional locking mechanism 240 can be integrated into a module, which can be referred to herein as a directional lock module or, simply, a module. In the arrangements shown, the directional locking mechanism 240 can be positioned at a connection between the headgear 220 and the mask 210, such as incorporated into an attachment fixture 260 (e.g., clip) to the mask body as illustrated in FIG. 14. Alternatively, as illustrated in FIG. 15, the directional locking mechanism can be positioned at a suitable location within the headgear 220, such as between a rear portion of the headgear 220 and the strap portions 230 connecting the rear portion of the headgear 220 with the mask 210, as illustrated in FIG. 15. Similar arrangements can be utilized in other configurations that use multiple retention planes.

In some arrangements, the directional locking mechanism or module utilizes a lock coupled to or otherwise movable with one portion of the interface assembly and an adjustment member coupled to or otherwise movable with a second portion of the interface assembly. The adjustment member can move relative to the lock to allow adjustment of the circumference or perimeter length of the headgear or interface assembly. The adjustment member can be in form of a core member, which can be a wire or filament or can be a strap, for example. A portion of the adjustment member is utilized to define a portion of the circumference or perimeter length at any given size adjustment of the interface assembly and another portion may be excess or surplus length that is not utilized at the given adjustment size. The surplus length will change along with changes in the circumference or perimeter length of the headgear or interface assembly. The accumulation of the surplus length can be accommodated by any suitable arrangement, such as accommodated within the mask frame or within an integral component within the headgear system.

Figure 16:
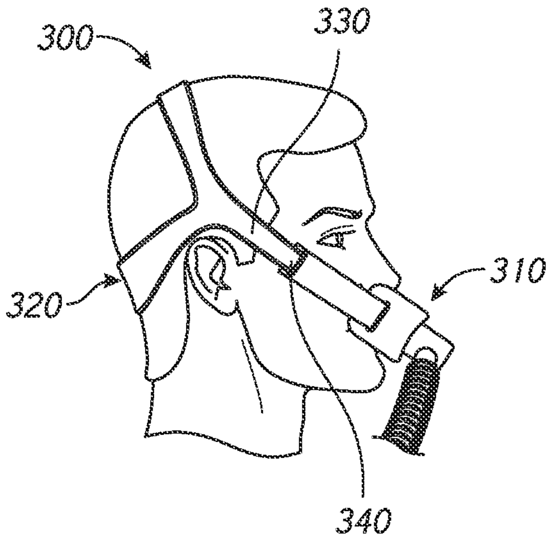
FIG. 16 is a side view of a nasal mask having a directional locking mechanism on a flat strap.
Figure 17:
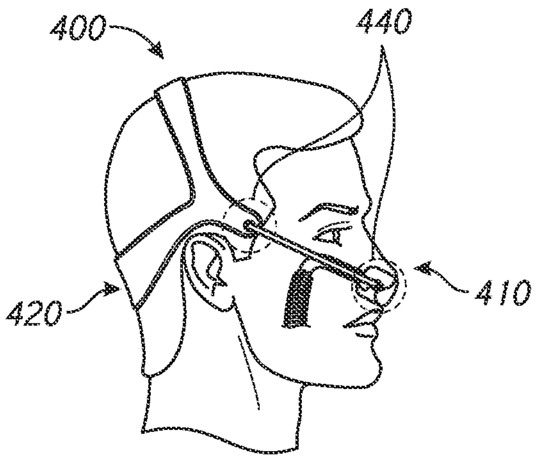
FIG. 17 is a side view of a nasal mask having directional locking mechanisms with a flexible core design.

FIGS. 16 and 17 illustrate arrangements that are applicable to nasal interfaces 300, such as nasal masks 310, (with or without a forehead rest or T-Piece, but often without a forehead rest or T-piece) or nasal cannula. In these arrangements, the directional locking mechanism 340 can incorporate or operate on a flat strap 330 or web, as discussed above. The use of the flat strap 330 is especially beneficial in applications in which the force vectors between the pressurised mask seal and the headgear are not aligned. This results in a situation where moments are generated which preferably are sufficiently resolved through rigidity within the headgear system. This is achievable by the selection of the torsional rigidity and bending rigidity characteristics of the headgear straps, the combination of which significantly increases the level of rotational stability for the mask system.

In situations in which a straight line between the mounting point on the headgear and the mounting point on the mask 410 provides an acceptable location for a headgear component or a component that provides a connection between the mask and a rear portion of the headgear 420, the use of a flexible core design 430 may be desirable, as illustrated in FIG. 17. That is, unless constrained into a modified shape, the flexible core will assume a straight line between mounting points. Thus, flexible core designs are well-suited for use in arrangements in which a straight line path for the directional locking mechanism 440 (e.g., between the rear portion of the headgear 420 and the mask 430) is a desirable or acceptable location for the mechanism 440.

Figure 20:
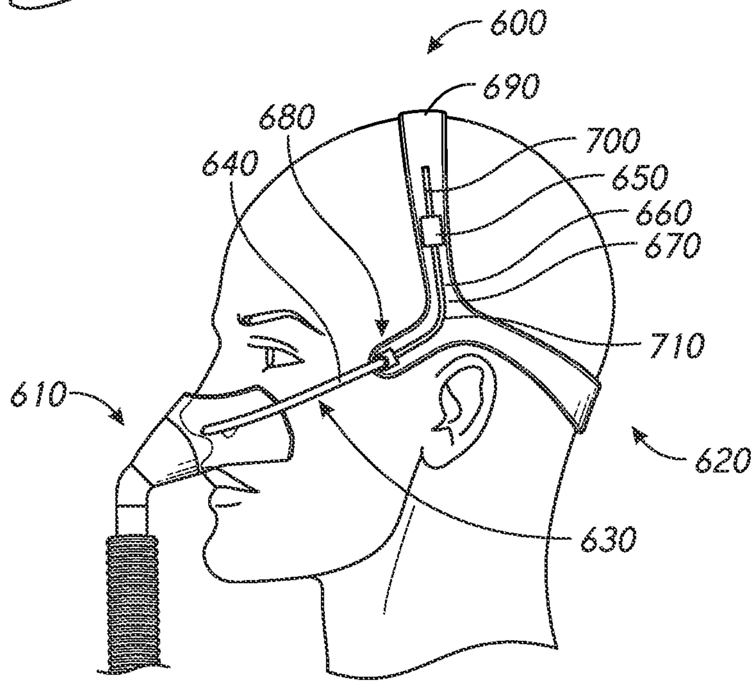
FIG. 20 is a side view of an exemplary interface assembly.

In some arrangements, the flat strap arrangement and the flexible core arrangement may be used in combination, such as in applications in which two or more retention planes are desirable or required. For example, the arrangements of FIGS. 11 and 12 or the arrangements of FIGS. 14 and 15 could utilize a flat strap arrangement along one of the upper or lower retention planes and a flexible core arrangement along the other of the upper or lower retention planes. In some configurations, the lower strap may be configured to use the flat strap arrangement and the top strap may be configured to use the flexible core arrangement. For instance, as illustrated, the lower strap may have a curved shape along its length to pass below and provide space to accommodate the user's ear. The upper strap, however, can be generally straight along its length. In some configurations, the upper strap can utilize a flat strap arrangement and the lower strap can utilize a flexible core arrangement. For example, the rear portion of the headgear can be configured to locate the mounting point such that a straight line between the headgear mounting point and the mounting point on the mask is appropriately located. Furthermore, as shown in FIG. 18 and FIG. 20, the use of a flat or relatively rigid headgear portion to aid in torsional or bending stability along the sides of the user's head, when connected in series with a flexible core arrangement, enables flexibility with the positioning of the directional locking mechanism.

A significant performance benefit of the directional locking-type of headgear system or interface assembly occurs when used in connection with respiratory ventilation patterns in which there is either a high constant pressure or a variable pressure waveform, such as non-invasive ventilation or bi-level ventilation, because the headgear system does not elongate during use or the circumference or perimeter length of the interface assembly remains constant. As described above, current state-of-the-art headgear arrangements can be generally categorized into elastic or inelastic systems. As described, inelastic systems can accommodate high constant pressure or variable pressure; however, such systems are prone to over-tightening and are difficult and time-consuming to adjust. Current state-of-the-art elastic headgear systems tend to elongate in response to high constant pressure or elongate and retract in response to pressure waves in a variable pressure waveform. Such elongation and retraction results in cyclic movement of the mask on the user's face, which can result in leaks. Leaks, in turn, can lead to loss of therapy and/or false triggering of breaths due the resulting volume and related pressure change within the mask. Furthermore, cyclic movement of the mask can result in abrasions and, potentially, skin damage due to movement or migration of the mask on the user's face.

Figure 18:
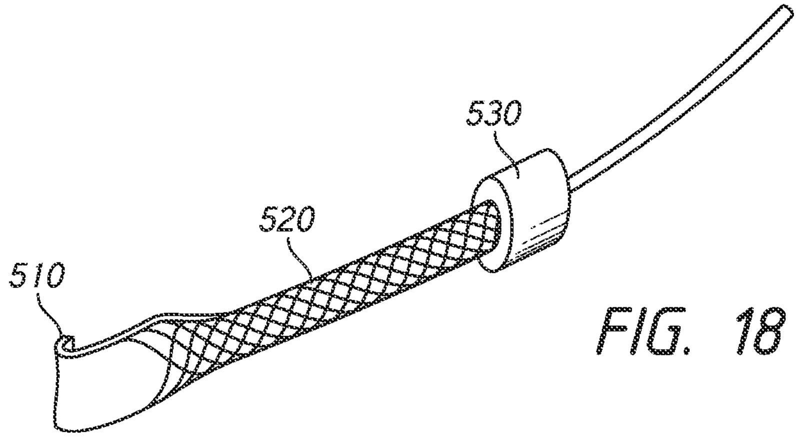
FIG. 18 illustrates a module of an interface assembly configured to extend between a mask or other interface and a rear portion of headgear that incorporates a directional lock arrangement.
Figure 19:
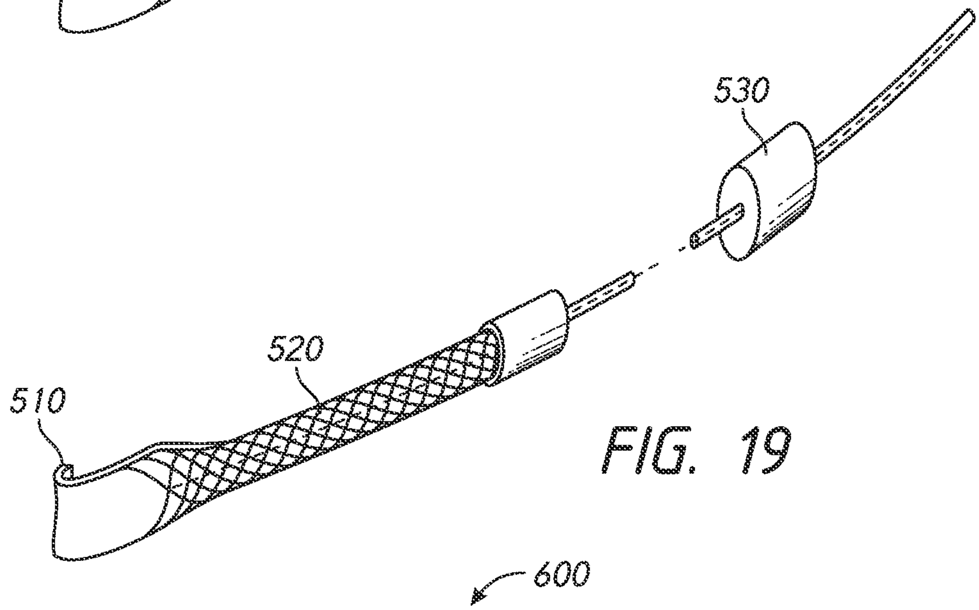
FIG. 19 illustrates a module of an interface assembly configured to extend between a mask or other interface and a rear portion of headgear that incorporates a directional lock arrangement that is spaced from a biasing arrangement.

FIGS. 18 and 19 illustrate examples of a portion or module of an interface assembly configured to extend between a mask or other interface and a rear portion of the headgear that incorporates a directional lock arrangement. Each of the illustrated module arrangements comprise a detachable clip 510 that defines a coupling between the mask body and the overall headgear system, which includes the module. The module includes an elastic section 520 extending between the detachable clip 510 and the directional lock 530, which produces a contraction force tending to move the clip 510 and the directional lock 530 toward one another. The elastic section 520 can be of any suitable arrangement, such as a braided member with one or more elastic elements, for example. FIG. 18 illustrates a variant that has the directional lock 530 located at the rearward end of the elastic section 520 and/or at a connection point between the module and a rearward portion of the headgear, which would position the directional lock 530 spaced from the mask, such as in the locations shown in FIG. 15 and FIG. 17, for example.

FIG. 19 illustrates an alternative variant that locates the directional lock 530 at a spaced location from the module and/or the connection point between the module and a rear portion of the headgear. Such an arrangement can be referred to herein as a "remote" lock arrangement. In some configurations, the lock can be positioned elsewhere within the headgear system, such as within a rear portion of the headgear, with a hollow conduit bridging the distance between the connection point between the module and the rear portion of the headgear and the location of the directional lock. Such an arrangement offers the ability to position the directional lock at a more suitable or desirable location with the headgear system, such as the location shown in FIG. 20, for example.

With reference to FIG. 20, the interface assembly 600 includes a mask 610 or interface (such as a nasal interface in the illustrated arrangement) and a headgear arrangement comprising a rear headgear portion 620 that engages a rear and/or upper portion of the user's head. The interface assembly 600 also includes an adjustment portion 630 that permits adjustment of a distance between the mask 610 and the rear portion of the headgear 620. The adjustment portion 630 can be a portion of the headgear arrangement, a portion of the interface or can be a separate component of the interface assembly.

In the illustrated arrangement, the adjustment portion 630 comprises a stretchable material 640, which can be configured to return toward its un-stretched position. Thus, the stretchable material 640 can exhibit a contraction force tending to reduce a circumference or perimeter length of the interface assembly. In some configurations, the stretchable material 640 is a braided material incorporating non-stretch and stretch elements. The non-stretch elements can provide a hard stop or maximum extension and the stretch elements can provide the contraction force. In other configurations, the stretch elements 640 or other biasing arrangement can be located remotely from the stretchable material of the adjustment portion 630.

The illustrated interface assembly also comprises a transformational lock arrangement, such as a directional lock arrangement. The illustrated directional lock arrangement comprises a directional lock 650, a filament core 660 and a filament guide 670 or housing (e.g., conduit or tube). Such an arrangement allows the directional lock 650 to be spaced from or remote from an attachment location 680 between the adjustment portion 630 and the rear headgear portion 620. In addition, the filament arrangement allows the directional lock 650 to be located in a non-linear arrangement with the adjustment portion 630. In other words, a functional axis of the directional lock 650 can be offset or angled relative to an axis of the adjustment portion 630 and/or a retention plane of the interface assembly 600.

The filament housing 670 can extend between the directional lock 650 and the attachment location 680 between the adjustment portion 630 and the rear headgear portion 620. In the illustrated arrangement, the filament housing 670 follows a curved path between the directional lock 650 and the attachment location 680 between the adjustment portion 630 and the rear headgear portion 620. For example, the directional lock 650 can be located on a crown strap 690 of the rear headgear portion 620 and the filament housing 670 can curve upwardly at a point rearward of the attachment location 680 onto the crown strap 690. The directional lock 650 can be located at any desired point on the crown strap 690, including a side portion or an upper or top portion, for example. In other configurations, the directional lock 650 can be located on other portions or at other locations on the rear headgear portion 620, such on a side or back of a rear strap of the rear headgear portion 620. Such arrangements can allow the directional lock 650 to be provided in a location that is more desirable than the attachment point between the adjustment portion 630 and the rear headgear portion 620 (referred to as "remote" mounting herein). For example, positioning the directional lock 650 on the top of the crown strap 690 may avoid contact with other objects (e.g., pillow) under many circumstances (e.g., the user lying face up or on his or her side). The particular location of the directional lock 650 can be selected based on a variety of relevant factors, such as comfort, clearance (e.g., for eyeglasses), filament length, among others.

In some configurations, the filament housing 670 extends past the directional lock 650 to accommodate excess filament 660 that is not being utilized to carry a load within the interface assembly 600. A portion of the filament housing 670 beyond the directional lock 650 can be referred to as an accumulation portion 700 or accumulation conduit. A portion of the filament housing 670 between the directional lock 650 and the attachment location 680 between the adjustment portion 630 and the rear headgear portion 620 can be referred to as a connecting portion 710 or connecting conduit. Although illustrated as a tube herein, the filament housing 670 can be provided in other forms, as well, such as a filament guide, for example. A filament guide arrangement may not entirely enclose the filament, but may simply provide guide surfaces at particular, discrete locations to direct the filament along a desired path.

One or more adjustment portions and/or transformational lock arrangements can be provided on each side of the interface assembly. Portions of the transformational lock arrangements on opposing sides of the interface assembly can be integrated with one another or share components. For example, the accumulation portion of the filament housing can connect a directional lock on one side of the interface assembly with a directional lock on the other side of the interface assembly. In some configurations, a single housing can be provided on the top or back of the interface assembly and can contain two separate lock mechanisms, which interact with elements (e.g., filaments) associated with transformational lock arrangements on opposite sides of the interface assembly. Alternatively, separate transformational or directional lock housings associated with lock arrangements on opposite sides of the interface assembly could be positioned near one another (longitudinally or laterally adjacent) on a top or rear portion of the rear headgear portion, for example.

A headgear system that incorporates a transformational mechanism as disclosed enables a portion of the headgear to be selectively switched from inelastic-type behaviour to an elastic-type behaviour to provide for convenient fitting and removal has a number of user advantages. Example mechanisms to achieve this behavior are disclosed herein and in Applicant's Application No. PCT/NZ2014/000074, the entirety of which is incorporated by reference herein. In some configurations, one or more of the advantages relate to the ability to provide an auto-adjusting, self-sizing or more intuitive adjustment interaction for the user. In addition, in at least some configurations, the headgear systems incorporating a transformational mechanism as disclosed enables undesirable movement of the mask body to be reduced or minimized in comparison with state-of-the-art headgear systems, which are typically constructed from either laminations of elasticated materials with the addition of stitching or stitched components or from an elasticated knitted construction. With these prior designs, movement of the mask caused by either hose pull or the interaction of applied respiratory pressure with the mask is likely to occur. Such movement may result in conditions ranging from leaks, loss of therapy, false triggering of breath patterns due to the resulting volume and pressure changes to skin abrasion or potential skin damage. To counteract this movement, a common practice is to over-tighten the headgear (either by providing a high elastic force in elastic systems or manual over-tightening in adjustable inelastic systems), such that the force required to elongate the headgear is greater than that which is produced by either hose pull or that generated via the pressurization of the mask. The application of additional pressure to the user as a result of this excess tightening can result in user discomfort, skin irritation or skin damage.

Due to the functionality of one or more of the auto-fit or transformational headgear systems disclosed herein, the elasticated behavior can be constrained to specific areas of a headgear system, where it is selectively switched on or off depending on usability conditions, rather than being a generic property of the headgear. This creates the opportunity to "engineer" the remaining portions of the headgear system to deliver specific performance attributes. In at least some configurations, a principal result of the combination of an engineered, transformational headgear system is to provide a behavior in which there is little to no movement in the mask body when in use.

Figure 21:
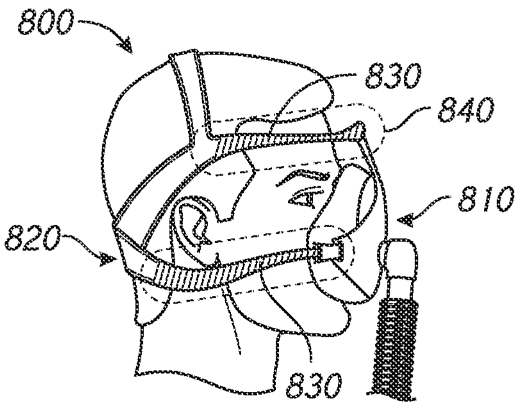
FIG. 21 is a side view of an exemplary full face mask.
Figure 22:
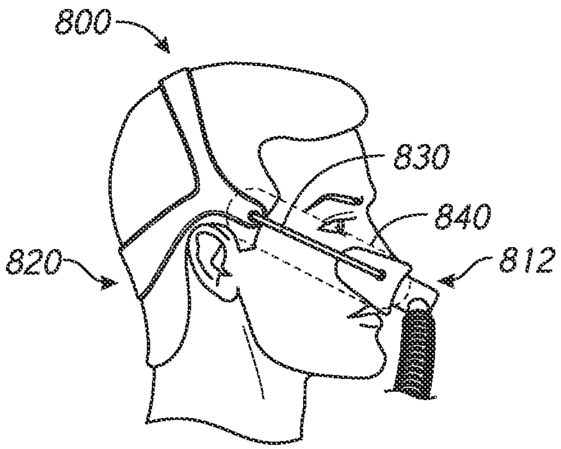
FIG. 22 is a side view of an exemplary nasal pillows mask.

FIGS. 21 and 22 illustrate example headgear systems 800 for a full face mask 810 (FIG. 21) and a nasal pillows mask 812 (FIG. 22). The indicated areas 840 illustrate presently preferred locations for the portions where the selectable elastic/inelastic functionality exists. In each application, the selectable elastic/inelastic portion 830 is positioned between the mask 800 and a rear portion of the headgear system 820 and extends along the sides of the user's head. The remaining rear portion of the headgear system ideally is a relatively rigid three-dimensional (3D) structure, which has very little elastic behaviour in the force ranges encountered during normal or anticipated use. To achieve such behavior, in some configurations, both the form of the headgear and the material construction have a significant impact.

Form

Figure 23:
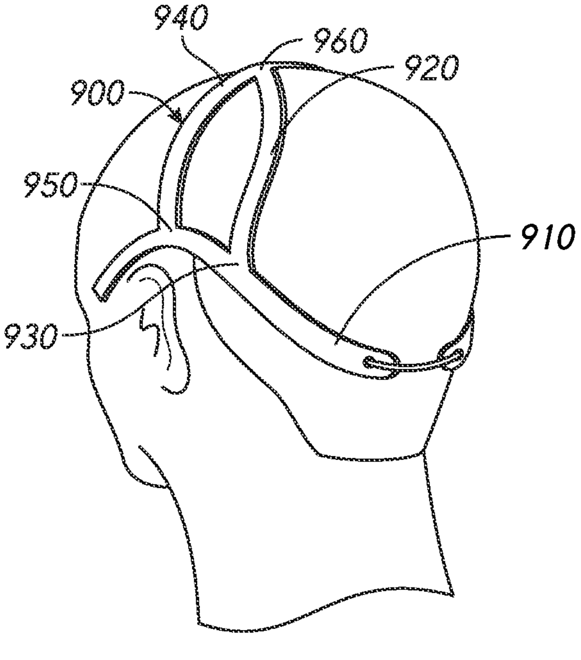
FIG. 23 is a rear perspective view of an exemplary headgear assembly positioned on a user.
Figure 24:
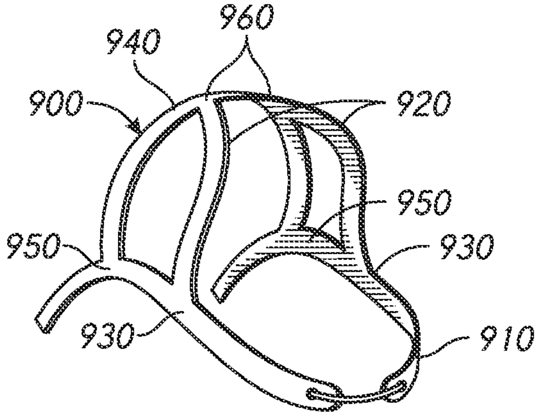
FIG. 24 is a rear perspective view of the exemplary headgear assembly in FIG. 23.

Referring to FIGS. 23 and 24, the use of a top or crown strap 940 and a strap passing around the back of the user's head (rear strap 910) as disclosed herein utilizes the geometry of the human head to provide repeatability with fitment location and to provide stability of the headgear 900 when in use. Additional design features can be added to this basic crown strap 940 and rear strap 910 arrangement to further enhance these desirable properties, namely, the addition of a gusset 920 or web that links the rear or lower strap 910 to the crown strap 940, as illustrated in FIGS. 23 and 24. The addition of the gusset 920 or web member(s) reduce the relative movement between the rear and crown straps 910, 940, resulting in a more laterally stable design.

The gussets 920 can be attached to the rear strap 910 and the crown strap 940 at any suitable location. The attachment points 930, 960 of the gusset 930 on the rear strap 910 and the crown strap 940 can be substantially equidistant or equidistant from a junction 950 between the rear strap 910 and the crown strap 940 or can be spaced at different distances from the junction 950. In the illustrated arrangement, the gusset 920 attaches to the crown strap 940 at a distance further from the junction 950 than a distance from the junction 950 at which the gusset 920 is attached to the rear strap 910. The distance from the junction 950 to the gusset 920 on the crown strap 940 can be approximately twice or more than the distance from the junction 950 to the gusset 920 on the rear strap 910. In the illustrated arrangement, a distance between the attachment points 960 of the gussets 920 on each side of the headgear 900 can be less than a distance between the junction 950 and the attachment point 960 of one of the gussets 920 on the crown strap 940. That is, the length of the distance between gussets 920 on the crown strap 940 is less than one-third of the overall length of the crown strap 940. The rear strap 910 and/or crown strap 940 can be continuous or can be interrupted. Sections of an interrupted rear or crown strap 910, 940 can be connected by a suitable coupling, which can be a fixed length, elastic or adjustable.

Construction/Fabrication

The overall form of the headgear can be produced by a number of different techniques. For example, the headgear can be cut from a single sheet of at least relatively or substantially inelastic material. In other configurations, the headgear can be injection molded from a single or multiple thermoplastic or thermoset materials. In some configurations, the headgear or head frame is constructed from a single material with variations in cross sectional geometry providing portions of increased or decreased torsional and/or bending stiffness to enable the headgear to smoothly contour to the human head form, as illustrated in FIGS. 25-28. In other configurations, the headgear can be constructed by co-molding or multi-molding different materials in various portions to achieve the same or similar behaviour, as illustrated in FIG. 29.

The various portions of the headgear can be constructed to have desirable properties in desirable portions or areas of the headgear. For example, for the portion extending over the user's ear (section 1), it can be desirable to provide limited flexibility such that bending movement about a lateral axis or torsional movement about a longitudinal axis is limited. The portions rearward of section 1 (sections 2 and 3) desirably conform closely to the shape of the human head. Desirably, each of the sections 1, 2 and 3 exhibit relatively inelastic behaviour in force ranges normally encountered or expected in use. To achieve such behavior, various combinations of materials can be used. In the illustrated example, thermoplastic elastomers or thermoplastic urethanes of various shore hardness's are used to achieve the desired behaviours.

As described above, the headgear can comprise various portions having various cross-sectional dimensions such that the properties of the headgear can be varied in different areas of the headgear. With reference to FIGS. 25-28, a rear headgear portion, which ends generally forward and above the user's ears is shown and referred to simply as the headgear 1000. Three vertical sections of the headgear 1000 are illustrated. Section 1 is taken in a portion of the headgear 1000 that extends above and forward of the user's ear. Section 2 is taken in a portion of the headgear 1000 that is rearward of section 1 and can be generally positioned rearward of the user's ear. In the illustrated arrangement, section 2 is located between the crown strap 1010 and the gusset 1030. Section 3 is taken in a location of the headgear rearward of section 1 and section 2. In the illustrated arrangement, section 3 is taken in a location on the back portion of the headgear 1000, which can contact the back of the user's head.

Preferably, the portion containing section 1 is relatively tall to provide resistance to vertical bending loads, which would attempt to move a forward end of the headgear 1000 in a vertical direction. In the illustrated arrangement, the portion containing section 1 has a greater height than the portion containing section 2. In some configurations, the portion containing section 3 has a greater height than the portion containing section 2. In some configurations, the portion containing section 3 has a greater height than the portion containing section 1. A portion of the headgear 1000 at the rear of the user's head (e.g., the portion containing section 3) typically applies a greater force to the user's head as a result of directly opposing the blow-off force of the interface. As a result, it can be preferable to enlarge the area of the rear portion by providing the rear portion with a relatively large height to improve user comfort. In the illustrated configuration, the height at section 1 is about 10 mm, the height at section 2 is about 3 mm and the height at section 3 is about 15 mm. In other configurations, other dimensions can be used. For example, the dimensions may be different, but the headgear 1000 can retain the same height ratio between any or all of sections 1, 2 and 3. In other configurations, the dimensions may vary by a specific number (e.g., 1 mm, 2 mm or 3 mm) or by a percentage either taller or shorter than the illustrated dimensions. In some configurations, the height of the headgear 1000 changes gradually between the sections 1, 2 and 3. The actual height at any point on the headgear 1000 can be selected to address appropriate performance parameters, such as resistance to bending, force distribution and fit or clearance considerations.

In some configurations, the headgear 1000 can decrease in thickness in a direction from a forward end toward a rearward end. For example, the portion containing section 1 can have a thicker cross-section relative to the portion containing sections 2 and 3 such that the portion containing section 1 (a forward end portion) has a greater resistance to torsional loads. In addition, the portion containing section 2 can have a thicker cross-section relative to the portion containing section 3. Thus, the portion containing section 2 has a greater resistance to torsional loads than the portion containing section 3. In some configurations, the difference in thickness between the portion containing section 1 and the portion containing section 2 is greater than the difference in thickness between the portion containing section 2 and the portion containing section 3. The reduced thickness of the portions containing sections 2 and 3 allow those portions to bend in a transverse direction to better conform to the particular shape of the user's head. In the illustrated arrangement, the thickness at section 1 is about 1.5 mm, the thickness at section 2 is about 1 mm and the thickness at section 3 is about 0.8 mm. In other configurations, other dimensions can be used. For example, the dimensions may be different, but the headgear 1000 can retain the same thickness ratio between any or all of sections 1, 2 and 3. In other configurations, the dimensions may vary by a specific number (e.g., 0.1 mm, 0.2 mm or 0.3 mm) or by a percentage either thicker or thinner than the illustrated dimensions. In some configurations, the thickness of the headgear 1000 changes gradually between the sections 1, 2 and 3. The actual thickness at any point on the headgear 1000 can be selected to address appropriate performance parameters, such as resistance to torsional loads and lateral flexibility to improve fit.

With reference to FIG. 29, as discussed above, the headgear 1100 could alternatively or additionally vary in material type throughout the headgear 1100 to provide different properties in different portions of the headgear 1100. The headgear 1100 of FIG. 29 illustrates three sections taken at three different locations within the headgear 1100, which can be the same as or substantially the same as the locations of the headgear 1100 of FIGS. 25-28. The portion containing section 1 can be constructed of a first material or combination of materials, such as polypropylene, for example. Similar to the headgear 1000 of FIG. 25-28, the material selection for the portion containing section 1 can take into consideration a desire to provide resistance to bending in a vertical direction. The material or combination of materials of the portion containing section 2 can be different than the material(s) of one or both of the portions containing sections 1 and 3. For example, the portion containing section 2 can be constructed of a second material or combination of materials, such as a combination of thermoplastic polyurethane (TPU) and thermoplastic elastomer (TPE). The material or combination of materials of the portion containing section 3 can be different than the material(s) of one or both of the portions containing sections 1 and 2. For example, the portion containing section 3 can be constructed of a third material or combination of materials, such as TPE. Considerations in material selection for the different portions of the headgear 1100 can be the same as or similar to the considerations described with respect to dimensional selection in FIGS. 25-28.

In some configurations, the material selection results in the headgear 1100 having a different durometer or hardness in different portions. For example, the portion containing section 1 can have the highest durometer. In some configurations, the portion containing section 1 can have a durometer of about 65-70 shore D. The portion containing section 2 can have a durometer that is less than the durometer of the portion containing section 1. In some configurations, the portion containing section 2 has the lowest durometer of the portions containing sections 1, 2 and 3. For example, the portion containing section 2 can have a durometer of about 70 shore A. The portion containing section 3 can have a durometer that is between the durometers of the portions containing sections 1 and 2. For example, the portion containing section 3 can have a durometer of about 40 shore D. Considerations in hardness selection for the different portions of the headgear 1100 can be the same as or similar to the considerations described with respect to dimensional selection in FIGS. 25-28. Variations in hardness can be achieved by material selection or other methods, such as manipulation of the material, for example.

Combinations of these techniques are also possible. For example, two or more of the dimensions, material and hardness can be selected to provide varying properties throughout the headgear. In some cases, the headgear is in a 3D form that contours to the human head, behaves in a substantially non-elasticated manner and provides a stable connection point for the transformational lock arrangement.

The material selection for one or more portions of the headgear can involve other considerations, as well. For example, in some configurations, a portion or the entire headgear can comprise a material that exhibits little or no tendency to absorb moisture. In some configurations, a portion or the entire headgear can comprise a material that exhibits water vapor permeability. Advantageously, with such configurations, the headgear can avoid or prevent the absorption of moisture, such as sweat, or can allow moisture to move through the headgear material. Either configuration can improve comfort for the user.

The headgear can be further enhanced by the integration of textile-based lining or padding to either or both of the interior or exterior surfaces to engineer the textural and/or tactical properties of the headgear. In some configurations, hair pull and/or the detectable edge of the headgear by the wearer is reduced or minimized. When lining or padding is provided on only one side of the headgear (interior or exterior), or is otherwise distinguishable between sides (e.g., different color on the interior than on the exterior), the feature assists with usability of the overall device as it provides visual clues to the user regarding orientation of the headgear for fitment.

In some configurations, the headgear can comprise one or more adjusters that permit the headgear to be adjusted in size. For example, an adjuster can be provided in a strap portion of the headgear to allow a length of the strap portion to be adjusted. An adjuster could also be provided between strap portions to allow a relative position of the strap portions to be adjusted. In some configurations, the adjusters are self-adjusting or permit self-adjusting of the headgear. As used herein, self-adjusting refers to adjusters that allow adjustment of the headgear from a first position (e.g., a first length or relative position) to a second position (e.g., a second length or relative position) and retains the headgear in the second position without manipulation (e.g., manual locking) by a user. In some configurations, the adjusters can comprise biasing elements or arrangements. For example, the adjuster can comprise a biasing arrangement that tends to bias the strap portions in a first direction (e.g., toward a reduced length). Thus, the adjusters can simply allow a user to manipulate the headgear and then automatically secure the headgear in the desired position or the adjusters can assist in moving the headgear toward an appropriate fit position and then automatically secure the headgear in the appropriate fit position. Such adjusters can comprise any of the transformational locking arrangements disclosed in Applicant's Application No. PCT/NZ2014/000074.

Figure 30:
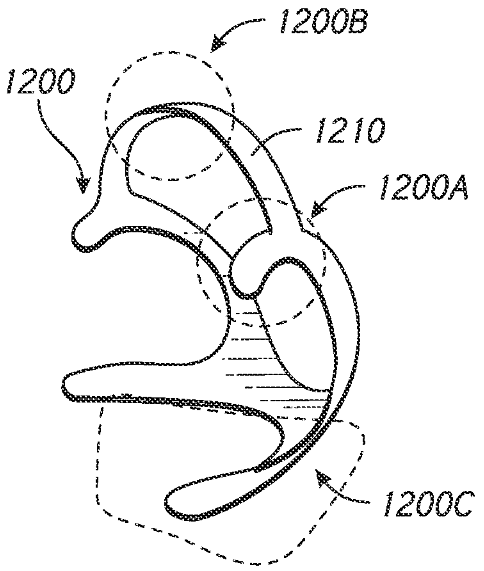
FIG. 30 illustrates locations where an automatic adjuster can be positioned within an exemplary headgear assembly.
Figure 31:
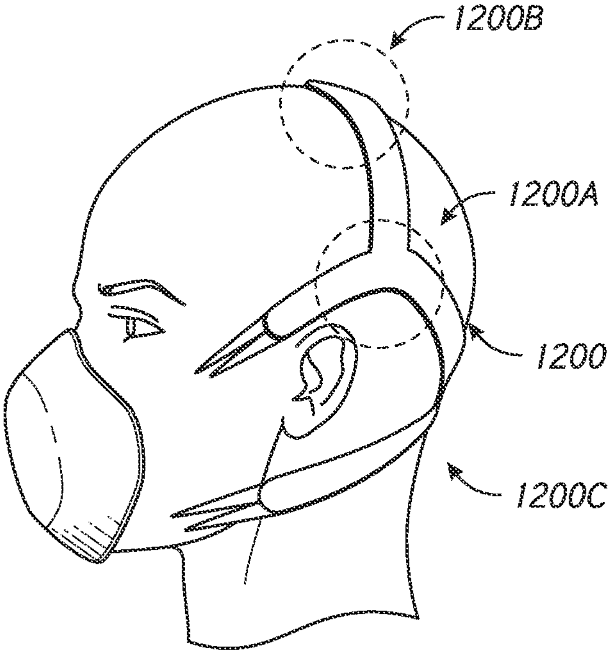
FIG. 31 illustrates locations where an automatic adjuster can be positioned within an exemplary headgear assembly worn by a user.

FIGS. 30 and 31 illustrate examples of locations in which an automatic adjuster can be positioned within the headgear 1200. For example, an automatic adjuster can be positioned at location 1200A, which is at or near a junction between a top or crown strap portion and a circumferential portion or upper portion that is located above the user's ear. An automatic adjuster can be positioned at location 1200A on each side of the headgear 1200. An automatic adjuster at location 1200A can allow a relative position of the upper portion of the headgear 1200 to be adjusted relative to the crown strap 1210, such as in a forward-rearward direction. Alternatively, an automatic adjuster at location 1200A can allow a circumferential length of a portion of the headgear 1200 to be adjusted. In other words, a length of the upper portion of the headgear 1200 can be adjusted by an automatic adjuster at location 1200A. An automatic adjuster can be positioned at location 1200B, which is within the top or crown strap 1210. An automatic adjuster at location 1200B can allow a length of the crown strap 1210 to be adjusted. An automatic adjuster can be positioned at location 1200C, which is within a rear or lower portion of the headgear 1200. A single automatic adjuster can be positioned within the rear portion or an automatic adjuster can be provided within each side of the lower portion of the headgear 1200. An automatic adjuster at location 1200C can permit a circumferential length of the lower portion of the lower portion of the headgear 1200 to be adjusted.

Automatic adjusters can be positioned in any one, any combination or all of the locations 1200A, 1200B and 1200C, and/or elsewhere within the headgear. In some configurations, the provision of automatic adjusters is to allow the rear headgear portion to be adjusted to fit the user's head. Thus, such automatic adjusters can be in addition to the transformational locking arrangements between the rear headgear portion and the interface, which can be configured to adjust the relative position of the interface and the rear headgear portion, as well as apply an appropriate sealing or retention force to the interface.

Figure 32:
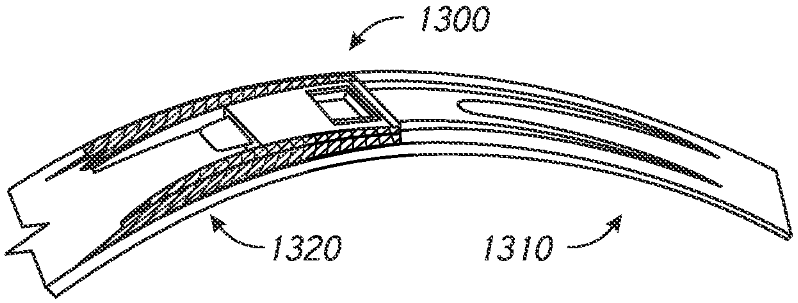
FIG. 32 illustrates an exemplary strap adjustment mechanism in assembled form.
Figure 33:
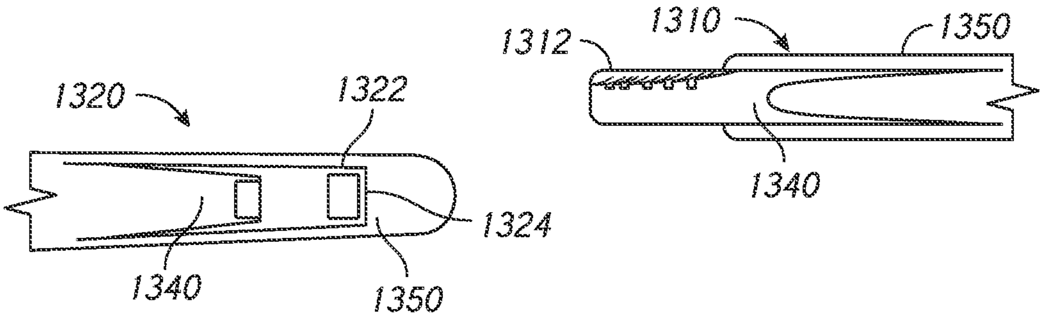
FIG. 33 is a plan view of the exemplary strap adjustment mechanism in FIG. 32 separated into first and second portions.
Figure 34:
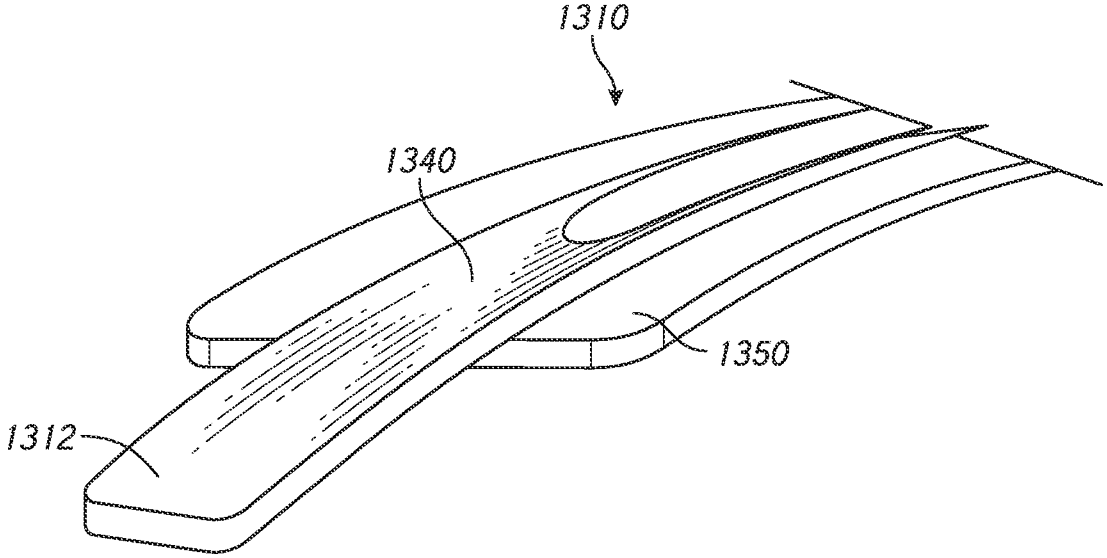
FIG. 34 is a perspective view of the second portion of the exemplary strap adjustment mechanism in FIG. 32.
Figure 40:
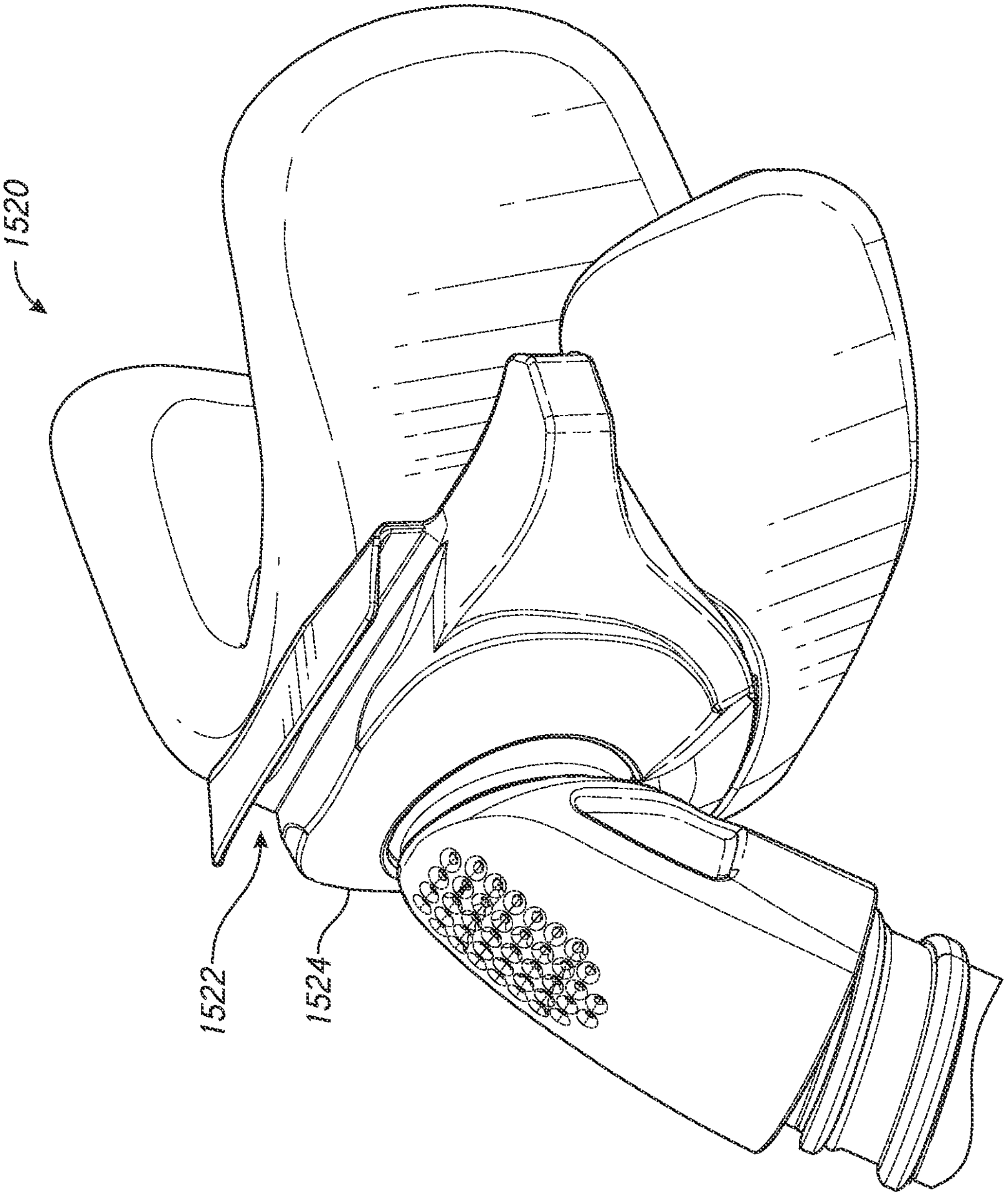
FIG. 40 is a perspective view of an exemplary interface assembly.
Figure 41:
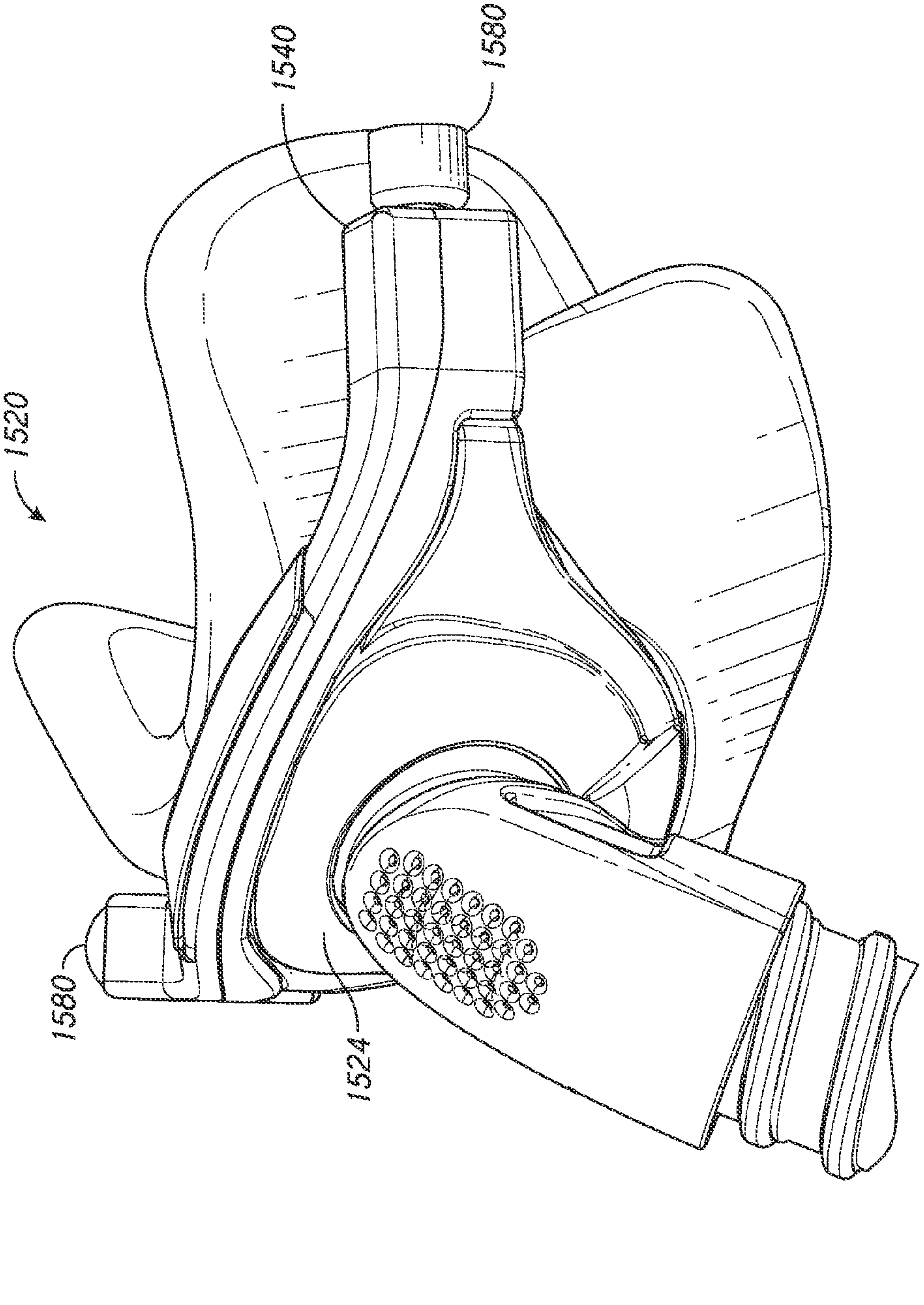
FIG. 41 is a left-side perspective view of an exemplary interface assembly attached to an interface coupling portion.
Figure 42:
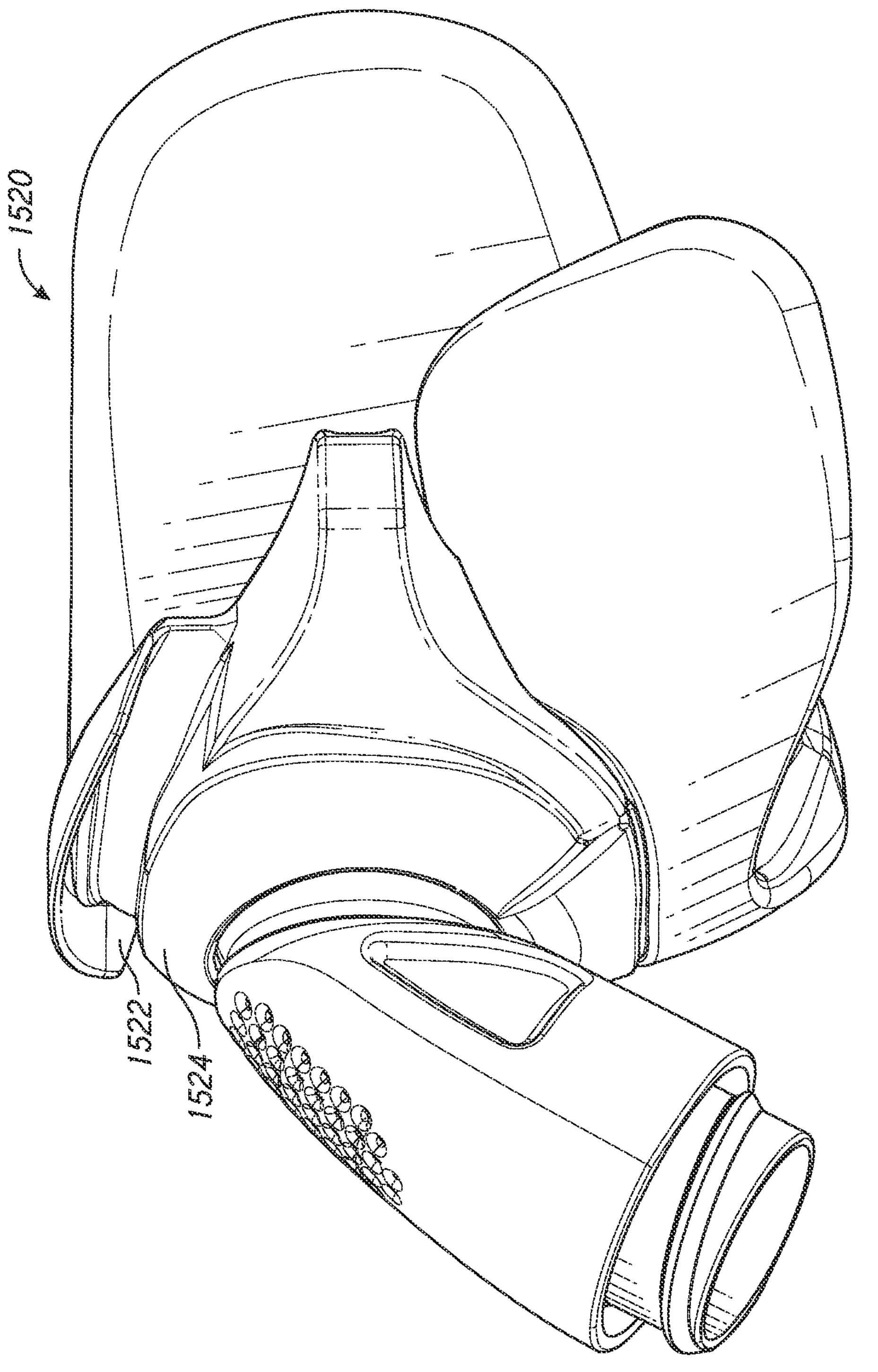
FIG. 42 is a side view of an exemplary interface assembly.
Figure 43:
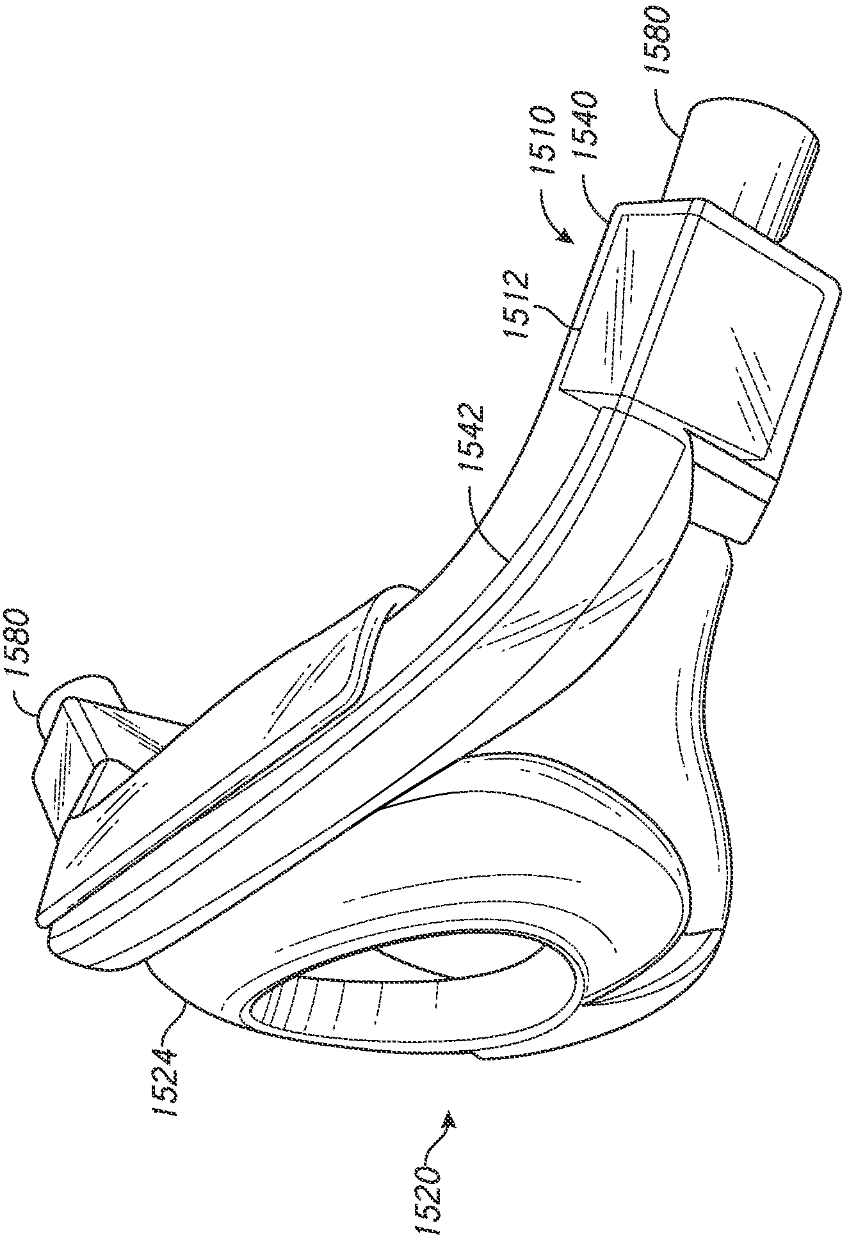
FIG. 43 is a perspective view of a frame element of an interface member attached to an interface coupling portion.
Figure 44:
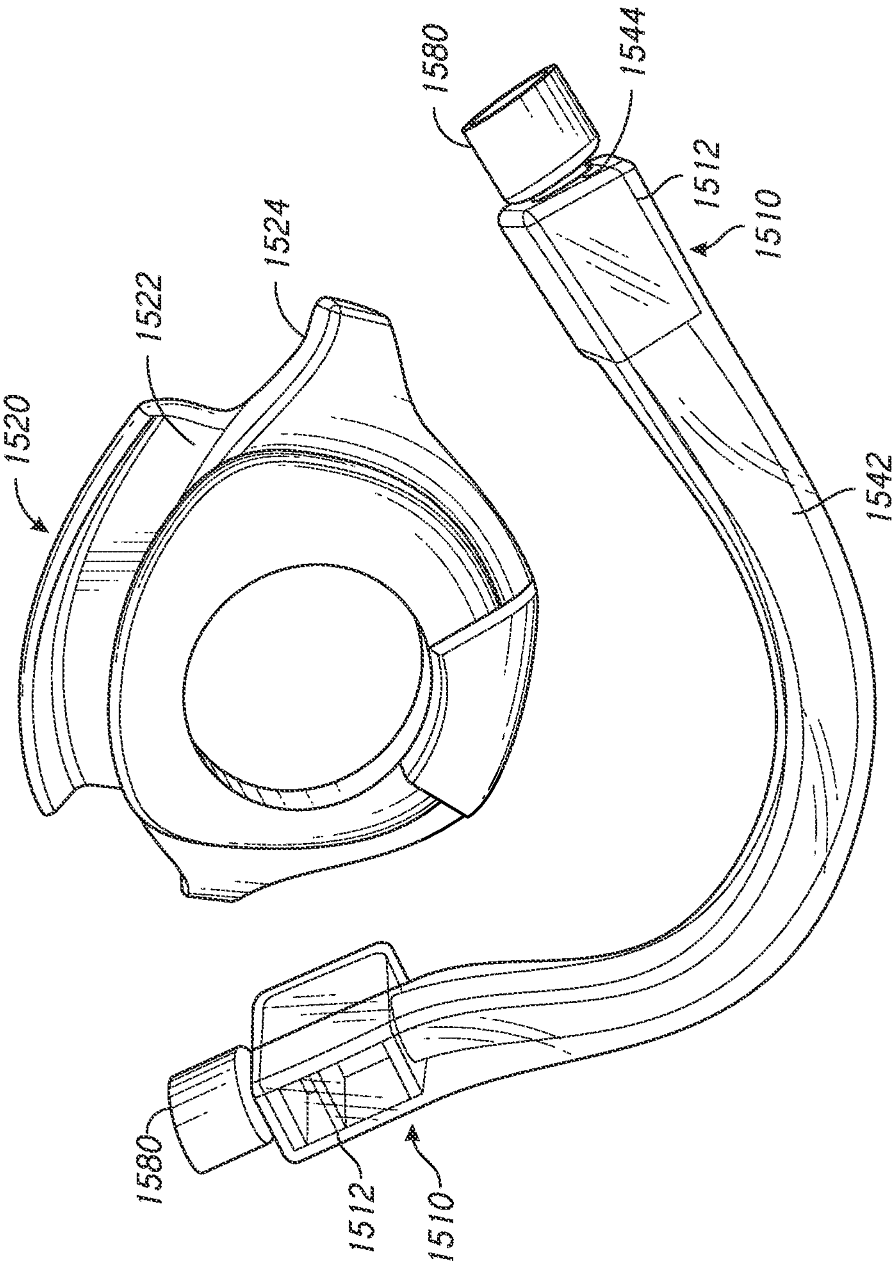
FIG. 44 is a front view of a frame element of an interface member and an interface coupling portion.
Figure 45:
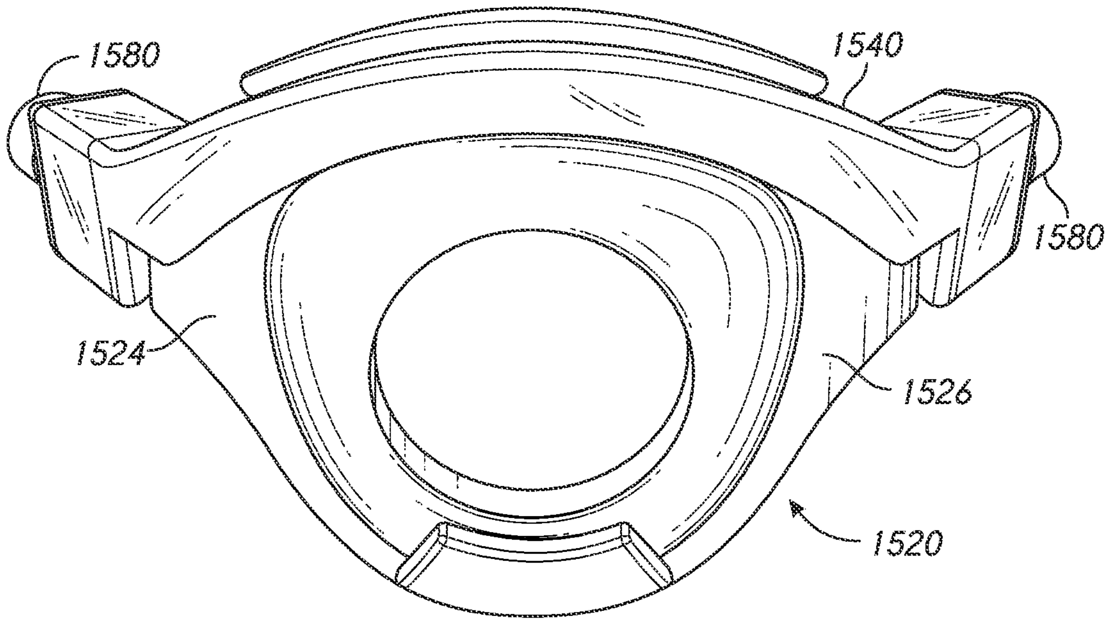
FIG. 45 is a front view of a frame element of an interface member attached to an interface coupling portion.
Figure 46:
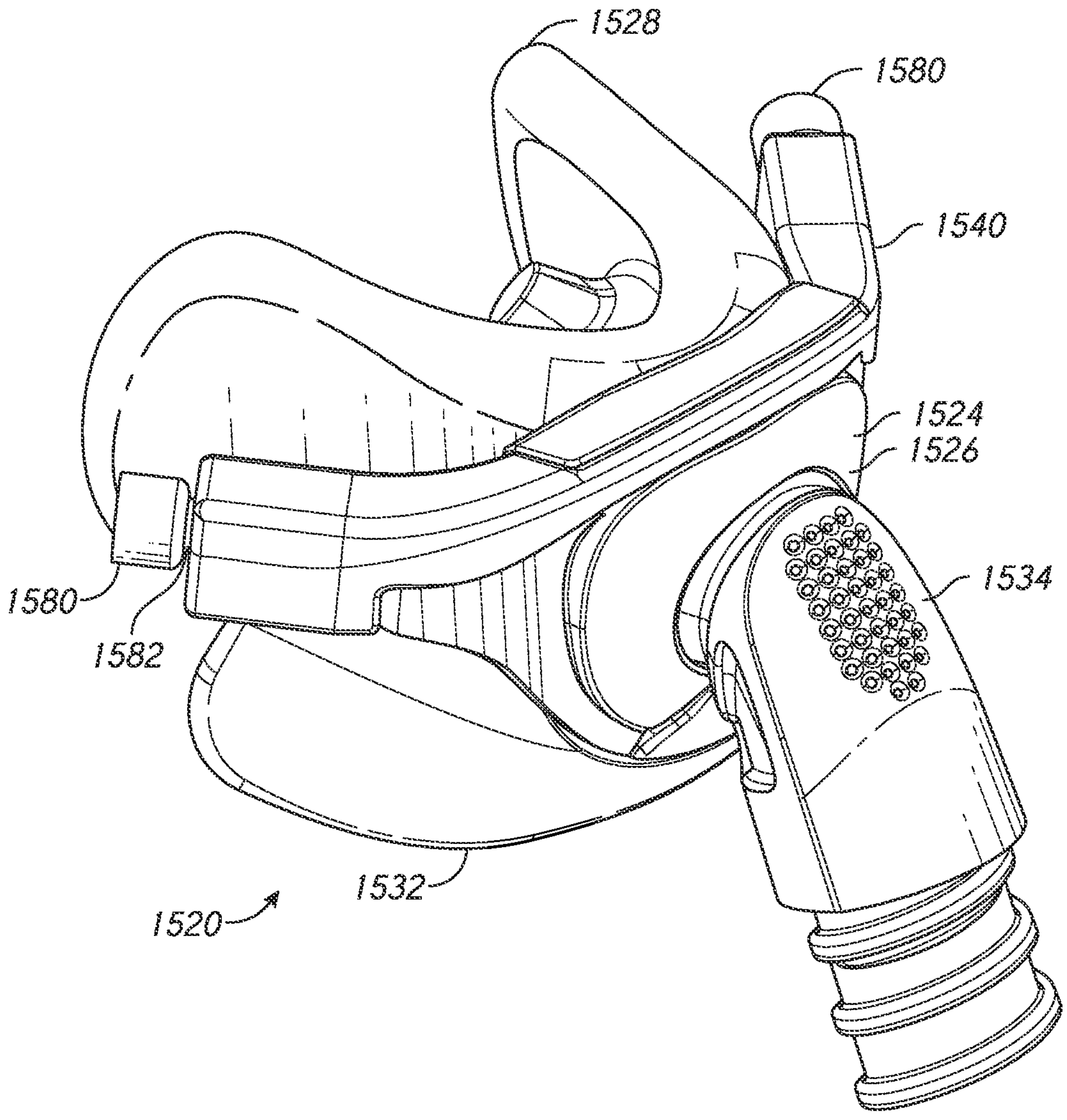
FIG. 46 is a right-side perspective view of an exemplary interface assembly attached to an interface coupling portion.
Figure 47:
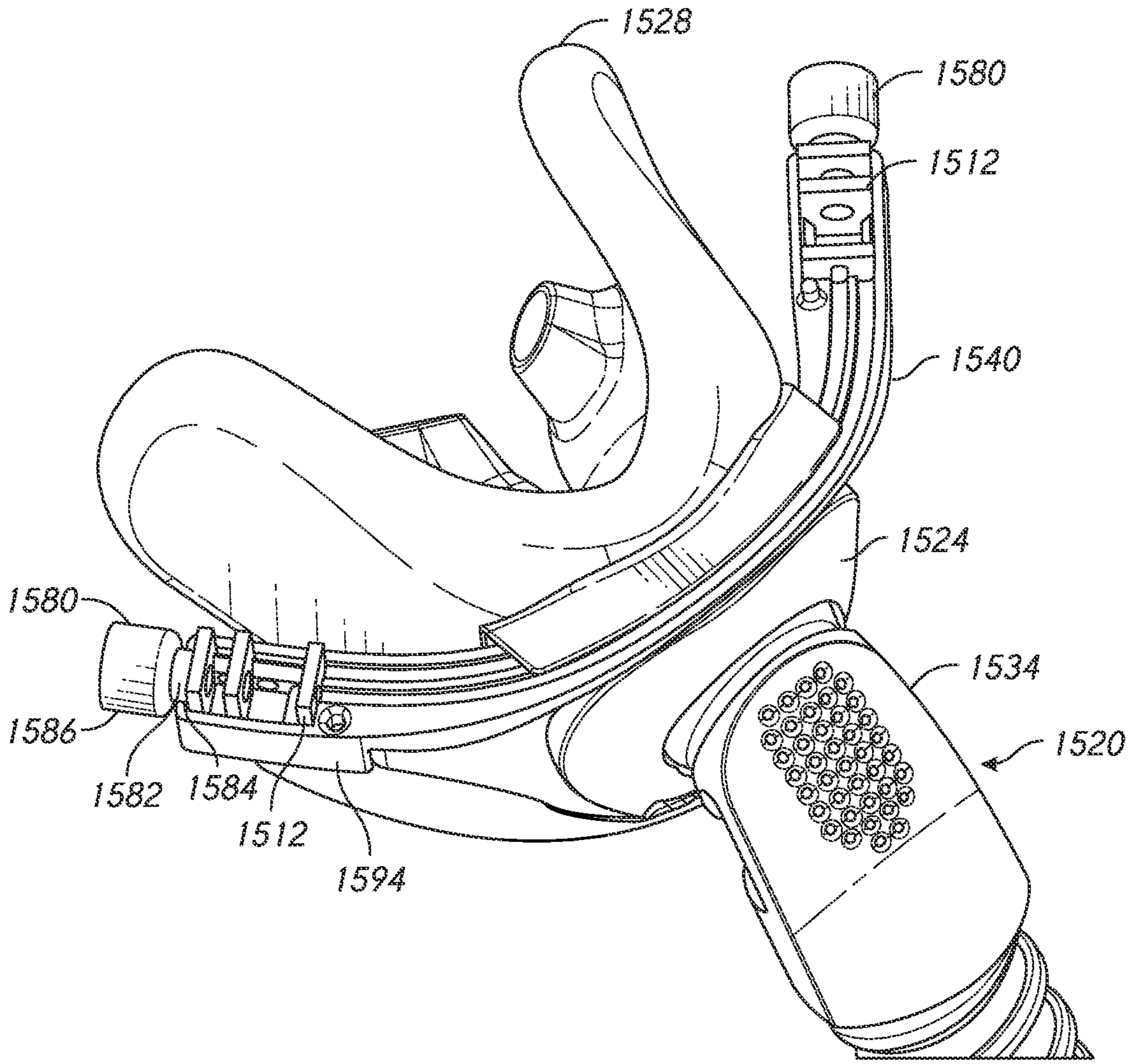
FIG. 47 is a top perspective view of an exemplary interface assembly attached to a second piece of an interface coupling portion.
Figure 48:
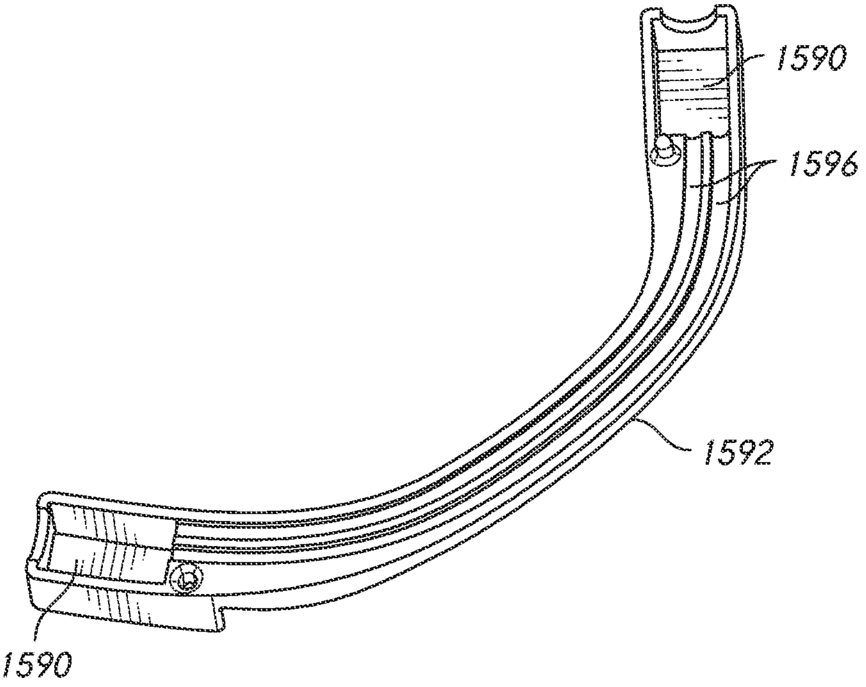
FIG. 48 is a top perspective view a first piece of an interface coupling portion.
Figure 49:
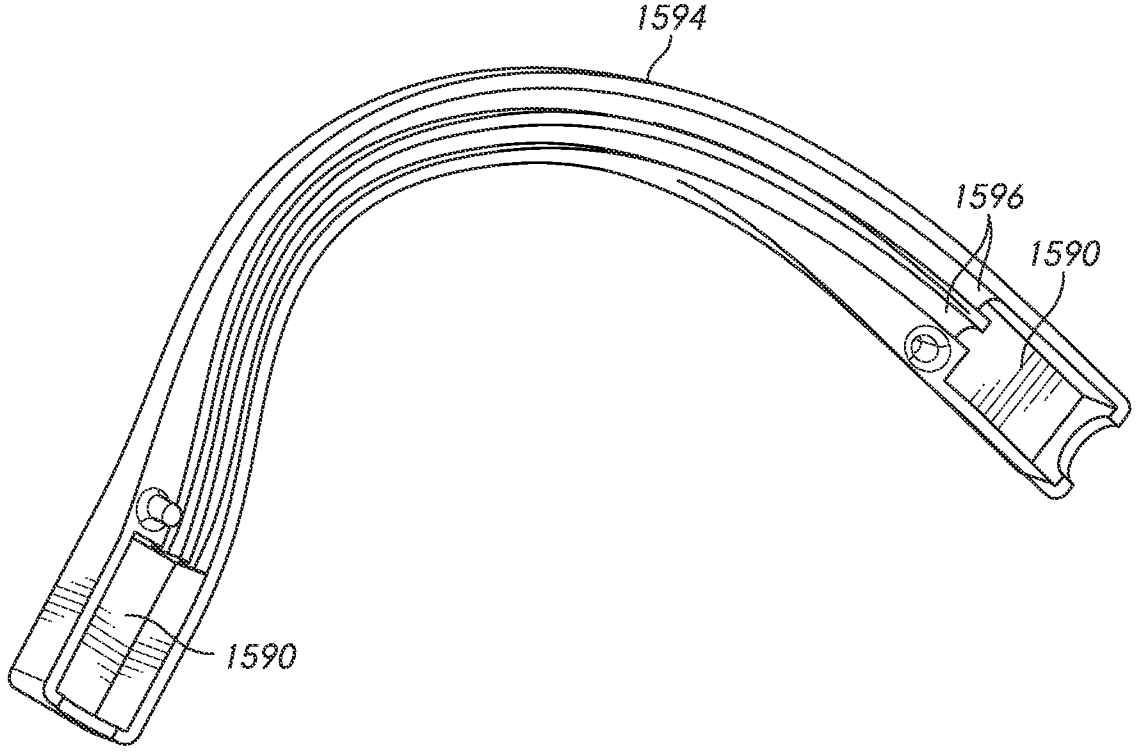
FIG. 49 is a top perspective view a second piece of an interface coupling portion.
Figure 50:
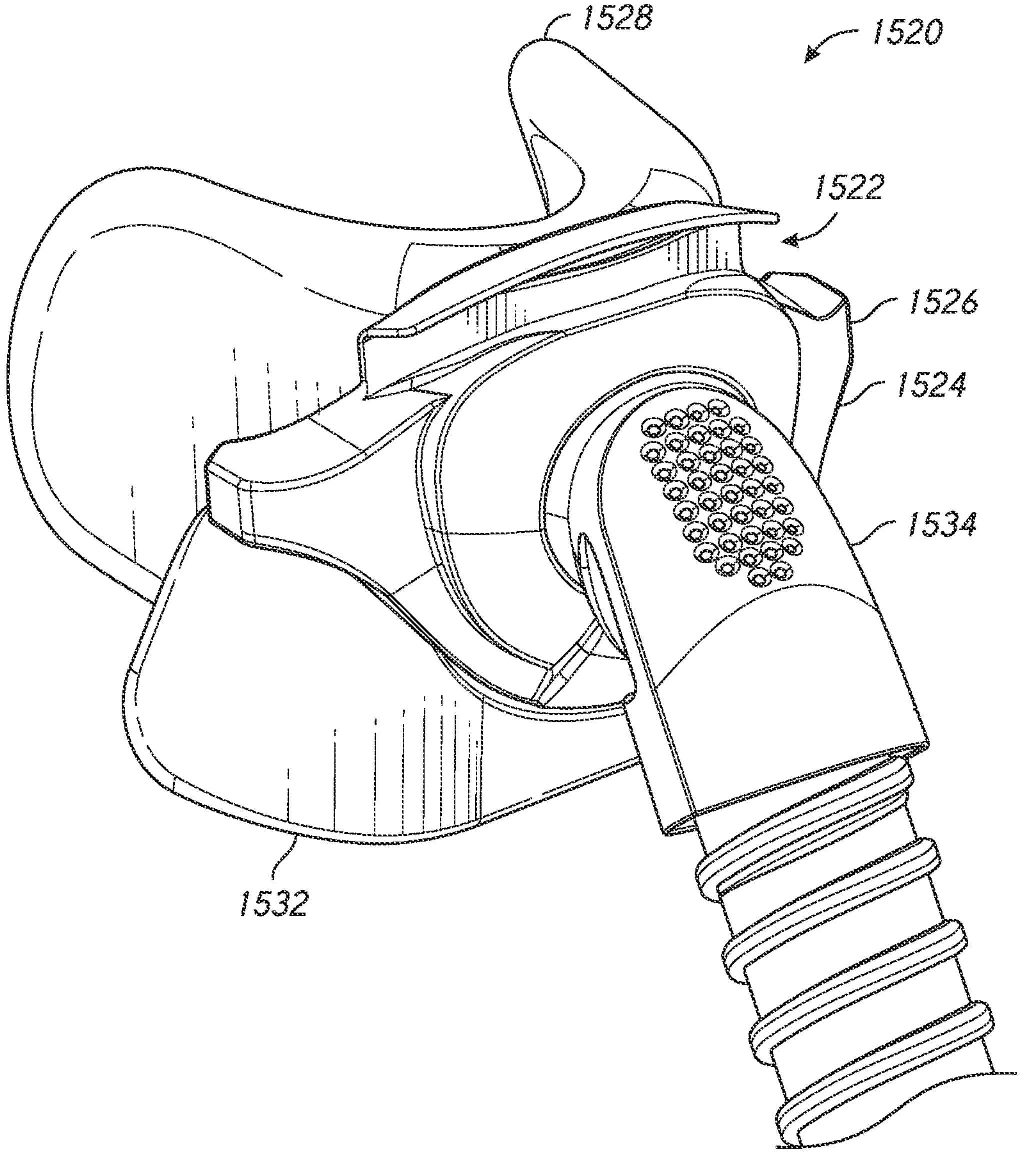
FIG. 50 is a right-side perspective view of an exemplary interface assembly.
Figure 51:
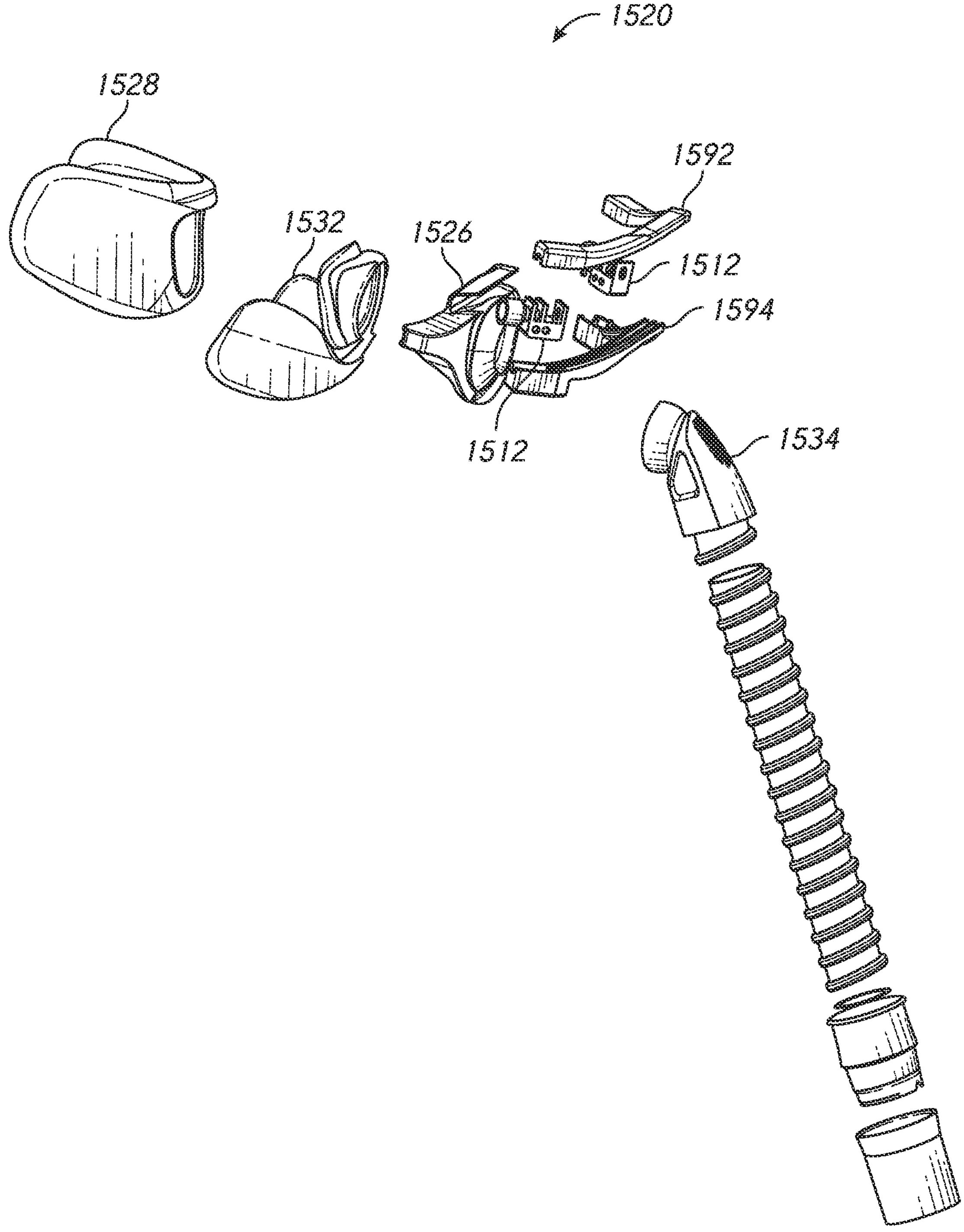
FIG. 51 is an exploded view of an exemplary interface assembly.
Figure 52:
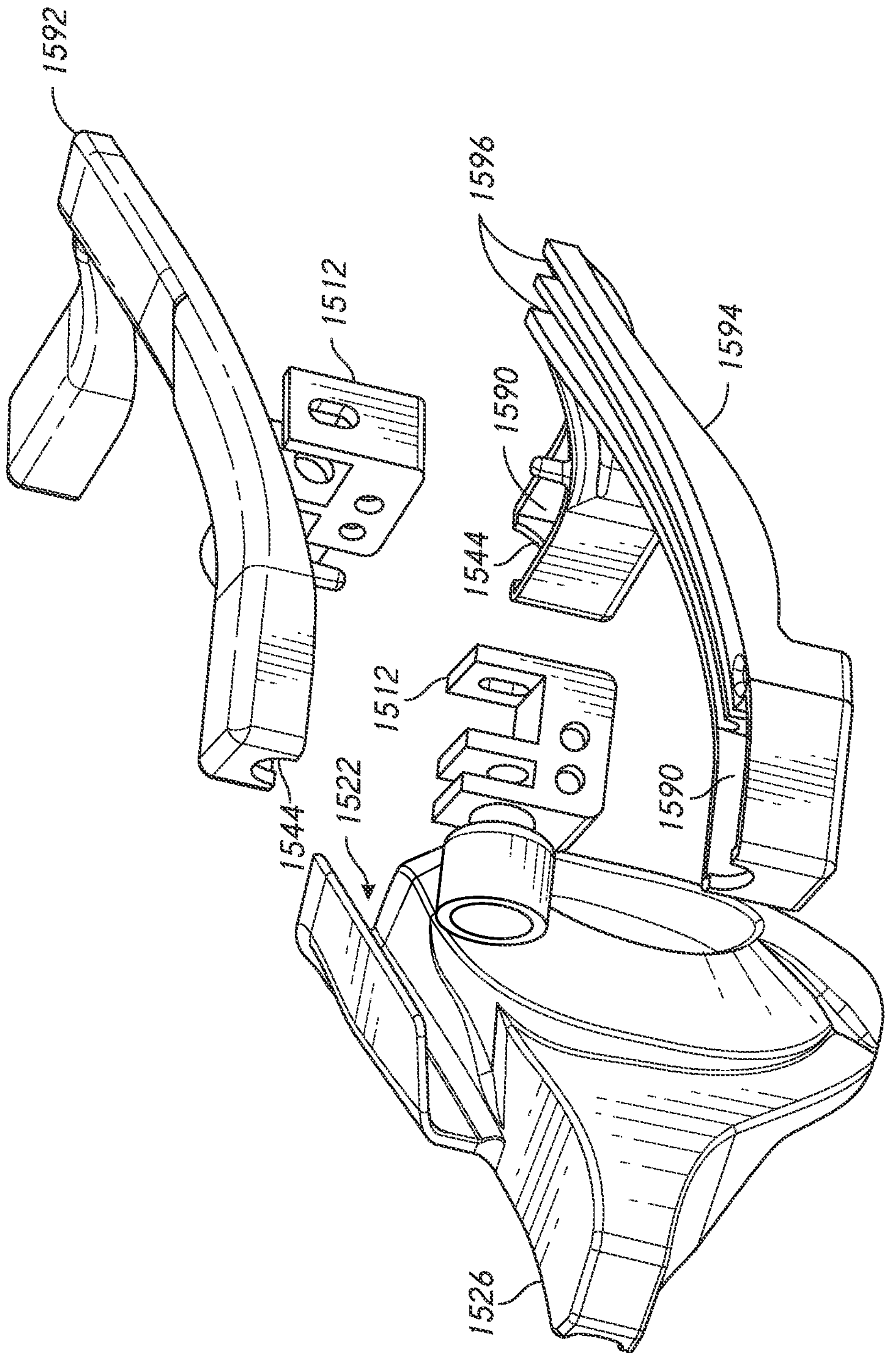
FIG. 52 is an exploded view of an exemplary interface coupling portion.
Figure 53:
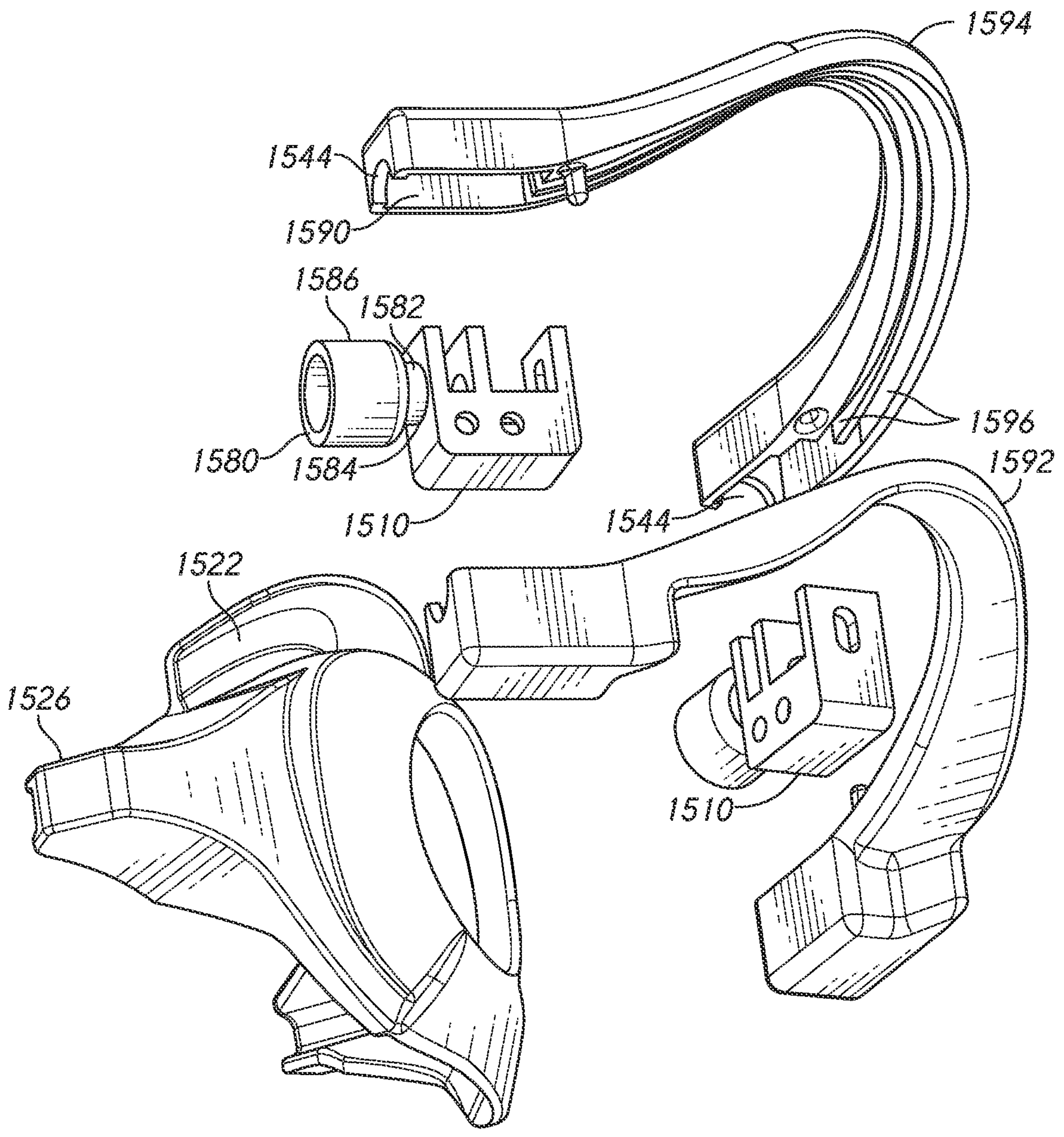
FIG. 53 is an inverted exploded view of an exemplary interface coupling portion.

With reference to FIGS. 32-34, a particular strap adjustment mechanism 1300 is shown. The adjustment mechanism 1300 of FIGS. 32-34 is substantially similar to the flat strap adjustment or directional locking mechanism shown and described in connection with FIGS. 40-42 in Applicant's PCT Application No. PCT/NZ2014/000074. However, in some configurations, the strap adjustment mechanism 1300 of FIGS. 32-34 incorporates an integrated padding or lining, as described above. In some configurations, the components of the strap adjustment mechanism 1300 are constructed by molding a moldable material onto a textile-based material.

FIGS. 32-34 illustrate the adjustable strap 1300 in assembled form and illustrates the portions of the adjustable strap separated and in plan view to illustrate the various components of the adjustment mechanism. The adjustment mechanism 1300 comprises a first portion 1310 that can be coupled to a second portion 1320 in multiple adjustment positions. In some configurations, the first portion 1310 and the second portion 1320 can be infinitely adjustable within the provided range of adjustment. The illustrated first and second portions 1310, 1320 are first and second portions of an adjustable top or crown strap; however, the adjustable strap can be provided in other locations as described in connection with FIGS. 30 and 31, for example. As described above, a biasing arrangement could be provided to bias the first and second portions 1310, 1320 relative to one another, such as toward a shortened position, for example.

Preferably, the adjustment mechanism 1300 comprises a directional lock 1330 that allows relative movement of the first portion 1310 and the second portion 1320 in a first direction (e.g., toward a shortened position) and provides a yield force that inhibits movement in a second direction. The yield force preferably is sufficient to prevent substantial movement in the second direction under normal or expected operating conditions, but may be overcome by an applied force to permit desired adjustment of the first portion 1310 and the second portion 1320.

The first portion 1310 of the adjustment mechanism 1300 can comprise a substantially flat strap 1312, which forms a male portion of the adjustment mechanism 1310. The second portion 1320 of the adjustment mechanism can comprise a receiver or a lock housing 1322, which forms a female portion of the adjustment mechanism. The lock housing 1322 can comprise a space 1324 that receives a lock member, such as a lock washer. The flat strap 1312 is movable within the receiver 1322 and passes through the space 1324 that receives the lock washer. The flat strap 1312 also passes through the lock washer. The lock washer is movable within the space 1324 of the lock housing 1322 between a release position and a lock position. In some configurations, the release position is defined by the lock washer being oriented substantially perpendicular to the length direction of the flat strap 1312 and the lock position is defined by the lock washer being tilted from the perpendicular orientation of the release position.

The position of the lock washer can be controlled by any suitable arrangement, such as being urged into the desired position by an end of the space 1324 of the lock housing 1322. For example, one end of the space 1324 of the lock housing 1322 can have a perpendicular surface and the other end can have a tilted surface. When the flat strap 1312 is moved in a direction toward the perpendicular surface, the lock washer is urged into the perpendicular orientation or release position and the flat strap 1312 is able to move relative to the lock housing 1322 with relatively low resistance. When the flat strap 1312 is moved in a direction toward the tilted surface, the lock washer is urged into the tilted orientation or lock position and relative movement between the flat strap 1312 and the lock housing 1322 is resisted by the yield force. The flat strap 1312 can comprise a gripping portion that facilitates movement of the lock washer. The gripping portion can be a higher friction material or material having a higher gripping force on the lock washer compared to the base material of the flat strap 1312.

In some configurations, each of the flat strap 1312 and the lock housing 1322 are constructed by molding a material onto the textile-based material of the first strap portion 1310 and the second strap portion 1320, respectively. In the illustrated configuration, a portion of the flat strap 1312 extends beyond an end of the textile-based material of the first strap portion 1310. In contrast, the textile-based material of the second strap portion 1320 extends beyond the lock housing 1322. Desirably, the portion of the flat strap 1312 that is received within the lock housing 1322 extends beyond the textile-based material of the first strap portion 1310 to avoid interference between the textile-based materials of the first strap portion 1310 and the second strap portion 1320 throughout an adjustment range of the adjustment mechanism. The portion of the second strap portion 1320 that extends beyond the lock housing 1322 can be configured such that the textile-based material of the first strap portion 1310 abuts or overlaps the textile-based material of the second strap portion 1320 in the largest position or most-separated position of the first portion 1310 and the second portion 1320.

In some configurations, the molded material extends along the textile-based material of the strap portions beyond the flat strap and/or lock housing. For example, the molded material can be provided as reinforcement for or as a stiffening member of the textile-based material of the strap portions. The additional molded material may be provided to increase the surface area between the molded material and the textile-based material to improve the connection therebetween and/or increase the holding force therebetween. In the illustrated arrangement, the additional molded material is in the form of strips or ribs that are separated from one another in a width direction of the strap portions and extend generally in the length direction of the strap portions.

In the illustrated configurations, the strap portions 1310, 1320 are desirably be relatively rigid in one direction (in a width direction to inhibit bending), but retain flexibility in another direction (in a thickness direction to allow the strap to bend and conform to the user's head). This can be achieved by the geometric design of the textile-based strap portion and/or the over-molded feature and/or through the use of different over-molded materials. In other configurations, such as other locations of the adjustment mechanism, other properties may be desired. Thus, other geometric shapes and/or materials can be selected to provide the strap portions with the desired properties.

In some configurations, the composite strap portions are constructed by an over-molding process involving molding a moldable material 1340 onto a textile or fabric material 1350. In some configurations, the moldable material 1340 can be a plastic material. The textile or fabric material 1350 preferably is selected to provide good adhesion of the moldable material.

The textile-based material can be placed into a mold. The mold can be closed and portions (e.g., edges) of the textile-based material can be captured between separable portions (e.g., halves) of the mold. The moldable material can then be injected into the mold and onto the textile-based material.

As disclosed in Applicant's patent application no. PCT/NZ2014/000074, many different types of directional locking mechanisms can be utilized in a headgear exhibiting balanced fit characteristics. In at least some configurations, a directional lock inhibits or prevents relative movement between two portions of the headgear in a first direction at least below a yield force of the directional lock. The directional lock also permits relative movement of the two portions of the headgear in a second direction opposite the first direction. Preferably, the movement in the second direction is permitted with no more than a relatively small amount of resistance.

Figure 35:
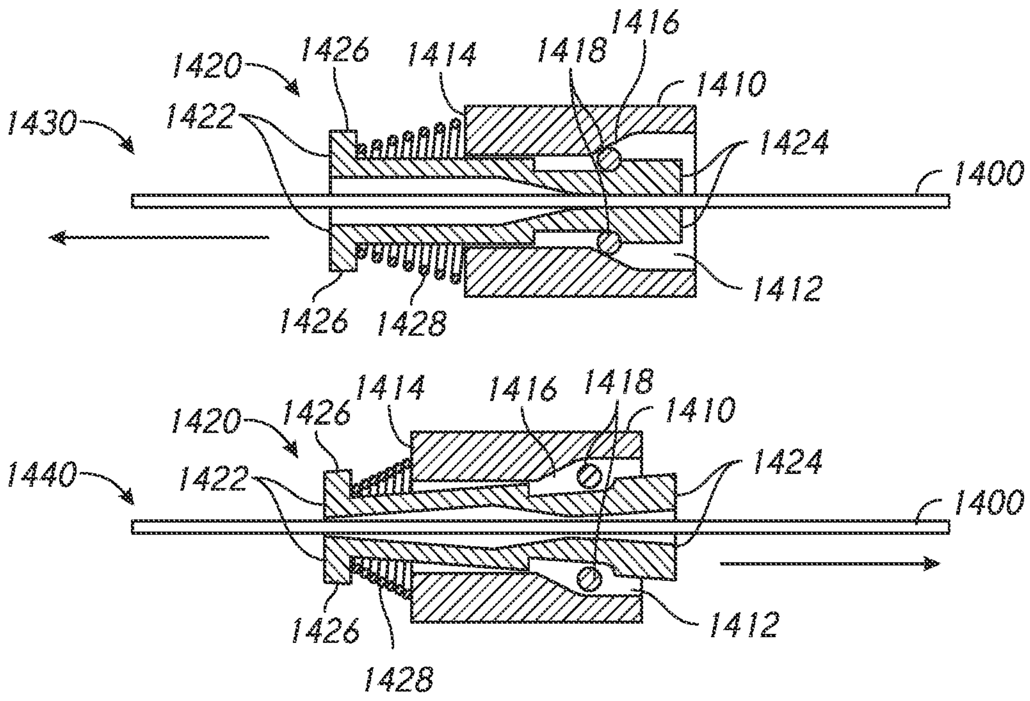
FIG. 35 is a sectional view of a directional lock in a lock position and release position.

With reference to FIG. 35, in some configurations, a first portion of the headgear comprises a core member 1400. The core member 1400 can be a wire, wire-like element or filament. A second portion of the headgear can comprise a housing 1410. The first portion and second portion of the headgear can be coupled to any suitable portions or components of the headgear that are movable relative to one another to vary or adjust a circumference of the headgear. The housing 1410 can be an element or receptacle that defines a space 1412 for receiving a lock arrangement 1420. The housing 1410 can be a separate component from the headgear or can be an integral component or portion of the headgear. The lock arrangement 1420 can engage the core member 1400 to inhibit or prevent movement of the core member 1400 relative to the housing 1410 in a first direction at least below a yield force of the directional lock. The lock arrangement 1420 can also disengage the core member 1400 to permit movement of the core member 1400 relative to the housing 1410 in a second direction opposite the first direction.

The lock arrangement 1420 can comprise two or more lock elements that are movable between a first or lock position 1430 and a second or release position 1440. The illustrated lock arrangement 1420 comprises a pair of lock elements in the form of lock jaws 1422. Each of the lock jaws 1422 is a generally semi-cylindrical member. The lock jaws 1422 cooperate to surround the core member 1400. An interior surface of each of the lock jaws 1422 facing the core member 1400 is concave. Each of the lock jaws 1422 comprises an engagement portion 1424 that contacts the core member 1400 in the lock position 1430 such that the lock jaws 1422 cooperate to engage the core member 1400. In the illustrated arrangement, the engagement portion 1424 is defined by an end portion of each of the lock jaws 1422.

An opposite end of each of the lock jaws 1422 extends through the housing 1410 and includes a radially-extending flange 1426. The directional lock can comprise a biasing arrangement that, in some configurations, provides a relatively light biasing force tending to move the lock arrangement toward the lock position or toward the left of the page in FIG. 35. The biasing arrangement can comprise a biasing element 1428, such as a spring, which acts against the flanges 1426 of the locking jaws 1422 and an end surface 1414 of the housing 1410. Preferably, the biasing arrangement provides a light biasing force that assists initial movement of the lock jaws 1422 toward the lock position 1430 when the core member 1400 is moved in a direction (to the left in FIG. 35) tending to increase a circumference of the headgear. The lock jaws 1422 can be moved toward the release position 1440 against the biasing force of the biasing arrangement when the core member is moved in a direction (to the right in FIG. 35) tending to decrease a circumference of the headgear.

As described above, the housing 1410 defines a space or passage for receiving the lock jaws 1422 and through which the core member 1400 can pass. The passage 1412 can define a chamfered, angled or tapered surface 1416 that facilitates movement of the lock jaws 1422 between the lock position 1430 and the release position 1440. One or more locking or roller elements 1418 can be positioned between each of the lock jaws 1422 and the housing 1410. Movement of the lock jaws 1422 along the longitudinal axis of the housing 1410 or passage 1412 in the direction toward the lock position 1430 causes engagement of the roller elements 1418 with the tapered surface 1416, which moves the roller elements 1418 and, thus, the lock jaws 1422 closer to one another such that the core member 1400 is clamped between the lock jaws 1422. Movement of the lock jaws 1422 along the horizontal axis in the direction toward the release position 1440 results in the roller elements 1418 being free to move away from the lock jaws 1422 in a radial direction thereby releasing the clamp force from the lock jaws 1422 and allowing the core member 1400 to move relatively free of substantial resistance. Such movement of the core member 1400 may result in axial movement of the lock jaws 1422 via frictional forces against the biasing force of the biasing arrangement.

The core member 1400, lock jaws 1422, tapered surface 1416 and/or roller elements 1418 can be configured such that the directional lock applies a clamping force to the core member 1400 that substantially inhibits or prevent movement of the core member 1400 relative to the housing 1410 when a force below a yield force acts on the core member 1400 attempting to elongate the headgear and allows movement of the core member 1400 attempting to elongate the headgear when a force above the yield force acts on the core member 1400. As described above, such an arrangement can allow a headgear incorporating one or more of the directional locks to resist normal or expected forces relating to therapy, while also permitting elongation of the headgear for fitment to or removal from the user. The directional lock can release the core member 1400 in response to movement of the core member 1400 attempting to retract the headgear to allow movement of the core member 1400 relative to the housing 1410 with relatively little resistance. Such an arrangement can allow headgear incorporating one or more of the directional locks to retract to fit the head size of the particular user. A retraction force tending to retract the headgear can be provided by any suitable method or mechanism, including manual retraction or automatic retraction caused by an elastic arrangement or elastic element(s) of the headgear.

Figure 36:
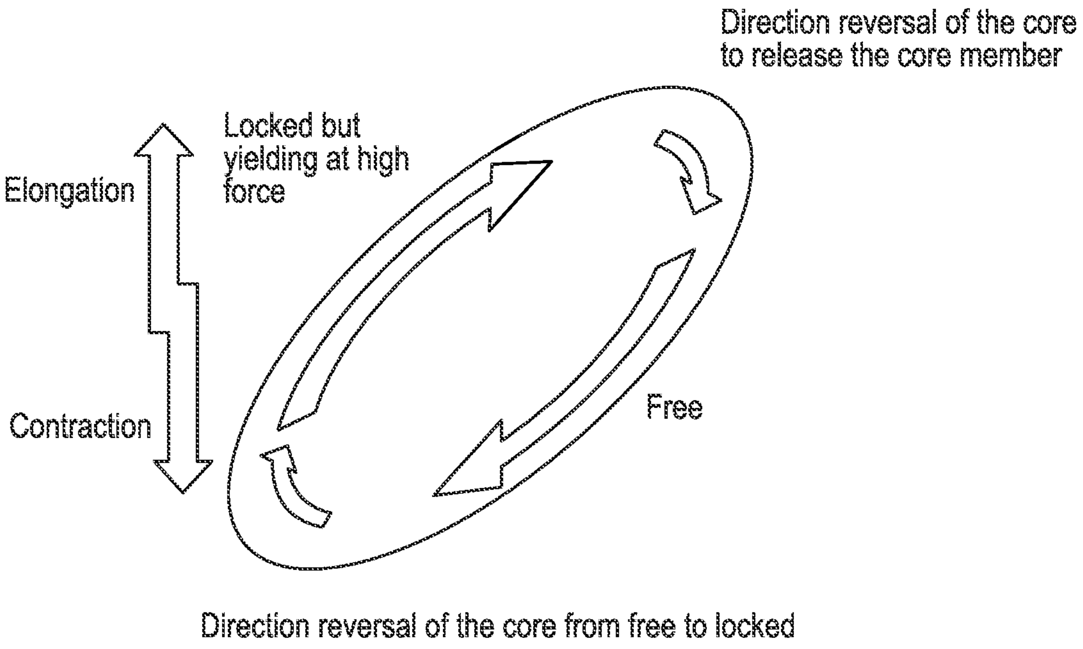
FIG. 36 illustrates an operation cycle for a headgear incorporating a directional lock.
Figure 37:
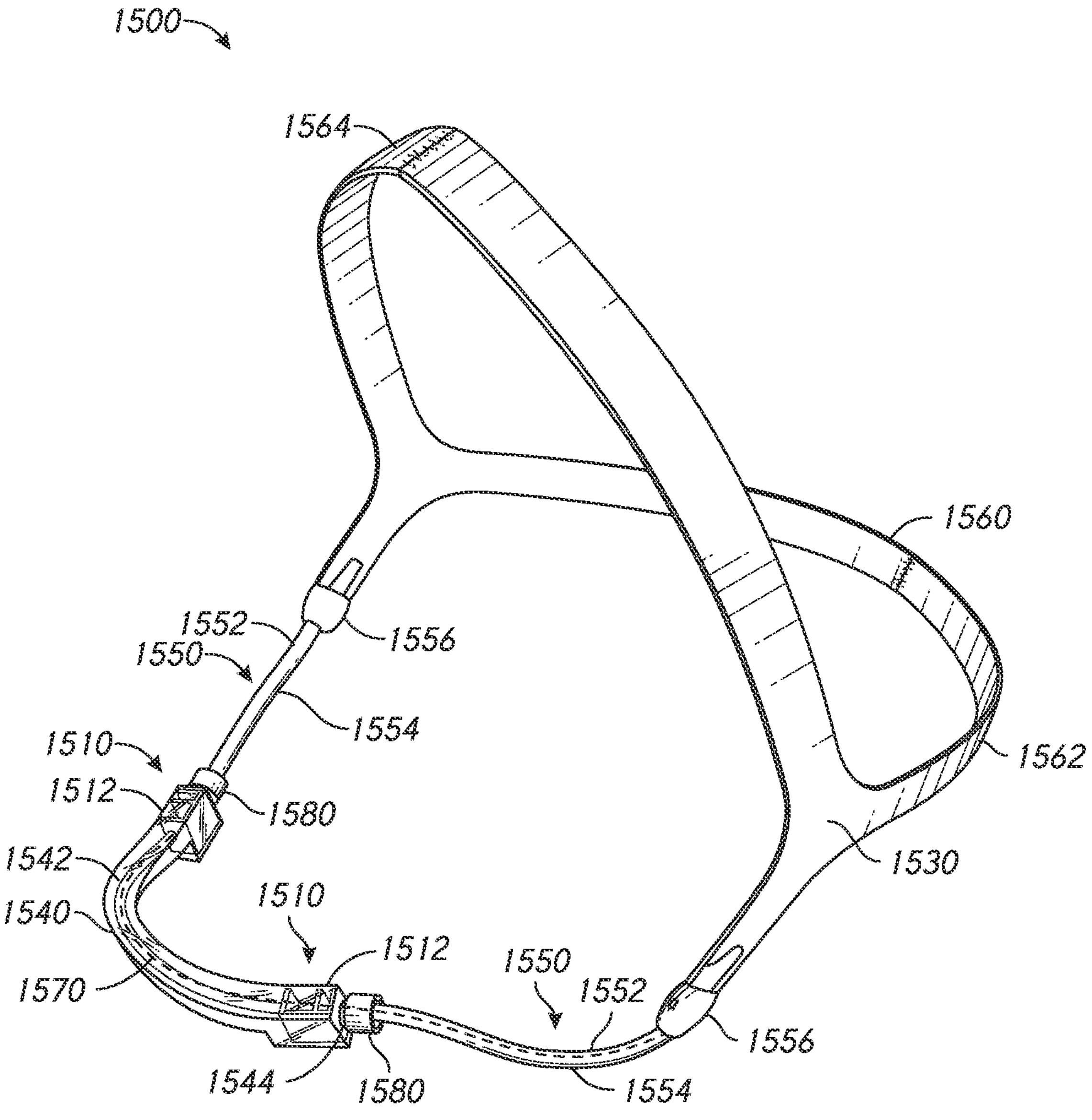
FIG. 37 is a perspective view of an exemplary headgear assembly incorporating one or more directional locks.
Figure 38:
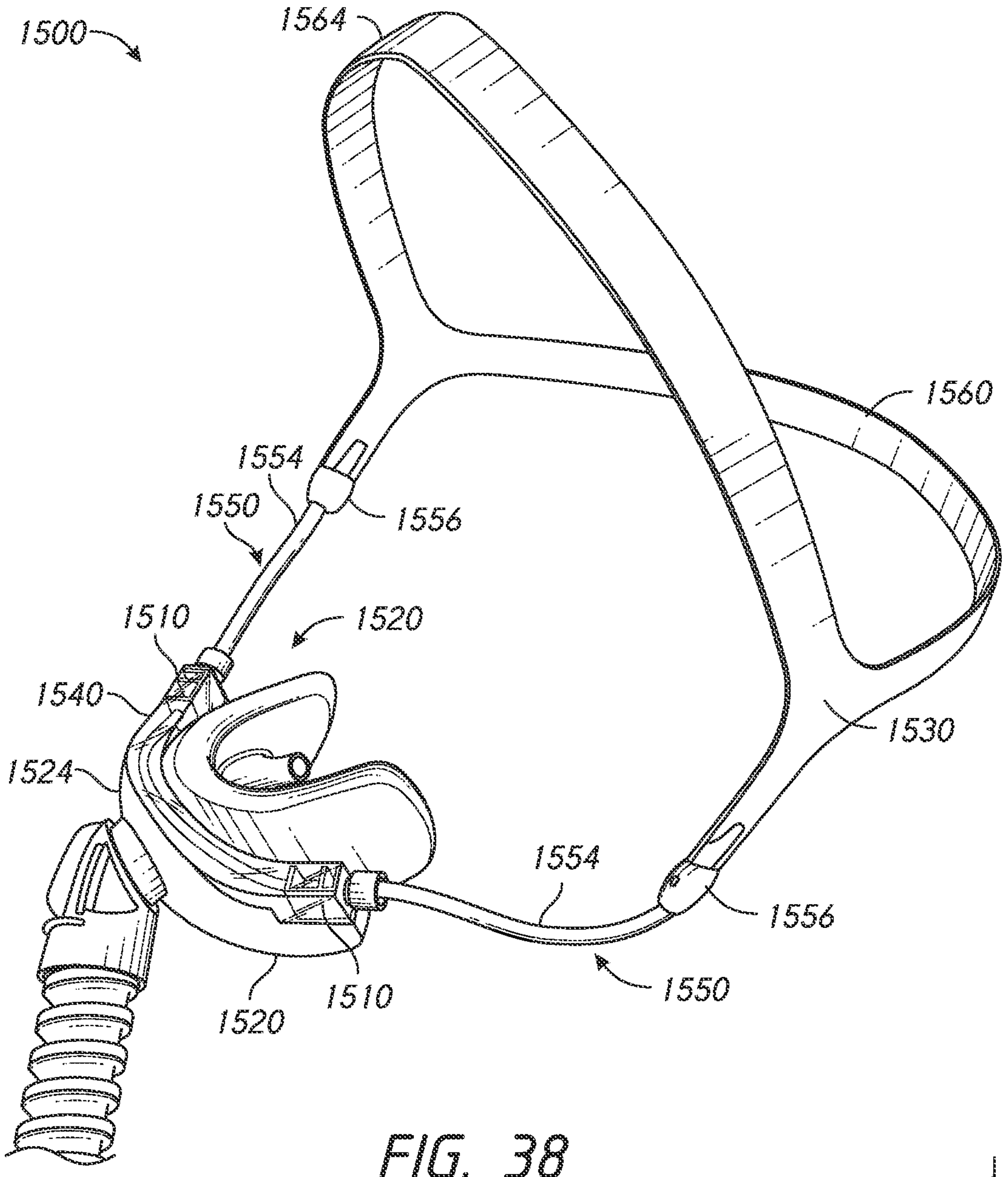
FIG. 38 is a perspective view of an exemplary headgear assembly incorporating one or more directional locks.
Figure 39:
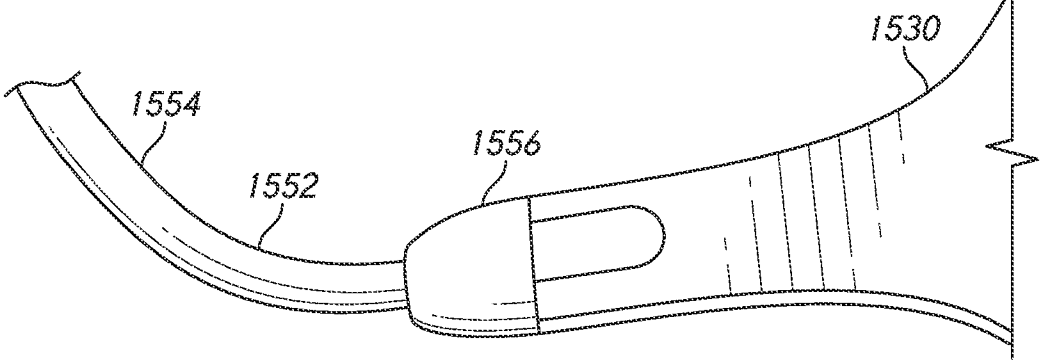
FIG. 39 is a side view of an attachment member attached to a headgear rear portion of the exemplary headgear assembly in FIG. 38.

FIG. 36 illustrates an operation cycle for a headgear incorporating a directional lock, such as the direction lock described above, any other directional lock described or incorporated by reference herein or any other suitable directional lock. In the operation cycle graphic, a component of an arrow in an upward direction represents elongation of the headgear (an increase in a circumference of the headgear) and a component of an arrow in a downward direction represents contraction of the headgear (a decrease in a circumference of the headgear). A component of an arrow to the right in FIG. 36 represents elongation movement of the headgear and a component of an arrow to the left represents retraction movement of the headgear.

FIG. 36 is described with reference to the structure of the directional lock described immediately above; however, the basic concepts highlighted by the description are equally applicable to many or all of the other directional locks described or incorporated herein. The upper, center arrow represents movement of the core member in a direction tending to elongate the headgear as a result of an application of force above the yield force of the directional lock. Thus, the core member is able to slip through the lock jaws, which are clamped against the core member by the interaction of the roller elements and the tapered surface of the passage of the housing. Such force may be applied in the application or removal of the headgear.

The next arrow in a clockwise direction represents a change in direction of the core member from elongation to retraction. Such a change in direction results in release of the clamping force on the core member.

The next arrow in the clockwise direction represents retraction movement of the core member. Thus, the core member movement can move the locking jaws such that the roller elements are no longer forced into the narrow portion of the tapered surface. As a result, relatively free retraction motion of the core member can occur. Such movement can allow the headgear to retract to fit the particular user or to retract to a minimum circumference when not in use.

The next arrow in the clockwise direction represents a change in direction of the core member from retraction to elongation. Such a change in direction results in the application of the clamping force to the core member. In each case of a change in direction, some movement of the core member may occur before the change in clamping force, or the change in the position of the direction lock, occurs or is fully reached. This cycle can be repeated each time the headgear is applied or removed from a user. In some cases, the cycle can occur when a user makes fine adjustments to the headgear.

FIGS. 37-53 illustrate an example of a headgear assembly 1500 incorporating one or more directional locks 1510. The illustrated headgear assembly 1500 is configured to be coupled to a portion of an interface 1520. In particular, the illustrated headgear assembly 1500 includes a headgear rear portion 1530, an interface coupling portion 1540 and a length or circumference adjusting portion 1550 that is interposed between the headgear rear portion 1530 to the interface coupling portion 1540. The headgear rear portion 1530 is configured in use to contact a rear portion of the user's head. The interface coupling portion 1540 is configured in use to be coupled to an interface 1520 such that the headgear assembly 1500 can support the interface 1520 in an appropriate position on the face of the user. The length or circumference adjusting portion 1550 is configured in use to permit a position of the interface coupling portion 1540 to be adjusted relative to the headgear rear portion 1530 such that the headgear assembly 1500 can be adjusted to the head size of a particular user. Thus, the length or circumference adjusting portion 1550 can permit a perimeter length or circumference of the headgear to be adjusted to allow the headgear assembly 1500 to fit the head size of a particular user.

Although illustrated and described as a headgear assembly 1500, in some configurations, the portions of the illustrated headgear assembly 1500 can be incorporated in any other suitable portion of an overall interface assembly. For example, the interface coupling portion 1540 can comprise a component or portion of an interface that is separate from and connectable to a headgear assembly 1500. The length or circumference adjusting portion 1550 can comprise a component or portion of an interface that is separate from and connectable to a headgear assembly 1500 or a component or portion of a headgear assembly 1500 that is separate from and connectable to an interface 1520. Advantageously, however, and as described further below, the illustrated headgear assembly 1500 can comprise a self-contained, automatic-fit headgear unit that exhibits balanced-fit characteristics and can be coupled to at least one and possible multiple types of interfaces. Thus, in at least some configurations, one type of the illustrated headgear assembly 1500 can be utilized with multiple types of interfaces. Accordingly, a seller can stock a lesser number of unique products while providing the same interface options. In addition, a user can utilize a single headgear assembly and interchange interfaces as desired, without requiring manual adjustment of the headgear assembly when changing from one interface to another.

In the illustrated arrangement, the headgear rear portion 1530 comprises at least one strap portion 1560 that contacts the head of the user. Preferably, the at least one strap portion 1560 contacts a rear portion or back of the head of the user such that the at least one strap portion 1560 can counteract forces induced in the headgear assembly 1500 by the pressurization of the interface during therapy. In some configurations, the strap portion 1560 extends generally or substantially in a lateral direction around the rear of the user's head and has an end one each side of the user's head. Each end can be coupled to another portion of the headgear assembly 1500, such as the circumference adjusting portion 1550, for example.

In some configurations, the at least one strap portion 1560 comprises a first strap portion and a second strap portion. The first strap portion can be a rear strap portion 1562 that extends around the back of the user's head and the second strap portion can be a top or upper strap portion 1564 that extends over the top of the user's head. The rear strap portion 1562 can be positioned to contact portions corresponding to one or both of the occipital or parietal bones of the user's head. The top strap portion 1564 can be positioned to contact portions corresponding to one or both of the parietal and frontal bones of the user's head. Thus, the top strap 1564 can be configured as either one of a crown strap or a forehead strap as such straps are sometimes characterized in the art. Other suitable arrangements can also be used.

Preferably, the headgear rear portion 1530 engages the user's head and provides a relatively stable platform for connection of the interface, such as utilizing the interface coupling portion 1540 and the circumference adjusting portion 1550. Thus, in at least some configurations, the headgear rear portion 1530 is substantially inelastic such that it holds its shape and effective length in response to applied forces within a range that is typical or expected for the intended application. In some configurations, the headgear rear portion 1530 can comprise a layer constructed from a relatively rigid material, such as a plastic material, coupled to one or more layers of a fabric material. Preferably, a fabric layer is provided at least on a user-contacting surface of the rigid material layer. In some configurations, a fabric layer is provided on each side of the rigid material layer. Furthermore, in some configurations, the rigid material layer can be formed between the material layers, such as by injection molding the rigid material into a space between two material layers within a mold. An example of such a headgear and a method of making such a headgear is disclosed in Applicant's U.S. Provisional Application No. 62/050,925, the entirety of which is incorporated by reference herein.

The circumference adjusting portion 1550 can comprise a pair of adjustment elements 1552 in which one adjustment element 1552 is positioned on each side of the headgear assembly 1500. In particular, each of the adjustment elements 1552 can couple one side of the headgear rear portion 1530 with one side of the interface coupling portion 1540. The adjustment elements 1552 can be coupled at or near a junction between the top strap 1564 and the rear strap 1562. In the illustrated arrangement, the adjustment elements 1552 are coupled to forward extensions of the headgear rear portion 1530 that extend in a forward direction from a junction between the top strap 1564 and the rear strap 1562. The adjustment elements 1552 are adjustable in length between a retracted length and an extended length. In some configurations, the adjustment elements 1552 cooperate to provide all or substantially all of the adjustment of a circumference of the headgear assembly 1500. Each of the adjustment elements 1552 can also include an elastic element or biasing arrangement that biases the adjustment element 1552 toward one of the retracted or extended lengths. Preferably, the adjustment elements 1552 are biased toward a retracted length, such that the headgear assembly 1500 is biased toward its smallest circumference. Such an arrangement permits the headgear assembly 1500 to be extended and then automatically retract to fit the particular user under the biasing force of the elastic element or other biasing arrangement of the adjustment element(s) 1552. In addition, preferably, the adjustment elements 1552 define a hard stop at a maximum extended length to limit extension of the headgear 1500 and define a maximum circumference of the headgear 1500.

In some configurations, the adjustment elements 1552 comprise a braided element 1554, which can extend or retract in length. The braided element 1554 can comprise one or more elastic elements in parallel with the braided element 1554. The elastic elements can be separate from the braided element 1554 or incorporated in the braided element 1554. In some configurations, the elastic elements are contained in internal spaces between filaments of the braided element 1554. An example of suitable braided elements is described in connection with FIGS. 46-54 of Applicant's patent application no. PCT/NZ2014/000074. However, other suitable constructions or arrangements can also be used. Alternatively, elastic element(s) or biasing element(s) can be located within the interface coupling portion and can interact with the core members to pull the core members into the interface coupling portion.

The interface coupling portion 1540 of the headgear assembly 1500 can extend between the pair of adjustment elements 1552 that comprise the circumference adjusting portion 1550. In some configurations, the interface coupling portion 1540 is coupled directly to the adjustment elements 1552. As described above, the interface coupling portion 1540 can facilitate connection of the headgear assembly 1500 to an interface 1520. However, the interface coupling portion 1540 can also accommodate at least a portion of one or more directional locks 1510. In the illustrated arrangement, a pair of directional locks 1510 is provided, with one directional lock 1510 associated with one of the pair of adjustment elements 1552. Portions (e.g., housings 1512) of the directional locks 1510 can be located at each end of the interface coupling portion 1540. In some configurations, a core member 1570 associated with each of the directional locks 1510 is coupled to the headgear rear portion 1530, extends along or through the adjustment element 1552, through the housing 1512 of the directional lock 1510 and into a collection space 1542 of the interface coupling portion 1540. The housing 1512 of the directional lock 1510 can comprise one or more members or elements (e.g., lock washers or lock jaws) that interact with the core member 1570 to selectively allow retraction of the headgear assembly 1500 or lock the headgear assembly 1500 in a particular circumference and inhibit or prevent extension of the headgear 1500 at least at forces below the yield force provided by of the directional lock(s) 1510. Additional particulars of the operation of the directional locks 1510 are described above and in Applicant's patent application no. PCT/NZ2014/000074.

In some configurations, one or both of the core member 1570 and the adjustment element 1552 are secured to the headgear rear portion 1530 by encapsulation of the core member 1570 and/or adjustment element 1552 within the headgear rear portion 1530. For example, the core member 1570 and/or adjustment element 1552 can be positioned within a mold and the rigid material portion of the headgear rear portion 1530 can be formed by injection molding such that it encapsulates the core member 1570 and/or adjustment element 1552. In the illustrated arrangement, an end portion of the adjustment element 1552 and an end portion of the core member 1570 are encapsulated within the rigid material portion of the headgear rear portion 1530. However, other suitable arrangements can also be used.

In some configurations, the adjustment element 1552 includes end cap portions 1556 that couple the braided element 1554 with the elastic element(s). The end cap portions 1556 can be applied to the ends of the adjustment element 1552 by an overmolding process. In particular, the braided element 1554 and elastic element(s) can be placed in a mold and the end cap portions 1556 can be created by injection molding over the end portions of the braided element 1554 and elastic element(s). In some configurations, the braided element 1554 and/or the elastic element(s) are held in a stretched state during the overmolding process. In some configurations, the adjustment element sub-assemblies are then coupled to the headgear rear portion 1530, such as by the above-described overmolding process. Thus, the end cap portion 1556 of the adjustment element 1552 can be encapsulated by the headgear rear portion 1530.

The end cap portion 1556 of each of the adjustment elements 1552 opposite the headgear rear portion 1530 can be coupled to the interface coupling portion 1540 by any suitable arrangement. In the illustrated configuration, the end cap portion 1556 of the adjustment element 1552 is coupled to a ferrule or socket 1580, which is, in turn, coupled to the interface coupling portion 1540. For example, the end cap portion 1556 can be press-fit or otherwise secured within the socket 1580. The socket 1580 can comprise a neck portion 1582 that spaces a retention portion 1584 from the main body 1586 of the socket 1580. The neck portion 1582 can extend through an opening 1544 in the interface coupling portion 1540 and the retention portion 1584 of the socket 1580 can prevent separation of the socket 1580 from the interface coupling portion 1540. In some configurations, the retention portion 1584 of the socket 1580 can be integrated with the housing 1512 of the directional lock 1510.

In some configurations, the interface coupling portion 1540 can be constructed from multiple pieces that cooperate to define the collection space. The multiple pieces can also cooperate to define a space 1590 for receiving the housing 1512 of each directional lock 1510. In the illustrated arrangement, the interface coupling portion 1540 comprises a first piece 1592 and a second piece 1594 that can be connected to define the collection space 1596 and a pair of spaces 1590 for receiving the housings 1512 of the directional locks 1510. The first and second pieces 1592, 1594 can be upper and lower pieces, respectively. In other arrangements, the first and second pieces 1592, 1594 could be forward and rearward pieces, for example. Provision of separate pieces facilitates assembly of the housings 1512 of the directional locks 1510, the core members 1570 of the directional locks 1510 and the sockets 1580 to the interface coupling portion 1540.

The collection space 1596 of the interface coupling portion 1540 is configured as an accumulator to receive end portions of the core members 1570 that, in the illustrated arrangement, are excess or inactive portions and do not form an operative portion of the core members 1570. That is, the portions of the core members 1570 between the mounting point at the headgear rear portion 1530 and the housing 1512 of the directional lock 1510 (or at the lock element(s) of the directional lock), are active and form a portion of the headgear circumference. Such portions of the core members 1570 are placed under tension when a force is applied tending to elongate the headgear. The lengths of the active core member portions and the inactive core member portions will vary along with variations in the adjusted or instantaneous circumference of the headgear assembly 1500. Thus, the collection space 1596 provides a location to accumulate and protect the inactive portions of the core members 1570.

Desirably, a length of the collection space 1596 is at least as great as a stretch distance (difference between the extended and retracted lengths) of one of the adjustment members 1552. In other words, the stretch distance of the adjustment members 1552 preferably is less than or equal to the length of the collection space 1596 so that ample space exists in the collection space 1596 for excess core member portion of sufficient length to allow movement of the adjustment members 1552 from a retracted position to an extended position with at least some excess core member 1570 length left within the collection space 1596 such that the core member 1570 is not pulled completely through the housing 1512 of the directional lock 1510. In some configurations, the collection space 1596 can comprise separate spaces or channels for each of the core members 1570.

A portion of the interface coupling portion 1540 can be configured for connection to an interface 1520 or a portion of an interface 1520. In some configurations, the interface coupling portion 1540 is able to be selectively coupled or removably coupled to an interface 1520. In the illustrated arrangement, a portion of the interface coupling portion 1540 that defines the collection space 1596 is configured to be received within a receiving channel 1522 of an interface member 1524. The receiving channel 1522 can be a semi-cylindrical space defined by the interface member 1524 and configured to receive the interface coupling portion 1540 in a snap-fit arrangement. The central portion of the interface coupling portion 1540 that defines the collection space 1542 can be generally columnar or cylindrical in outer shape. In the illustrated arrangement, the central portion of the interface coupling portion 1540 is curved along its length.

The interface member 1524 can be any portion of an interface 1520. For example, the interface member 1524 can be a relatively rigid portion of an interface 1520, such as a shell or frame element 1526. In the illustrated arrangement, the interface member 1524 is a frame element 1526, which can directly or indirectly support a mask seal 1528, cushion 1532 or other interface element. The frame element 1526 (or another portion of the interface) can support a conduit connector, such as an elbow 1534. In some configurations, the interface member 1524 can be configured to support several different types of mask seals 1528, cushions 1532 or other interface elements. In some configurations, the interface member 1524 can be integrated with or designed for use with a specific mask seal 1528, cushion 1532 or other interface element and different interface members 1524 can be integrated or associated with each type of mask seal 1528, cushion 1532 or interface element. In any event, in at least some configurations, the headgear assembly 1500 can be utilized with multiple types of mask seals 1528, cushions 1532 or other interface elements, including nasal cannula, nasal pillows, nasal masks or full face masks, for example.

Figure 54:
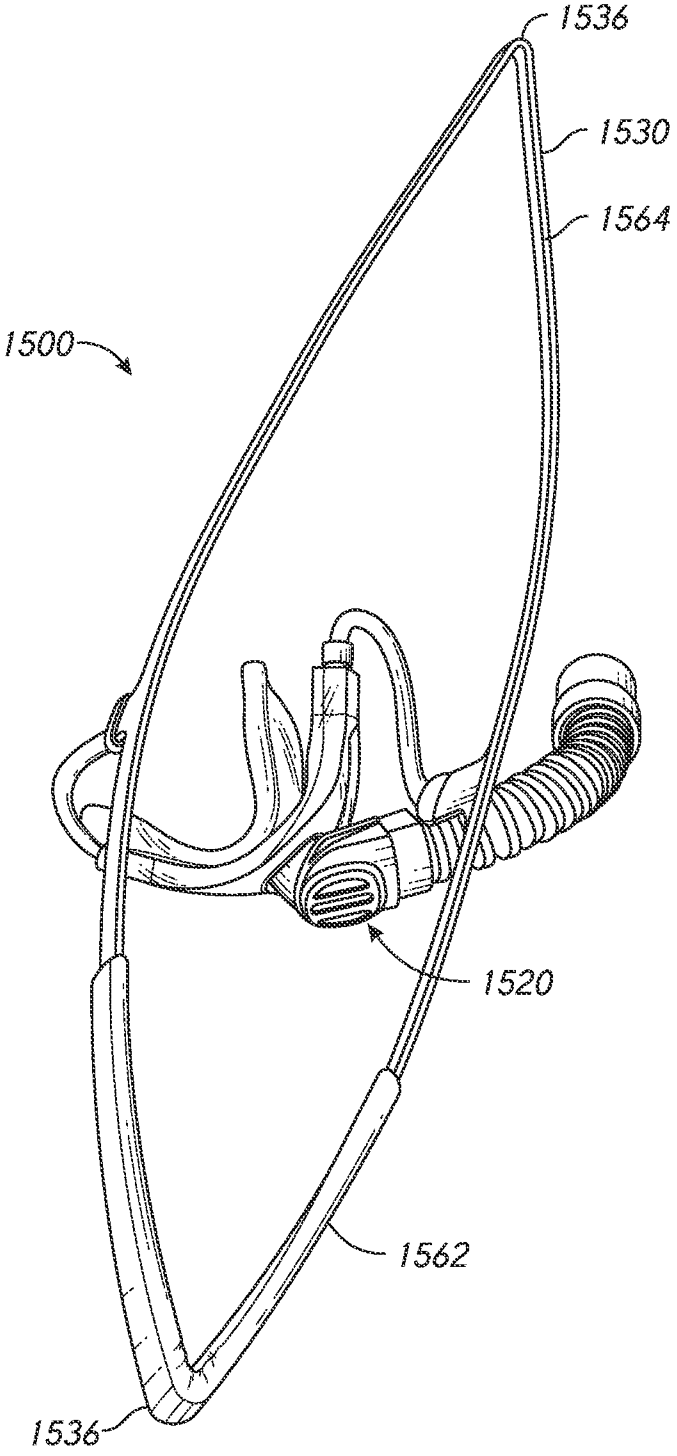
FIG. 54 is a top view of an exemplary collapsible headgear assembly.
Figure 55:
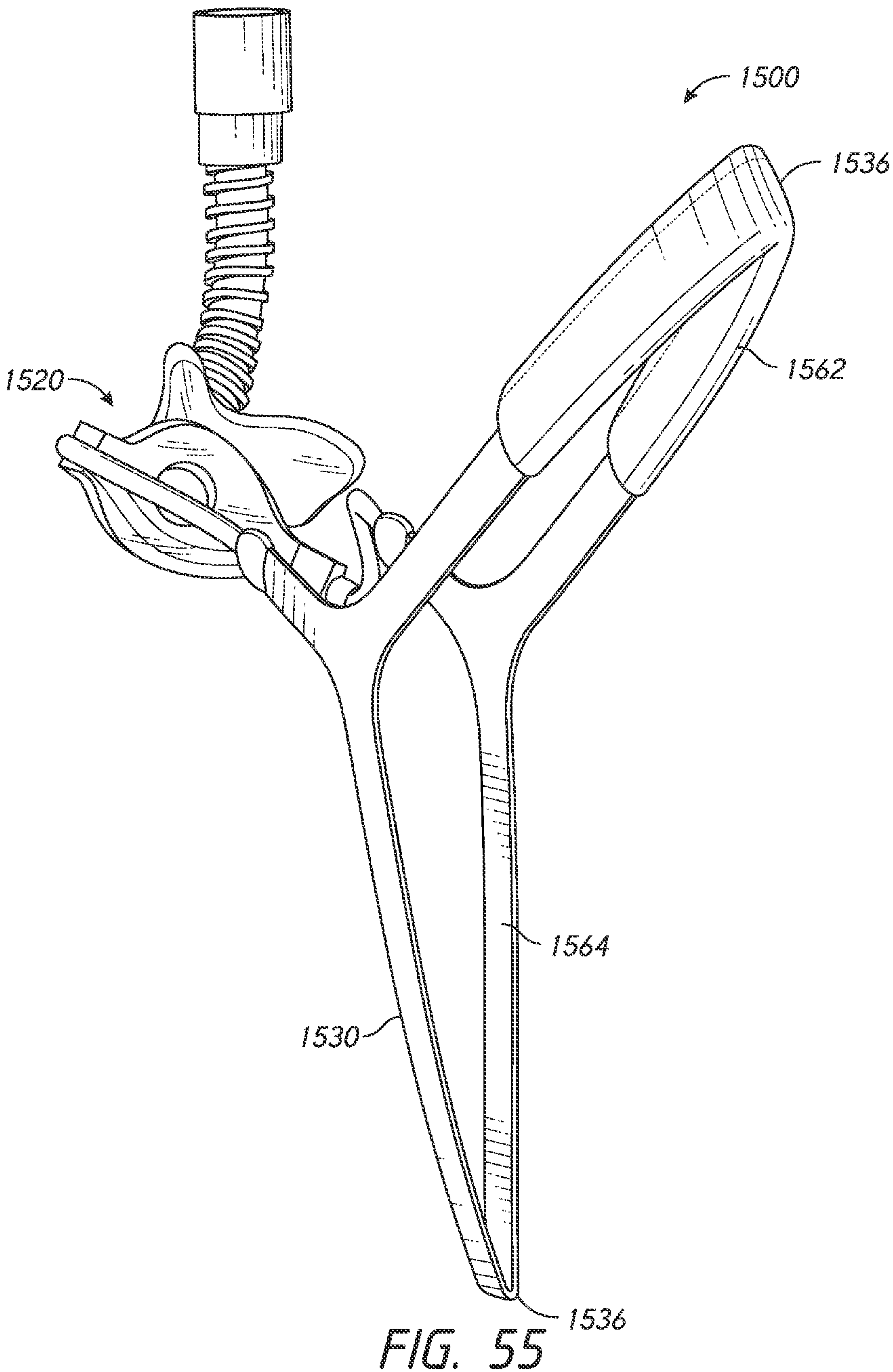
FIG. 55 a rear view of an exemplary collapsible headgear assembly.
Figure 56:
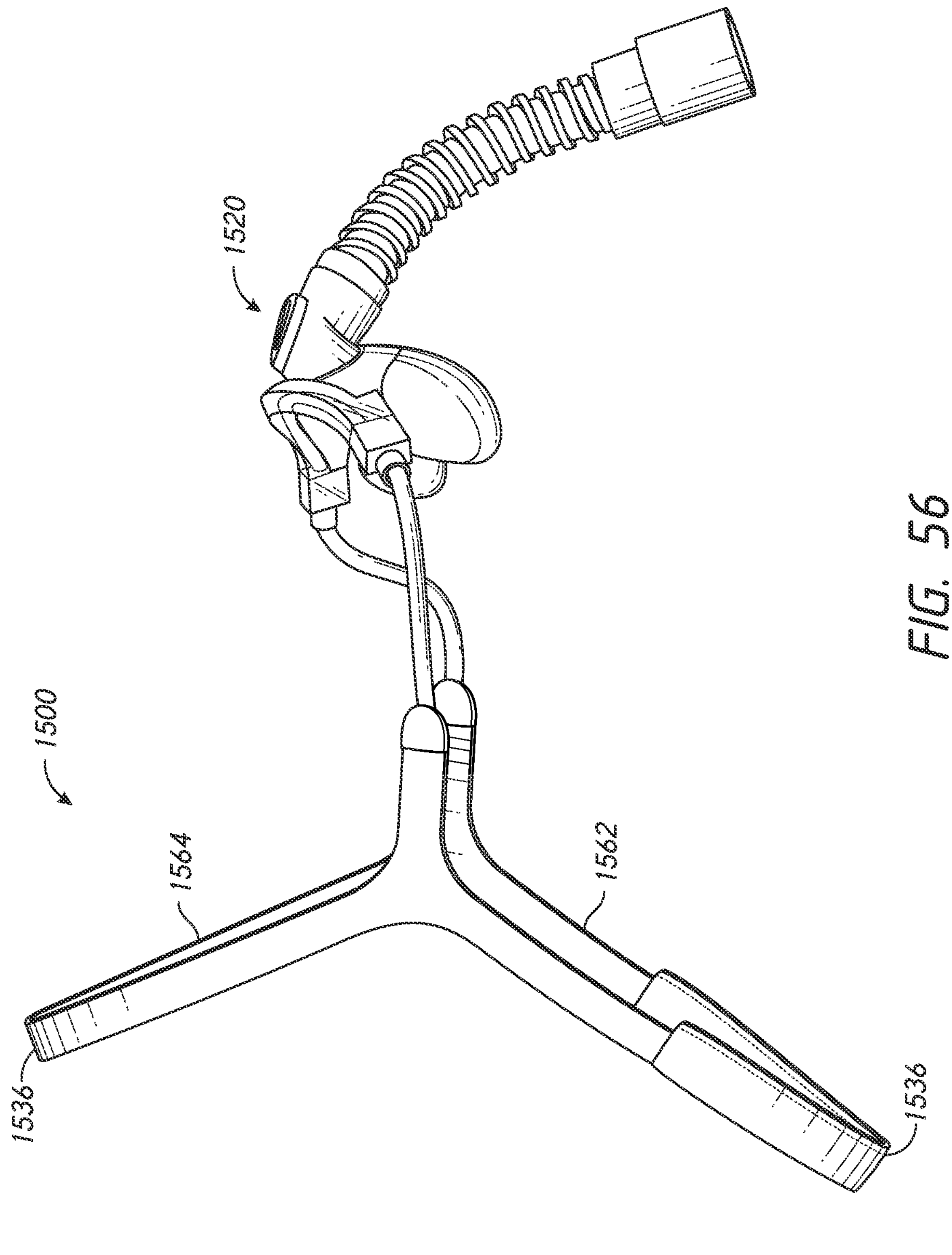
FIG. 56 a side view of an exemplary collapsible headgear assembly.

FIGS. 54-56 illustrate an interface assembly incorporating a headgear assembly 1500, which can be the same as or substantially to the headgear assembly 1500 described immediately above, or can be of another suitable arrangement. In the illustrated arrangement, the headgear rear portion 1530 is collapsible. In some configurations, the headgear rear portion 1530 can be collapsed or folded from an expanded configuration, in which the headgear rear portion 1530 assumes a three-dimensional form, to a collapsed configuration, in which the headgear rear portion 1530 can lay relatively flat. In the illustrated arrangement, a hinge, joint or fold 1536 is provided in one or both of the rear strap and the top strap. The hinge, joint or fold 1536 can comprise a section of the headgear rear portion 1530 that has less rigidity than other portions of the headgear rear portion 1530. The hinge, joint or fold 1536 can comprise a reduced thickness portion of the rigid headgear material, a separation between rigid headgear material portions such that the one or more fabric layers define the hinge, joint or fold 1536, or a coupling between separate portions of the headgear rear portion 1530, such as a sewn joint, for example. A separate hinge member could be utilized to join portions of the headgear rear portion.

Such an arrangement enables the headgear to be laid relatively flat, which can help with it being packed it the user is travelling with the mask. Having a designed fold point or line enables the headgear unit to have the shape sustaining behaviour, but also lets it be a compact unit if it has to be packed in a suitcase, etc. The fold line or hinge line 1536 could be constructed by any suitable process, such as with the use of stitching or injection molding both the left and right sides of the rigid material portion up to that point and then leaving an un-backed piece or pieces of fabric to act as the hinge.

Figure 58:
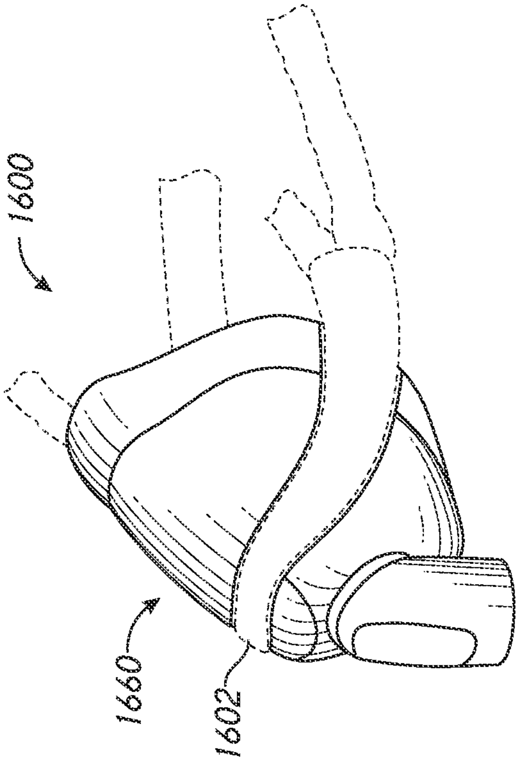
FIG. 58 illustrates the exemplary headgear assembly in FIG. 57 coupled to a nasal mask.
Figure 59:
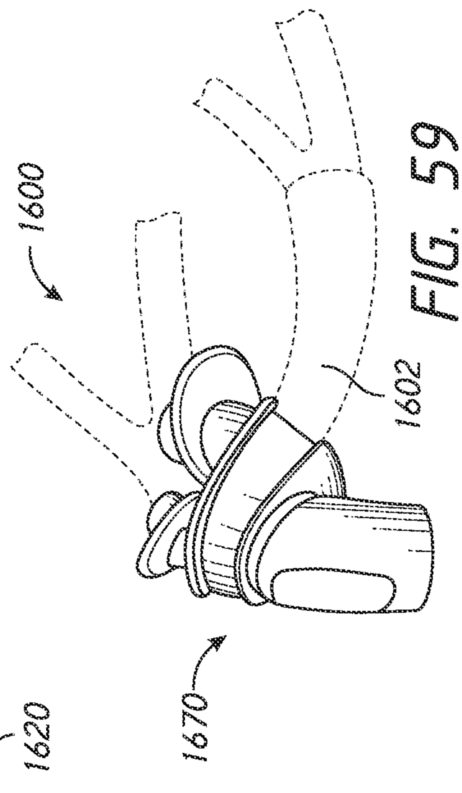
FIG. 59 illustrates the exemplary headgear assembly in FIG. 57 coupled to a nasal pillows/prongs mask.
Figure 57:
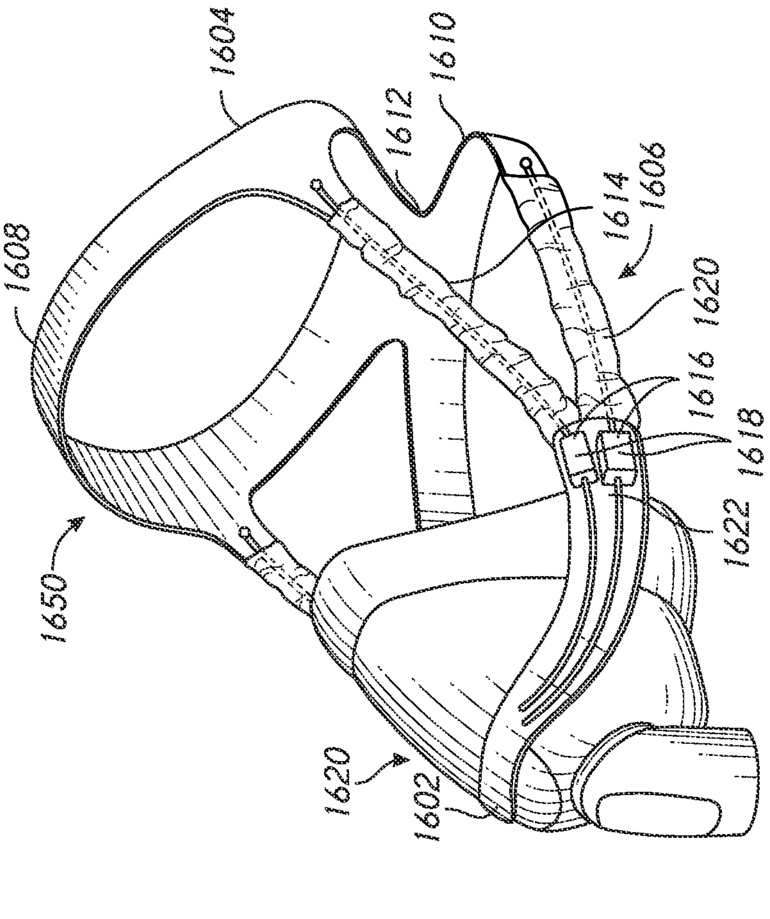
FIG. 57 illustrates an exemplary headgear assembly coupled to a full face mask type interface.

FIGS. 57-59 illustrate another headgear assembly 1600 that, in at least some configurations, can be utilized with two or more interface types. For example, FIG. 57 illustrates the headgear assembly 1600 as forming a modular component of an interface assembly comprising a full face mask type interface 1650. The headgear assembly 1600 can comprise a portion 1602 that engages the interface 1650 or can otherwise be coupled to the interface 1610. In some configurations, the engagement or coupling portion 1602 of the headgear assembly 1600 can be engaged or coupled with at least one other type of interface. For example, FIG. 58 illustrates the headgear assembly 1600 of FIG. 57 (shown in dashed line) supporting a nasal mask 1660 and FIG. 59 illustrates the headgear assembly 1600 of FIG. 57 (shown in dashed line) supporting a nasal pillows/prongs mask 1670. Thus, with such a modular arrangement, a single headgear assembly can be utilized with multiple types of interfaces. Advantageously, the on-demand resistance feature of the headgear assembly as described herein allows the single headgear assembly to operate in a suitable manner with the different interface types. For example, the retention force provided by the headgear can automatically adjust to the force applied to the headgear by the particular interface that is used. The engagement or coupling portion 1602 can be of any suitable arrangement, such as the same as or similar to the arrangement disclosed in connection with FIGS. 37-53, for example.

The headgear assembly 1600 can be generally similar to the other headgear assemblies disclosed herein or in Applicant's Application No. PCT/NZ2014/000074. In particular, the illustrated headgear assembly 1600 includes a headgear rear portion 1604, an interface coupling portion 1602 and a length or circumference adjusting portion 1606 that is interposed between the headgear rear portion 1604 to the interface coupling portion 1602. The headgear rear portion 1604 is configured in use to contact a rear portion of the user's head. The interface coupling portion 1602 is configured in use to be coupled to an interface such that the headgear assembly 1600 can support the interface in an appropriate position on the face of the user. The length or circumference adjusting portion 1606 is configured in use to permit a position of the interface coupling portion 1602 to be adjusted relative to the headgear rear portion 1604 such that the headgear assembly 1600 can be adjusted to the head size of a particular user. Thus, the length or circumference adjusting portion 1606 can permit a perimeter length or circumference of the headgear to be adjusted to allow the headgear assembly 1600 to fit the head size of a particular user.

The headgear rear portion 1604 can be of any suitable arrangement, such as the same as or similar to any of those described herein or in Applicant's Application No. PCT/NZ2014/000074. Preferably, the headgear rear portion 1604 engages the user's head and provides a relatively stable platform for connection of the interface, such as utilizing the interface coupling portion 1602 and the circumference adjusting portion 1606. Thus, in at least some configurations, the headgear rear portion 1604 is substantially inelastic such that it holds its shape and effective length in response to applied forces within a range that is typical or expected for the intended application. The headgear rear portion 1604 can include a top strap portion 1608 that extends over the top of the user's head and a rear strap portion 1610 that extends around the back of the user's head. The top strap portion 1608 and rear strap portion 1610 can be separate or coupled in any suitable manner, such as by an intermediate connecting portion 1612.

The length or circumference adjusting portion 1606 can be of any suitable arrangement, such as the same as or similar to any of those described herein or in Applicant's Application No. PCT/NZ2014/000074. The circumference adjusting portion 1606 can comprise two pair of adjustment elements 1614 in which one pair of adjustment elements 1614 are positioned on each side of the headgear assembly 1600. Thus, the illustrated headgear arrangement 1600 can be generally described or categorized as a two retention plane headgear type. The headgear arrangement 1600 can be described as a two retention plane, forward converge headgear type or possibly a hybrid of a two retention plane, forward converge headgear type and a two retention plane, separated/angled headgear type.

Each pair of the adjustment elements 1614 can couple one side of the headgear rear portion 1604 with one side of the interface coupling portion 1602. The pair of adjustment elements 1614 one each side are coupled to the headgear rear portion 1604 at spaced locations. For example, one of the adjustment elements 1614 is coupled to the headgear rear portion 1604 at or near a portion of the top strap 1608 and the other of the adjustment elements 1614 is coupled the headgear rear portion 1604 at or near a portion of the rear strap 1610. In the illustrated arrangement, the upper adjustment elements 1614 are coupled to forward extensions of the headgear rear portion 1604 that extend in a forward direction from a portion of the top strap 1608 at or near a location above the user's ear. The lower adjustment elements 1614 are coupled to ends of the rear strap 1610 of the headgear rear portion 1604.

The adjustment elements 1614 are adjustable in length between a retracted length and an extended length. In some configurations, the adjustment elements 1614 cooperate to provide all or substantially all of the adjustment of a circumference of the headgear assembly 1600. Each of the adjustment elements 1614 can also include an elastic element or biasing arrangement that biases the adjustment element 1614 toward one of the retracted or extended lengths. Preferably, the adjustment elements 1614 are biased toward a retracted length, such that the headgear assembly 1600 is biased toward its smallest circumference. Such an arrangement permits the headgear assembly 1600 to be extended and then automatically retract to fit the particular user under the biasing force of the elastic element or other biasing arrangement of the adjustment element(s) 1614. In addition, preferably, the adjustment elements 1614 define a hard stop at a maximum extended length to limit extension of the headgear 1600 and define a maximum circumference of the headgear 1600.

In some configurations, each of the adjustment elements 1614 comprise a braided element, which can extend or retract in length. The braided element can comprise one or more elastic elements in parallel with the braided element. The elastic elements can be separate from the braided element or incorporated in the braided element. In some configurations, the elastic elements are contained in internal spaces between filaments of the braided element. An example of suitable braided elements is described in connection with FIGS. 46-54 of Applicant's patent application no. PCT/NZ2014/000074. However, other suitable constructions or arrangements can also be used. Alternatively, elastic element(s) or biasing element(s) can be located within the interface coupling portion and can interact with the core members to pull the core members into the interface coupling portion.

The interface coupling portion 1602 of the headgear assembly 1600 can extend between the pair of adjustment elements 1614 that comprise the circumference adjusting portion 1606. In some configurations, the interface coupling portion 1602 can be relatively rigid. In some configurations, the interface coupling portion 1602 is coupled directly to the adjustment elements 1614. As described above, the interface coupling portion 1602 can facilitate connection of the headgear assembly 1600 to an interface. However, the interface coupling portion 1602 can also accommodate at least a portion of one or more directional locks 1616. In the illustrated arrangement, two pair of directional locks 1616 is provided, with one directional lock 1616 associated with each one of the adjustment elements 1614. Portions (e.g., housings 1618) of the directional locks 1616 can be located at each end of the interface coupling portion 1602. In some configurations, a core member 1620 associated with each of the directional locks 1616 is coupled to the headgear rear portion 1604, extends along or through the adjustment element 1614, through the housing 1618 of the directional lock 1616 and into a collection space 1622. The collection space 1622 can be defined by a collection tube or conduit, which can be a separate member from or can be incorporated into the interface coupling portion 1602. The housing 1620 of the directional lock 1616 can comprise one or more members or elements (e.g., lock washers or lock jaws) that interact with the core member 1618 to selectively allow retraction of the headgear assembly 1600 or lock the headgear assembly 1600 in a particular circumference and inhibit or prevent extension of the headgear at least at forces below the yield force provided by of the directional lock(s). Additional particulars of the operation of the directional locks 1616 are described above and in Applicant's patent application no. PCT/NZ2014/000074.

In the illustrated arrangement, the directional locks 1616 on each side of the interface coupling portion 1602 are vertically stacked or positioned side-by-side. Although the directional locks 1616 are illustrated as separate units, in some configurations portions of the directional locks 1616 can be integrated. For example, a single housing could contain individual lock elements that interact with the separate core members of each adjustment element.

The interface coupling portion 1602 can be curved and the collection spaces 1622 (e.g., defined by collection tubes or channels) can be curved along with the interface coupling portion 1602. In the illustrated arrangement, a center portion of the interface coupling portion 1602 is located above end portions of the interface coupling portion 1602. Furthermore, when viewed from the front, side portions of interface coupling portion 1602 curve downwardly from the center portion. Thus, the interface coupling portion 1602 can complement or correspond to the shape of a body or shell portion of the full face mask interface 1650. The center portion of the interface coupling portion 1602 can be located above an elbow or other conduit connector of the mask 1650. Similarly, the interface coupling portion 1602 can be configured to complement or correspond to the shape of a body or shell portion of the nasal mask interface 1660. The center portion of the interface coupling portion 1602 can be located above an elbow or other conduit connector of the nasal mask 1660. The interface coupling portion 1602 can be configured to complement or correspond to the shape of a body of the nasal pillows/prongs mask 1670. The center portion of the interface coupling portion 1602 can be located above an elbow or other conduit connector of the nasal pillows/prongs mask 1670. In some configurations, the interface coupling portion 1602 can be located between the elbow or other conduit connector and the pillows/prongs of the nasal pillows/prongs mask 1670.

Figure 60:
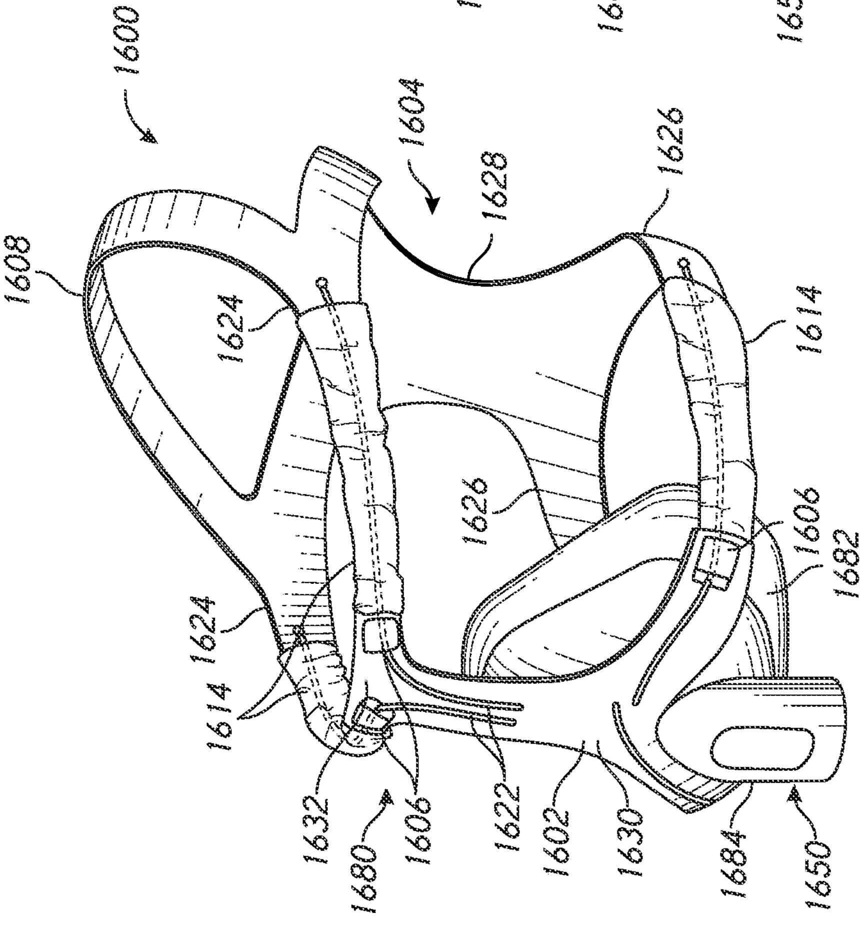
FIG. 60 illustrates an exemplary headgear and interface assembly with a T-piece.

FIG. 60 illustrates an interface assembly 1680 that is similar in many respects to other interface assemblies disclosed herein, such as the interface assemblies of FIGS. 37-53 and FIGS. 57-59. The interface assembly 1680 of FIG. 60 comprises a headgear assembly 1600 and an interface in the form of a full face mask 1650 or nasal mask. The headgear assembly 1600 generally comprises a headgear rear portion 1604, a length or circumference adjusting portion 1606 and an interface coupling portion 1602. The headgear 1600 of FIG. 60 is described in the context of the differences relative to the interface assemblies of FIGS. 37-53 and FIGS. 57-59. Features or details not described can be the same as or similar to corresponding features or details of the interface assemblies of FIGS. 37-53, FIGS. 57-59, other interface assemblies disclosed herein or in Applicant's Application No. PCT/NZ2014/000074 or can be of any other suitable arrangement.

The headgear assembly 1600 of FIG. 60 can be described as or categorized as a two retention plane, parallel headgear type. The illustrated headgear rear portion 1604 comprises a top strap 1608, a pair of upper straps 1624 and a pair of lower straps 1626. The headgear rear portion 1604 comprises a vertically-elongated intermediate rear portion 1628 that extends between and couples the upper straps 1624 and the lower straps 1626. The illustrated interface coupling portion 1602 is in the form of a support frame 1630 for the shell portion 1682 of the full face mask or nasal mask. The shell portion 1682 and the elbow 1684 or other conduit connector (collectively referred to as the "elbow") can be secured, directly or indirectly, to the support frame 1630 by any suitable arrangement. For example, the shell portion 1682 and the elbow 1684 can be separately coupled to the support frame 1630 (directly or indirectly), the shell portion 1682 can be directly coupled to the frame 1630 and the elbow 1684 can be coupled to the shell portion 1682 or the elbow 1684 can be directly coupled to the frame 1630 and the shell portion 1682 can be coupled to the elbow 1684.

In the illustrated arrangement, the interface coupling portion or support frame defines a forehead rest or T-piece 1632. The upper pair of adjustment elements 1614 that comprise the circumference adjusting portion 1606 can be coupled to the T-piece 1632 such that the upper adjustment elements 1614 are positioned above the user's eyes and extend above the user's ears. The lower pair of adjustment elements 1614 that comprise the circumference adjusting portion 1606 can be coupled to a lower portion of the support frame 1630 (directly or through another member, such as the shell) such that the lower adjustment elements 1614 are positioned below the user's eyes and ears. The collection spaces 1622 (e.g., defined by collection tubes or channels) for the upper adjustment elements 1614 can curve and extend downwardly along the T-piece 1632 toward the elbow. The upper directional locks 1616 can be carried by the T-piece 1632. The lower directional locks 1616 can be carried (directly or indirectly) by a lower portion of the support frame 1630.

The micro-adjustment capability provided by the headgear assembly or interface assembly 1680 of FIG. 60 is particularly advantageous in a T-piece configuration because it allows for small adjustments of the fit around the bridge of the user's nose, which can be a particularly sensitive region, to be accomplished quickly and easily. Although each connection between the headgear rear portion 1604 and the interface coupling portion 1602 or interface is illustrated as an automatic adjustment arrangement, in some configurations a combination of automatic adjustment and manual adjustment arrangements could be used. For example, upper connections (e.g., to the T-piece 1632) could be manually adjustable (such as hook-and-loop fastened straps) and the lower connections could be automatically adjustable. With such an arrangement, the upper connections could be set and maintained in position throughout multiple fitting cycles with the lower connections providing all of the elongation necessary for donning and removal ("doffing") of the headgear assembly or interface assembly 1600. Such an arrangement could provide some of the advantages of automatic adjustment at a lower price point, for example. Other suitable combinations could also be used, such as lower manual adjustment and upper automatic adjustment or manual adjustment on one side and automatic adjustment on the opposite side.

Figure 61:
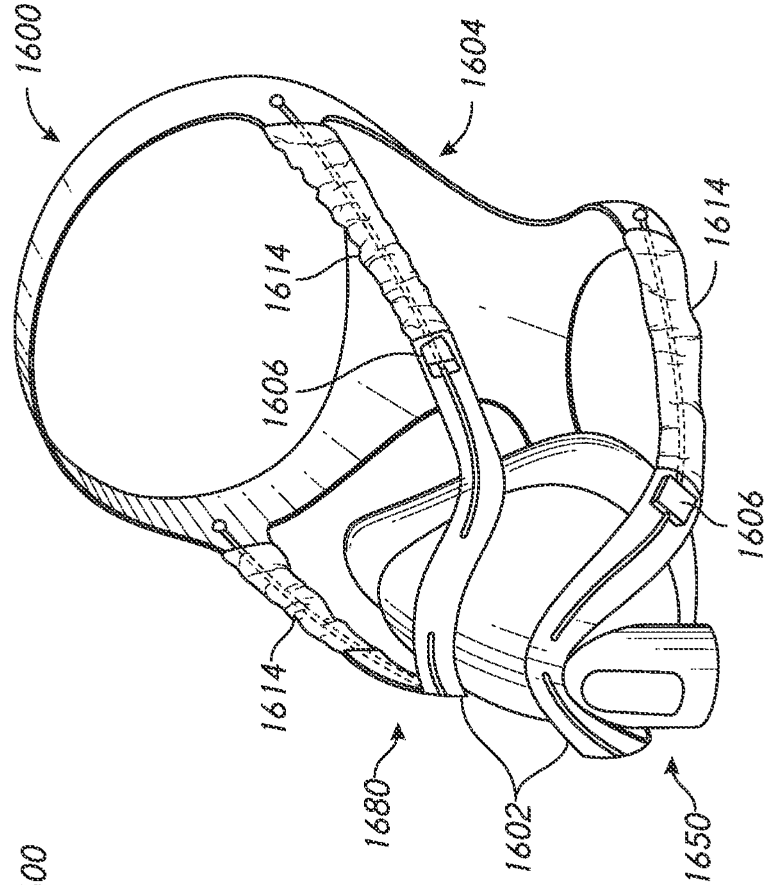
FIG. 61 illustrates an exemplary headgear and interface assembly without a T-piece.

FIG. 61 illustrates an interface assembly 1680 that is similar in many respects to other interface assemblies disclosed herein, such as the interface assemblies of FIGS. 37-53, FIGS. 57-59 and FIG. 60. The headgear 1600 of FIG. 61 is described in the context of the differences relative to the interface assemblies of FIGS. 37-53, FIGS. 57-59 and FIG. 60. Features or details not described can be the same as or similar to corresponding features or details of the interface assemblies of FIGS. 37-53, FIGS. 57-59, FIG. 60, other interface assemblies disclosed herein or in Applicant's Application No. PCT/NZ2014/000074 or can be of any other suitable arrangement.

The interface assembly 1680 of FIG. 61 comprises a headgear assembly 1600 and an interface in the form of a full face mask 1650 or nasal mask. The headgear assembly generally comprises a headgear rear portion 1604, a length or circumference adjusting portion 1606 and an interface coupling portion 1602. However, unlike the interface assembly of FIG. 60, the interface assembly 1680 of FIG. 61 does not include a forehead rest or T-piece 1632. As a result, each of the upper pair of adjustment elements 1614 connects to the interface coupling portion 1602 or interface at a lower position relative to the interface assembly 1680 of FIG. 60. For example, the upper adjustment elements 1614 can pass generally along the cheeks and below the eyes of the user.

The headgear assembly 1600 of FIG. 61 can be described as or characterized as a two retention plane, separated/angle headgear type. The upper and lower adjustment elements 1614 are spaced from one another on the mask 1650 to provide a retention force to the mask 1650 at spaced vertical locations, which can provide stability to the mask 1650. The headgear assembly 1600 can be coupled to the mask 1650 by separate interface coupling portions 1602, each of which can be substantially similar to the interface coupling portion 1602 described in connection with FIGS. 57-60. One of the interface coupling portions 1602 can be located on a lower portion (e.g., a lower half) of the mask 1650 and the other of the interface coupling portions 1602 can be located on an upper portion (e.g., an upper half) of the mask 1650. The lower interface coupling 1602 can pass above the elbow or other conduit connector. In some configurations, the upper and lower interface coupling portions 1602 could be coupled to one another or integrated with one another. For example, a bridge portion could extend between and connect the upper and lower interface coupling portions 1602. The bridge portion could be separate from or unitary with one or both of the interface coupling portions.

Figure 62:
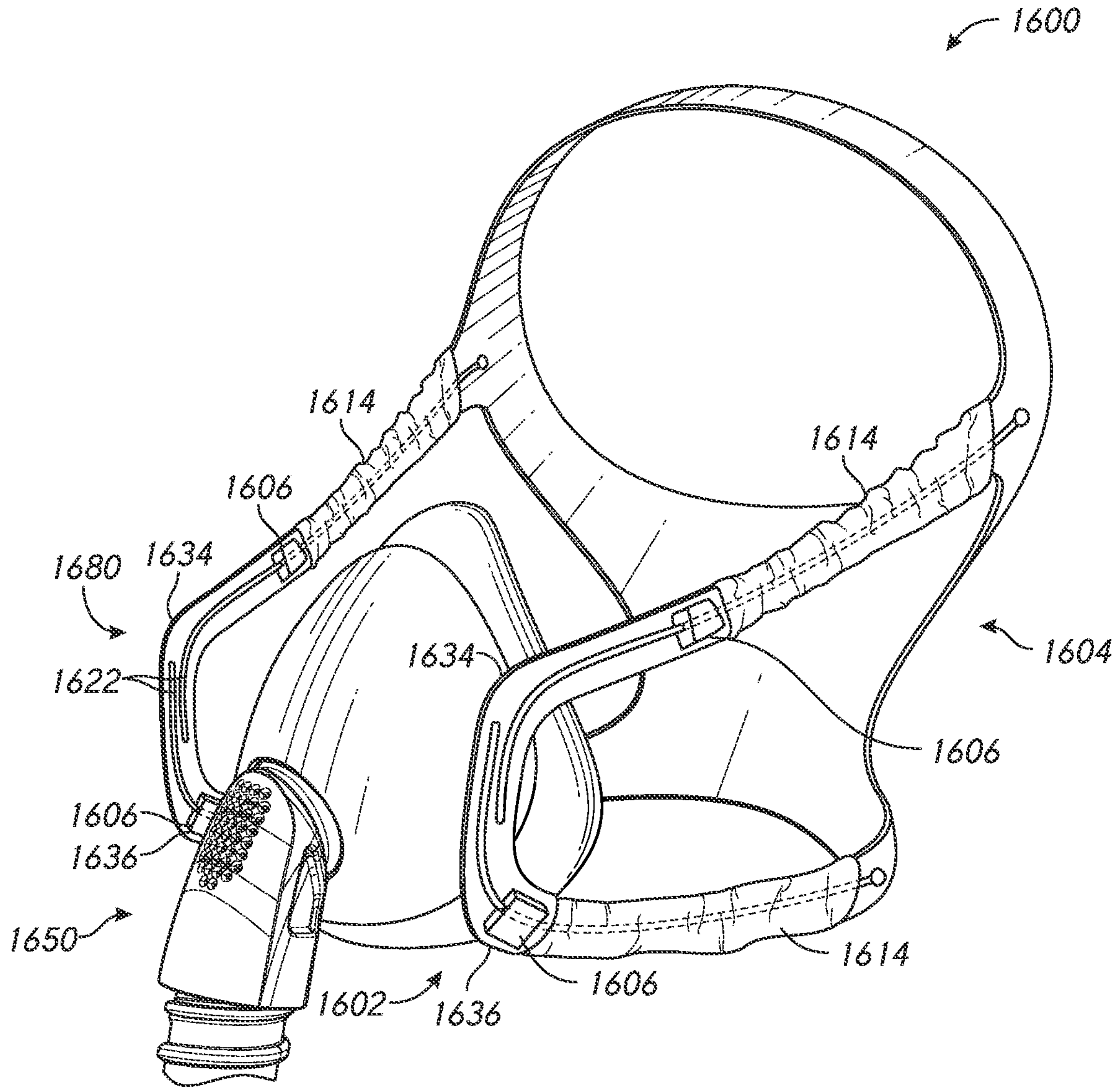
FIG. 62 illustrates an exemplary headgear and interface assembly with an interface coupling portion removably attached to an interface.

FIG. 62 illustrates an interface assembly 1680 that is similar in many respects to other interface assemblies disclosed herein, such as the interface assemblies of FIGS. 37-53, FIGS. 57-59, FIG. 60 and FIG. 61. The headgear 1600 of FIG. 62 is described in the context of the differences relative to the interface assemblies of FIGS. 37-53, FIGS. 57-59, FIG. 60 and FIG. 61. Features or details not described can be the same as or similar to corresponding features or details of the interface assemblies of FIGS. 37-53, FIGS. 57-59, FIG. 60, FIG. 61, other interface assemblies disclosed herein or in Applicant's Application No. PCT/NZ2014/000074 or can be of any other suitable arrangement.

The interface assembly 1680 of FIG. 62 comprises a headgear assembly 1600 and an interface in the form of a full face mask 1650 or nasal mask, for example. The headgear assembly 1600 generally comprises a headgear rear portion 1604, a length or circumference adjusting portion 1606 and an interface coupling portion 1602. However, unlike the interface assembly 1680 of FIGS. 60 and 61, for example, the interface coupling portions 1602 of the interface assembly 1680 of FIG. 62 do not extend between adjustment elements on opposite sides of the interface assembly 1680 or headgear assembly 1600. Instead, the interface coupling portions 1602 couple the adjustment elements 1614 on the same side of the interface assembly 1680 or headgear assembly 1600. That is, each of the pair of interface coupling portions 1602 couple to one another the upper and lower adjustment elements 1614 of one side of the interface assembly 1680 or headgear assembly 1600.

In the illustrated arrangement, the interface coupling portions 1602 are generally U-shaped members having an upper end portion 1634 coupled to the upper adjustment element 1614 and a lower end portion 1636 coupled to the lower adjustment element 1614. A curved portion of the interface coupling portion 1602 extends between the upper and lower end portions 1634, 1636. The directional lock 1616 for the upper and lower adjustment elements 1614 can be carried by the respective upper and lower end portions 1634, 1636. The collection spaces 1622 (e.g., defined by collection tubes or channels) can curve along the central curved body portion of the interface coupling portion 1602 and, in some configurations, may overlap one another.

In the arrangement of FIG. 62, the headgear assembly 1600 itself may not define an entire closed perimeter. Rather, the interface 1650 may form a portion of the closed perimeter and, thus, a portion of the circumference or perimeter length of the interface assembly 1680. Advantageously, such an arrangement allows for the interface assembly 1680 to be optionally configured have the closed perimeter quickly and easily opened for donning or doffing of the interface assembly 1680. That is, one (or both) of the interface coupling portions 1602 can be removably attached to the interface 1650 (such as by one or more clips) such that one (or both) of the interface coupling portions 1602 can be disconnected and the closed perimeter can be opened. In some configurations, an automatic adjustment mechanism(s) may be provided on only one side of the interface assembly. Similarly, other interface assemblies or headgear assemblies disclosed herein or in Applicant's Application No. PCT/NZ2014/000074 could be of a single-sided or asymmetric arrangement in which the automatic adjustment mechanism(s) may be provided on only one side.

Figure 65:
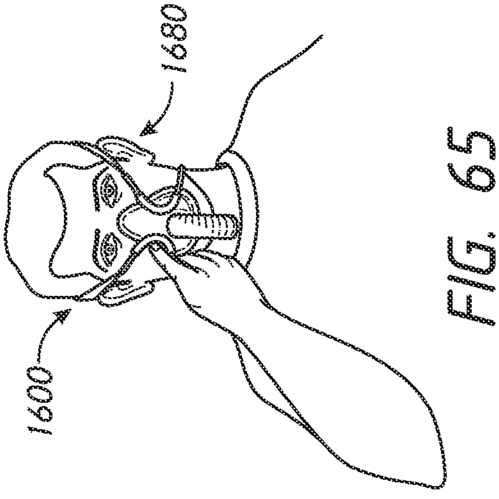
FIG. 65 illustrates a third position when donning the exemplary interface assembly of FIG. 62.
Figure 64:
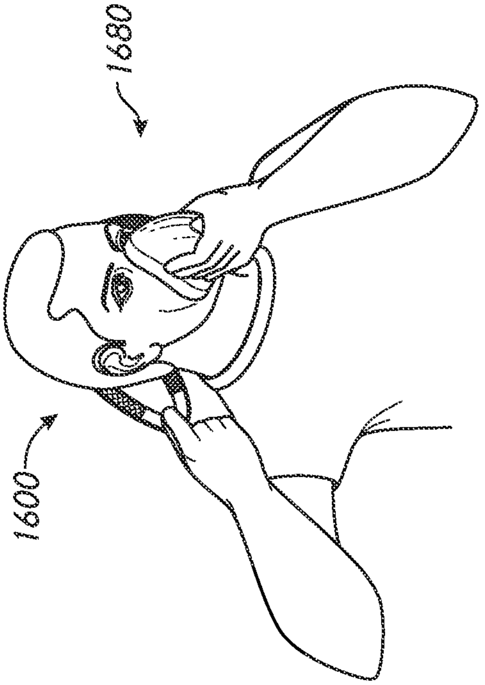
FIG. 64 illustrates a second position when donning the exemplary interface assembly of FIG. 62.
Figure 63:
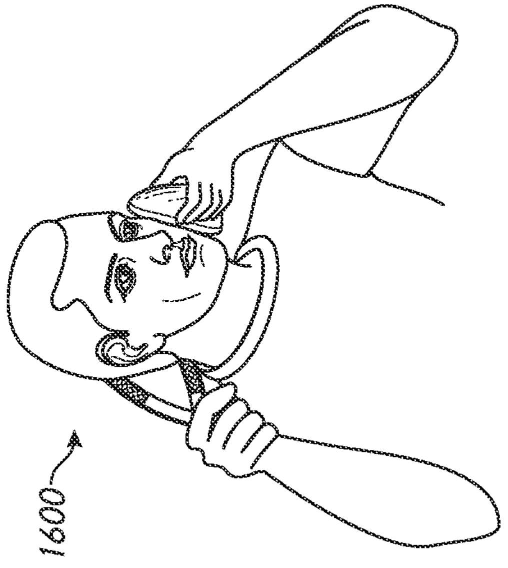
FIG. 63 illustrates a first position when donning the exemplary interface assembly of FIG. 62.

FIGS. 63-65 illustrate a series of discrete positions or steps of donning the interface assembly 1680 of FIG. 62. FIG. 63 illustrates a user placing the interface with interface coupling portion 1602 attached on one side of the head, looping the interface assembly 1600 around the back of the head and pulling the disconnected interface coupling portion 1602 toward the face. In FIG. 64, the interface is brought toward the appropriate position on the face and the disconnected interface coupling portion 1602 is brought toward the interface 1680. FIG. 65 illustrates the interface 1680 in place on the user's face and the user reconnecting the loose or disconnected interface coupling portion 1602 to close the perimeter loop. A portion or all of the movement between FIGS. 64 and 65 may require overcoming of the yield force of the directional locks, as described above. To remove or doff the interface assembly 1680, the procedure can be reversed.

Figure 67:
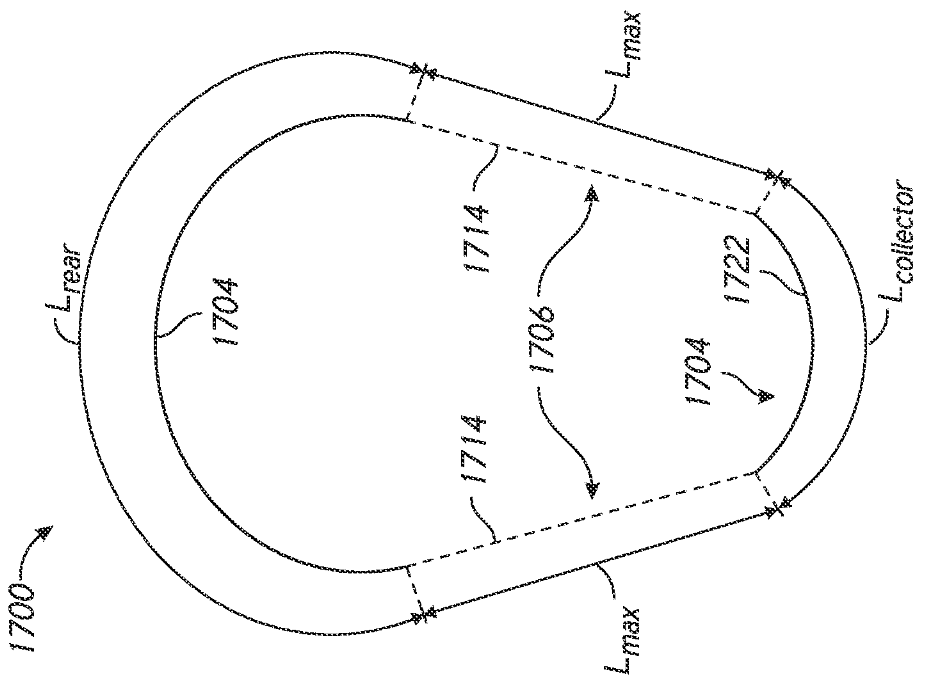
FIG. 67 illustrates a perimeter of an adjustable interface assembly or headgear assembly at a maximum length.
Figure 66:
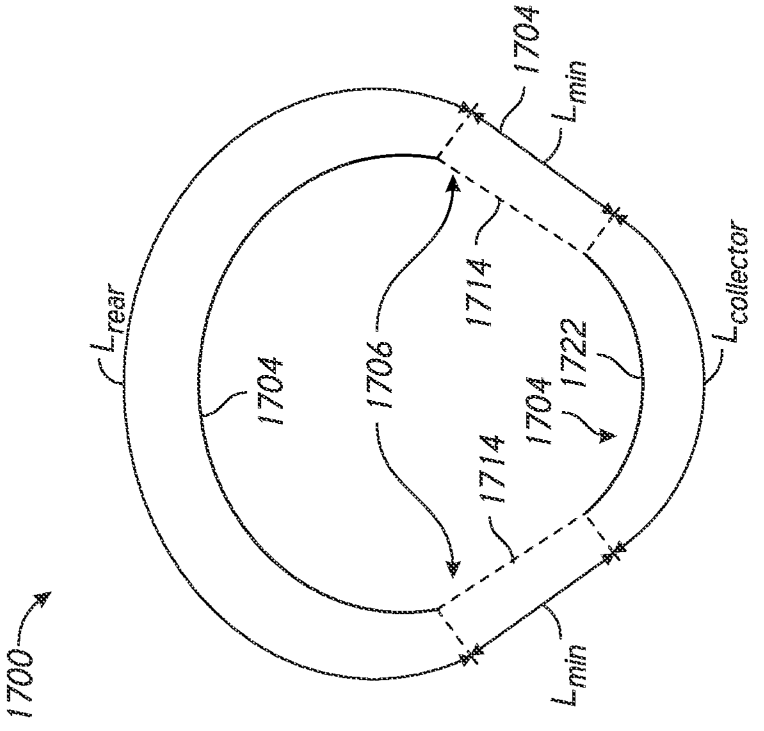
FIG. 66 illustrates a perimeter of an adjustable interface assembly or headgear assembly at a minimum length.

FIGS. 66 and 67 illustrate a perimeter of an automatically adjustable interface assembly or headgear assembly 1700 in a first position (e.g., a minimum perimeter length) and a second position (e.g., a maximum perimeter length), respectively. As described with respect to interface assemblies and headgear assemblies disclosed herein, the perimeter can comprise a length $L_{rear}$ defined by a headgear rear portion 1704. In some configurations, the length $L_{rear}$ can be zero. In other words, a fixed length headgear rear portion 1704 can be omitted and the rear section can be formed by a length adjusting portion or elastic component. In addition, one or more of the portions of the illustrated perimeter can be located in alternative locations or can be split into multiple portions.

The perimeter can also comprise a length $L_{elastic}$ defined by a circumference or length adjusting portion 1706, which in the illustrated arrangement is defined by a pair of elastic or adjustable elements 1714. However, in other configurations, the circumference or length adjusting portion 1706 could be defined by one elastic or adjustable element 1714 or more than two elastic or adjustable elements 1714, among other suitable arrangements. As described above, in some configurations the headgear rear portion 1704 defining the length $L_{rear}$ can be omitted and the length adjusting portion 1706 could extend the entire perimeter portion from one end of the interface coupling portion 1702 to the other end of the interface coupling portion 1702. In FIGS. 66 and 67, the $L_{elastic}$ lengths are labeled with the relative position indicators of minimum length $L_{min}$ and maximum length $L_{max}$, respectively.

The perimeter can further comprise a collector length $L_{collector}$, which can represent an individual or total available length of collection spaces 1722 that receive excess portions of the core elements of the directional lock arrangements. As described above, the collector spaces 1722 do not necessarily extend from one adjustable element 1714 to the other adjustable element 1714 and thereby define a physical section of the perimeter length. For example, in the interface assembly 1680 of FIG. 62, the collector spaces 1622 do not extend between opposite adjustable elements 1614. Thus, in a physical sense, the interface coupling portion(s) 1602, interface 1650 or other structures can define a portion of the perimeter length. However, in a conceptual sense, the elastic length(s) $L_{elastic}$ (minimum length $L_{min}$ and maximum length $L_{max}$) define a length adjustable portion of the perimeters of FIGS. 66 and 67, with the remaining portions (headgear rear portion length $L_{rear}$ and collector length $L_{collector}$) being of a fixed length.

In the illustrated arrangement, the perimeter length can comprise or be defined by the sum of the headgear rear portion length $L_{rear}$, the collector length $L_{collector}$ and the total elastic length $L_{elastic}$, which in the illustrated configuration is two times (2×) $L_{elastic}$ because two equal length adjustable elements 1714 are provided. The total elastic length $L_{elastic}$ at any point in time or for any particular position of the interface or headgear assembly 1700 is equal to or somewhere between the minimum length $L_{min}$ and maximum length $L_{max}$. As described herein, the length of each core member $L_{core}$ preferably is greater than or equal to the maximum length $L_{max}$ of each adjustable element and, therefore, the total core member length $L_{core}$ is preferably greater than or equal to the total maximum length $L_{max}$ such that the headgear assembly can be expanded to its maximum perimeter length without pulling the core member(s) completely through the directional locking element(s). In other words, it is preferable that a portion of the core member(s) is available for engagement by the directional locking element(s) when the headgear assembly is expanded to its maximum perimeter length.

In addition, it is preferable that the collector length $L_{collector}$ is sufficient to accommodate the total excess or unutilized portion(s) of the core members at the minimum and maximum perimeter lengths of the headgear assembly. Thus, in at least some configurations, the individual or total core length $L_{core}$ is less than or equal to the individual or total maximum length $L_{max}$ plus the individual or total collector length $L_{collector}$. In at least some configurations, the individual or total core length $L_{core}$ is less than or equal to the individual or total minimum length $L_{max}$ plus the individual or total collector length $L_{collector}$. In some configurations, the individual or total maximum length $L_{max}$ is less than or equal to the individual or total core length $L_{core}$, which is less than the individual or total maximum length $L_{max}$ plus the individual or total collector length $L_{collector}$. The length of the directional lock mechanism(s) is not specifically shown within the perimeter, but could be considered to form a portion of any of the length of the headgear rear portion $L_{rear}$, elastic length $L_{elastic}$ or collector length $L_{collector}$. In any event, the length of the directional lock mechanism(s) can be accounted for in determining the minimum length of the core $L_{core}$.

In at least some configurations, the individual or total core length $L_{core}$ can be greater than the sum of the individual or total elastic length $L_{elastic}$ and the collector length $L_{collector}$. In at least some configurations, the individual or total core length $L_{core}$ can be between the individual or total maximum length $L_{max}$ and the headgear rear portion length $L_{rear}$, or can be equal to either one of the individual or total maximum length $L_{max}$ and the headgear rear portion length $L_{rear}$.

The perimeters of FIGS. 66 and 67 can be representative of an actual perimeter of an interface assembly or a headgear assembly. That is, the perimeters of FIGS. 66 and 67 could represent the physical construction of a single retention plane interface or headgear assembly or a physical construction of one retention plane in a multi-retention plane interface or headgear assembly. However, as described, the perimeters of FIGS. 66 and 67 can be representative of other interface or headgear types in a conceptual sense. The illustrated perimeters could represent a single retention plane (e.g., upper or lower) of a multiple retention plane headgear type or could represent an average of two or more retention planes of a multiple retention plane headgear type, for example and without limitation.

FIGS. 68A to 68D show an embodiment of a directional lock comprising a housing 1810, a first and a second lock element (e.g., washer 1820, 1822) and a core member 1830. The housing comprises a first and a second chamber 1840, 1842 wherein the first and second chambers 1840, 1842 are configured to house the first and second lock washers 1820, 1822, respectively. In the illustrated arrangement, the first and second chambers 1840, 1842 are separated by an internal wall 1812 of the housing 1810. However, in other arrangements, the first and second chambers 1840, 1842 are not necessarily physically separate spaces, but can be portions of a chamber. The housing 1810 has two end walls 1814, which along with the internal wall 1812, have an elongate core opening 1860 for the core member 1830 pass through. The core openings 1860 are substantially aligned with each other. The core opening 1860 of the end wall 1814 shown on the right side of the figures is larger than the core opening of the internal wall 1812 and the end wall 1814 shown on the left of the figures. This allows for manipulation of the path of the core member 1830 through the housing 1810. The first and second chambers 1840, 1842 are each delimited by the internal wall 1812, one of the end walls 1814 and a pair of side walls 1816; wherein the side walls 1816 extend between the end walls 1814 of the housing 1810. The first and second chambers 1840, 1842 are configured to be open at one or both of a top and a bottom of the housing 1810.

Each of the first and second chambers 1840, 1842 has a pair of washer retainers 1850 that are aligned on opposing side walls 1816 of the housing 1810. Each pair of washer retainers 1850 is configured to pivotally retain one of the first or second lock washers 1820, 1822 within the respective first or second chamber 1840, 1842. The washer retainers comprise a circular bush 1852 and an elongate slot 1854, wherein circular bushes 1852 intersect with the bottom of the housing such that an entrance is formed. The entrance is configured to allow the first and/or second lock washers 1820, 1822 to be received into the washer retainers 1850. The slot 1854 extends radially from the circular bush 1852 towards the top of the housing 1810.

The first and second washers 1820, 1822 comprise a cylindrical shaft 1824 and an arm 1826 that extends from the shaft 1824. The cylindrical shaft 1824 is substantially the same width W, as the housing 1810 and the arm 1826 is narrower to fit within the first and second chambers 1840, 1842. In the illustrated arrangement, the arm 1826 comprises a first section 1872 and a second section 1874, wherein the first section 1872 extends radially or perpendicularly from the cylindrical shaft 1824 and the second section 1874 extends at an obtuse angle from the end of the first section 1872. The first section 1872 of the arm 1826 of the first washer 1820 is shorter than the first section 1872 of the arm 1826 of the second washer 1822. The angle between the first and second sections 1872, 1874 of the arm 1826 of the first washer 1820 is greater than the corresponding angle of the second washer 1822. The angles can be selected such that the second section 1874 of one or both of the first and second washers 1820, 1822 lies substantially flat against the corresponding wall (e.g., internal wall 1812 and end wall 1814, respectively) of the housing 1810 in one position of the washers 1820, 1822. The second section 1874 of the arm 1826 comprises a centrally located circular aperture 1876 configured to receive the core member 1830. The first and second chambers 1840, 1842 differ in size according to the size of the washer that is to be housed within it, i.e. the first chamber 1840 is smaller than the second chamber 1842 because the first washer 1820 is smaller than the second washer 1822.

The cylindrical shafts 1824 of the first and second lock washers 1820, 1822 have a diameter substantially the same as that of the circular bushes 1852 of the washer retainer 1850, and are configured to be received and retained by the circular bush 1852 in a snap-fit configuration. The snap-fit configuration is provided by the entrance of the circular bush 1852 being narrower than the diameter of the cylindrical shaft 1824. The slots 1854 of the washer retainers 1850 are configured to allow the entrance to be flexed open to increase the ease with which the first and second lock washers 1820, 1822 can be pushed through the entrances and assembled to the housing 1810. Once assembled within the first and second chambers 1840, 1842 of the housing 1810, the first and second washers 1820, 1822 can pivot back and forward around a central axis that runs through the cylindrical shaft 1824.

Figure 68A:
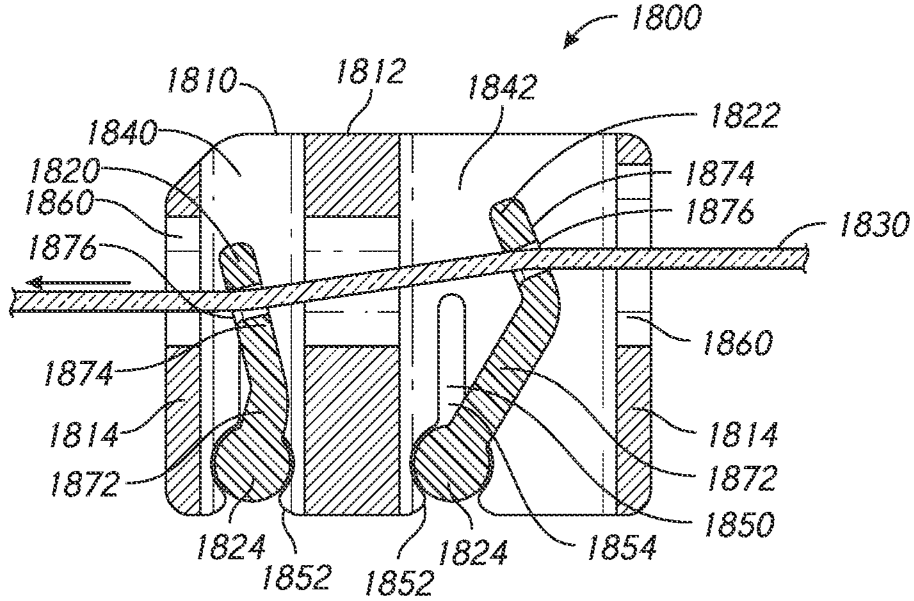
FIG. 68A is a cross-sectional view of a directional lock in a locked position.
Figure 68B:
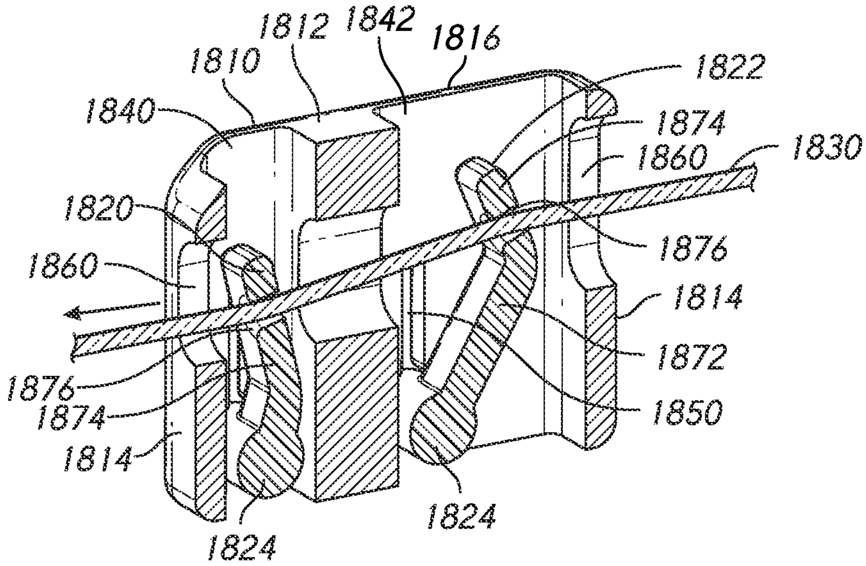
FIG. 68B is a perspective cross-sectional of the directional lock in FIG. 68A in the locked position.
Figure 68C:
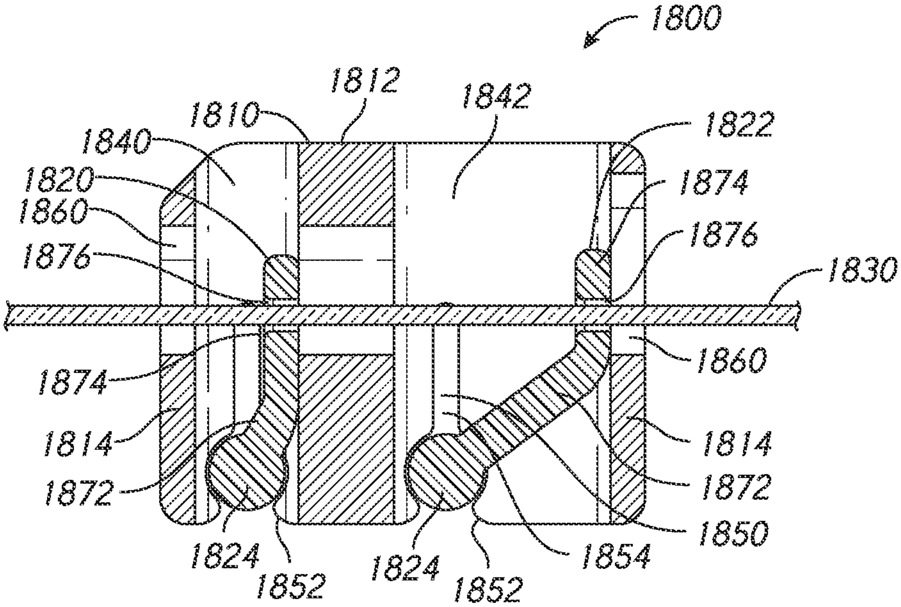
FIG. 68C is a cross-sectional view of the directional lock in FIG. 68A in the unlocked position.
Figure 68D:
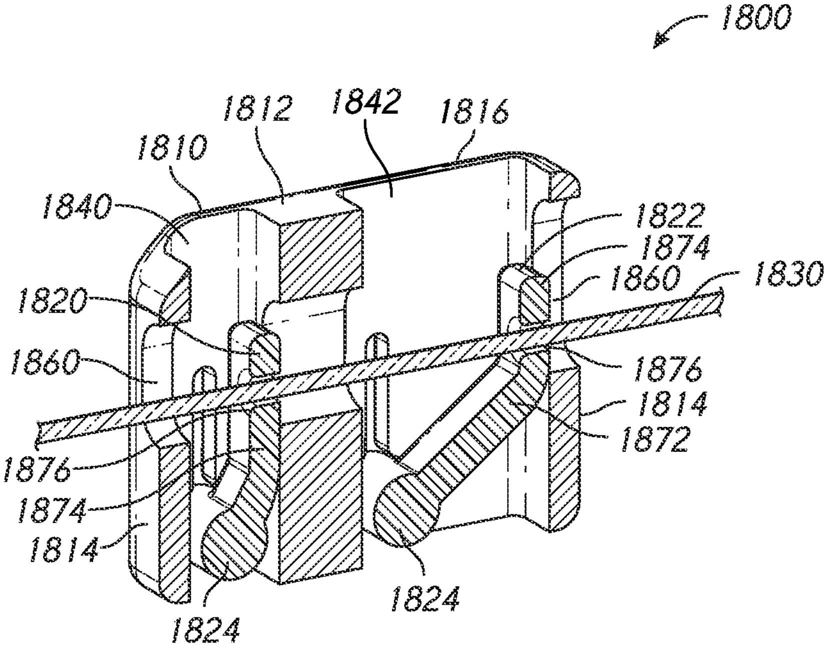
FIG. 68D is a perspective cross-sectional of the directional lock in FIG. 68A in the unlocked position.

The core member 1830 is configured to pass through the core openings 1860 of the housing 1810 and the apertures 1876 of the first and second washers 1820, 1822. Application of a tension force to the core member 1830 causes the first and second lock washers 1820, 1822 to pivot back and/or forward between a locked position and/or open position. FIGS. 68A and 68B show the directional lock in a locked configuration in which a force is applied to the core member 1830 in a direction towards the left side of the figure (as indicated by the arrow). The force applied to the core member 1830 in this configuration causes the first and second lock washers 1820, 1822 to pivot in an anti-clockwise direction, such that the path of the core member 1830 through the directional lock 1800 is non-linear or tortuous and movement of the core member 1830 is restricted. FIGS. 68C and 68D show the directional lock in an open configuration in which a force is applied to the core member 1830 in a direction towards the right side of the figure (as indicated by the arrow). In this configuration, the first and second lock washers 1820, 1822 are pivoted in a clockwise direction such that the circular apertures 1876 and core openings 1860 are aligned in a substantially straight line. This provides a smooth path for the core member 1830 to be pulled substantially freely through the directional lock 1800. Additional particulars of the operation of the directional locks 1800 are described above and in Applicant's patent application no. PCT/NZ2014/000074.

Figure 69A:
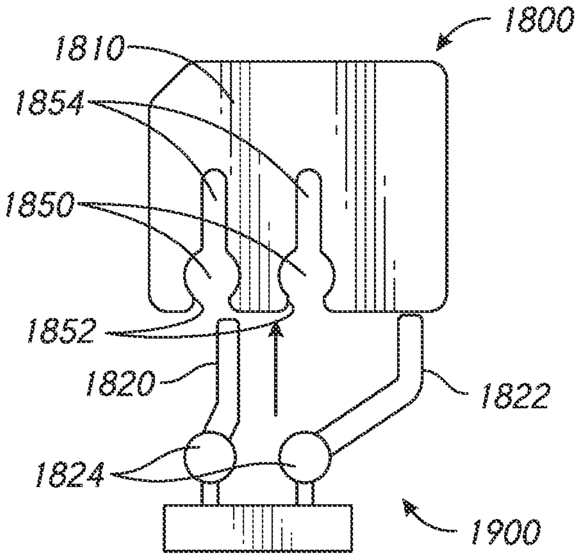
FIG. 69A is a view of a first assembly step for attaching lock washers to a housing of an exemplary directional lock.
Figure 69B:
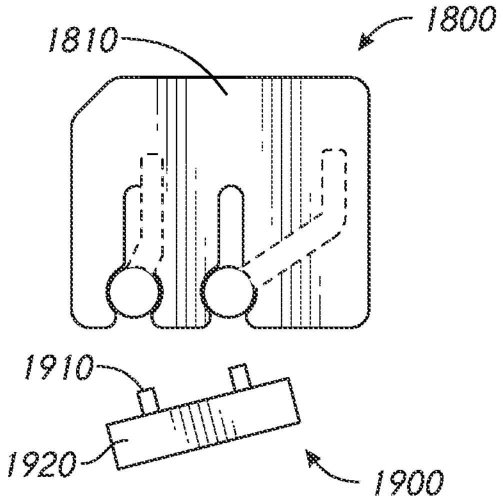
FIG. 69B is a view of a second assembly step for attaching lock washers to the housing of the exemplary directional lock of FIG. 69A.

FIGS. 69A-B show a non-limiting exemplary embodiment of a housing 1810 and first and second lock washer 1820, 1822. The first and second lock washers 1820, 1822 are configured to be moulded as a single component wherein they are connect by a runner and gate system 1900, as in known in the art. The runner and gate system is configured to be used as an assembly aid for the first and second lock washers 1820, 1822, wherein the runner and gate system 1900 can be gripped by a person or machine in order to align the first and second washers 1820, 1822 with the washer retainers 1850 of the housing 1810. A force (as shown by the arrow) can be applied to the lock washers 1820, 1822 through the gate and runner system 1900 to provide relative movement between the housing 1810 and the lock washers 1820, 1822. Such relative movement can be utilized to engage the first and second lock washers 1820, 1822 with the housing 1810 such that the cylindrical shafts 1824 of the lock washers 1820, 1822 are snap-fitted into the circular bush 1852 of the washer retainer 1850.

As shown in FIG. 69B, once the first and second lock washers 1820, 1822 are assembled within the housing 1810, the gate and runner system 1900 can be disconnected or broken away from the lock washers 1820, 1822. A force (shown by the arrow) can be applied to the gate and runner system 1900 in a direction that is substantially perpendicular to the direction in which the assembly force is applied (arrow in FIG. 69A) to detach the gate and runner system 1900 from the lock washers 1820, 1822. When the gate and runner system 1900 is detached, the lock washers 1820, 1822 remain assembled with the housing 1810. The gates 1910 of the gate and runner system 1900 can be designed to have a weak point that encourages them to break as close as possible to the cylindrical shaft 1824 of the lock washer 1820, 1822, such that the range of pivoting motion of the lock washer 1820, 1822 is not limited by excess gate material.

Figure 70A:
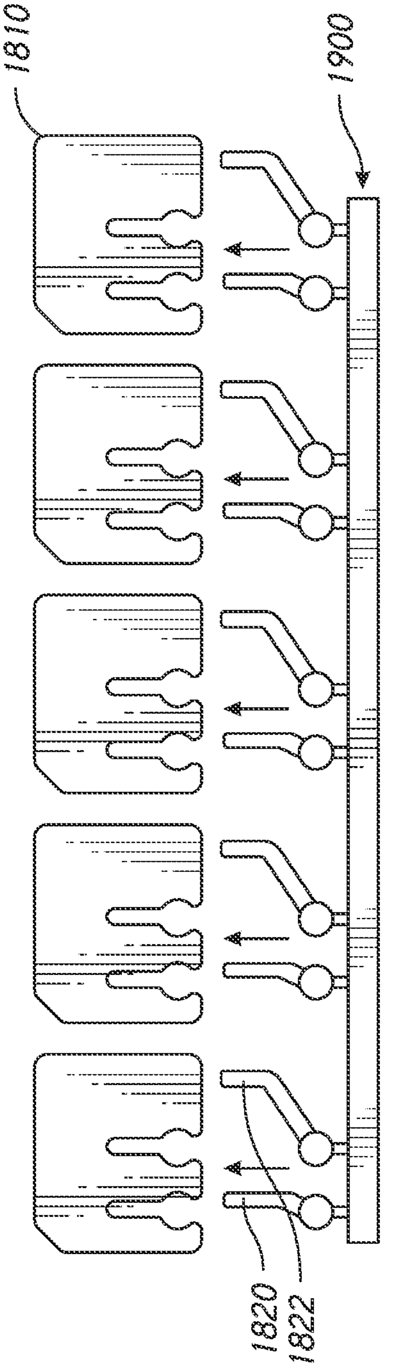
FIG. 70A is a view of a first assembly step for attaching lock washers to housings of a plurality of exemplary directional locks.
Figure 70B:
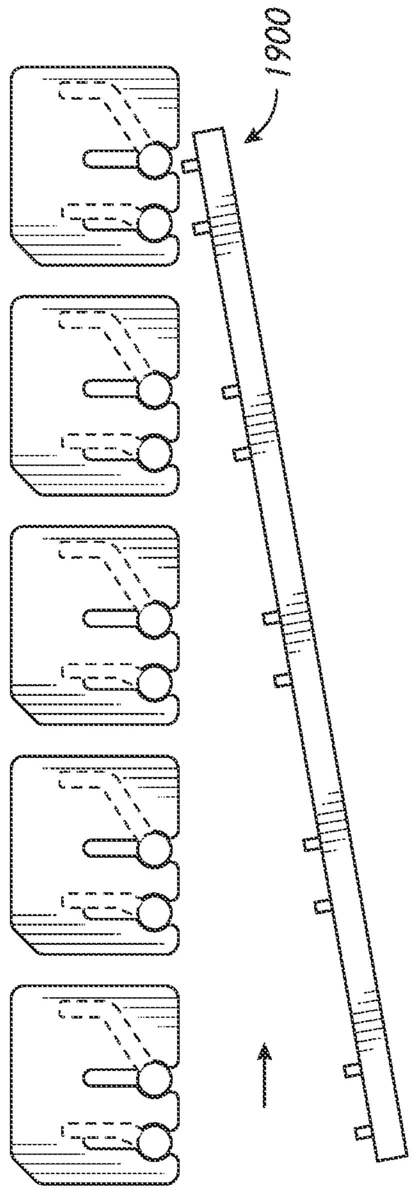
FIG. 70B is a view of a second assembly step for attaching lock washers to housings of the plurality of exemplary directional locks of FIG. 70A.

FIGS. 70A and 70B show an embodiment wherein multiple sets of first and second lock washers 1820, 1822 are moulded together on a single gate and runner system 1900. This configuration allows multiple directional locks 1820, 1822 to be assembled at once or sequentially, thus improving manufacturing efficiencies. To assemble the sets of lock washers 1820, 1822 to the housings 1810, the runner and gate system 1900 can be gripped by a person or machine in order to align the first and second washers 1820, 1822 with the washer retainers 1850 of each of the housings 1810. A force (as shown by the arrow) can be applied through the gate and runner system 1900 to engage the sets of first and second lock washers 1820, 1822 with the housings 1810 such that the cylindrical shafts 1824 of the lock washers 1820, 1822 are snap-fitted into the circular bushes 1852 of the washer retainers 1850.

Figure 71:
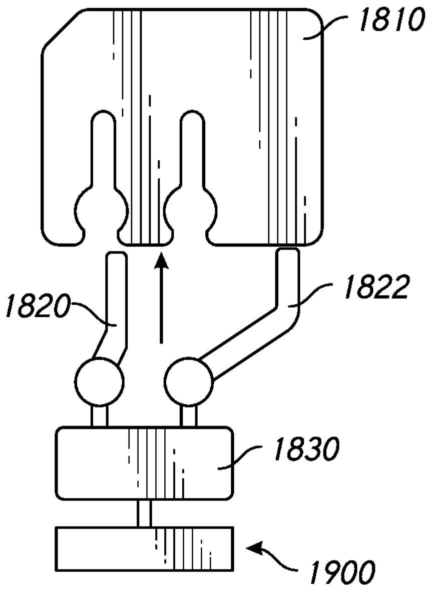
FIG. 71 is a view of an assembly step for attaching lock washers to a housing of an exemplary directional lock.

FIG. 71 shows a non-limiting exemplary configuration for assembling the first and second lock washers 1820, 1822 to the housing 1810 of a directional lock 1800. This configuration includes a grip portion or element, such as a grip tab 1930, that is used to align and apply an assembly force to the lock washers 1820, 1822. The grip tab 1930 is formed between the lock washers 1820, 1822 and the gate and runner system 1900 and can have a geometry specifically configured to be easily gripped by a person or a machine. In some configurations, the gate and runner system 1900 is configured to be removed from the grip tab 1930 during the moulding process. In a variation of this configuration (not shown) multiple pairs of first and second lock washers 1820, 1822 can be connected by a single grip tab 1930, which is then used to assemble the directional lock in a single action.

Figure 72:
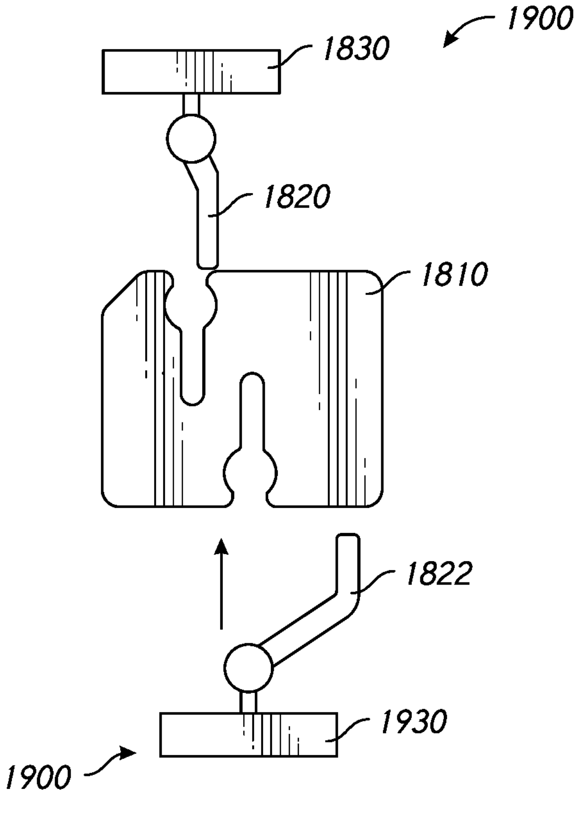
FIG. 72 is a view of an assembly step for attaching lock washers to a housing of an exemplary directional lock.

FIG. 72 shows a non-limiting exemplary embodiment of the direction lock. In this embodiment, the washer retainers 1850 are positioned in an opposing arrangement wherein the first washer retainer 1850 extends downwardly from the top of the housing and the second washer retainer 1850 extends upwardly from the bottom of the housing. The first and second lock washers 1820, 1822 are assembled to the housing 1810 in opposing directions. For example, a grip tab 1930 or the gate and runner system 1900 as described in relation to the embodiment of FIGS. 69*a* to 71 can be used to aid in the assembly of the lock washers 1820, 1822 to the housing 1810.

FIGS. 73-80 illustrate interfaces with headgear arrangements configured to allow the interface to be donned and doffed in the manner of a baseball cap. Preferably, the headgear arrangements do not include a strap that passes below the user's ear. Therefore, the interface with such as headgear arrangement can be fitted or donned by passing the interface over the user's head from above. The headgear arrangement could be positioned onto the rear of the user's head and then the interface arrangement rotated downward and the interface positioned on the user's face, or vice-versa. The headgear arrangements can include a portion forward of the user's ear, which can provide a mounting location for direction or indirect connection to the interface. In some configurations, the rear portion of the headgear arrangement is relatively rigid (e.g., to maintain an open shape when not on a user) and/or relatively inextensible.

Figure 73:
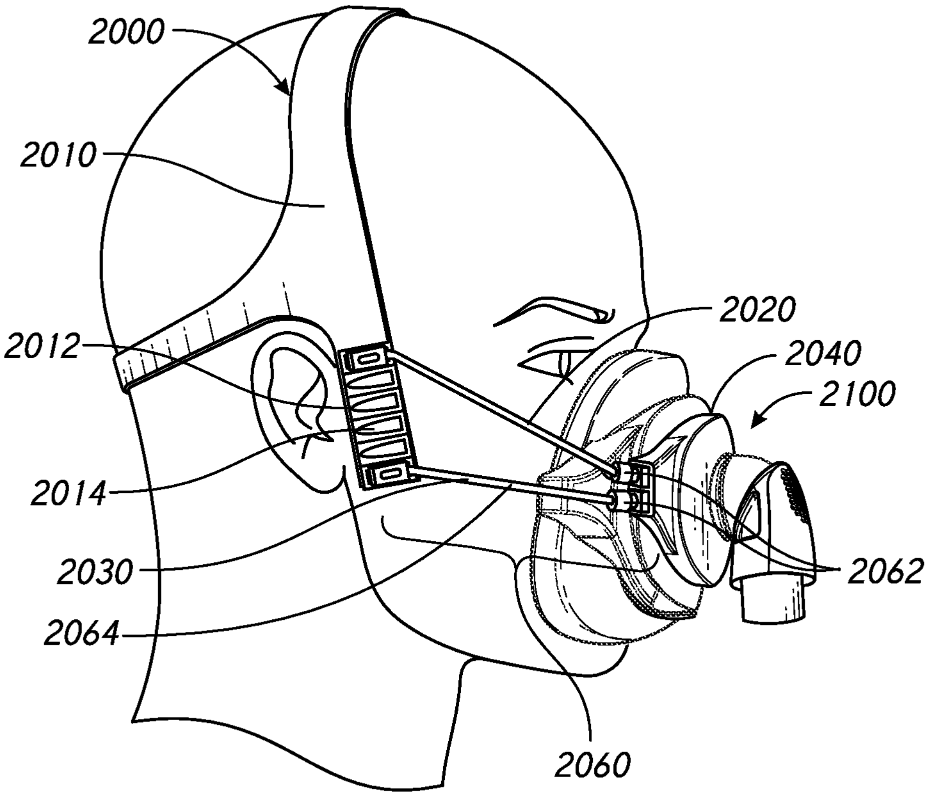
FIG. 73 is a side view of an exemplary full face mask without a forehead support.

FIG. 73 illustrates an alternate arrangement for a headgear system 2000 that is configured for use in combination with a full face mask 2100 that has no forehead support. However, the headgear system 2000 or portions thereof can also be used in combination with other types of interfaces, including interfaces having a forehead support, if desired. The full face mask 2100 is configured to seal around a user's nose and mouth, wherein it contacts the nasal bridge, cheeks and a lower lip or chin region. The headgear system 2000 comprises a headgear rear portion 2010, an upper retention plane 2020 and a lower retention plane 2030.

Preferably, the headgear rear portion 2010 engages the user's head and provides a relatively stable platform for connection of the interface, such as utilizing the interface coupling portion 2040 and the circumference adjusting portion (e.g., directional locking modules 2060). Thus, in at least some configurations, the headgear rear portion 2010 is substantially inelastic such that it holds its shape and effective length in response to applied forces within a range that is typical or expected for the intended application. In some configurations, the headgear rear portion 2010 can comprise a layer constructed from a relatively rigid material, such as a plastic material, coupled to one or more layers of a fabric material. Preferably, a fabric layer is provided at least on a user-contacting surface of the rigid material layer. In some configurations, a fabric layer is provided on each side of the rigid material layer. Furthermore, in some configurations, the rigid material layer can be formed between the material layers, such as by injection molding the rigid material into a space between two material layers within a mold. An example of such a headgear and a method of making such a headgear is disclosed in Applicant's U.S. Provisional Application No. 62/050,925, the entirety of which is incorporated by reference herein.

The headgear rear portion 2010 comprises an arm 2012 that extends in front of the user's ear. The arm 2012 comprises a plurality of vertically spaced connectors 2014 configured to provide a series of locations at which one or more directional locking modules 2060 may be connected. Full face masks are generally larger and heavier than the direct nasal masks of previous embodiments. As a result of this, the full face masks may require more than one retention plane to provide the desirable or required level of stability to achieve a substantially airtight seal with a user's face.

The two retention planes 2020, 2030 converge towards a single point on the side of or possibly forward of the full face mask 2100, wherein they may or may not intersect. The retention planes 2020, 2030 can be vertically spaced from one another, such that they are spaced apart further at the point where they connect with the headgear than the point where they connect with the mask. This provides some degree of stability to the interface. For example, an upper retention plane 2020 can pass from the top of the ear through or above the underside of the nose of the user and a lower retention plane 2030 can pass from the bottom of the ear to near or below the mouth of the user.

Each of the two retention planes 2020, 2030 can be provided by two directional locking modules 2060, wherein one is located on each side of the headgear system 2000. The directional locking modules 2060 each comprise a directional lock 2062 and an elastic portion 2064, which is connected to the directional lock 2062 at one end and one of the plurality of connectors 2014 at the other end. The angle of the retention planes 2020, 2030 can be adjusted by connecting the end of the elastic portion 2064 to a different connector 2014 on the headgear arm 2012. The illustrated full face mask 2100 does not include a forehead rest or "T-piece." However, in some configurations, a T-piece could be provided. If desired, additional headgear element(s) or strap(s) could couple a rear portion of the headgear to the T-piece of the mask.

Figure 74:
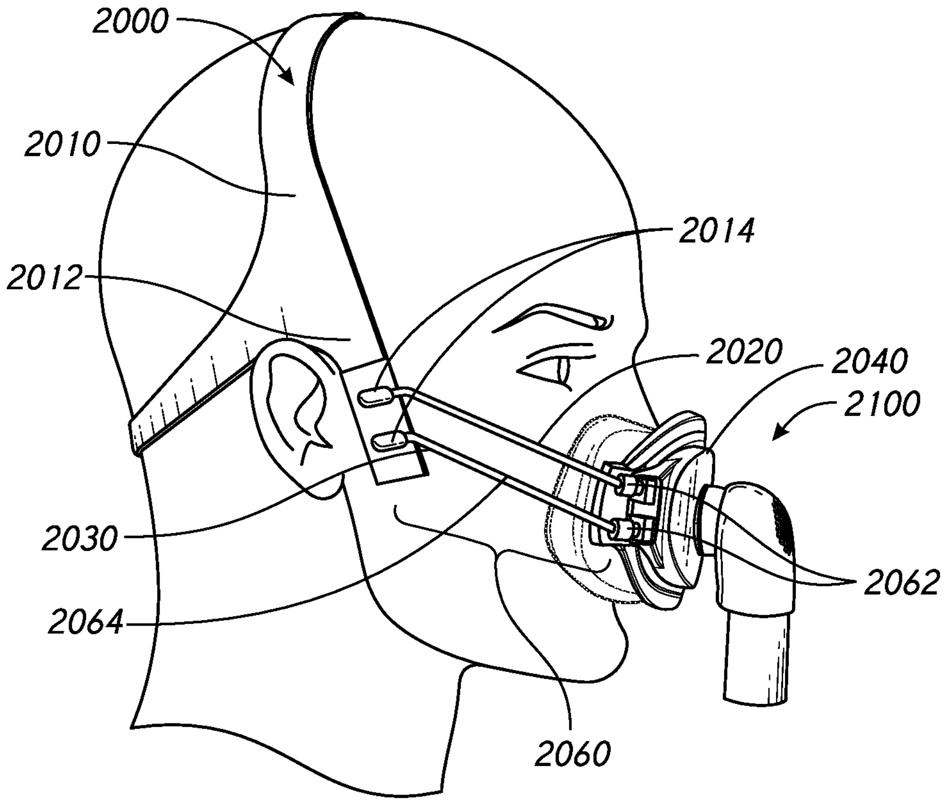
FIG. 74 is a side view of an another exemplary full face mask without a forehead support.

FIG. 74 illustrates a headgear system arrangement 2000 that comprises a headgear rear portion 2010 and two retention planes 2020, 2030 that are configured to secure a full face mask 2100 to a user's face. In this arrangement the full face mask 2100 is configured to seal on the underside of a user's nose and around their mouth, such that the nasal bridge is not contacted by the mask 2100. The different sealing locations, relative to the previous embodiment, require or at least make it desirable that the angles of the retention planes 2020, 2030 differ in order to apply forces to the mask in an optimal or desirable direction. In FIG. 74, the two retention planes 2020, 2030 are shown to be vertically spaced and attached to an arm 2012 of the headgear rear portion 2010 such that there is an upper retention plane 2020 and a lower retention plane 2030 that are substantially parallel to each other. The upper retention plane 2020 is more horizontal than the upper retention plane 2020 of the previous embodiment and sits lower down on the user's face. The angle of the retention planes 2020, 2030 may be adjustable via a plurality of connectors 2014, such as those shown in the embodiment of FIG. 73.

Each of the retention planes 2020, 2030 is shown to comprise a directional lock module 2060, which further comprises an elastic portion 2064 and a directional lock 2062. In a variation of this arrangement, each directional lock module 2060 may comprise more than one directional lock 2062.

Figure 75:
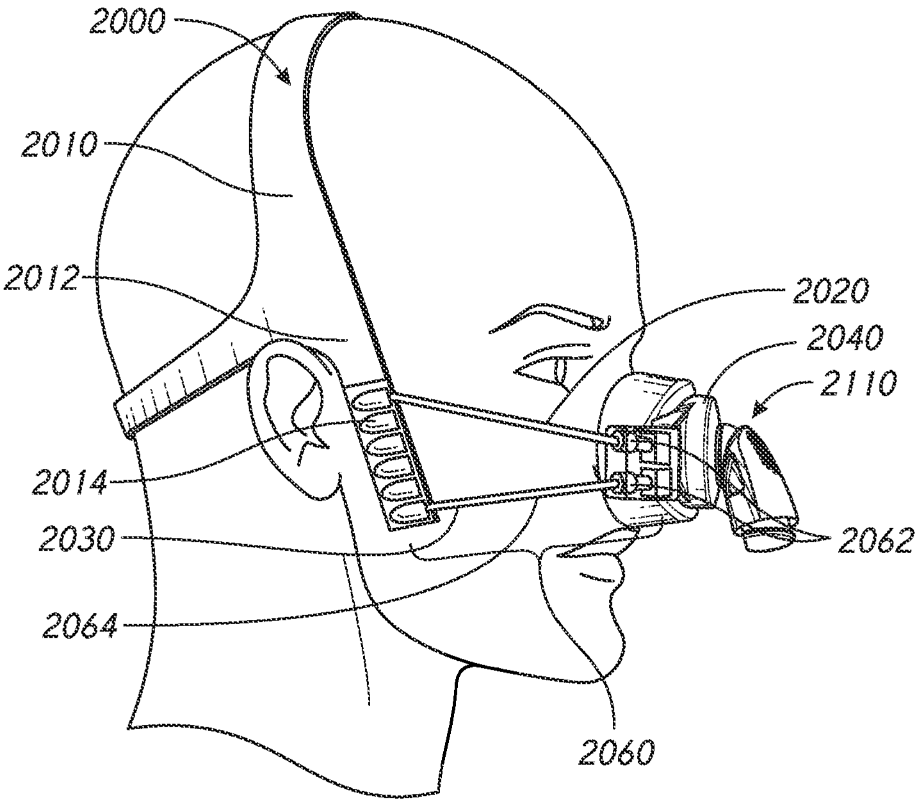
FIG. 75 is a side view of an exemplary nasal mask.

FIG. 75 shows the headgear system 2000 of FIG. 73 in combination with a nasal mask 2110. The nasal mask 2110 is configured to seal around the nose of a user, contacting the nasal bridge, cheeks and the upper lip. Two retention planes 2020, 2030 are desired or possibly required to provide appropriate stability to the mask 2110 when fitted to a user's face.

Figure 76:
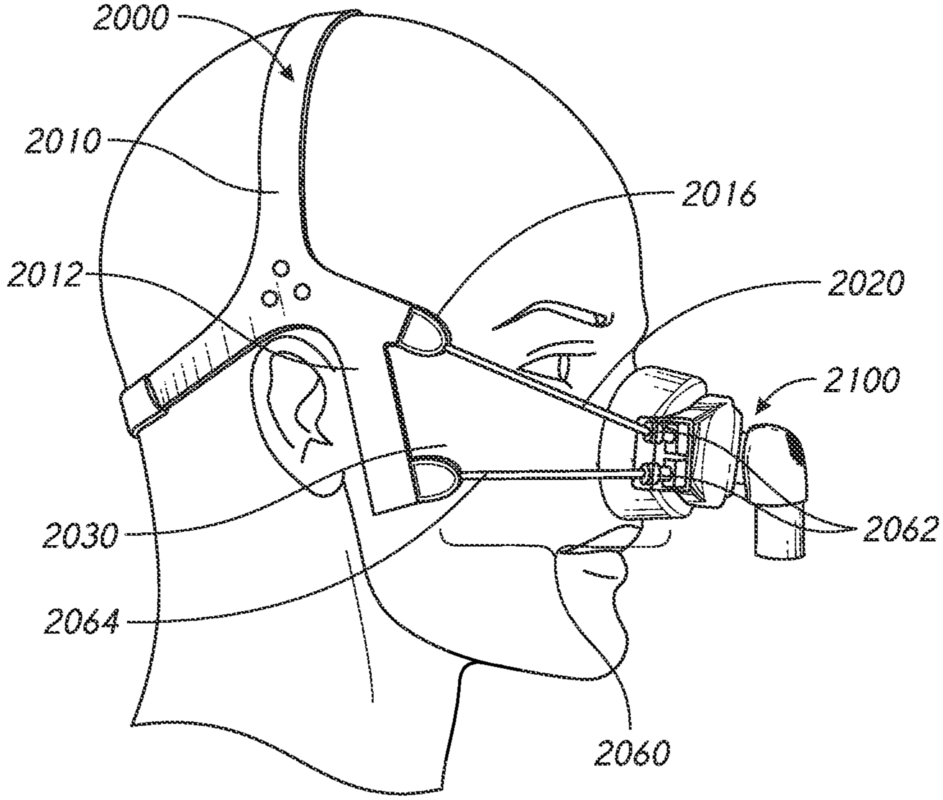
FIG. 76 is an exemplary headgear system having a headgear rear portion and two retention planes.

FIG. 76 illustrates a non-limiting exemplary embodiment of a headgear system 2000 that comprises a headgear rear portion 2010 and two retention planes 2020, 2030 configured to secure a nasal mask 2110 to a user's face. The headgear rear portion 2010 comprises a moulded plastic structure 2016, with an integrally formed fabric covering, having arms that extend downward in front of a user's ear. Upper and lower retention planes 2020, 2030 are provided by directional lock modules 2060 on each side of the headgear. The upper retention plane 2020 extends from the top of the arm 2012 to a location just above the tip of a user's nose. The lower retention plane 2030 extends from the bottom of the arm 2012 to a position that is approximately on the underside of the user's nose. In the illustrated arrangement, the directional lock modules 2060 comprise a braided elastic portion, core filament (not shown) and a directional lock, wherein the braided elastic portion and core filament are joined permanently to the arm 2012 of the headgear and the directional lock 2060 by an over-molded connection. The angle of the retention planes 2020, 2030 is fixed by the over-moulded connections 2016.

Figure 77:
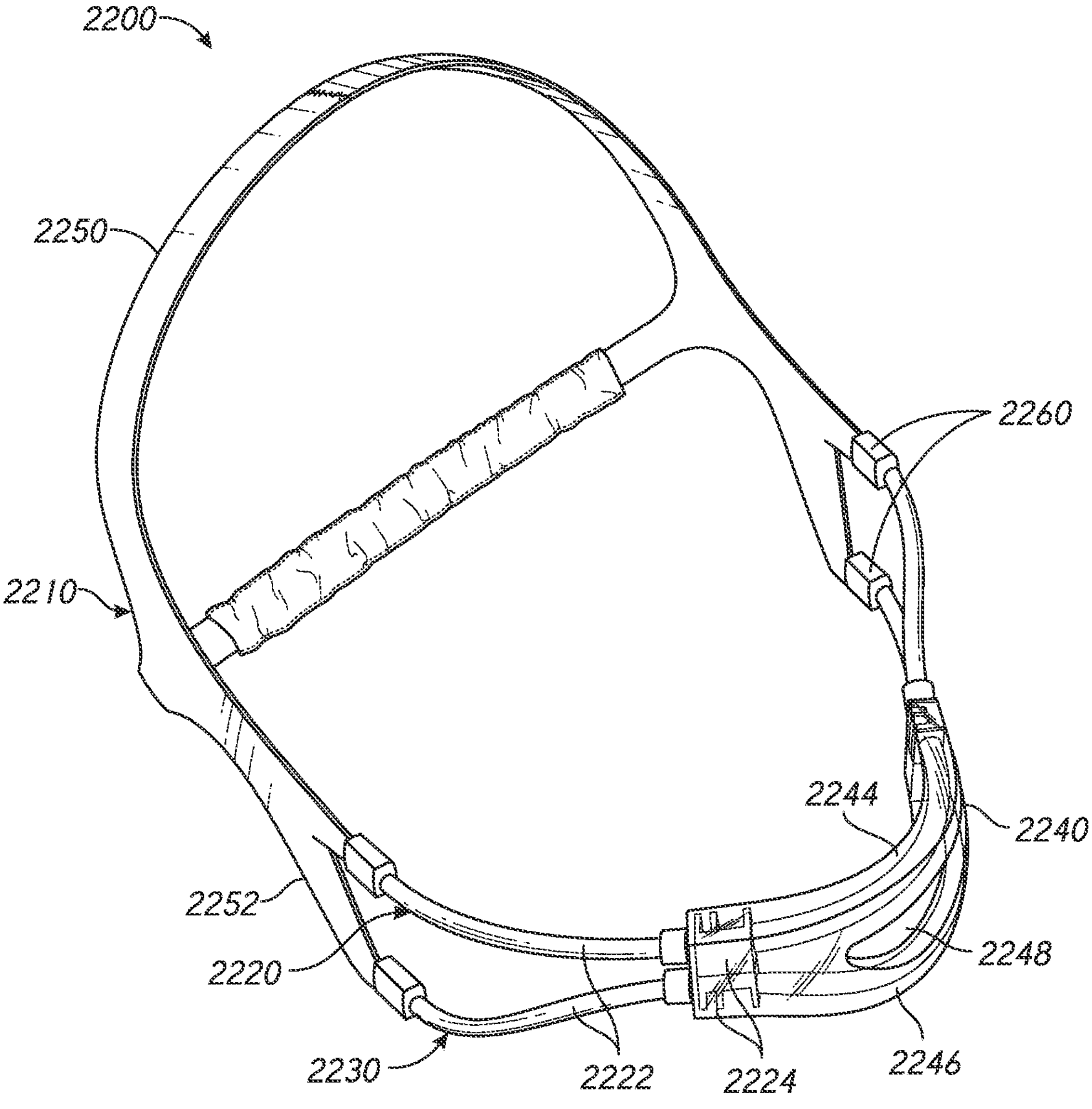
FIG. 77 is a front perspective view of an another exemplary headgear.
Figure 78:
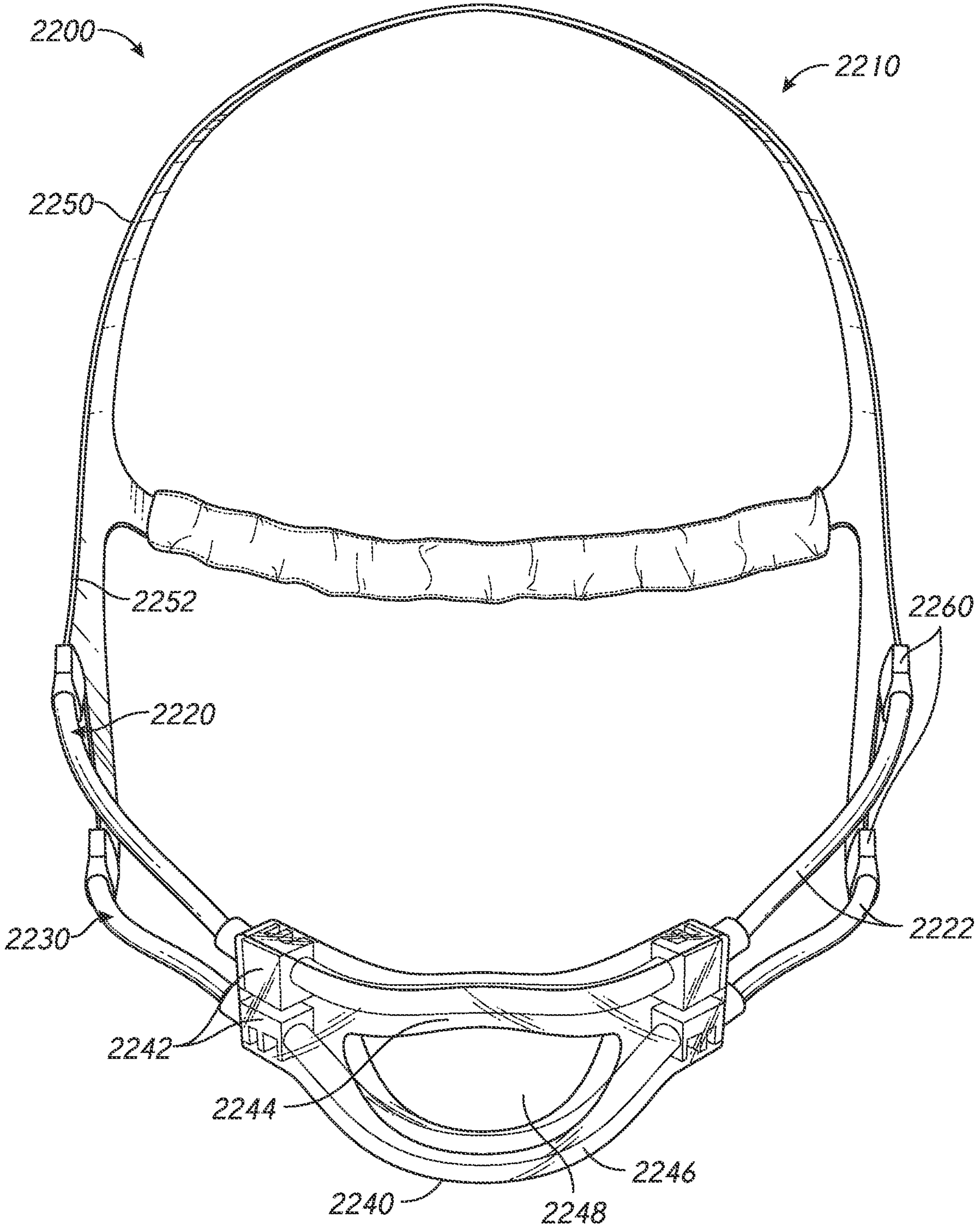
FIG. 78 is a front view of the exemplary headgear system in FIG. 77.
Figure 79:
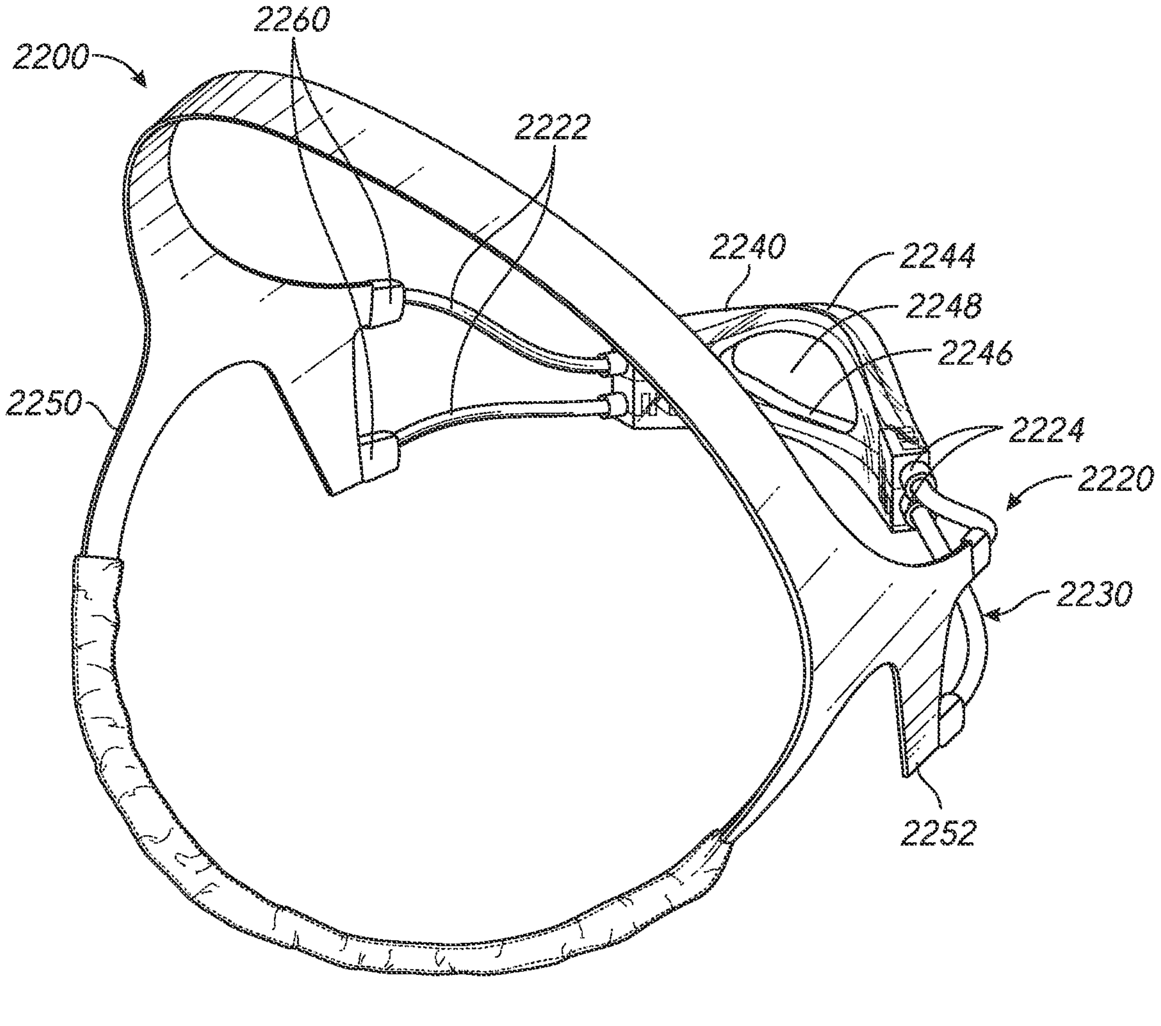
FIG. 79 is a rear perspective view of the exemplary headgear system in FIG. 77.

FIGS. 77 to 79 show views of a headgear system 2200 according to the presently disclosed subject matter. The headgear system 2200 is a closed loop and comprises a headgear 2210, two upper directional lock modules 2220, two lower directional lock modules 2230 and a housing 2240. The headgear rear portion 2250 comprises a bifurcated molded plastic structure with an integrally formed fabric cover, and a pair of arms 2252 configured to extend downwardly in front of a user's ears, in use.

The upper and lower directional lock modules 2220, 2230 comprise an elastic portion 2222, a core filament (not shown) and a directional lock 2224. The core filament is configured to extend partially or throughout the length of the elastic portion 2222 and through the directional locks 2224. The directional locks 2224 are configured to interact with the core filament to allow the length of the directional lock module 2220, 2230 to automatically adjust. The core filament and elastic portions 2222 are permanently joined to the arms 2252 of the headgear 2210 by an over-molded connection 2260, wherein the upper directional lock modules 2220 are joined to an upper region of the arms 2252 and the lower directional lock modules 2230 are joined to a lower region of the arms 2252. The elastic portions 2222 are permanently joined to the directional lock 2220, 2230 by an over-molded connection 2260. The directional locks 2220, 2230 are contained within the housing 2240. The two upper directional lock modules 2220 form an upper retention plane, and the two lower directional lock modules 2230 form a lower retention plane that are substantially the same as those of FIG. 76.

The housing 2240 comprises substantially rigid body having four directional lock brackets 2242, an upper conduit 2244, a lower conduit 2246 and a central opening 2248 formed there between. Two directional lock brackets 2242 are positioned, one above the other, at each of the lateral ends of the housing 2240. The directional lock brackets 2242 are configured to retain the directional locks 2224. The upper conduit 2244 extends laterally between the two upper lock brackets 2242 and the lower conduit 2246 extends laterally between the lower lock brackets 2242. The upper and lower conduits 2244, 2246 are configured to house a free end of the core filaments. The central opening 2248 that is formed between the upper and lower conduits 2244, 2246 is configured to receive a nasal mask arrangement.

Figure 80:
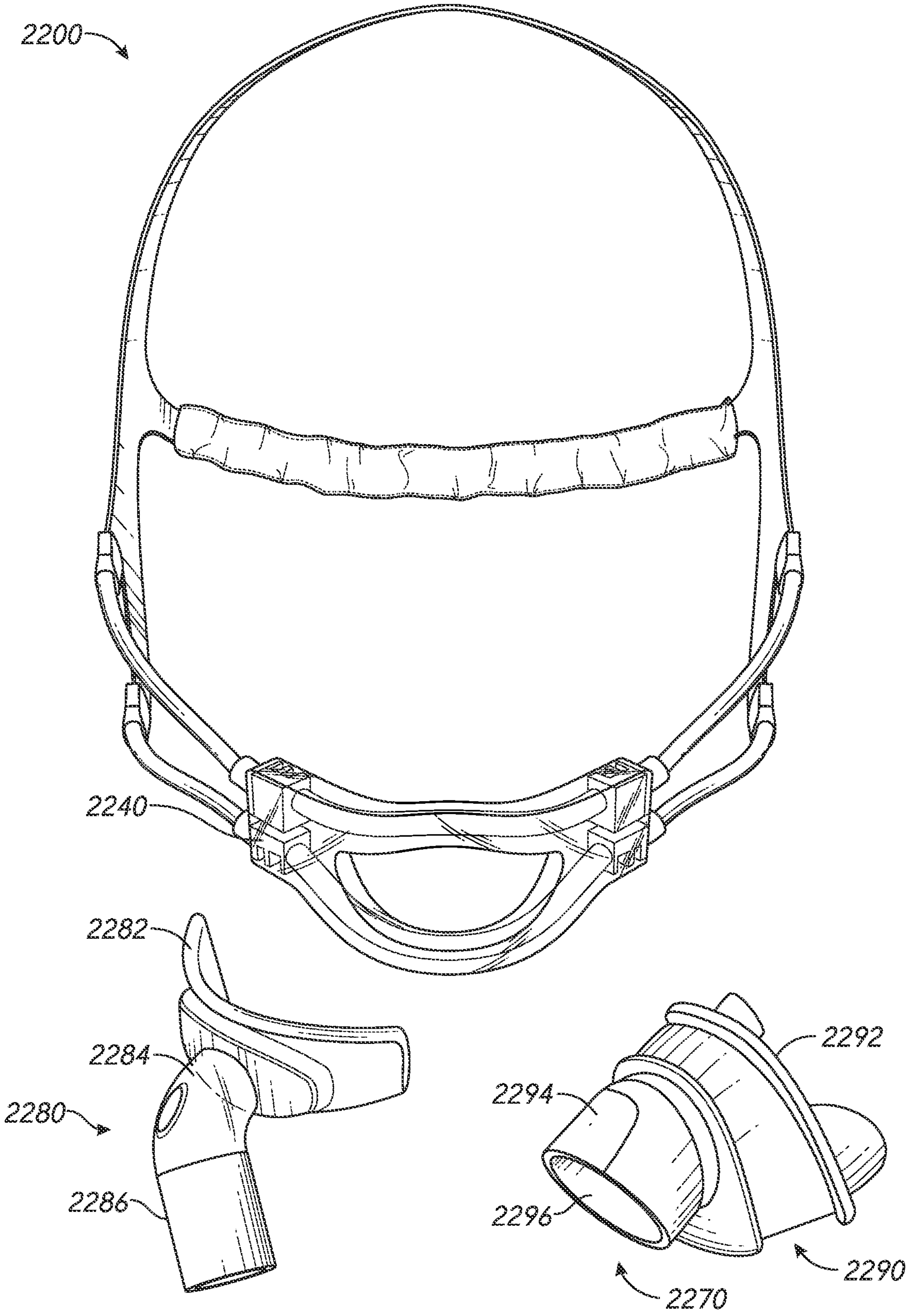
FIG. 80 is a front view of the exemplary headgear system in FIG. 77 with a mating nasal mask arrangement.

FIG. 80 shows the headgear system of FIG. 79 along with the nasal mask arrangement 2270 that is configured to assemble with it. The nasal mask arrangement 2270 comprises a frame assembly 2280 and a cushion module 2290. The frame assembly 2280 includes a frame 2282, elbow 2284 and a tube connector 2286. The frame 2282 and the elbow 2284 are configured to be joined together by a ball and socket connection, wherein the frame 2282 includes the socket 2410 and the elbow 2284 includes the ball 2400. The frame 2282 comprises a nylon component with geometry that provides a repeatably removable snap-fit connection with the housing 2240 of the headgear system 2200. In some configurations, the elbow is made of a different material to the frame 2282, such as polycarbonate, so that the two parts do not stick together when assembled. This can improve the freedom with which that elbow can move relative to the frame 2282 and may reduce hose drag. It is envisaged that other material combinations may also be used.

The tube connector 2286 connects to an end of the elbow 2284, which opposes the end that is connected to the frame 2282, in a snap fit configuration. The tube connector 2286 can swivel or rotate about the end of the elbow 2284. In some embodiments the tube connector 2286 can be made of a different material to the elbow 2284, such as nylon. Tube connector 2286 is configured to provide a means for connecting the nasal mask arrangement 2270 to a CPAP tube, which provides a pressurized air supply.

Figure 81:
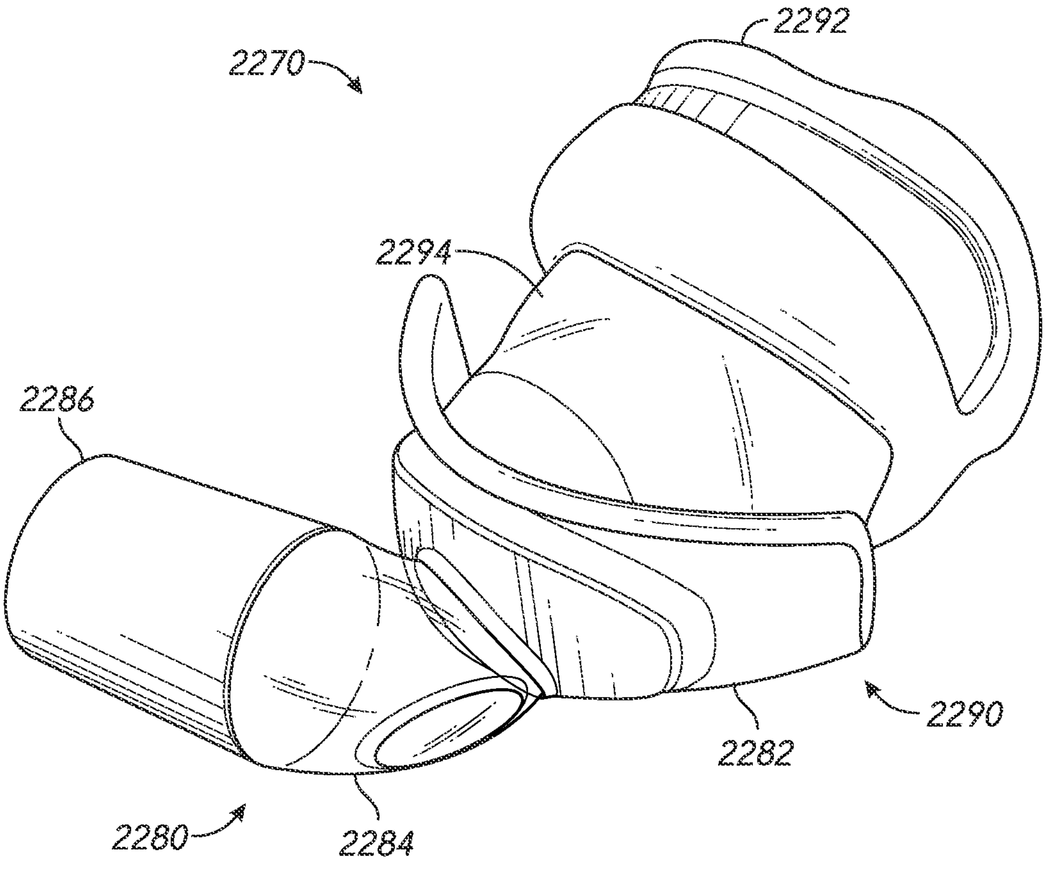
FIG. 81 is a front perspective view of an exemplary cushion module and frame assembly.

The cushion module 2290 comprises a sealing cushion 2292 that is integrally formed with a connector portion 2294, by means such as but not limited to over-molding. The sealing cushion 2292 comprises a compliant interface that is made from a flexibly resilient material such as, but not limited to, silicone or a thermoplastic elastomer. It is configured to form a substantially air tight breathing chamber that seals about the nose of a user. The connector portion 2294 is made of a substantially rigid material, such as but not limited to polycarbonate, and comprises a circular opening 2296 opposing the sealing cushion 2292. It is configured to provide a repeatably removable connection between the cushion module 2290 and the frame assembly 2280. The cushion module 2290 and frame assembly 2280 connect together such that an air path is formed through the tube connector 2286 and elbow 2284 and into the cushion module 2290, as shown in FIG. 81.

Figure 82:
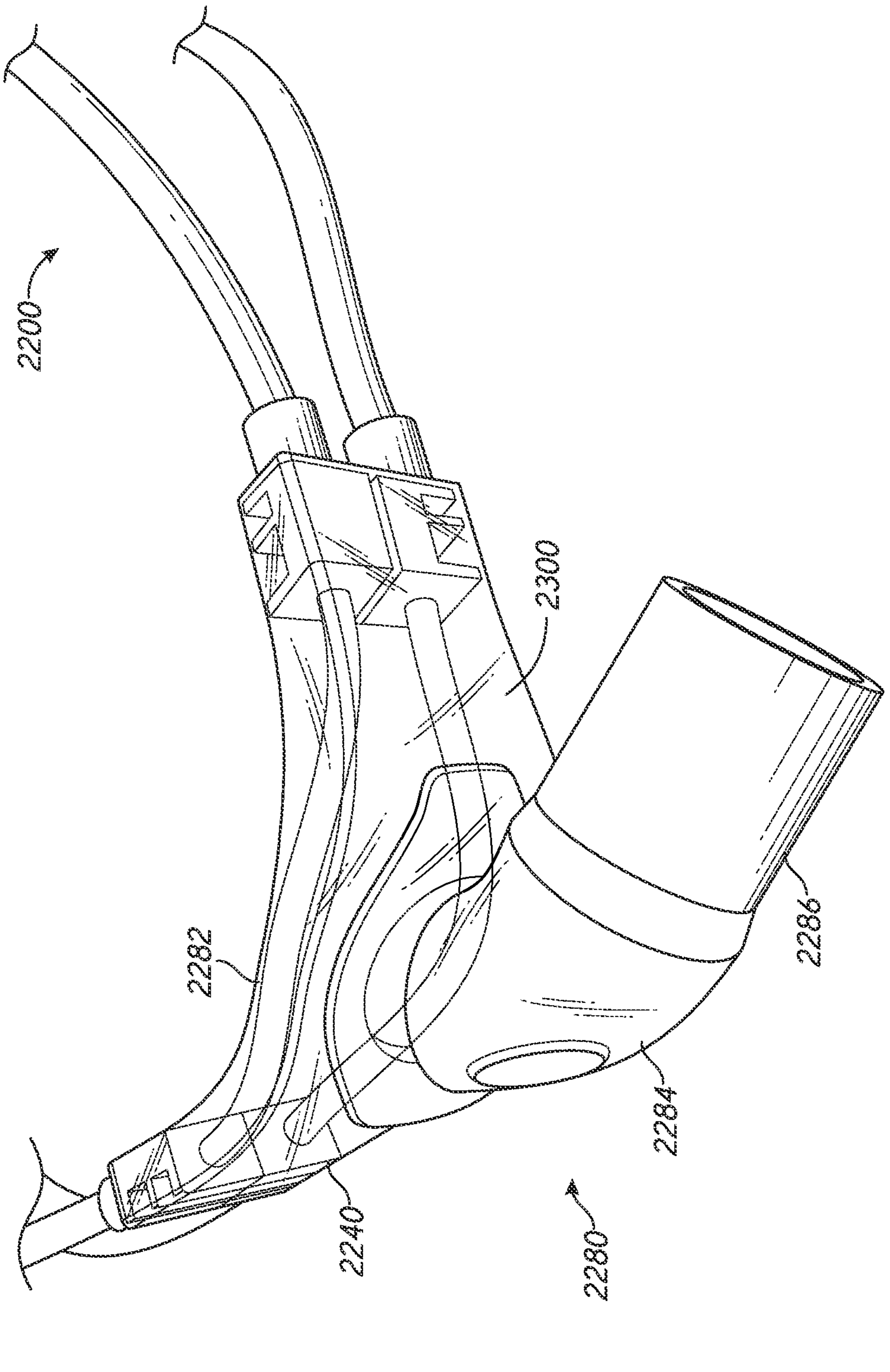
FIG. 82 is a front perspective view of the frame assembly connected to the housing of the headgear system.
Figure 83:
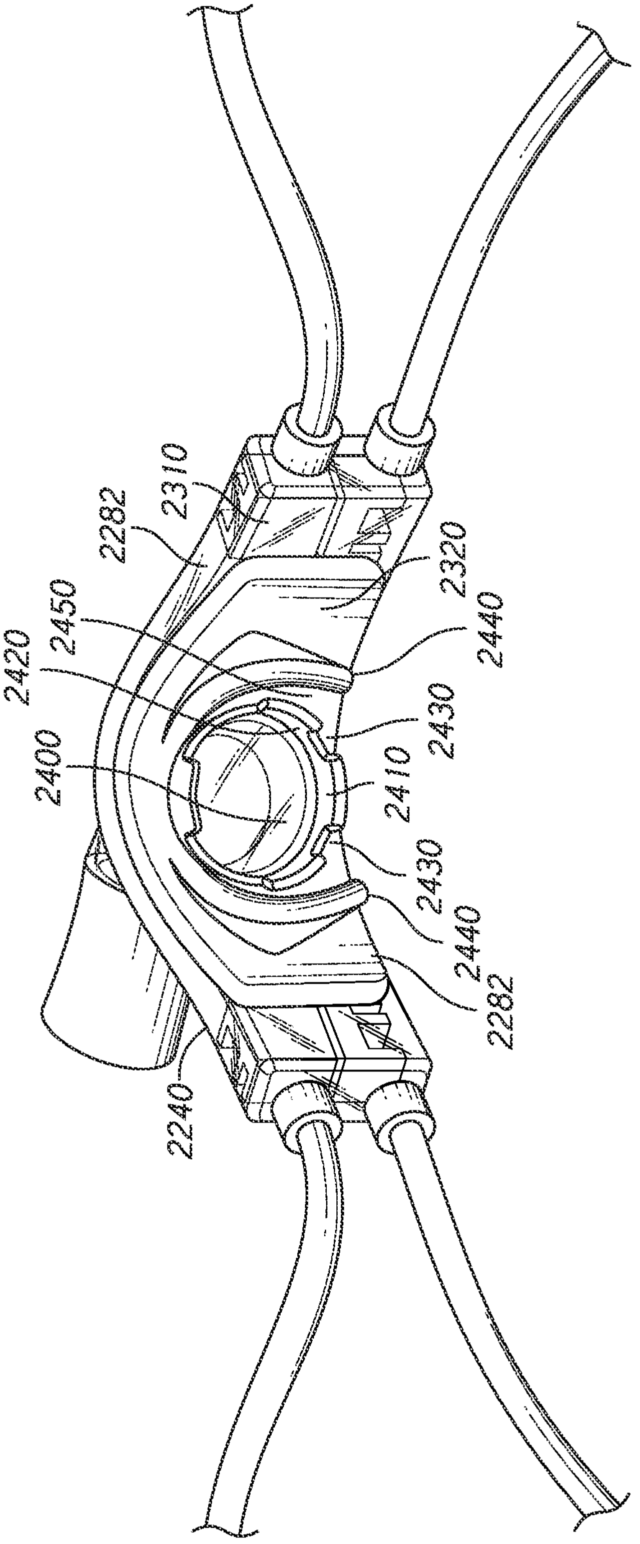
FIG. 83 is a rear view of the frame assembly connected to the housing of the headgear system.

FIGS. 82 and 83 show how the frame assembly 2280 connects to the housing 2240 of the headgear system 2200. The elbow 2284 and tube connector 2286 are configured to pass through the central opening of the housing 2240 in order to connect the frame 2282 to a rear surface 2310 of the housing 2240. A portion of the frame 2282 extends through the central opening 2248 of the housing 2240 and sits substantially flush with a front surface 2300 of the housing 2240.

Figure 84:
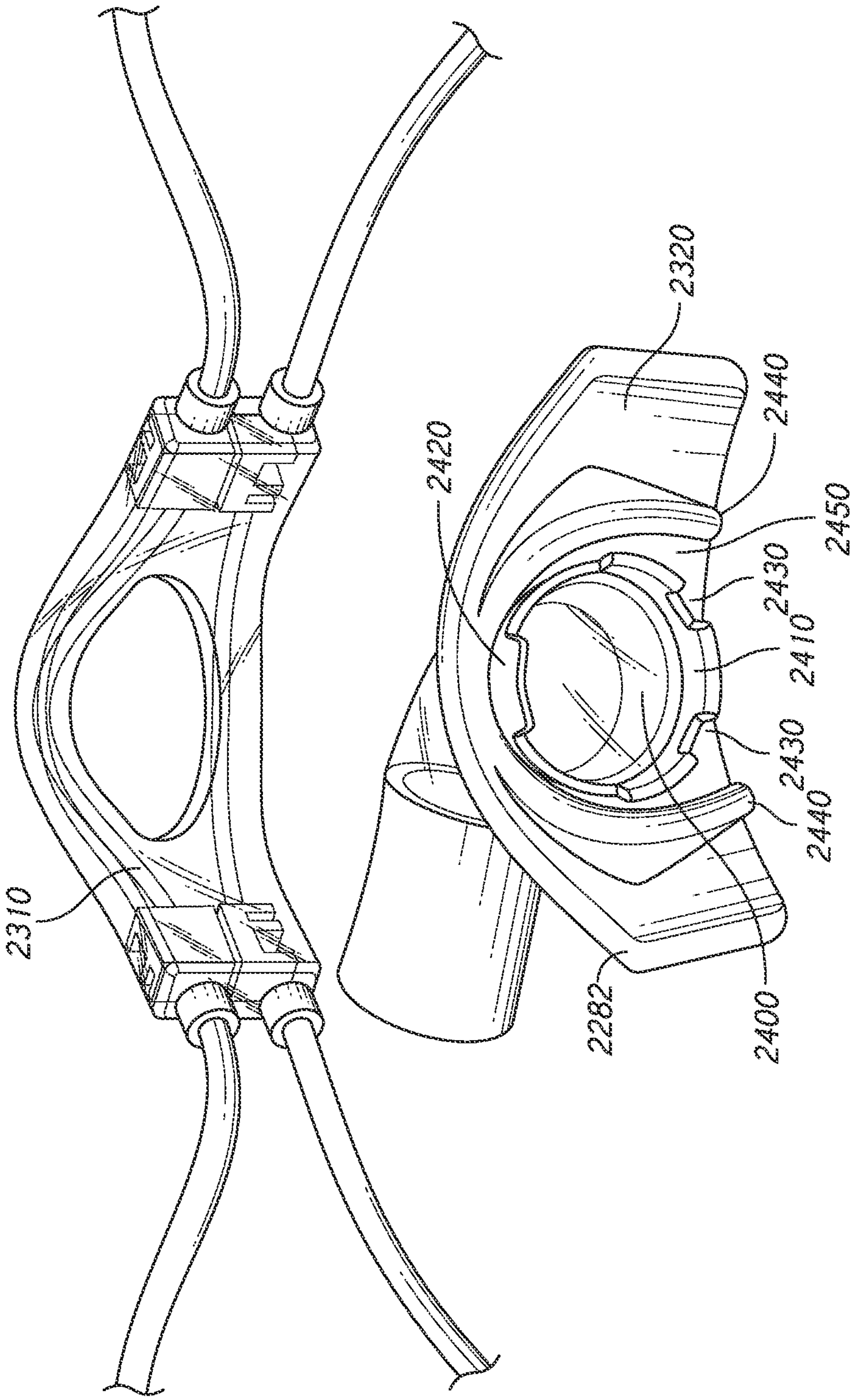
FIG. 84 is a rear view of the frame assembly removed from the housing of the headgear.

A rear surface 2320 of the frame 2282 is shown in FIGS. 83 and 84. It can be seen that the rear surface 2320 of the frame 2282 comprises a number of protrusions that form a circular inner cuff 2420 around the perimeter of the socket of the ball 2400 and socket 2410 connection. The inner cuff 2420 has a plurality of cut-outs 2430 that provide flexibility. A recessed channel 2450 extends around the periphery of the inner cuff 2420. The recessed channel 2450 retains the circular opening 2296 of the cushion module 2290 in a snap-fit configuration. There is one or more (e.g., a pair of) keying features 2440 located on the lower perimeter of the recessed channel 2450. The keying features 2440 are configured to interact with a corresponding feature on the connector portion 2294 of the cushion module 2290, such that rotation of the cushion module 2290 is prevented.

An advantage of the headgear adjustment systems disclosed in the previously described embodiments is that it provides a silent adjustment means. Hook and loop fastening systems (such as Velcro) are commonly used in the art to provide size adjustment to headgear systems for respiratory masks. When the tightness of the headgear system requires adjusting, the hook and loop fastener components must be separated from each other. The separation of hook and loop fastener components usually generates a ripping sound, which may be annoying to the mask user and in some circumstances may wake a bed partner of the user. The headgear system of the present disclosure is less likely to require the user to make a manual adjustment to achieve an improved size and fit and any adjustment that is required will not generate a noise, or at least not a significant level of noise, thus improving ease of use and comfort for the user and their bed partner.

Figure 85:
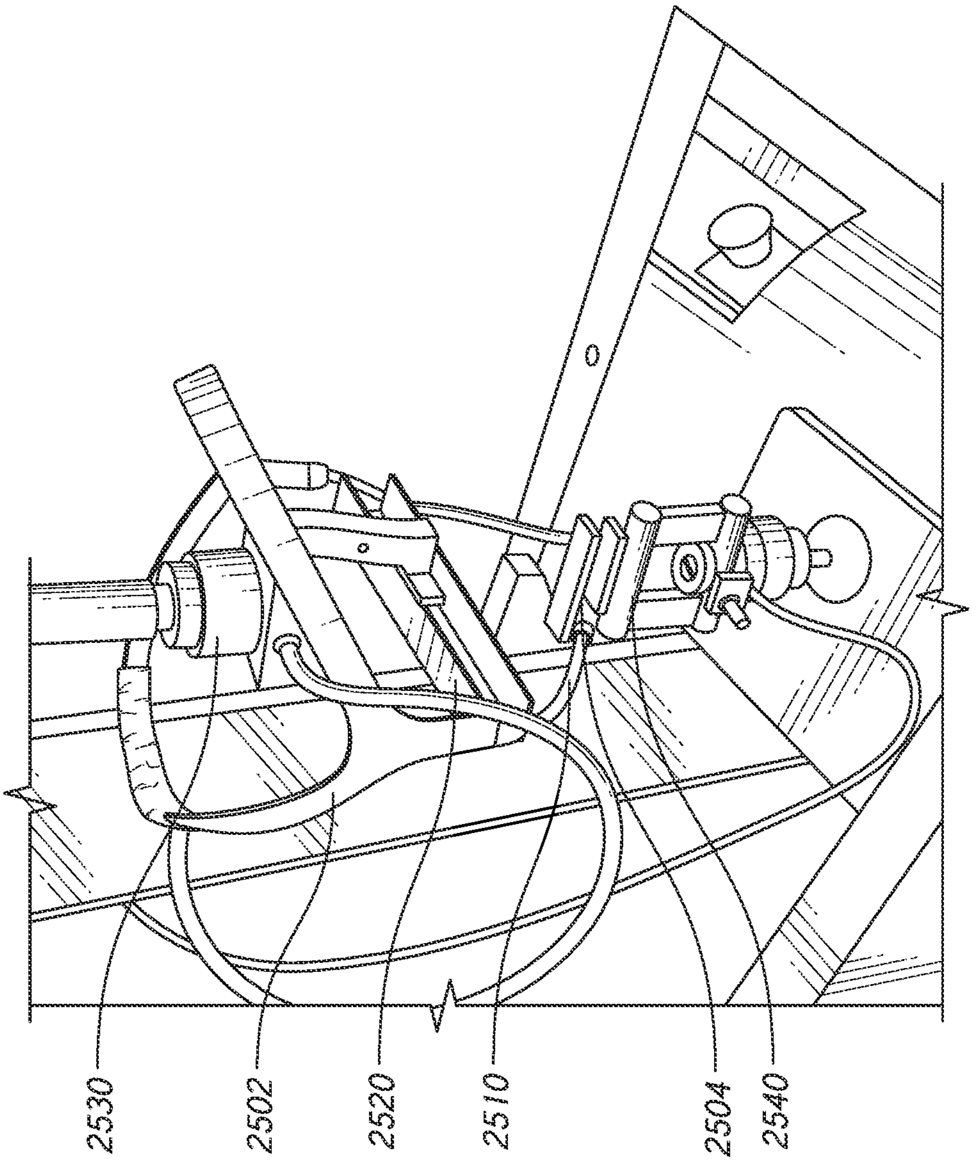
FIG. 85 illustrates a validation testing of the function of a headgear arrangement that includes at least one directional locking module.

Headgear Testing:

FIG. 85 shows a test set-up for validating the function of a headgear arrangement 2500 that includes at least one directional locking module 2510. The headgear arrangement 2500 being tested in FIG. 85 comprises a headgear 2502 and a mask frame 2504 that are connected together by a pair of lateral directional lock modules 2510. The frame 2504 is configured to receive a nasal pillows seal. The ends of the directional lock modules 2510 that are connected to the headgear 2500 are retained within a test jig 2520 that secures the headgear arrangement 2500 to a moving cross head 2530 of a universal testing machine. The mask frame 2504 is secured to a fixed cross head 2540 of the universal testing machine. The universal testing machine can run a test which simulates the donning and wearing of the mask in several phases. It is to be understood that this test set-up can be modified to test headgear arrangements that are configured to be used with different mask types, such as full-face and nasal masks.

The first phase of the test simulates the donning of the mask and headgear arrangement. The moving cross head is programmed to pull the headgear away from the frame, elongating the directional lock modules, until the headgear arrangement is near its maximum circumference. The second phase of the test simulates the fitting of the mask and headgear arrangement to a user's head. The universal testing machine is programmed to return the headgear back towards the mask frame to a distance wherein the circumference of the headgear arrangement is approximately half way between the maximum and minimum circumferences. This simulates the point at which the circumference of the headgear arrangement matches the circumference of the user's head. The third step of the test comprises extending the headgear arrangement back to its maximum circumference, which simulates the application of CPAP pressure and use of the mask system. The force profile is recorded during all three of the test phases.

During the first phase of the test it is expected that a force-extension plot should show an initial steep rise in the force as the lock, of the directional lock mechanism, engages during elongation of the headgear arrangement. If the plot does not show this there may be some slack in the headgear and the jig that needs to be taken up before the directional lock mechanism kicks in. Following this steep rise in force, a transition point will be reached at or near a predetermined yield force. Once the yield force has been reached the rate of increase of the force reduces and remains substantially constant until the maximum headgear circumference is reached.

The second phase of the test is expected to show the instant release of the directional lock mechanism, on the force-extension plot. An initial sharp drop in force indicates an instant release of the hold of the washer (or other appropriate locking mechanism), when the extension force is released from the headgear arrangement. The return force is driven by the elasticated component of the directional lock module. In this particular case; 4 strands of lycra in a braided sleeve. The return force can be controlled by selection of materials and manufacturing methods of the elasticated component. The return force should be below the expected blow-off force, which will change depending on the type mask (i.e. full-face, nasal or nasal pillows etc.).

The third phase simulates use, wherein the headgear has contracted to an imaginary user's head circumference. The application of CPAP pressure (blow off force) to the mask should result in the force-extension plot showing a steep increase in force, at substantially the same rate as the initial elongation force, before the yield force is reached. The application of the CPAP pressure should activate the washer (or other lock mechanism) and show a sharp rise in force against a short elongation. The balanced fit of the mask and headgear arrangement should fall somewhere along this force-extension curve, and will be dependent on the CPAP pressure that is applied. As the extension of the headgear arrangement continues towards the maximum circumference the yield force will be reached. This portion of the plot should follow or approximate the elongation of the headgear after the yield point during the first phase of the test. A close overlap indicates a repeatable yield force.

Figure 86:
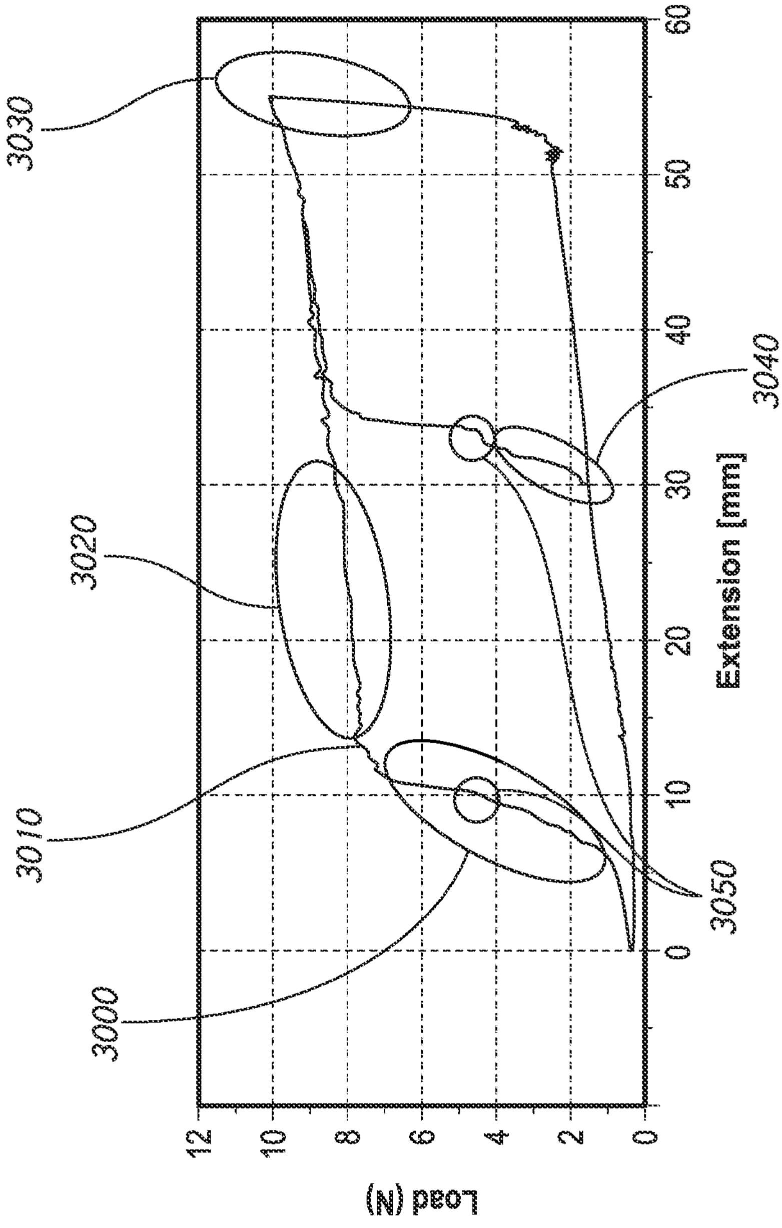
FIG. 86 is a graph illustrating a relationship between force versus extension of tested exemplary headgear arrangements.
Figure 87:
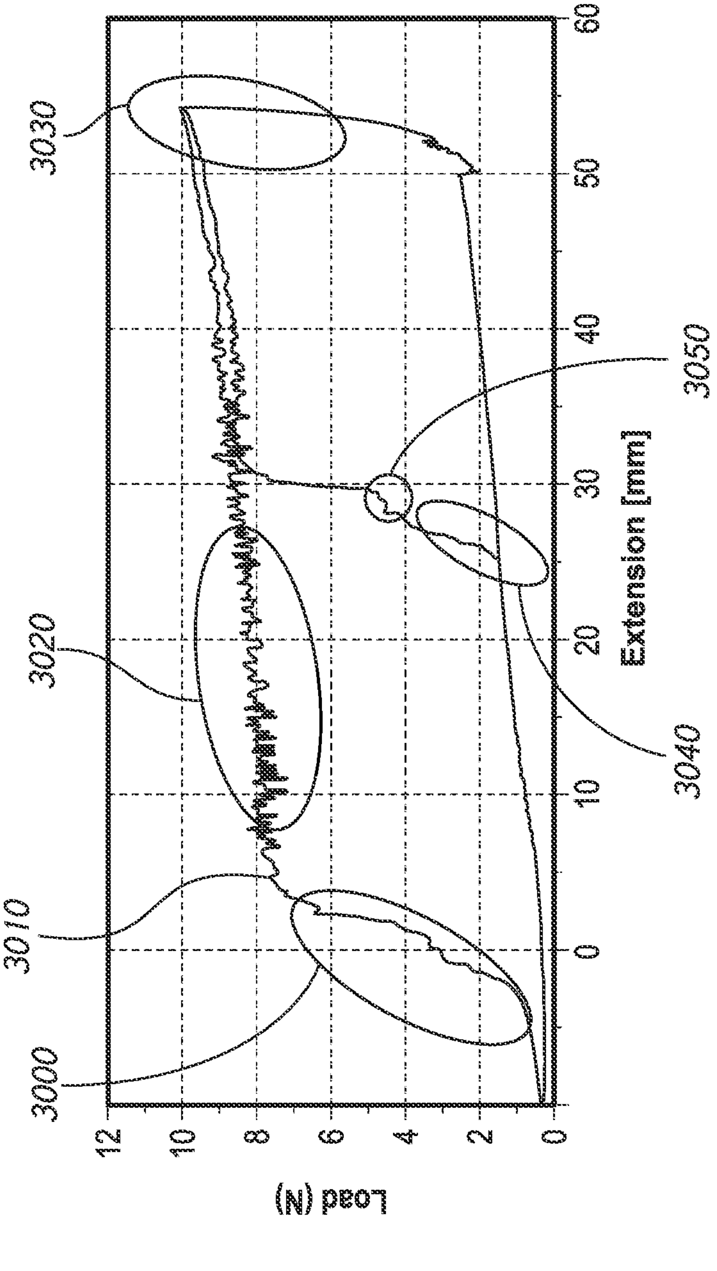
FIG. 87 is a force-extension graph illustrating force fluctuation during elongation after the transition.

FIGS. 86 and 87 show force-extension plots two headgear arrangement and mask samples (such as those shown in FIG. 85) obtained using the test set-up described above. The plots of both FIGS. 86 and 87 show that the headgear arrangement and mask samples that were tested meet the desired criteria as described above. Both plots show a steep increase in force during initial elongation 3000 followed by a lower rate of increase 3020 after the transition point 3010 has been reached. It can be seen in FIG. 87 that the force can fluctuate during elongation 3020 after the transition point 3010. This may be a result of imperfect tolerances between components of the directional lock module, or inaccuracies in how the sample is retained during the test. The two plots also show that both samples displayed a sharp drop 3030 in force indicating an instant release of the directional lock mechanism, and a low return force. A sharp increase 3040 in force was shown for both samples during the third phase of simulating use. The force-extension curve after the yield force also closely aligned with the initial elongation curve.

In both FIGS. 86 and 87, a hesitation/elongation 3050 can be seen approximately half way up the steep increases in force. This corresponds to the construction of the directional lock mechanism. In the samples that were tested the directional lock mechanisms included two washers, such the embodiments of FIGS. 68A to 68D. The hesitation is caused by the first washer having a lower yield force and allowing a small amount of elongation before the second washer is engaged and continues the steep slope.

FIGS. 88-102 illustrate several nasal cannula systems incorporating a headgear arrangement of the present disclosure, which can include at least one directional lock arrangement. The several nasal cannula systems are described below with emphasis on the differences between the several systems. Portions, components or features not specifically described can be the same as or similar to corresponding portions, components or features of other nasal cannula systems, or can be of another suitable arrangement. A number of example nasal cannula arrangements are disclosed in Applicant's PCT Application No. PCT/IB2015/054585 and PCT Publication No. WO2014/142681, the entireties of which are incorporated by reference herein. In addition, features of the several nasal cannula systems can be interchanged to create combinations in addition to those specifically illustrated. The same reference numbers are used to refer to the same or corresponding portions, features or components of the several nasal cannula systems.

In some configurations, the nasal cannula systems are configured for high flow therapy (HFT) and may be unsealed or may not create a substantial seal with the user's nares. However, in other arrangements, the nasal cannula systems could comprise sealing cannula. In addition, while well-suited for use with nasal cannula systems, the disclosed headgear arrangements could also be employed with systems utilizing other types of interfaces, such as nasal pillows, under-nose nasal masks, under-nose full face masks or traditional nasal or full-face masks, for example and without limitation. The headgear can be of any suitable configuration. For example, the headgear can be relatively rigid in at least one plane or can be soft. The headgear can be elastic (extensible or stretchable) or substantially inelastic (inextensible or non-stretchable).

Each of the nasal cannula systems preferably include at least one directional lock arrangement, which can be configured to provide different resistance to relative movement of portions of the system in different directions. For example, the directional lock arrangement(s) can be configured to allow movement tending to shorten an effective perimeter length or circumference of the system at a lesser resistance than movement tending to lengthen the effective perimeter length or circumference. In some configurations, the nasal cannula systems can also include a biasing arrangement, which can be configured to bias the system toward or to a minimum effective perimeter length or circumference. A resulting nasal cannula system can be applied onto the user's head and can automatically reduce in perimeter length or circumference to automatically adjust toward or to an appropriate size for the particular user. Such an automatically adjustable arrangement is useful in a nasal cannula application to maintain the position of the prongs in the user's nares. A similar, easily-adjustable arrangement (e.g., manually or otherwise adjustable) can also be useful in a nasal cannula application. In some cases, the nasal cannula does not require seal (and, thus, does not produce any or at least a substantial blow-off force), but there is still a moment arm that exists as a result of the weight of the nasal cannula and/or hose pull forces, possibly among other forces acting on the system. At least some of the configurations disclosed herein help to accommodate the nasal cannula in the operational position, such as by automatically or otherwise adjusting to a desired perimeter length or circumference and then resisting normal or expected forces acting on the nasal cannula. The directional lock arrangement(s) and biasing arrangement(s) can be the same as or similar to any of those disclosed herein, the same as or similar to any of those disclosed in Applicant's PCT Publication No. WO 2014/175752, published Oct. 30, 2014, entitled AUTOMATICALLY ADJUSTING HEADGEAR FOR PATIENT INTERFACE, the entirety of which is incorporated by reference herein, or can be of any other suitable arrangement.

Figure 88:
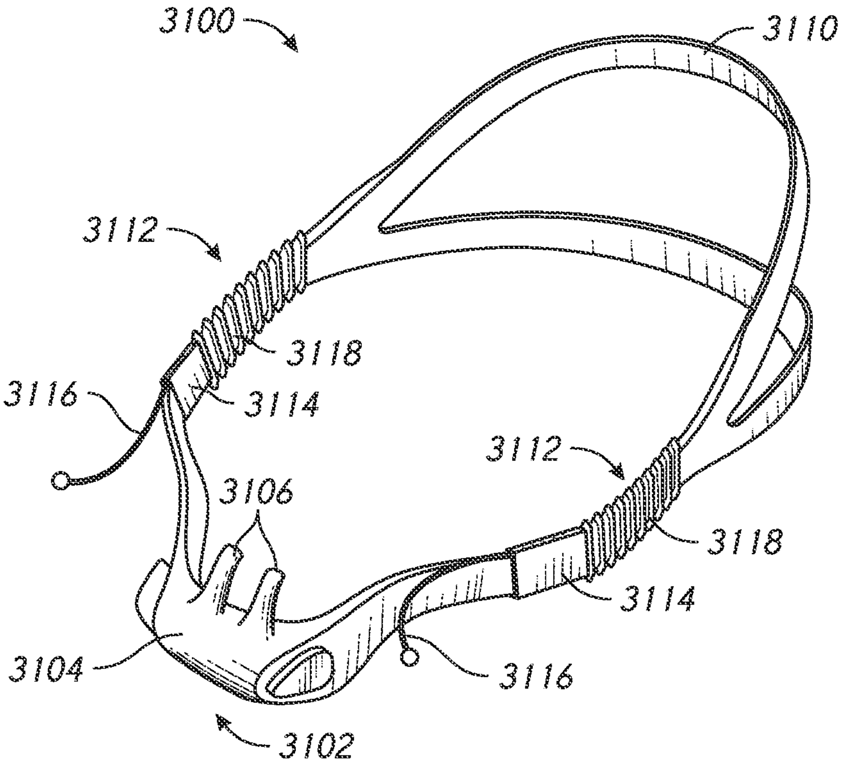
FIG. 88 is a perspective view of a respiratory cannula incorporating a headgear arrangement of the present disclosure, which can include at least one directional lock arrangement.

With reference to FIG. 88, a nasal cannula system 3100 comprises a cannula 3102 having a cannula body 3104 and at least one nozzle 3106, such as a pair of nozzles 3106. The cannula body 3104 can comprise an internal gas space that communicates with openings of the nozzles 3016. A suitable conduit can be connected to the cannula body 3104 to deliver a flow of breathing gases to the internal gas space and, ultimately, to the user. The nasal cannula system 3100 can also comprise a headgear 3110, which in the illustrated arrangement is a bifurcated headgear comprising a pair of straps (e.g., an upper strap and a lower strap). Opposing ends of the headgear 3110 connect directly or indirectly to opposing sides of the cannula body 3104. The illustrated headgear 3110 is a relatively rigid, non-stretch headgear, which can comprise an inner core and a cover. The cover can comprise one or more layers that partially or completely surround the inner core. In some configurations, the inner core is a plastic material and the cover comprises one or more fabric or textile materials. A suitable arrangement is disclosed in Applicant's U.S. Provisional Patent Application No. 62/198,104, filed Jul. 28, 2015, entitled HEADGEAR, PORTIONS, ASSEMBLIES AND METHODS, the entirety of which is incorporated by reference herein.

In some configurations, at least one and preferably a pair of adjustment arrangements 3112 are positioned within the nasal cannula system 3100 to allow for adjustment of a perimeter length or circumference of the nasal cannula system 3100 (hereinafter, "circumference"). In the illustrated arrangement, a pair of adjustment arrangements 3112 are positioned between the nasal cannula 3102 and the headgear 3110. The adjustment arrangements 3112 can comprise a portion of or be integrated with one or both of the nasal cannula 3102 and the headgear 3110 or can be a separate component from one or both of the nasal cannula 3102 and the headgear 3110. The adjustment arrangements 3112 can each comprise a directional lock 3114, a core member or filament 3116 that moves relative to and is selectively engaged by the directional lock 3114, and a biasing element or arrangement 3118 (hereinafter, "biasing element"). In the illustrated arrangement, the biasing elements 3118 are configured to shorten a circumference of the nasal cannula system 3100. The directional locks 3114 are configured to provide greater resistance to lengthening of the circumference than to shortening of the circumference. Preferably, the directional locks 3114 are configured to substantially inhibit or prevent lengthening of the circumference of the nasal cannula system 3100 at least in response to normal or expected forces applied during therapy, such as forces caused by the flow of gases during therapy, the weight of the cannula system 3100 and/or hose pull forces. The directional locks 3114, the core members 3116 and the biasing elements 3118 can be located together or near one another to form a sub-assembly or can be dispersed throughout the nasal cannula assembly 3110.

In the illustrated system 3100 of FIG. 88, the core members 3116 are coupled to the headgear 3110 and the directional locks 3114 are coupled to the nasal cannula 3102. The biasing elements 3118 have one end coupled to the headgear 3110 and one end coupled to the nasal cannula 3102. The core members 3116 extend from each side of the headgear 3110 toward the front of the nasal cannula system 3100. The core members 3116 can be secured to the nasal cannula 3102, such as by a guide, for example. The adjustment arrangements 3112 are symmetrically positioned on each side of the nasal cannula system 3100. With such an arrangement, the adjustment of the circumference of the nasal cannula system 3100 can be symmetrical, such that a center line of the headgear 3110 remains aligned with the center line of the nasal cannula 3102. The pair of adjustment arrangements 3112 provide for a greater range of circumference adjustment in comparison to a single adjustment arrangement 3112. Such an arrangement can, in some configurations, allow for a single size nasal cannula system 3100 to cover a substantial portion or an entirety of an intended user population (e.g., an adult population). In addition, the adjustment arrangements 3112 positioned on the sides of the nasal cannula system 3100 keeps the adjustment arrangements 3112 away from the front and rear of the nasal cannula system 3100, which are the locations often grasped when applying (donning) or removing (doffing) the nasal cannula system 3100.

Figure 89A:
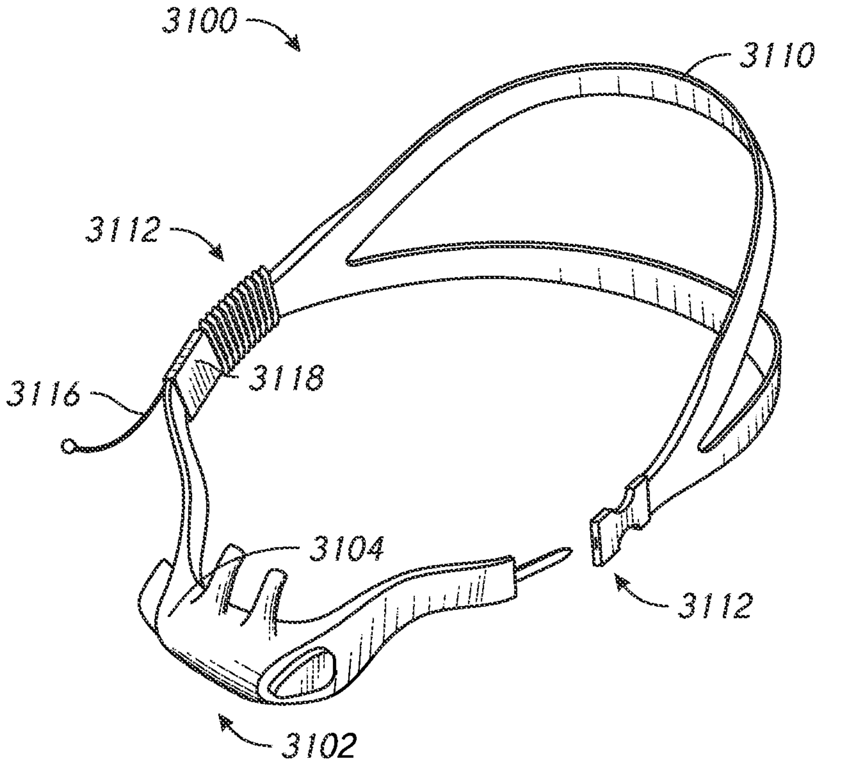
FIGS. 89*a*-89*c* are perspective views of additional respiratory cannulas incorporating headgear arrangements of the present disclosure, which headgear arrangements can include at least one directional lock arrangement and a headgear quick release arrangement.
Figure 89B:
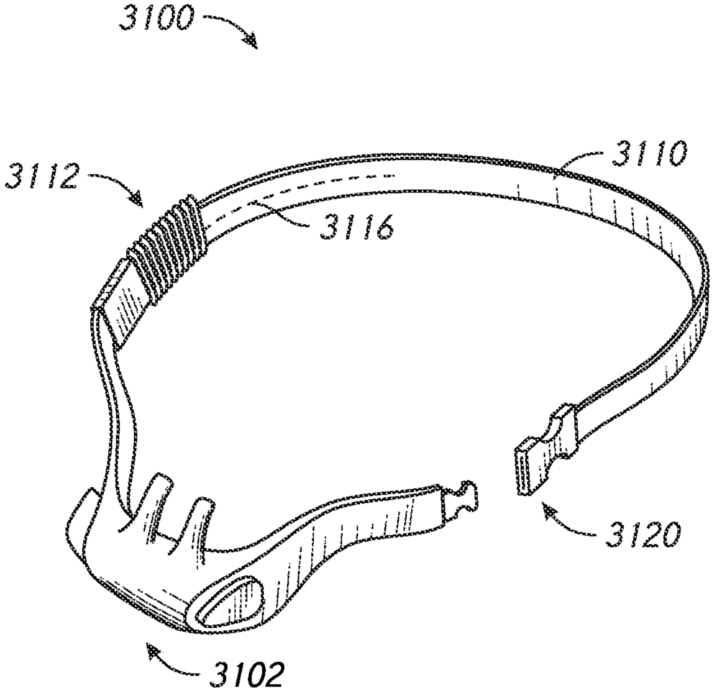
Figure 89C:
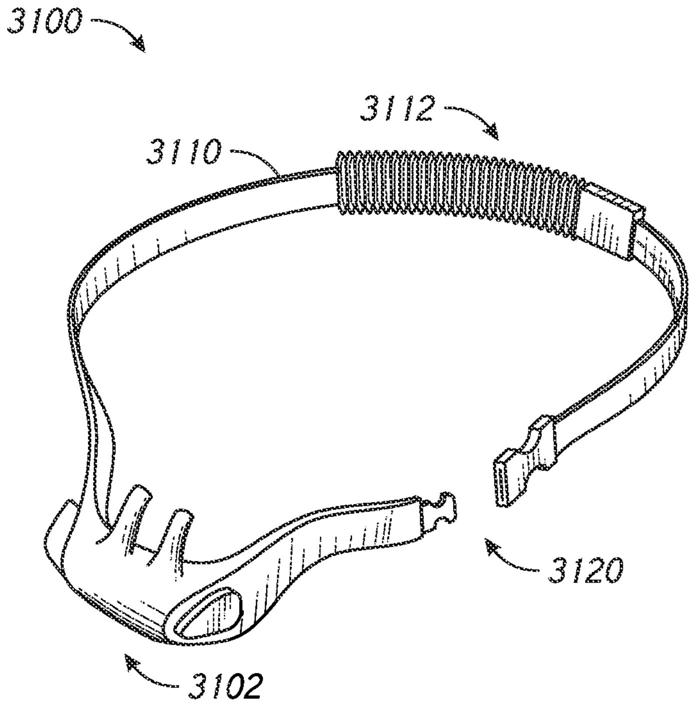

With reference to FIG. 89*a*, the illustrated nasal cannula system 3100 is similar to that of FIG. 88; however, the nasal cannula system 3100 of FIG. 89*a* includes an adjustment arrangement 3112 on one side of the nasal cannula system 3100 and a quick release arrangement 3120 on the opposite side of the nasal cannula system 3100. In the illustrated arrangement, the quick release arrangement 3120 is a buckle. However, other suitable arrangements (e.g., clip, latch, magnet, etc.) can also be used. The quick release arrangement 3120 can permit the nasal cannula system 3100 to be quickly and easily applied to or removed from the user. For example, in the context of an unresponsive patient, such as in a hospital environment, the quick release arrangement 3120 can permit a caregiver to quickly and easily break the closed loop of the nasal cannula system 3100 to facilitate removal of the system 3100 from the user. In addition, the single adjustment arrangement 3112 can result in a lower manufacturing cost compared to a similar system having two or more adjustment arrangements. FIG. 89*b* illustrates a similar system 3100 that incorporates a single strap headgear 3110 instead of the bifurcated headgear 3110 of the system 3100 of FIG. 89*a*. FIG. 89*c* illustrates a nasal cannula system 3100 having the adjustment arrangement 3112 integrated into a single strap headgear 3110. In the illustrated arrangement, the adjustment arrangement 3112 is positioned in a rearward portion of the headgear 3110; however, the adjustment arrangement 3112 could be positioned in other locations, as well.

Figure 90:
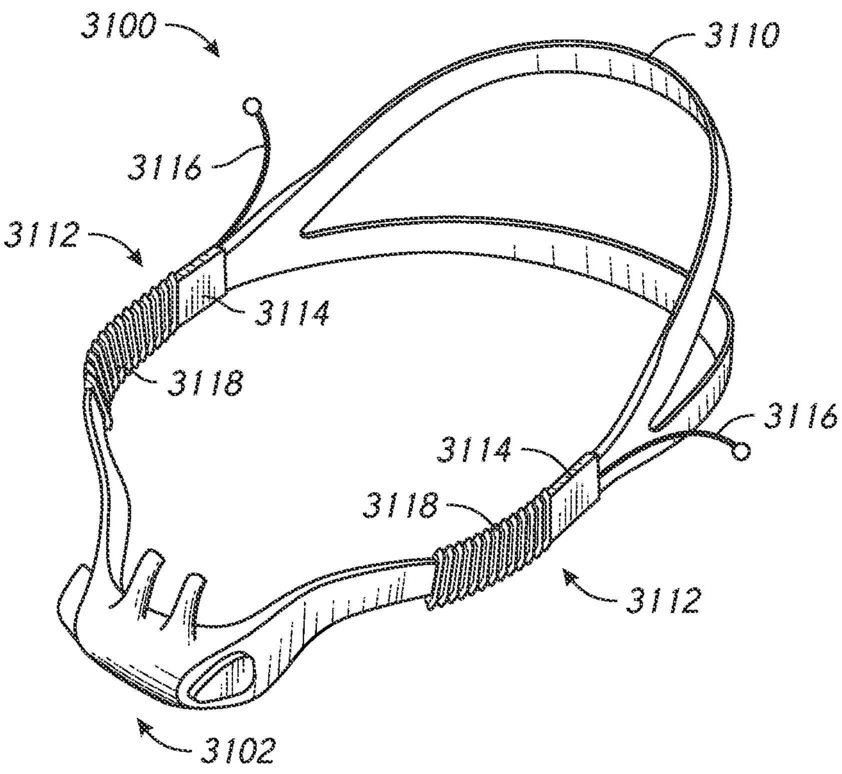
FIG. 90 is a perspective view of another respiratory cannula incorporating a headgear arrangement of the present disclosure, which can include at least one directional lock arrangement.

FIG. 90 illustrates a nasal cannula system 3100 that is similar to the system 3100 of FIG. 88 except, in the system 3100 of FIG. 90, the direction of the adjustment arrangements 3112 are reversed relative to the arrangements 3112 of FIG. 88. In particular, the core members 3116 are coupled to the nasal cannula 3102 and the directional locks 3114 are coupled to the headgear 3110. Although shown free of the headgear 3110, the excess portions of the core members 3116 can be secured to the headgear 3110 if desired, such as by a guide or accumulator. Locating the excess portions of the core members 3116 on the headgear 3110 can provide a greater accumulator length and, thus, can permit the system 3100 of FIG. 90 to have a greater adjustment range than other systems, such as the system 3100 of FIG. 88.

Figure 91:
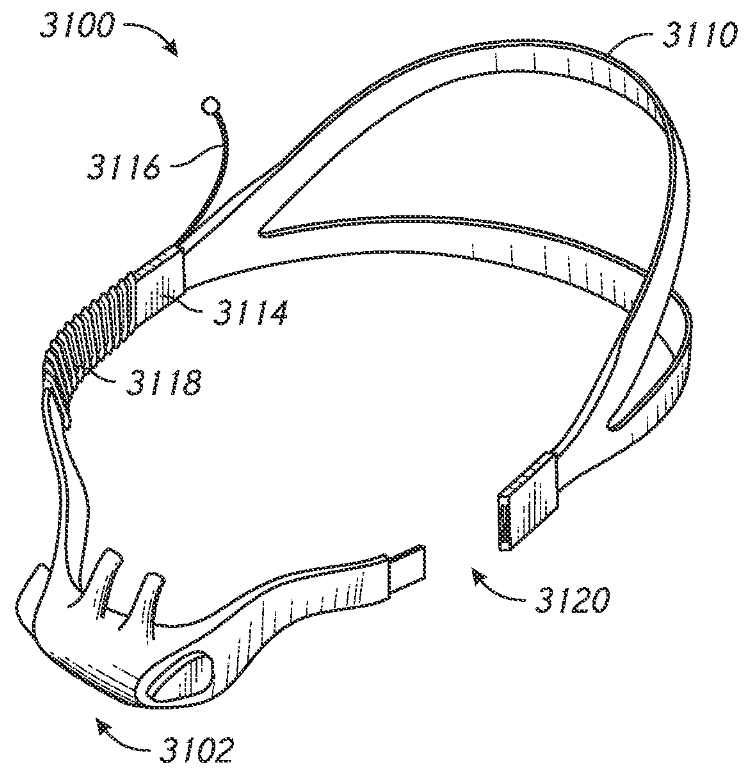
FIG. 91 is a perspective view of a respiratory cannula incorporating a headgear arrangement of the present disclosure, which can include at least one directional lock arrangement and a headgear quick release arrangement.

FIG. 91 illustrates a nasal cannula system 3100 that is similar to the system 3100 of FIG. 89*a* except, in the system 3100 of FIG. 91, the direction of the adjustment arrangement 3112 is reversed relative to the arrangement 3112 of FIG. 89*a*. In particular, the core member 3116 is coupled to the nasal cannula 3102 and the directional lock 3114 is coupled to the headgear 3110. Although shown free of the headgear 3110, the excess portion of the core member 3116 can be secured to the headgear 3110 if desired, such as by a guide or accumulator. Locating the excess portion of the core member 3116 on the headgear 3110 can provide a greater accumulator length and, thus, can permit the system 3100 of FIG. 91 to have a greater adjustment range than other systems, such as the system 3100 of FIG. 89*a*.

Figure 92:
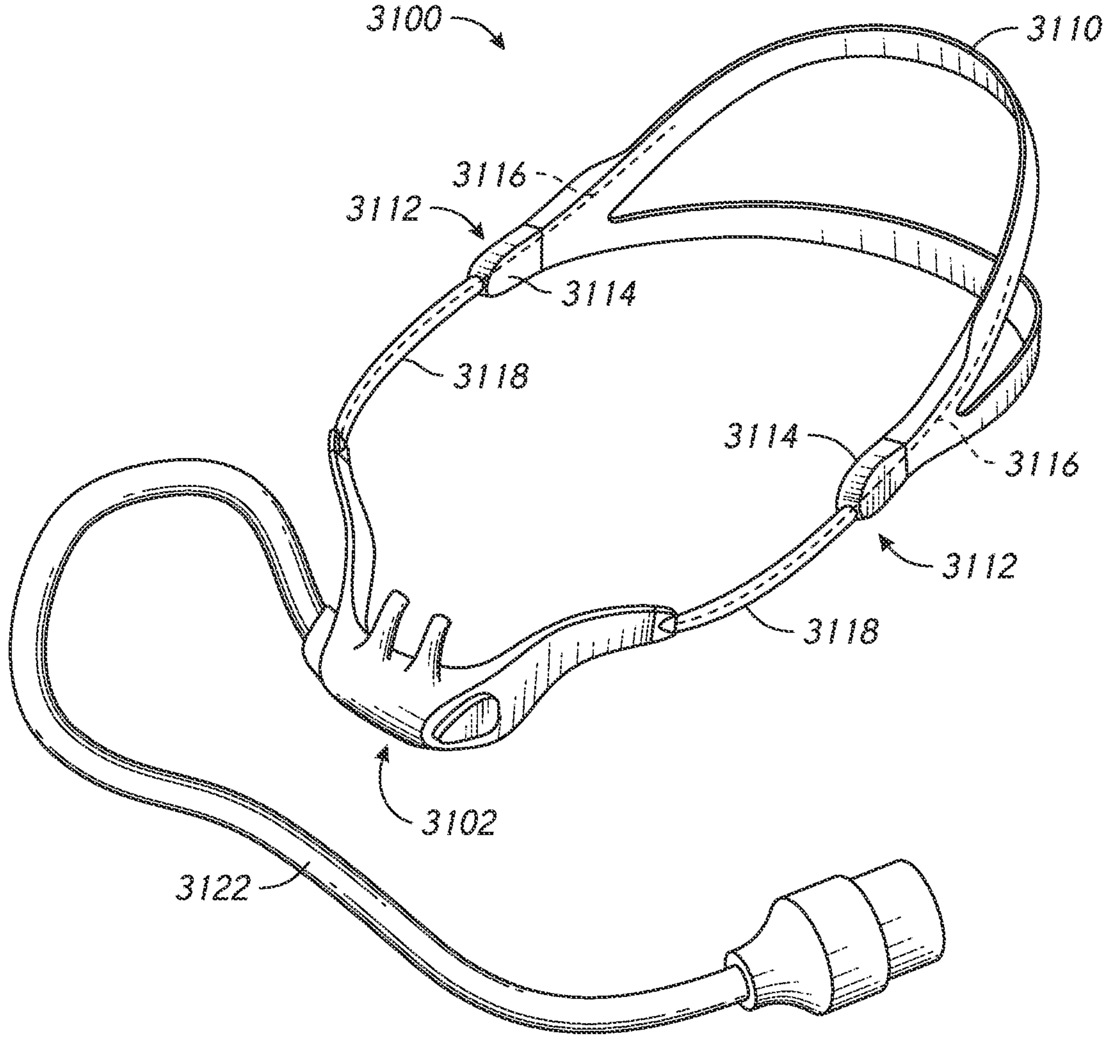
FIG. 92 is a perspective view of a respiratory cannula incorporating a headgear arrangement of the present disclosure, which can include at least one directional lock arrangement.

FIG. 92 illustrates a nasal cannula system 3100 that is similar to the system 3100 of FIG. 90 except, in the system 3100 of FIG. 92, the excess portions of the core members 3116 are contained within the nasal cannula system 3100. In particular, the core members 3116 are coupled to the nasal cannula 3102 and the directional locks 3114 are coupled to the headgear 3110. The core members 3116 extend through the biasing elements 3118, which in some configurations can be elastic tubular members. The biasing elements 3118 can be braided tubular elements that incorporate elastic elements that provide some or all of a biasing force of the biasing elements 3118. The excess portions of the core members 3116 are received within an interior of the headgear 3110, such as within a guide or accumulator. Locating the excess portions of the core members 3116 within the headgear 3110 can protect the excess portions of the core members 3116 to inhibit or prevent damage to the core members 3116, which could result in reduced performance. In some configurations, the headgear 3110 comprises an inner core and a cover, as described above. The headgear 3110 can define elongate interior spaces configured to receive the excess portions of the core members 3116 within the inner core, between the inner core and the cover, or elsewhere (e.g., a dedicated guide element). In FIG. 92, the breathing gases supply conduit 3122 is illustrated.

Figure 93:
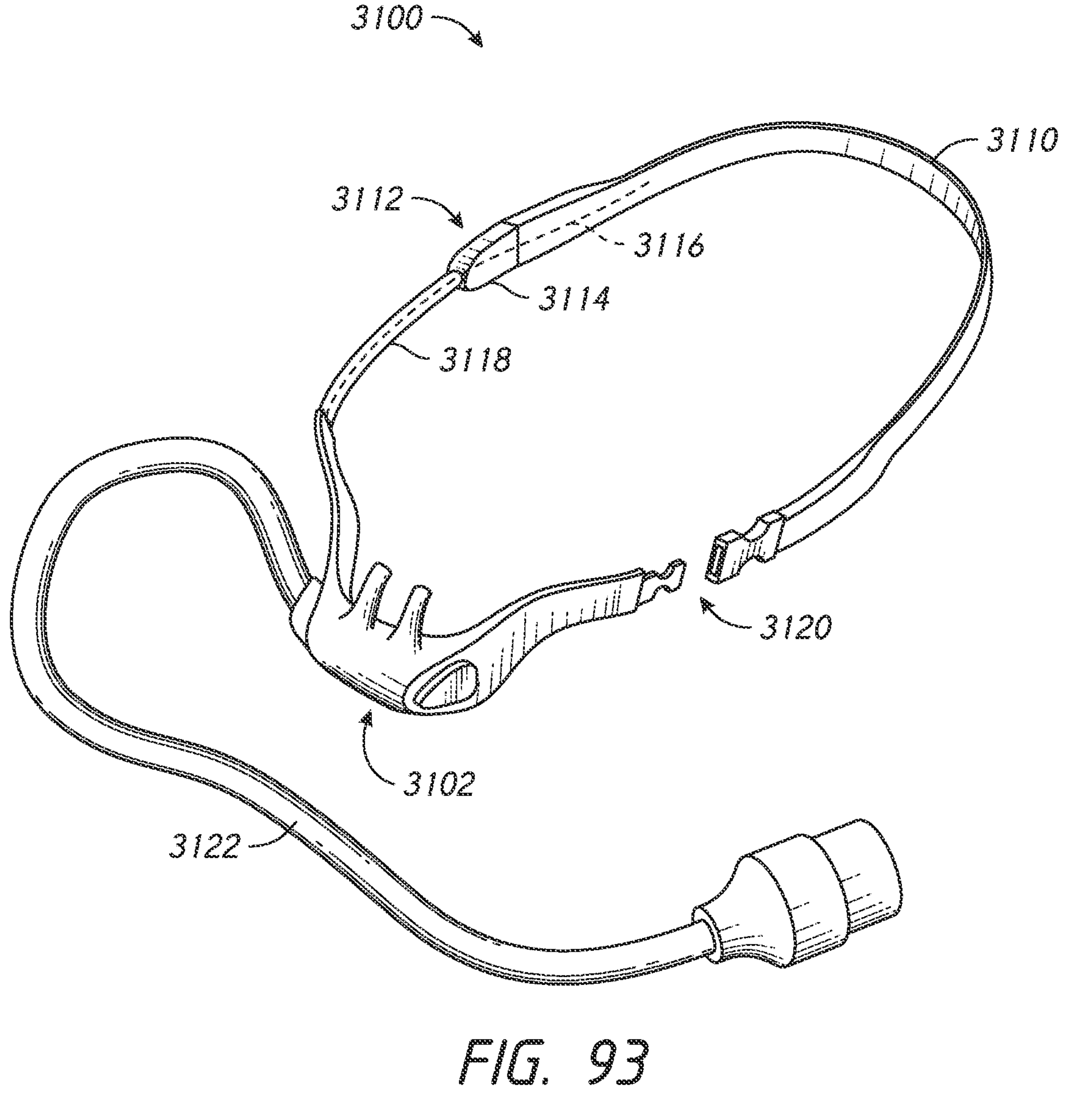
FIG. 93 is a perspective view of a respiratory cannula incorporating a headgear arrangement of the present disclosure, which can include at least one directional lock arrangement and a headgear quick release arrangement.

FIG. 93 illustrates a nasal cannula system 3100 that comprises a single adjustment arrangement 3112 in combination with a quick release arrangement 3120 similar to the systems 3100 of FIGS. 89*a*-89*c*. In the illustrated arrangement, the adjustment arrangement 3112 is located on one side of the system 3100 and the quick release arrangement 3120 is located on the opposite side of the system 3100. However, other locations for one or both of the adjustment arrangement 3112 and the quick release arrangement 3120 (e.g., a rearward location) can also be used. In addition, the nasal cannula system 3100 is configured such that the excess portion of the core member 3116 of the adjustment arrangement 3112 is contained within the headgear 3110 in a manner similar to the system 3100 of FIG. 92. That is, the headgear 3110 comprises an internal space configured to receive the excess portion of the core member 3116. In the illustrated system 3100, the headgear 3110 is a single strap arrangement; however, other types of headgear arrangements can also be used.

Figure 94:
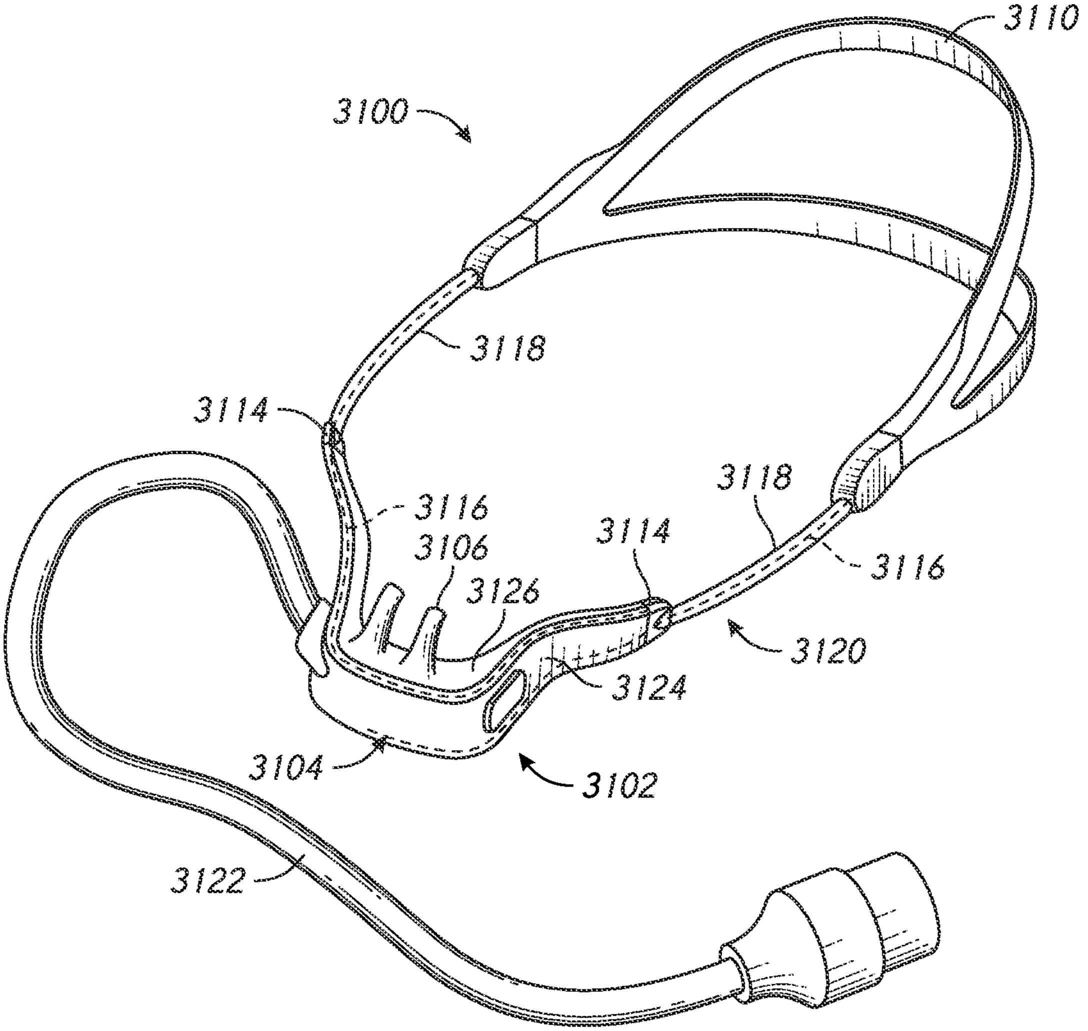
FIG. 94 is a perspective view of a respiratory cannula incorporating a headgear arrangement of the present disclosure, which can include at least one directional lock arrangement.

FIG. 94 illustrates a nasal cannula system 3100 similar to the system 3100 of FIG. 88; however, the system 3100 of FIG. 94 is configured such that the excess portions of the core members 3116 are internally contained. In particular, the nasal cannula 3102 can comprise internal spaces (e.g., conduits) configured to receive the excess portions of the core members 3116. The internal spaces can be defined by the cannula body 3104, by a guide member or by another suitable component or arrangement. In the illustrated arrangement, the cannula body 3104 comprises a rigid portion or frame 3124 that is coupled to the headgear 3110/adjustment arrangements 3112 and a softer, user-contacting portion 3126 supported by the frame 3124. The user-contacting portion 3126 can define or support the prongs 3106. The user-contacting portion 3126 can be permanently or removably coupled to the frame 3124. Such an arrangement provides for some amount of decoupling or independent movement between the frame 3124 and the user-contacting portion 3126. The internal spaces that receive the excess portions of the core members 3116 can be spaces molded into the frame 3124. In other configurations, the internal spaces can be defined between the frame 3124 and the user-contacting portion 3126. The biasing elements 3118 can be the same as or similar to those of FIG. 92 or can be of another suitable arrangement.

Figure 95:
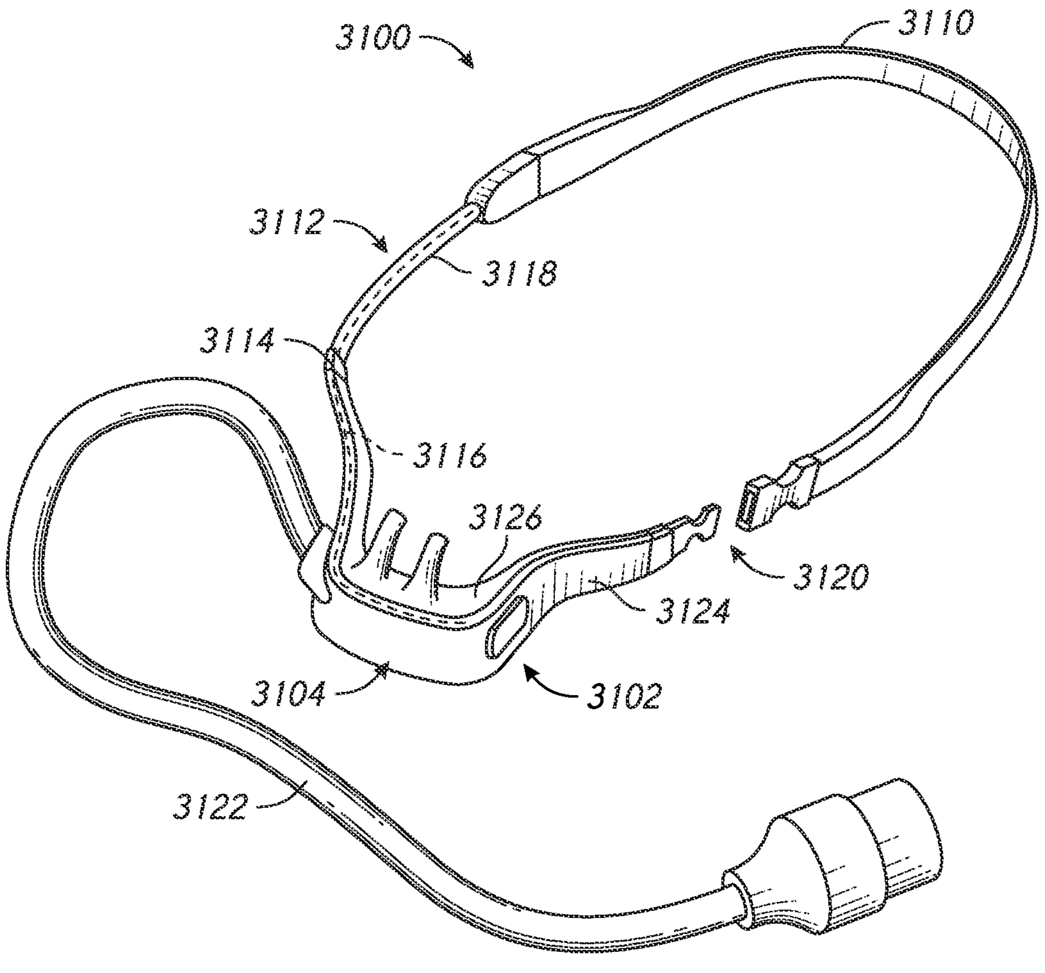
FIG. 95 is a perspective view of a respiratory cannula incorporating a headgear arrangement of the present disclosure, which can include at least one directional lock arrangement and a headgear quick release arrangement.

FIG. 95 illustrates a nasal cannula system 3100 that is similar to the system 3100 of FIG. 94. In particular, the system 3100 of FIG. 95 comprises a cannula body 3104 having a rigid portion or frame 3124 that is coupled to the headgear 3110/adjustment arrangement 3112 and a softer, user-contacting portion 3126 supported by the frame 3124. The nasal cannula 3102 can comprise an internal space configured to receive the excess portion of the core member 3116. However, similar to the system 3100 of FIG. 89*a*, the nasal cannula system 3100 of FIG. 95 includes a single adjustment arrangement 3112 and a quick release arrangement 3120. In the illustrated arrangement, the adjustment arrangement 3112 is located on one side of the nasal cannula system 3100 and the quick release arrangement 3120.

Figure 96:
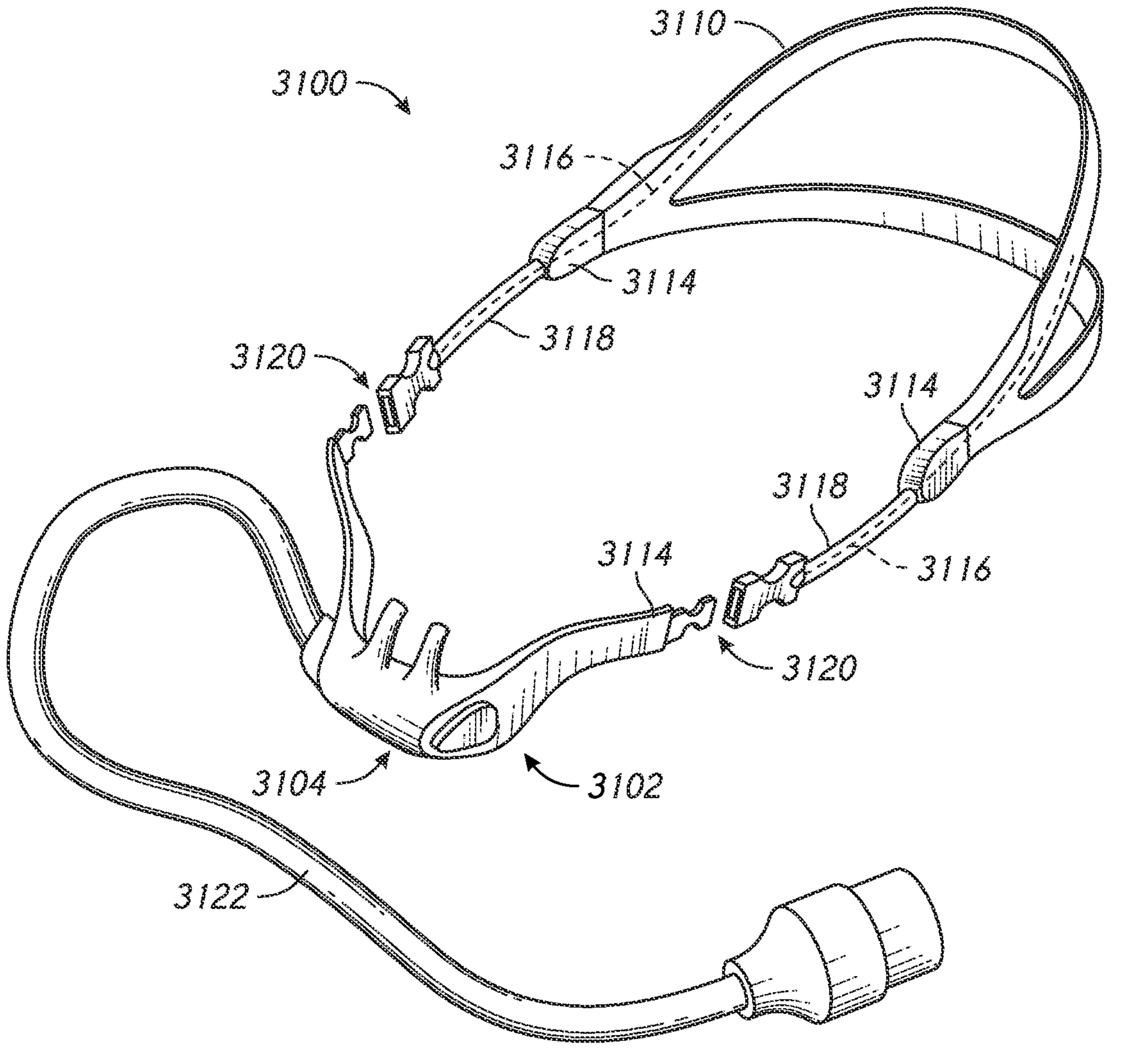
FIG. 96 is a perspective view of a respiratory cannula incorporating a headgear arrangement of the present disclosure, which can include a pair of directional lock arrangements and a pair of headgear quick release arrangements.

FIG. 96 illustrates a nasal cannula system 3100 that is similar to the system 3100 of FIG. 92 in that the excess portions of the core members 3116 are contained within the nasal cannula system 3100. In particular, the core members 3116 are coupled to the nasal cannula 3102 and the directional locks 3114 are coupled to the headgear 3110. The core members 3116 extend through the biasing elements 3118, which in some configurations can be elastic tubular members. In the illustrated arrangement, the excess portions of the core members 3116 are received within an interior of the headgear 3110, such as within a guide or accumulator. In some configurations, the headgear 3110 comprises an inner core and a cover, as described above. The headgear 3110 can define elongate interior spaces configured to receive the excess portions of the core members 3116 within the inner core, between the inner core and the cover, or elsewhere (e.g., a dedicated guide element). Unlike the system 3100 of FIG. 92, in the illustrated configuration of FIG. 96, the nasal cannula system 3100 also comprises one or more quick release arrangements 3120 between the headgear 3110/adjustment arrangements 3112 and the nasal cannula 3102. Preferably, a pair of quick release arrangements 3120 are provide, with one on each side of the nasal cannula system 3100.

Figure 97:
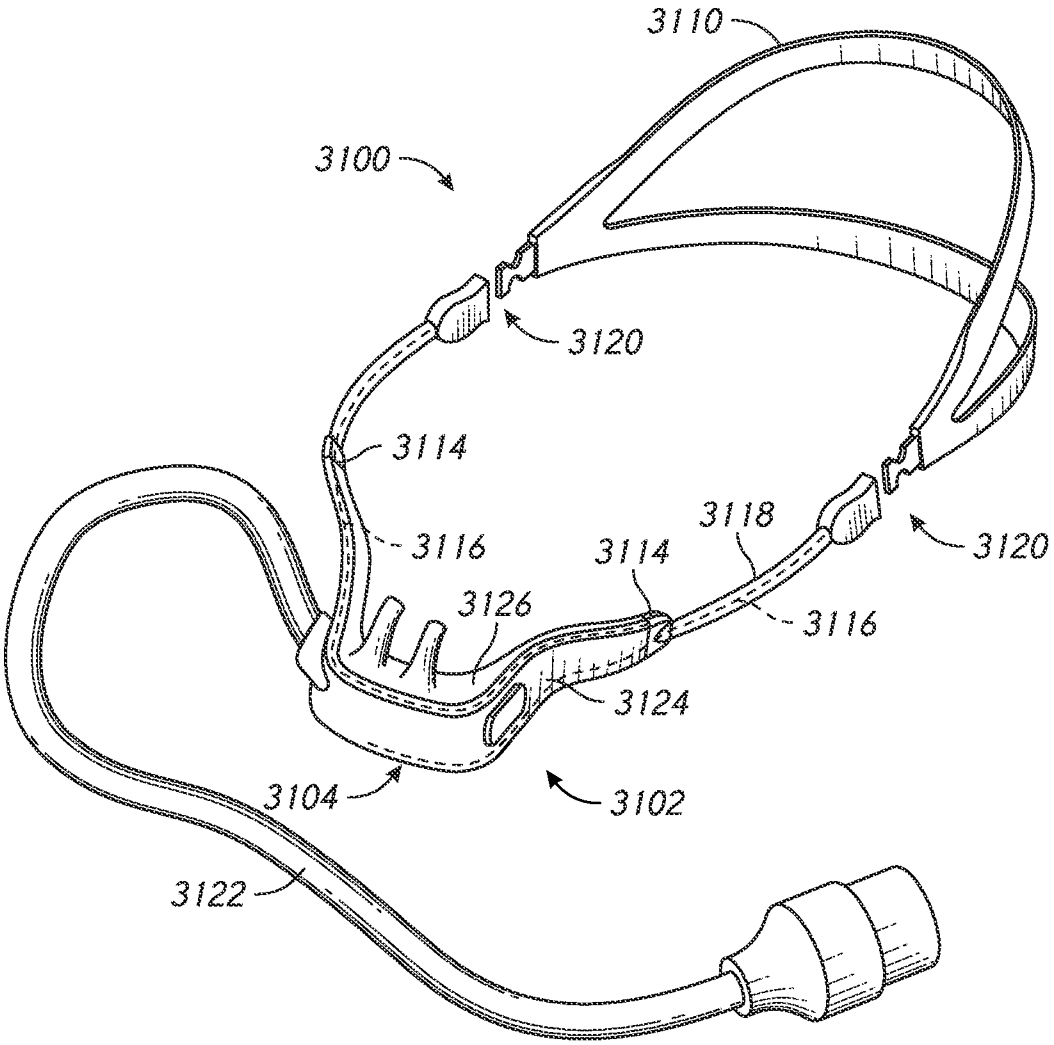
FIG. 97 is a perspective view of a respiratory cannula incorporating a headgear arrangement of the present disclosure, which can include a pair of directional lock arrangements and a pair of headgear quick release arrangements.

FIG. 97 illustrates a nasal cannula system 3100 that is similar to the system 3100 of FIG. 96 in that the system 3100 of FIG. 97 includes a pair of adjustment arrangements 3112 and a pair of quick release arrangements 3120. However, in the system of FIG. 97, the quick release arrangements 3120 are located between the headgear 3110 and the adjustment arrangements 3112. In addition, the directional locks 3114 are located at end portions of the cannula body 3104 of the nasal cannula 3102 or at forward ends of the biasing elements 3118. The excess portions of the core members 3116 are received within internal spaces of the cannula body 3104, which includes a frame 3124 and a user-contacting portion 3126 similar to the arrangements of FIGS. 94 and 95.

Figure 98:
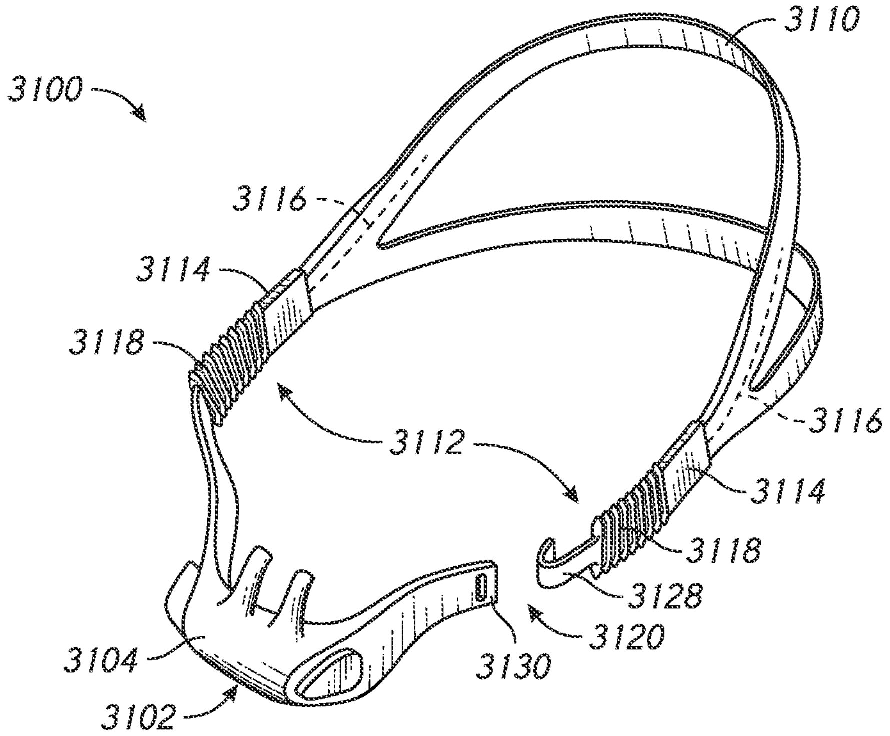
FIG. 98 is a perspective view of a respiratory cannula incorporating a headgear arrangement of the present disclosure, which can include a pair of directional lock arrangements and a headgear quick release arrangement.

FIG. 98 illustrates a nasal cannula system 3100 similar to the system 3100 of FIG. 92. For example, adjustment arrangements 3112 are provided on each side of the nasal cannula system 3100 and excess portions of the core members 3116 are received within the headgear 3110. However, the system 3100 of FIG. 98 includes a single quick release arrangement 3120. In the illustrated arrangement, the quick release arrangement 3120 is located on one side of the nasal cannula system 3100. In particular, the quick release arrangement 3120 is located between a forward end of one of the adjustment arrangements 3112 (e.g., at a forward end of the biasing element 3118) and the nasal cannula 3102. The illustrated quick release arrangement 3120 comprises a hook and post connection in which a hook 3128 is carried by the adjustment arrangement 3112 and a post 3130 is carried by the nasal cannula 3102. However, this arrangement could also be reversed. Other suitable quick release arrangements could also be used, including but not limited to any of those disclosed herein.

Figure 99:
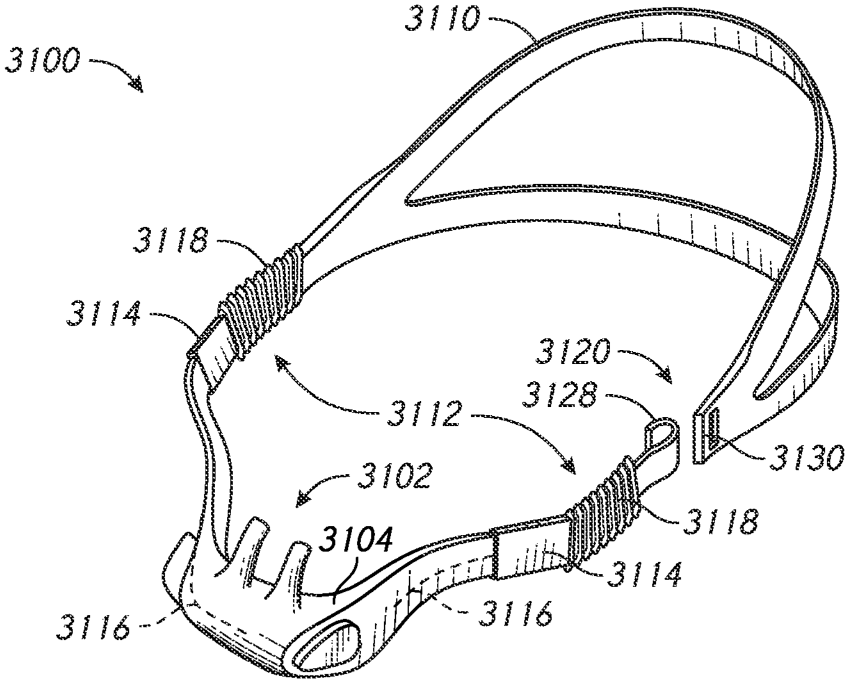
FIG. 99 is a perspective view of a respiratory cannula incorporating a headgear arrangement of the present disclosure, which can include a pair of directional lock arrangements and a headgear quick release arrangement.

FIG. 99 illustrates a nasal cannula system 3100 similar to the system 3100 of FIG. 98; however, in the system 3100 of FIG. 99, the direction of the adjustment arrangements 3112 are reversed. That is, the directional locks 3114 are located closer to the nasal cannula 3102 than the headgear 3110. In some configurations, the directional locks 3114 can be carried by the cannula body 3104 and the excess portions of the core members 3116 can be contained within the nasal cannula 3102. In addition, quick release arrangement 3120 is located between the adjustment arrangement 3112 and the headgear 3110. In particular, the hook 3128 is carried by the adjustment arrangement 3112 and the post 3130 is carried by the headgear 3110. However, this arrangement could be reversed and/or other suitable quick release arrangements could be used.

Figure 100:
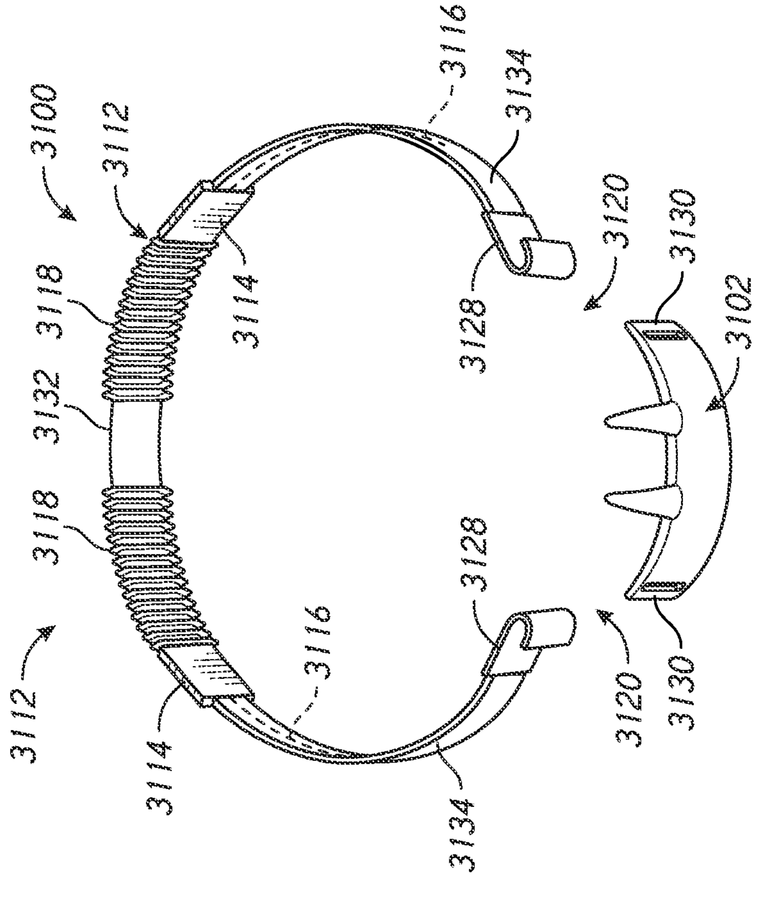
FIG. 100 is a perspective view of a respiratory cannula incorporating a headgear arrangement of the present disclosure, which can include a pair of directional lock arrangements and a pair of headgear quick release arrangements.

FIG. 100 illustrates a nasal cannula system 3100 in which the adjustment arrangement(s) 3112 are integrated into the headgear 3110, which is a single strap headgear in the illustrated arrangement. In the illustrated system 3100, a pair of adjustment arrangements 3112 are provided. In addition, each end of the headgear 3110 is connected to the nasal cannula 3102 by a quick release arrangement 3120, such as a hook 3128 and post 3130 coupling arrangement. The adjustment arrangements 3112 are located toward a rear of the headgear 3110. Ends of the adjustment arrangements 3112 are coupled to one another, either directly or via a rear head strap portion 3132, which can be a non-stretch or inextensible strap in some configurations. One end of each core member 3116 can be coupled to the head strap portion 3132 and can extend forward through a respective one of a biasing element 3118, a directional lock 3114, and into an internal accumulator space of a front head strap portion 3134. The front head strap portions 3134 can be non-stretch or inextensible straps in some configurations.

Figure 101:
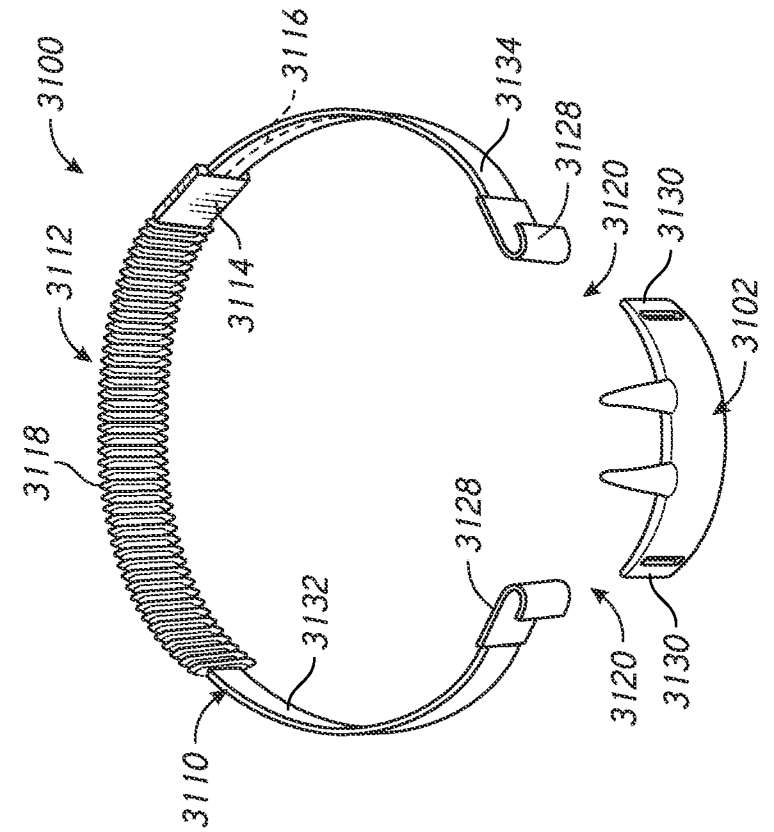
FIG. 101 is a perspective view of a respiratory cannula incorporating a headgear arrangement of the present disclosure, which can include at least one directional lock arrangement and a pair of headgear quick release arrangements.

FIG. 101 illustrates a nasal cannula system 3100 that is similar to the system 3100 of FIG. 100. However, the nasal cannula system 3100 of FIG. 101 includes a single adjustment arrangement 3112. The single adjustment arrangement is incorporated into the headgear 3110. The headgear 3110 is a single strap headgear arrangement having a first portion 3132 and a second portion 3134 coupled by the biasing element 3118. The core member 3116 is coupled to the first headgear portion 3132 and extends into an interior accumulation space of the second headgear portion 3134. The directional lock 3114 is coupled to the second headgear portion 3134 and selectively engages the core member 3116 to secure the headgear 3110 in a desired adjustment position of the circumference of the nasal cannula system 3100.

Figure 102:
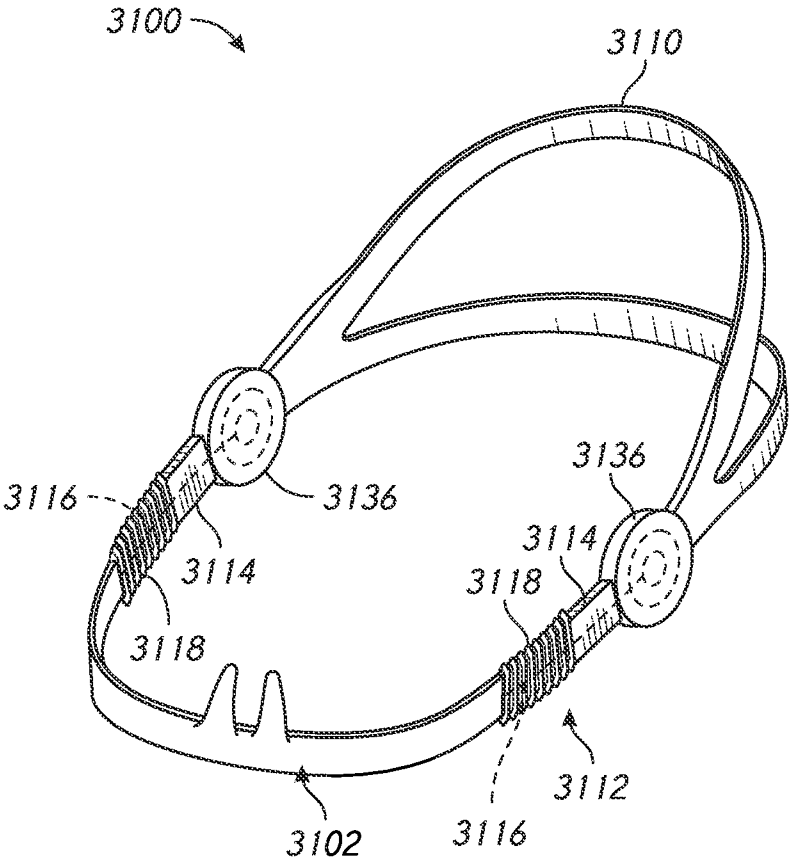
FIG. 102 is a perspective view of a respiratory cannula incorporating a headgear arrangement of the present disclosure, which can include a pair of directional lock arrangements.

FIG. 102 illustrates a nasal cannula system 3100 that is similar to the system 3100 of FIG. 90. In particular, the nasal cannula system 3100 comprises an adjustment arrangement 3112 on each side of the nasal cannula system 3100. In the illustrated arrangement, the excess portions of the core members 3116 are accumulated in disk-shaped accumulators 3136. Such an arrangement eliminates the need to provide for accumulation of the excess portions of the core members 3116 in the headgear 3110. In the illustrated arrangement, the adjustment arrangements include biasing elements 3118. However, in other configurations, the accumulators 3136 could be in the form of dial adjusters that take up or release the core members 3116. With such an arrangement, the circumference of the nasal cannula system 3100 can be adjusted by rotating the accumulators in one direction or the other to reduce or lengthen the circumference. In addition, although not specifically shown, the system 3100 of FIG. 102 can include one or more quick release arrangements 3120.

In at least some configurations, the core member ("filament") is circular in cross-sectional shape and the excess portion of the filament is received within an accumulator (e.g., tube or tubular pathway—hereinafter "tube") that is also circular in cross-sectional shape. In at least some configurations, the filament can be in the range of 0.6 mm to 0.8 mm in diameter. In at least some configurations, the diameter of the tube (the inner diameter) is approximately 0.1 mm greater than the filament diameter, when the filament is nylon and the tube is polyethylene (PE). Thus, in some configurations, the diameter of the tube is between about 10-20 percent greater, about 12-17 percent greater or about 12.5-16.67 percent greater than the diameter of the filament, including any sub-range or value within the above ranges.

In general, the smaller the tube diameter in relation to the filament diameter, the more friction will be applied to the filament by the tube. However, the bigger the diameter of the tube, the less guidance it will provide for the filament, which, in some cases, could negatively influence movement of the filament within the tube. As a result, the "return behavior" or shortening of the interface circumference or headgear length may feel rougher and/or less consistent. Furthermore, excessive movement of the filament within the tube could damage the internal walls of the tube. It has been determined that a nylon filament of 0.7 mm diameter sliding inside a PE tube of internal diameter of 0.8 mm increases the total force on the adjustment arrangement by about 1 N in the activation direction. It is possible that a similar excess force will be present in both the activation (lengthening) and return (shortening) directions. Excess force added as a result of movement of the filament within the tube preferably is reduced or minimized such that the return force provided by biasing element(s) can be kept low.

The ratio of the filament and tube diameters can be based, at least in part, on the curvature of the tube, the flexural modulus of both the tube and the filament, and the particular materials of the tube and filament. In addition, a factor of the tube design can include the external wall to internal wall ratio, where the higher that ratio is (external/internal), the higher the flexural modulus of the tube. Too high of a flexural modulus may reduce the flexibility of the tube. Reduced flexibility may cause the tube to kink if it is bent or curved in use. Different materials can also have different flexural moduli, as well as other properties that affect the forces resulting from the filament sliding within the tube. In some configurations, it is desirable that the tube has a higher Young's modulus relative to the filament because the tube acts as the guide to the filament. Therefore, it is desirable to reduce the possibility of the filament damaging the tube or creating excessive wear of the tube. In some configurations, it is preferable for the tube and the filament to be made of dissimilar materials to avoid cold welding through friction caused by sliding of the filament relative to the tube.

Figure 103:
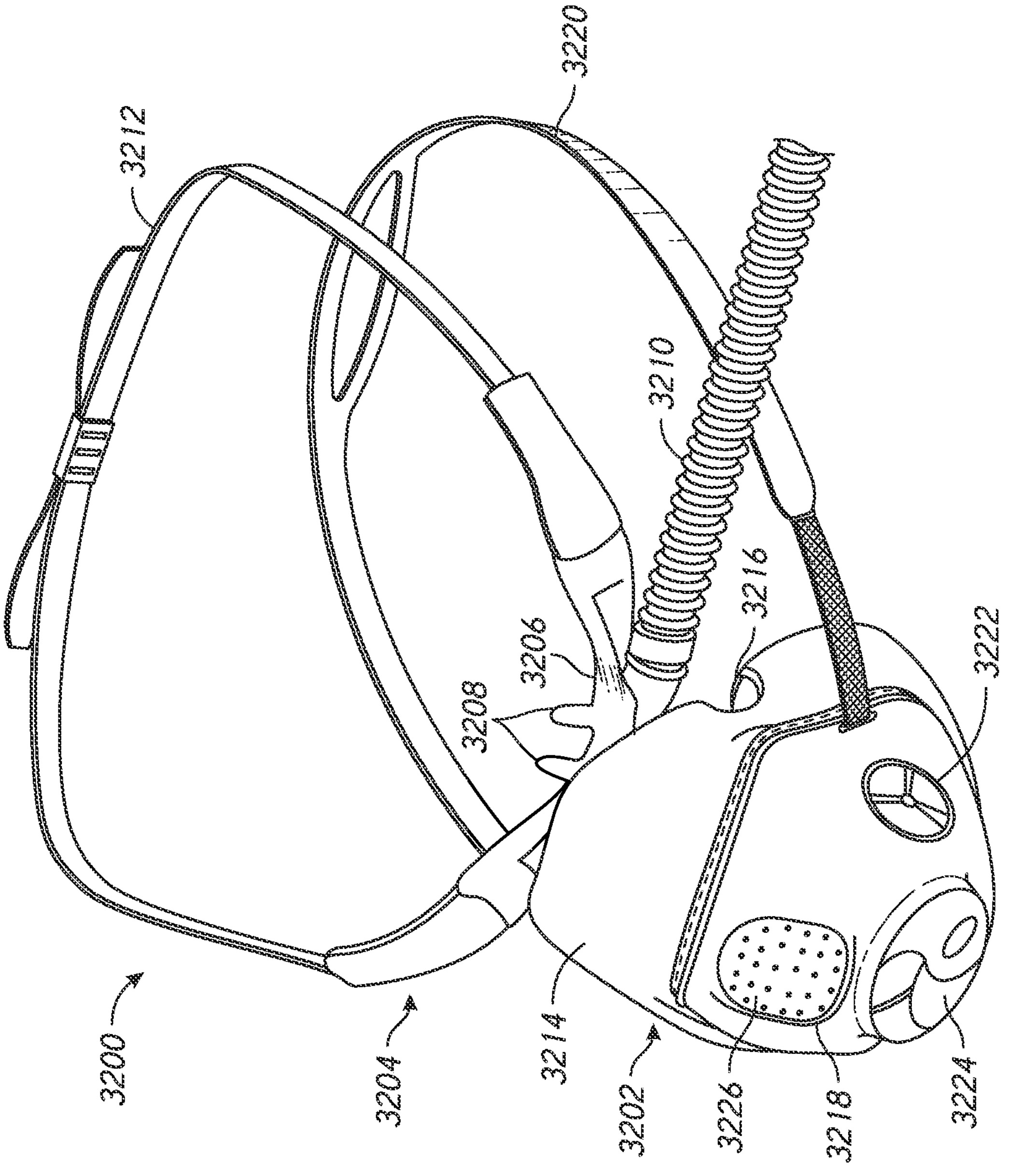
FIG. 103 is a perspective view of an increased or controlled expiratory pressure system comprising a respiratory mask for use in combination with a nasal high flow cannula. The respiratory mask can comprise one or more directional lock arrangements.
Figure 104:
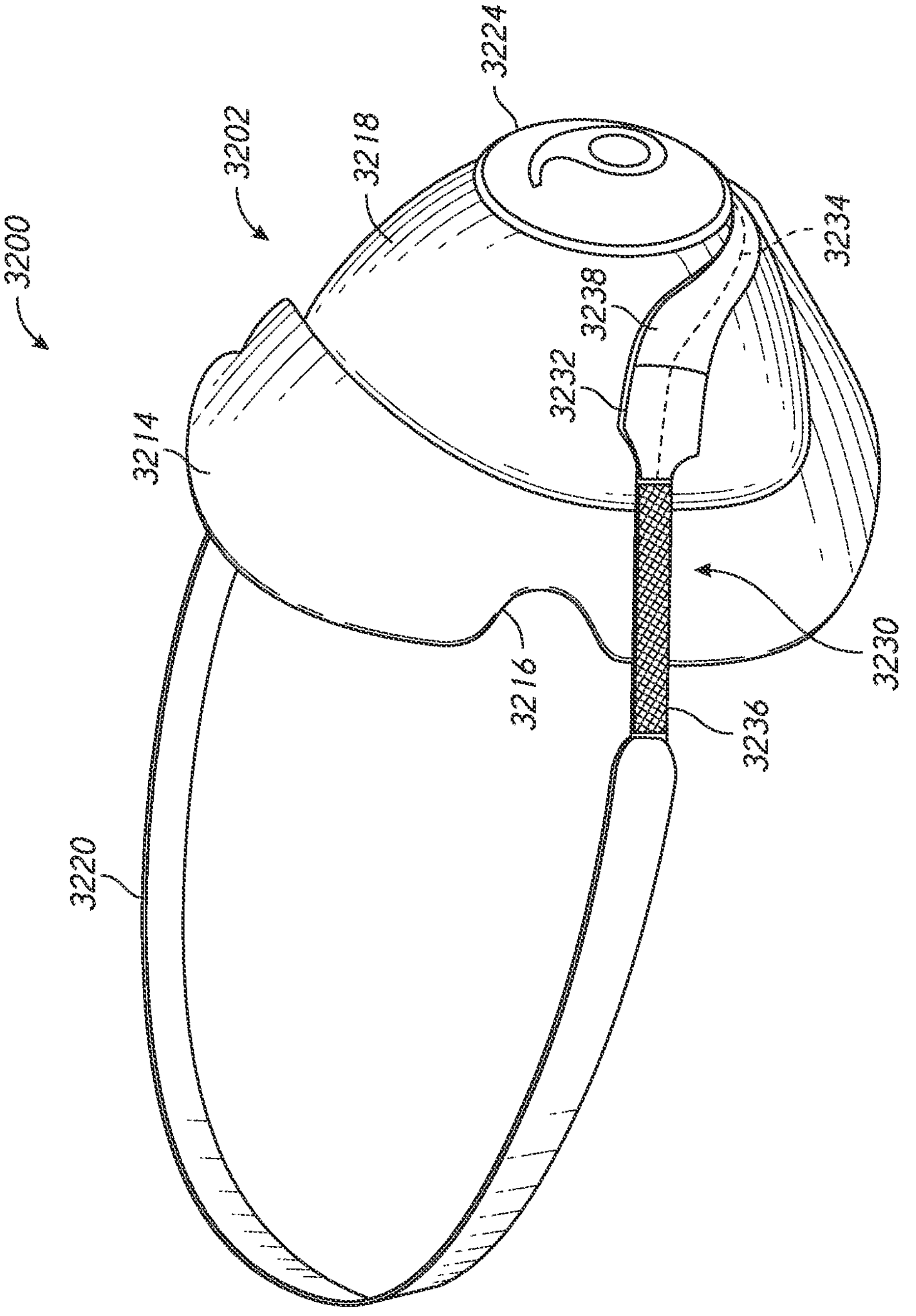
FIG. 104 is a perspective view of the respiratory mask of FIG. 103.

FIG. 103 illustrates a respiratory therapy system 3200 comprising a mask 3202 that covers a nasal cannula 3204 (e.g., nasal high flow cannula) to provide an increased or controlled expiratory pressure relative to the nasal cannula 3204 on its own. FIG. 104 illustrates the mask 3202 alone. Such a system is disclosed in Applicant's PCT Application No. PCT/IB2015/052257, entitled CANNULA PRESSURIZING MASK, the entirety of which is incorporated by reference herein. The mask 3202 and nasal cannula 3204 can be sold as a system or kit, in which the mask 3202 and nasal cannula 3204 are sold together or in a single package. In other configurations, the mask 3202 can be configured for use in combination with one or more particular models of nasal cannula 3204, but can be sold separately from such nasal cannula 3204.

The nasal cannula 3204 can be used to provide a flow of breathing gas to the user. Thus, the nasal cannula 3204 can be applied to the user separately from the mask 3202. The mask 3202 can be selectively applied to the user without removal of the nasal cannula 3204 and, preferably, without significant movement or other manipulation of the nasal cannula 3204. Similarly, the mask 3202 preferably can be removed from the user without removal of the nasal cannula 3204 and, preferably, without significant movement or other manipulation of the nasal cannula 3204.

The nasal cannula 3204 can be of any suitable configuration for the intended use, such as high-flow (HF) nasal therapy. The nasal cannula 3204 can have a body 3206 from which at least one nasal prong 3208 extends. In the illustrated arrangement, a pair of nasal prongs 3208 is provided. Preferably, when the nasal cannula 3204 is properly positioned on the user's head, the nasal prongs 3208 extend toward or into, but do not fully seal with, the user's nares. The nasal cannula 3204 includes a gases or breathing circuit that communicates with the nasal prongs 3208. In the illustrated arrangement, the gases circuit comprises at least one gases tube 3210 that supplies a flow of breathing gas to the nasal prongs 3208 and, thus, can be referred to as a supply tube. In the illustrated arrangement, a single supply tube 3210 is provided and extends to one side of the nasal cannula 3204. In other arrangements, the supply tube 3210 can extend in other directions and/or multiple supply tubes 3210 can be provided. For example, in some configurations, a supply tube 3210 can be provided on and extend to each side of the nasal cannula 3204. In use, the supply tube 3210 can be connected to a source of pressurized gas (e.g., a flow generator) and, optionally, a humidifier. The source of pressurized gas can be configured to supply supplemental oxygen to the user. Any suitable source of pressurized gas can be used.

The nasal cannula 3204 preferably also includes a retention or headgear arrangement that secures or retains the nasal cannula 3204 onto the user's head. In the illustrated cannula 3204, the headgear arrangement is in the form of a single strap 3212 that extends around the user's head from one side of the cannula body 3206 to the other side of the cannula body 3206. However, in other configurations, the headgear arrangement can more complex, such as including multiple straps or multiple strap portions. The headgear arrangement can include a rear portion that extends around the back of the user's head and/or an upper portion that extends over the top of the user's head. The headgear arrangement can include flexible or relatively rigid portions, elastic or relatively inelastic portions or any combination thereof. If desired, the headgear arrangement can comprise one or more adjustment arrangements as described herein.

The mask 3202 can comprise a sealing cushion 3214, one or more cannula cut-outs 3216, a mask frame 3218, a headgear arrangement or head strap 3220, a one-way valve 3222, a variable vent 3224 and a fixed bias flow vent 3226. Unlike non-invasive respiratory masks known in the art, the illustrated mask 3202 may not include an air supply conduit or connection port. Instead, a portion or most of the air flow to the user is supplied by the nasal cannula system 3204 with any deficit being supplied through the one-way valve(s) 3222. With such an arrangement, the mask 3202 can act as a pressure vessel that can increase the expiratory pressure within the airways of the user.

The mask 3202 can comprise a mask body, which can be made up of, in whole or in part, the mask frame 3218 and the sealing cushion 3214. The sealing cushion 3214 can be referred to herein as a "seal" or as a "cushion." The mask frame 3218 can be unitary with or can otherwise support the cushion 3214. The mask frame 3218 can be constructed from a material that is capable of at least substantially maintaining its shape in the absence of external forces applied to the mask frame 3218. In some configurations, the mask frame 3218 can be resilient. In other configurations, the mask frame 3218 can be relatively rigid or at least more rigid than the cushion 3214. For example, the mask frame 3218 can be constructed in whole or in part from polycarbonate, high-density polyethylene (HDPE) or another suitable material. The mask frame 3218 can be a one-piece structure or can be a multi-piece structure. For example, a first mask frame portion or element can support the cushion 3214 and a second mask frame portion or element can provide for connection of the headgear 3220. The first mask frame portion and the second mask frame portion can be permanently or, preferably, removably connected to one another.

The cushion 3214 can be configured to provide an interface between the user and the mask 3202 and can be made from a flexible material, such as silicone rubber, a thermoplastic elastomer or any other suitable seal material. The cushion 3214 can be secured to the mask frame 3218 by any suitable process or arrangement. For example, the cushion 3214 can be removably coupled to the mask frame 3218, such as by a flange-and-groove arrangement. In other configurations, the cushion 3214 can be attached to the mask frame 3218 by adhesives or during the forming process (e.g., overmolding or co-molding).

The cushion 3214 preferably includes one or more features configured to accommodate the nasal cannula 3204 when the mask 3202 is applied to a user while the nasal cannula 3204 is in use. For example, the cushion 3214 can include at least one cannula recess or cut-out 3216. In other configurations, the cushion 3214 can include other configurations to accommodate the nasal cannula 3204, such as regions of increased compliance or thin-walled regions that allow the cushion 3214 to stretch over the nasal cannula 3204. Such thin-walled regions may have a wall thickness that is significantly thinner than surrounding portions of the cushion 3214 and may be sized and/or shaped to generally correspond to the size and/or shape of the portion of the nasal cannula 3204 that passes underneath the cushion 3214. Examples of thin-walled regions are described in Applicant's PCT Publication No. WO2015/130179, published Sep. 3, 2015, entitled "RESPIRATORY MASK WITH NASOGASTRIC TUBE PATH," the entirety of which is incorporated by reference herein.

In the illustrated arrangement, the cushion 3214 includes a cannula cut-out 3216 on each side of the mask 3202. In particular, the illustrated cushion 3214 includes a cut-out 3216 on each lateral side of the mask 3202. The cut-outs 3216 can be configured to accommodate, complement or match the lateral geometry of a nasal cannula, in general, or a particular nasal cannula 3204. Such an arrangement enables a cannula to pass between the mask 3202 and a user's face, preferably with minimal or acceptable gaps between the cannula and mask 3202. Preferably, when properly positioned on the user in combination with the nasal cannula 3204, the mask 3202 can create a seal with the face of the user that is sufficient to allow for an increase in pressure within an interior space or breathing cavity of the mask 3202 and/or an increased expiratory pressure within the user's airways relative to the use of the nasal cannula 3204 without the mask 3202. Preferably, the mask 3202 also creates at least a substantial seal with the nasal cannula 3204. Preferably, the combination of the seal with the user's face and the nasal cannula 3204 is sufficient to allow for an increase in pressure within an interior space or breathing cavity of the mask 3202 and/or an increased expiratory pressure within the user's airways. In some configurations, the mask 3202 is capable of creating a seal with the user's face that is sufficient to allow for a therapeutically-significant increase in an increase in pressure within an interior space or breathing cavity of the mask 3202 and/or an increased expiratory pressure within the user's airways relative to the use of the nasal cannula 3204 without the mask 3202.

Preferably, the mask 3202 comprises at least one adjustment arrangement 3230, which can be the same as or similar to any of the adjustment arrangements disclosed herein, or can be of another suitable arrangement. With such an arrangement, the mask 3202 can be quickly and easily applied to a user over the nasal cannula 3204 to provide increased therapy pressure. In at least some configurations, the mask 3202 can automatically adjust toward or to an appropriate size for the particular user. Such an arrangement is beneficial for reducing the time that it takes a caregiver to apply the mask 3202 to initiate the increased therapy pressure by reducing the time needed to adjust the circumference of the mask 3202 and headgear 3220 to the particular user. Although not shown, the mask 3202 can include one or more quick release arrangements, such as any of those disclosed herein, to further facilitate the application or removal of the mask 3202 to a user.

In some configurations, the mask 3202 comprises a pair of adjustment arrangements 3230, with one adjustment arrangement 3230 positioned on each side of the mask 3202. The adjustment arrangements 3230 can each comprise a directional lock 3232, a core member or filament 3234 that moves relative to and is selectively engaged by the directional lock 3232, and a biasing element or arrangement 3236 that, in the illustrated arrangement, tends to shorten a circumference of the mask 3202 and headgear 3220. In the illustrated arrangement, one end of each of the core members 3234 is coupled to a respective end of the headgear 3220. The core members 3234 extend through the biasing elements 3236, the directional locks 3232 and into an accumulator 3238, which can be defined by any suitable structure. In the illustrated arrangement, the accumulator

3238 is a connector that clips onto the mask frame 3218 to connect the headgear 3220 to the mask frame 3218. In other configurations, a separate accumulator could be provided for each core member 3234. The excess portions of the core members 3234 could also be accommodated by other suitable structures, such as any of those disclosed herein. The illustrated direction of the adjustment arrangements 3230 could also be reversed. Furthermore, the number and/or location of the adjustment arrangements 3230 could be varied from that illustrated in FIGS. 103 and 104.

Figure 105:
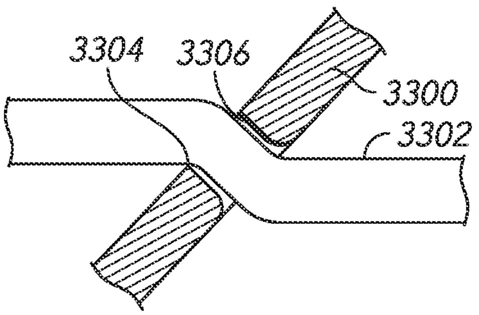
FIG. 105 is a side view of a lock member and core member of a directional lock arrangement.

FIG. 105 illustrates an example of a lock member, which in the illustrated arrangement is a lock washer 3300, in a locked position relative to a core member 3302. It has been discovered by the present inventors that a leading edge 3304 (relative to a direction of movement of the core member 3302 that tends to move the lock washer 3300 to the locked position) of the opening 3306 of the lock washer 3300 through which the core member 3302 passes can be an important design characteristic to achieve a desirable performance of the associated directional lock. Thus, the leading edge 3304 or a portion of the leading edge 3304 that engages the core member 3302 in a locked position of the lock washer 3300 can be referred to as the "working edge." In at least some configurations, it is desirable that at least a portion of the leading edge 3304 that engages the core member 3302 in the locked position (e.g., a lower portion or half) is relatively sharp. It is presently believed that the sharp leading edge 3304 provides a better grip on the core member 3302 than a more rounded edge. The sharpness of the leading edge 3304 can be defined as: 1/R, wherein R is the radius of the leading edge 3304 or at least a portion of the leading edge 3304 that contacts or engages the core member 3302 in a locked position of the lock washer 3300.

Figure 106:
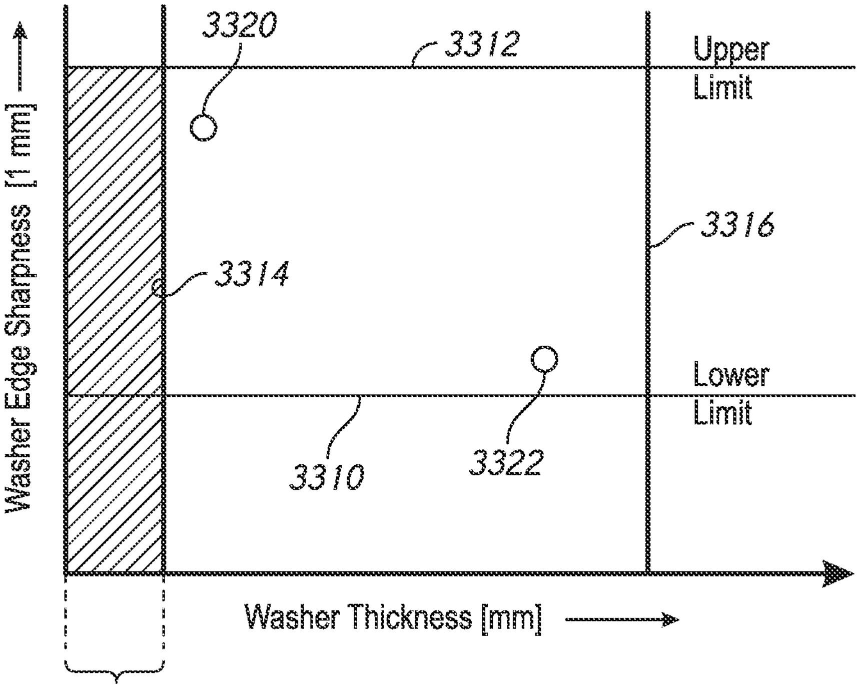
FIG. 106 is a graph of lock member edge sharpness versus lock member thickness illustrating a preferred operating envelope for the lock member.

FIG. 106 illustrates a graph of leading edge sharpness versus lock washer thickness. Performance and/or practical considerations can result in the creation of design limits on these variables with respect to a particular interface or application of use. Such design limits may be selected to achieve a desired level of performance, and values outside of the design limits may still be functional and suitable for use in at least some applications. Therefore, the design limits described herein are not considered limiting unless expressly indicated as such. Moreover, the design limits will likely vary between different interface or headgear types, or different applications of use.

The graph of FIG. 106 illustrates a target design envelope created by a lower limit 3310 and an upper limit 3312 of the leading edge sharpness and a lower limit 3314 and an upper limit 3316 of the lock washer thickness. As discussed above, if the leading edge sharpness of the lock washer 3300 (or other lock element) is too low, the associated directional lock may not provide a desired level of grip on the core member 3302 and the locking force of the directional lock may be lower than desirable. Thus, the lower limit 3310 of the lock washer sharpness may be determined by the desired lock force in view of the other relevant design characteristics, such as material selection, lock member angle, etc. The upper limit 3316 of the lock washer sharpness may be determined in view of practical considerations, such as manufacturability. That is, the upper limit 3316 of lock washer sharpness may be determined by the sharpness that can be produced by a given manufacturing process, which process may be selected on the basis of manufacturing cost.

The lower limit 3314 of lock washer thickness may be determined based on practical considerations, such as strength requirements or manufacturability. The upper limit 3316 of lock washer thickness can also be determined by practical considerations, such as space available for the lock washer 3300 and the associated directional lock. Thus, in at least some configurations, the lock washer thickness will not be substantially greater than necessary to provide adequate strength (or other physical characteristics) in order to allow the associated directional lock to be relatively small. In some configurations, the lower limit 3314 may be approximately 0.5 mm and the upper limit 3316 may be approximately 5 mm. However, these values can change depending on relevant design criteria, as described above.

FIG. 106 illustrates two points 3320, 3322 within the target design envelope that represent two different lock washers 3300 having a different thickness and leading edge sharpness relative to one another. Point 3320 represents a lock washer 3300 having relatively high leading edge sharpness and relatively low washer thickness. In other words, the lock washer 3300 represented by point 3320 is relatively thin. Such a lock washer 3300 represented by point 3320 can have a thickness of about 0.5 mm-1 mm (e.g., 0.8 mm). Point 3322 represents a lock washer 3300 having relatively low leading edge sharpness and relatively high washer thickness relative to the target design envelope and the washer 3300 represented by point 3320. Such a lock washer 3300 represented by point 3322 can have a thickness of about 2 mm-4 mm (e.g., 3 mm). The radius of the leading edge 3304 can be between 0.4 mm-0.6 mm (e.g., 0.5 mm).

Figure 107:
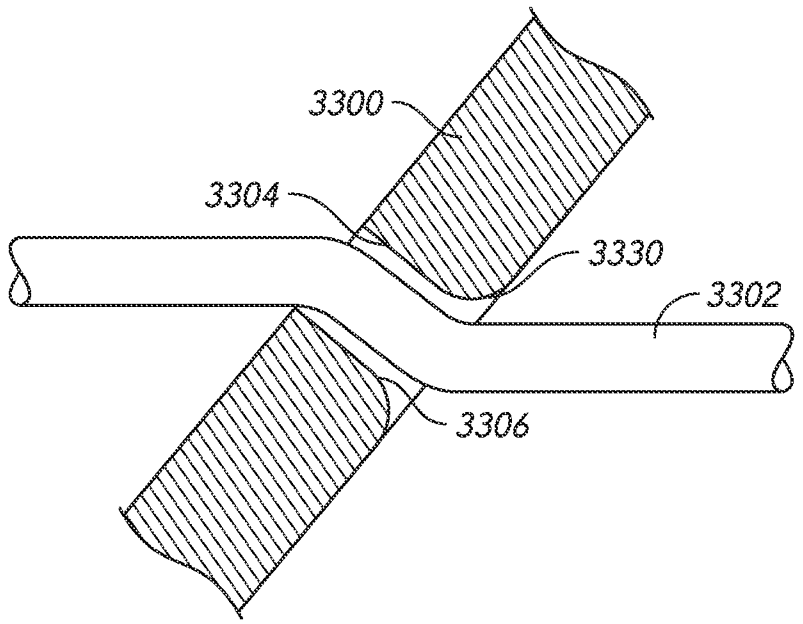
FIG. 107 is an enlarged view of a lock member in a locked position.
Figure 108:
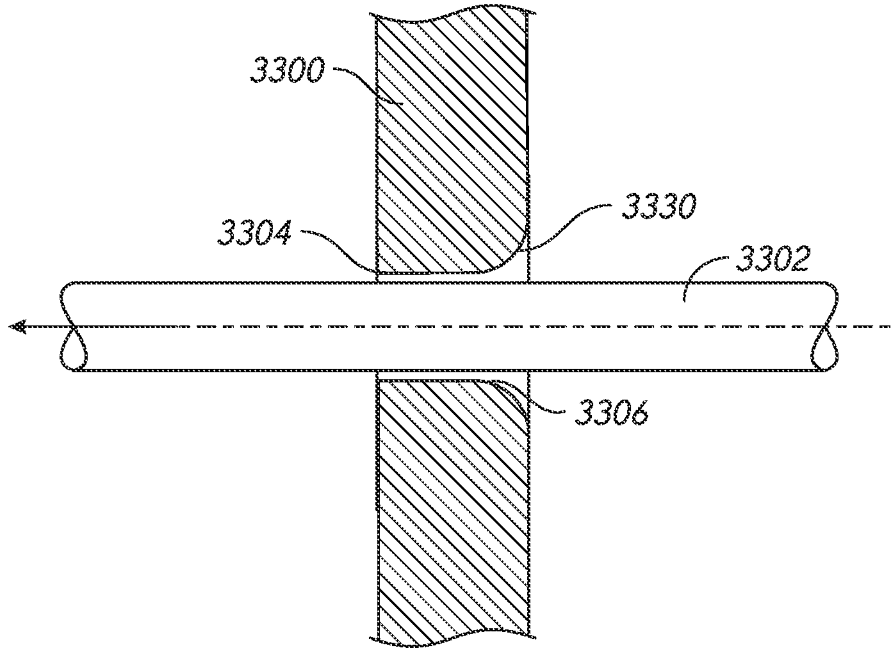

FIGS. 107 and 108 illustrate an embodiment of a lock member/lock washer 3300 and a core member 3302 in a locked position and a free or unlocked position, respectively. As illustrated, preferably, the leading edge 3304 of a portion of the lock washer 3300 that defines the opening 3306 and engages the core member 3302 is relatively sharp or has a relatively high sharpness, as described above. Preferably, the trailing edge 3330 of a portion of the lock washer 3300 that defines the opening 3306 for the core member 3302 has a lower sharpness than the leading edge 3304. In some configurations, the trailing edge 3330 is rounded or chamfered. Preferably, a diameter (or perimeter length) of the opening 3306 at the trailing edge 3330 is larger than a diameter (or perimeter length) of the opening 3306 at the leading edge 3304. Such an arrangement can provide a desirable locking force and can also allow the core member 3302 to move in a release direction (FIG. 108) at a reduced level of resistance compared to a constant diameter opening 3306. In addition, the arrangement of FIGS. 107 and 108 improves manufacturability by making it easier to pass the core member 3302 through the opening 3306 during assembly of the directional lock. That is, the core member 3302 can be inserted through the larger diameter (or perimeter length) trailing edge 3330, which can be easier and faster than attempting to insert the core member 3302 through the smaller diameter (or perimeter length) leading edge 3304.

FIGS. 109*a*-109*c* illustrate several core members 3300 having openings 3306 of different cross-sectional shapes between the leading edge 3304 and the trailing edge 3330. The opening 3306 of each of the core members 3300 of FIGS. 109*a*, 109*b* and 109*c* has a diameter (or perimeter length) at or near the leading edge 3304 that is less than the diameter (or perimeter length) at or near the trailing edge 3330. In FIG. 109*a*, the opening 3306 has a substantially constant diameter from the leading edge 3304 and extending toward the trailing edge 3330 through a substantial portion of a length of the opening 3306. However, the portion of the opening 3306 near the trailing edge 3330 is rounded or chamfered such that the diameter of the opening 3306 at the trailing edge 3330 is larger than the diameter of the opening

3306 at the leading edge 3304. The opening 3306 of FIG. 109*a* is substantially similar to the openings 3306 of FIGS. 107 and 108.

The opening 3306 of FIG. 109*b* is tapered along a portion or a substantial entirety of its length. In the illustrated arrangement, the opening 3306 tapers at a constant angle from a minimum diameter at the leading edge 3304 to a maximum diameter at the trailing edge 3330. However, in other configurations, the taper could be non-linear. The opening 3306 of FIG. 109*c* combines a linear or constant diameter portion and a tapered portion. The portion of the opening 3306 beginning at the leading edge 3304 and extending through a portion (e.g., one-third to two-thirds, or about one-half) of the thickness of the washer 3300 defines a constant diameter. The remaining portion of the opening 3306 defines an outwardly-tapered portion such that the diameter of the opening 3306 at the trailing edge 3330 is greater than the diameter of the opening 3306 at the leading edge 3304. The tapered portion can comprise a linear or non-linear taper.

FIGS. 110, 111*a* and 111*b* illustrate lock members or lock washers 3300 having openings 3306 with non-circular profile shapes. For example, the lock washer 3300 of FIGS. 110 and 111*a* includes an opening 3306 that tapers from an upper portion 3340 to a lower portion 3342. In the illustrated arrangement, the opening 3306 has an upside-down teardrop or raindrop shape. The upper portion 3340 of the opening 3306 is generally semi-circular. The lower portion 3342 of the opening 3306 can also be semi-circular in shape and defines a diameter or width that is less than the diameter or width of the upper portion of the opening 3306. Sidewalls 3344 of the opening 3306 can taper or reduce in width from the upper portion 3340 toward the lower portion 3342. The diameter or width of the upper portion 3340 of the opening 3306 preferably is larger than the diameter or width of the core member 3302, and can be only slightly larger than the diameter or width of the core member 3302. With such an arrangement, each of the sidewalls 3344 can define a working edge of the opening 3306 that engages the core member 3302 in the locked position of the lock washer 3300. A width or lateral distance between the sidewalls 3344 or working edges that engage the core member 3302 can reduce the further the lock washer is rotated toward the locked position. Such an arrangement results in a progressively increasing locking force with increasing rotation of the lock washer 3300.

FIG. 111*b* illustrates an alternative non-circular or tapered profile shape of an opening 3306 of a lock washer 3300. The opening 3306 of the lock washer 3300 of FIG. 111*b* defines a keyhole shape, in which an upper portion 3340 is circular in shape and a lower portion 3342 tapers starting from a width that is less than the diameter of the circular upper portion 3340. The working edges of the opening 3306 can also be defined by the sidewalls 3344 in a manner similar to the opening 3306 of FIGS. 110 and 111*a*. Similarly, the opening 3306 of FIG. 111*b* can also result in a progressively increasing locking force, which may initially start or abruptly rise to a higher initial value than the opening 3306 of FIGS. 110 and 111*a*.

FIG. 112 illustrates a graph of locking or holding force versus core member displacement comparing a linear curve, which may be provided by a circular opening 3306, to a progressive curve, which may be provided by a non-circular (e.g., tapering) opening 3306. As illustrated, the non-circular or tapered openings, such as the openings 3306 of FIGS. 110, 111*a* and 111*b*, can rise to a desired locking or holding force at a lesser displacement of the core member 3302 compared to the linear curve of a circular opening 3306. Thus, a lock washer 3300 comprising a non-circular or tapered opening 3306 may reach a desired locking or holding force more quickly than a circular opening 3306.

FIGS. 113*a* and 113*b* illustrate a directional lock 3400 having a first lock member or lock washer 3402 and a second lock member or lock washer 3404. The directional lock 3400 may be similar to the directional lock 1800 shown and described with respect to FIGS. 68A-68D. The first lock washer 3402 can be configured to move between a free position and a locked position, or throughout its available range of motion, with less displacement of the core member 3410 in comparison to the second lock washer 3404. The second lock washer 3404 can provide a greater holding or locking force than the first lock washer 3402, but has a greater range of motion between its free position and its locked position.

The directional lock 3400 of FIG. 113*a* includes a motion transfer arrangement to transfer motion from one of the first lock washer 3402 and the second lock washer 3404 to the other of the first lock washer 3402 and the second lock washer 3404. In the illustrated arrangement, the motion transfer arrangement comprises a motion transfer element 3420 positioned between the first lock washer 3402 and the second lock washer 3404. The illustrated motion transfer element 3420 is a tubular member carried on the core member 3410 and positioned between the first lock washer 3402 and the second lock washer 3404. The motion transfer element 3420 is configured to move the second lock washer 3404 along with movement of the first lock washer 3402 through at least a portion of the range of motion of one or both of the lock washers 3402, 3404. FIG. 113*a* illustrates the one or both of the lock washers 3402, 3404 in or relatively toward a free or unlocked position and FIG. 113*b* illustrates one or both of the lock washers 3402, 3404 in or relatively toward a locked position.

Thus, in at least some arrangements, the motion transfer element 3420 ensures that the second lock washer 3404 begins to move at substantially the same time as the first lock washer 3402, which may result in faster engagement of the second lock washer 3404 than without the motion transfer element 3420. As described above, because in at least some configurations, the range of motion of the second lock washer 3404 may be greater than the range of motion of the first lock washer 3402 (or vice-versa), the first lock washer 3402 and/or the second lock washer 3404 may be able to move relative to the motion transfer element 3420 such that the motion transfer element 3420 does not fix the lock washers 3402, 3404 to one another. In other words, in the illustrated arrangement, the motion transfer element 3420 pushes the second lock washer 3404 through a portion of its range of motion, but allows the second lock washer 3404 to move away from the motion transfer element 3420 and/or allows the motion transfer element 3420 to move away from the first lock washer 3402 such that the second lock washer 3404 can move through a longer range of motion than the first lock washer 3402.

FIGS. 114*a* and 114*b* illustrate an arrangement similar to that of FIGS. 113*a* and 113*b*. However, in the arrangement of FIGS. 114*a* and 114*b*, the motion transfer element 3420 comprises a linking element. The linking motion transfer element 3420 couples the first lock washer 3402 and the second lock washer 3404. However, in at least some configurations, the linking motion transfer element 3420 is configured to allow the second lock washer 3404 to move away from the first lock washer 3402 (or vice-versa). The illustrated linking motion transfer element 3420 is a beam that defines a living hinge. The beam 3420 is deformable from a first position (FIG. 114*a*) having a first length to a second position (FIG. 114*b*) having a second length, which can be greater than the first length. The beam 3420 can have a curved shape in the first position, which can be a relaxed position of the beam 3420. The beam 3420 can flex or deform to a less-curved shape in the second position. Thus, the deformation of the beam 3420 from the curved shape to the less-curved shape can allow the second lock washer 3404 to move away from the first lock washer 3402.

FIGS. 115-117 illustrate possible locations for placement of directional locks 3500 within a headgear 3502 of a patient interface 3504 relative to a user's head. The directional locks 3500 can be of any suitable arrangement, such as any of those disclosed herein. FIG. 115 illustrates the directional lock 3500 integrated within the headgear 3502, which is configured to position the directional lock 3500 aligned with an upper portion or slightly above the user's ear and/or aligned with a rearward portion or slightly behind the user's ear. In the illustrated arrangement, the excess portions of the core members can be accumulated in the rear strap of the headgear 3502; however, other suitable arrangements can also be used. The area in which the directional lock 3500 is positioned in FIG. 115 can be advantageous in that the user's ear projects from the user's head and creates a space that can accommodate the directional lock 3500. With the directional lock 3500 located as such, less pressure may be applied to the directional lock 3500 (such as from the user's pillow) when the user is lying on his or her side compared to other possible side locations for the directional lock 3500. In some cases, with such positioning of the directional lock 3500, there may be little to no significant pressure exerted on the directional lock 3500 when the user is lying on his or her side, which can provide a desirable level of comfort for the user. In addition, the reduced pressure or lack of any significant pressure on the directional lock 3500 can avoid crushing the directional lock 3500 to ensure operability or at least reduce the likelihood of malfunctioning due to crushing forces.

FIGS. 116 and 117 illustrate possible desirable zones relative to a user's head for placement of the directional lock 3500. For example, FIG. 116 illustrated that an area 3510 overlapping a portion of the ear and rearward and above the ear can provide a natural space for receiving the directional lock 3500 and inhibiting or preventing crushing or excessive pressure on the directional lock 3500 when the user is lying on his or her side. The portion of the area 3510 overlapping the ear preferably is the space behind or above the base of the ear. In addition, an area 3512 on top of the head can also provide a desirable location for placement of the directional lock 3500 to inhibit or prevent crushing or excessive pressure on the directional lock 3500 when the user is lying on his or her side or back.

FIG. 117 illustrates the area 3510 overlaid onto a user's head with the bones of the skull illustrated. The area 3510, as described above, can be overlapping a portion of the ear and rearward and above the ear. The area 3510 can be positioned on the temporal bone and can extend toward, to or somewhat beyond a boundary of the temporal bone and onto the parietal or occipital bones. However, in some configurations, the area 3510 does not extend significantly beyond the rearward or upper boundary of the temporal bone. The exact boundary of the area 3510 that would provide acceptable performance may vary between users; however, preferably, the area 3510 is configured to allow a large portion of the intended user population to comfortably utilize a patient interface 3504 and headgear 3502 having a directional lock 3500 positioned within the area 3510 when lying on his or her side. Although not specifically shown in FIG. 117, the area 3512 shown in FIG. 116 can be positioned on the top portions of the frontal and/or parietal bones. Preferably, the area 3512 is limited to substantially upward-facing portions of the frontal and/or parietal bones. The exact boundary of the area 3512 that would provide acceptable performance may vary between users; however, preferably, the area 3512 is configured to allow a large portion of the intended user population to comfortably utilize a patient interface 3504 and headgear 3502 having a directional lock 3500 positioned within the area 3512 when lying on his or her side or back.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A directional lock assembly for a respiratory mask headgear, the directional lock assembly comprising:

- a first lock element comprising a first lock element opening;
- a pair of first lock element retainers;
- a second lock element comprising a second lock element opening;
- a pair of second lock element retainers;
- a core member;
- a housing comprising:
  - a first end wall comprising a first end wall opening,
  - a second end wall comprising a second end wall opening,
  - a first side wall and a second side wall each extending between the first end wall and the second end wall, wherein the first side wall is opposite from the second side wall, and
  - a first chamber configured to house the first lock element and a second chamber configured to house the second lock element;

wherein the first end wall opening, the second end wall opening, the first lock element opening, and the second lock element opening allow the core member to pass through the first lock element opening and the second lock element opening;

wherein the first end wall opening and the second end wall opening are aligned with each other;

wherein a first one of the pair of first lock element retainers is positioned on the first side wall and a second one of the pair of first lock element retainers is positioned on the second side wall, and a first one of the pair of second lock element retainers is positioned on the first side wall and a second one of the pair of second lock element retainers is positioned on the second side wall;

wherein the pair of first lock element retainers are configured to pivotally retain the first lock element within the first chamber and the pair of second lock element retainers are configured to pivotally retain the second lock element within the second chamber; and wherein the first lock element and the second lock element are each configured to pivot between a first position and a second position.

2. The directional lock assembly of claim 1, wherein the application of a tension force to the core member causes the first lock element and the second lock element to pivot between the first position and the second position.

3. The directional lock assembly of claim 1, wherein the first position is an open position and the second position is a locked position.

4. The directional lock assembly of claim 1, wherein the first chamber and the second chamber are separated by an internal wall of the housing, wherein the internal wall comprises an internal wall opening for the core member to pass through, wherein the internal wall opening, the first end wall opening, and the second end wall opening aligned with each other.

5. The directional lock assembly of claim 4, wherein the first chamber accommodates the first lock element and the second chamber accommodates the second lock element, wherein the first chamber and the second chamber differ in size and the first lock element and the second lock element differ in size, wherein the size of the first chamber allows the first lock element to pivot between the first position and the second position, and wherein the size of the second chamber allows the second lock element to pivot between the first position and the second position.

6. The directional lock assembly of claim 1, wherein the first lock element comprises a first shaft and a first arm that extends from the first shaft, and the second lock element comprises a second shaft and a second arm that extends from the second shaft.

7. The directional lock assembly of claim 6, wherein the first shaft and the second shaft are cylindrical.

8. The directional lock assembly of claim 6, wherein the first arm comprises a first opening and the second arm comprises a second opening, and wherein the first opening and the second opening are configured to receive the core member.

9. The directional lock assembly of claim 6, wherein first arm comprises a first arm first section and a first arm second section, wherein the first arm first section extends radially or perpendicularly from the first shaft, and the first arm second section extends at an obtuse angle from an angle of the first arm first section; and wherein the second arm comprises a second arm first section and a second arm second section, wherein the second arm second section extends radially or perpendicularly from the second shaft, and the second arm second section extends at an obtuse angle from an angle of the second arm second section.

10. The directional lock assembly of claim 9, wherein the first arm first section is shorter than the second arm first section.

11. The directional lock assembly of claim 10, wherein the angle between the first arm first section and the first arm second section is greater than the angle between the second arm first section and the second arm second section.

12. The directional lock assembly of claim 6, wherein the first shaft and the second shaft are substantially the same width as the housing, the first arm is narrower than the first chamber, and the second arm is narrower than the second chamber.

13. The directional lock assembly of claim 6, wherein the first lock element retainers comprise a first circular bush and a first elongate slot, and the second lock element retainers comprise a second circular bush and a second elongate slot, and wherein the first circular bush and the second circular bush intersects with a bottom of the housing to form an entrance.

14. The directional lock assembly of claim 13, wherein the first shaft is cylindrical and the second shaft is cylindrical, wherein a diameter of the first shaft is substantially the same as a diameter of the first circular bush such that the first shaft is configured to be received and retained by the first circular bush, and wherein a diameter of the second shaft is substantially the same as a diameter of the second circular bush such that the second shaft is configured to be received and retained by the second circular bush.

15. The directional lock assembly of claim 13, wherein first elongate slot is configured to allow the first lock element to be received into the housing, and wherein the second elongate slot is configured to allow the second lock element to be received into the housing.

16. The directional lock assembly of claim 13, wherein the first elongate slot extends radially from the first circular bush towards a top of the housing, and wherein the second elongate slot extends radially from the second circular bush towards the top of the housing.

17. The directional lock assembly of claim 1, wherein the first chamber and the second chamber are configured to be open at one or both of a top and a bottom of the housing.

18. The directional lock assembly of claim 1, wherein when the directional lock assembly is in the first position, the first end wall opening, the second end wall opening, the first lock element, and the second lock element are all aligned.

19. The directional lock assembly of claim 1, wherein when the directional lock assembly is in the second position, a path of the core member through the directional lock assembly is nonlinear or tortuous and movement of the core member through the directional lock assembly is restricted.

* * * * *